US012084703B2

(12) United States Patent
Li et al.

(10) Patent No.: US 12,084,703 B2
(45) Date of Patent: Sep. 10, 2024

(54) SYNTHETIC SELF-AMPLIFYING MRNA MOLECULES WITH SECRETION ANTIGEN AND IMMUNOMODULATOR

(71) Applicant: SunVax mRNA Therapeutics Inc., Beverly, MA (US)

(72) Inventors: Yingzhong Li, Reading, MA (US); Libin Zhang, Lynnfield, MA (US)

(73) Assignee: SunVax mRNA Therapeutics Inc., Beverly, MA (US)

( * ) Notice: Subject to any disclaimer, the term of this patent is extended or adjusted under 35 U.S.C. 154(b) by 0 days.

(21) Appl. No.: 18/316,033

(22) Filed: May 11, 2023

(65) Prior Publication Data

US 2023/0366001 A1 Nov. 16, 2023

Related U.S. Application Data

(60) Provisional application No. 63/393,688, filed on Jul. 29, 2022, provisional application No. 63/341,018, filed on May 12, 2022.

(51) Int. Cl.
*C12P 19/34* (2006.01)
*C12N 15/88* (2006.01)

(52) U.S. Cl.
CPC .............. *C12P 19/34* (2013.01); *C12N 15/88* (2013.01)

(58) Field of Classification Search
CPC ........ C12P 19/34; C12N 15/88; C12N 15/113
USPC .... 435/6.1, 91.1, 91.31, 455, 458; 536/23.1, 536/24.5; 514/44 A, 44 R
See application file for complete search history.

(56) References Cited

U.S. PATENT DOCUMENTS

| | | | |
|---|---|---|---|
| 2006/0251678 A1 | 11/2006 | Frolov et al. | |
| 2021/0322541 A1 | 10/2021 | Akahata et al. | |

FOREIGN PATENT DOCUMENTS

| | | | | |
|---|---|---|---|---|
| CN | 110218734 * | 3/2018 | .............. C12P 19/34 |
| CN | 114317563 A | 4/2022 | |
| WO | 2018/213803 A1 | 11/2018 | |
| WO | 2020254804 A1 | 12/2020 | |
| WO | WO-2021072075 A1 * | 4/2021 | ............. A61K 39/00 |
| WO | 2021/156267 A1 | 8/2021 | |
| WO | 2021/178661 A1 | 9/2021 | |
| WO | 2021/183563 A1 | 9/2021 | |
| WO | 2021/191630 A1 | 9/2021 | |
| WO | 2021/209970 A1 | 10/2021 | |
| WO | 2021/213924 A1 | 10/2021 | |
| WO | 2021/213945 A1 | 10/2021 | |
| WO | 2021/216776 A2 | 10/2021 | |
| WO | 2021/229448 A1 | 11/2021 | |
| WO | 2021/236854 A1 | 11/2021 | |
| WO | 2021/255270 A1 | 12/2021 | |
| WO | 2022/137128 A2 | 6/2022 | |
| WO | 2022/159511 A2 | 7/2022 | |
| WO | 2023/008553 A1 | 2/2023 | |
| WO | 2023/066874 A1 | 4/2023 | |

OTHER PUBLICATIONS

Bloom et al (Gene Therapy, vol. 28, pp. 117-129 (2021)), (Year: 2021).*
Beissert et al (Human Gene Therapy, vol. 28, No. 12, pp. 1138-1146 (2017)) (Year: 2017).*
Beissert et al (Molecular Therapy, vol. 28, No. 1, pp. 119-128 (2020)) (Year: 2020).*
Geall et al (Seminars in Immunology, vol. 25, pp. 152-159 (2013)).*
Perri et al (J. Virol., Bol. 77, pp. 10,394-10,403 (2003)). (Year: 2003).*
Blakney et al (Molecular Therapy, vol. 29, No. 3, pp. 1174-1185 (2021)) (Year: 2021).*
Maruggi et al (Current Topics in Microbiology and Immunology, Self-amplifying mRNA-based Vaccine Technology and Its Mode of Action (http://doi.org/10.1007/82_2021_233, pp. 1-40 (2021)) (Year: 2021).*
Maruggi et al., "Self-amplifying mRNA-Based Vaccine Technology and Its Mode of Action", Current Topics in Microbiology and Immunology, Apr. 17, 2021, 40 pages, Springer Berlin Heidelberg, Berlin, Heidelberg.
Bloom et al., "Self-amplifying RNA vaccines for infectious diseases", Gene Therapy, vol. 28, No. 3-4, Oct. 22, 2020, pp. 117-129.
Database GenBank [Online] Sep. 28, 2021,Castruita J S.A.: "Synthetic construct HCV1146 Moderna (mRNA-1273) SARS-CoV-2 vaccine sequence", XP093093538, Database accession No. OK120841 abstract, 2 pgs.
Jeong Dae-Eun et al: "Assemblies of putative SARS-CoV2-spike-encoding mRNA sequences for vaccines BNT-162b2 and mRNA-1273",Apr. 15, 2021, XP093093539, Retrieved from the Internet, 2 pgs.
Frolov I et al: "Selection of RNA replicons capable of persistent noncytopathic replication in mammalian cells", Journal of Virology, the American Society for Microbiology, US, vol. 73, No. 5, May 1, 1999, pp. 3854-3865, XP002970391.
Yingzhong Li et al: "In vitro evolution of enhanced RNA replicons for immunotherapy", Scientific Reports, vol. 9, No. 1, May 6, 2019, XP055685185, 10 pgs.

(Continued)

*Primary Examiner* — Jane J Zara
(74) *Attorney, Agent, or Firm* — Rothwell, Figg, Ernst and Manbeck, P.C.

(57) ABSTRACT

Lipid nanoparticle (LNP) encapsulating self-amplifying mRNA, compositions, and methods of using the novel nucleic acid constructs and compositions are disclosed. LNP constructs include novel ionizable lipid. Novel sa-mRNA constructs encode a modified SARS-CoV-2 spike protein, wherein the polynucleotide has been truncated to not include nucleotides encoding a SARS-CoV-2 transmembrane domain and short cytosolic domain amino acids and immunomodulators. Sa-mRNAs are useful in for use as a therapeutic, diagnostic and/or prophylactic agent to mammalian cells or organs.

29 Claims, 23 Drawing Sheets

Specification includes a Sequence Listing.

(56) References Cited

OTHER PUBLICATIONS

Garmashova Natalia et al: "Sindbis virus nonstructural protein nsP2 is cytotoxic and inhibits cellular transcription", Journal of Virology, the American Society for Microbiology, US,vol. 80, No. 12, Jun. 1, 2006, pp. 5686-5696, XP009099860.
Harald Brussow: "Efforts towards a COVID-19 vaccine", Environmental Microbiology, Blackwell Science, GB, vol. 22, No. 10, Sep. 28, 2020, pp. 4071-4084, XP072191926.
Li Yen-Der et al: "Coronavirus vaccine development: from SARS and MERS to COVID-19", Journal of Biomedical Science, Dec. 20, 2020, pp. 1-23, XP055819408.
Tseng Hung Fu et al: "Effectiveness of mRNA-1273 against SARS-CoV-2 Omicron and Delta variants", Nature Medicine, vol. 28, No. 5, May 1, 2022, pp. 1063-1071, XP093093216.
Baden Lindsey R. et al: "Efficacy and Safety of the mRNA-1273 SARS-CoV-2 Vaccine", The New England Journal of Medicine, vol. 384, No. 5, Feb. 4, 2021, pp. 403-416, XP093093433.
Polack Fernando P. et al: "Safety and Efficacy of the BNT162b2 mRNA Covid-19 Vaccine", The New England Journal of Medicine, vol. 383, No. 27, Dec. 31, 2020, pp. 2603-2615, XP055820495.
Weisberg R.A. et al: "Transcriptional Regulation in Bacteriophage" In: "Encyclopedia of Virology", Jan. 1, 2008, Elsevier, XP093092166, ISBN: 978-0-12-374410-4 pp. 174-186.
Conrad Thomas et al: "Maximizing transcription of nucleic acids with efficient T7 promoters", Communications Biology, vol. 3, No. 1, Aug. 14, 2020, XP055780658, 8 pgs.
Hickson Sarah E. et al: "Sequence diversity in the 3' untranslated region of alphavirus modulates IFIT2-dependent restriction in a cell type-dependent manner", bioRxiv, Dec. 11, 2021, XP093092699, 37 pgs.
Dryga Sa et al: "Identification of mutations in a Sindbis virus variant able to establish persistent infection in BHK cells: the importance of a mutation in the nsP2 gene", Virology, Elsevier, Amsterdam, NL, vol. 228, No. 1, Feb. 3, 1997, pp. 74-83, XP002100720.
Petrakova et al: "Noncytopathic Replication of Venezuelan Equine Encephalitis Virus and Eastern Equine Encephalitis Virus Replicons in Mammalian Cells", Journal of Virology, vol. 79, No. 12, May 26, 2005, pp. 7597-7608, XP055295504.
International Search Report issued in PCT/US2023/066903 dated Oct. 31, 2023, 19 pgs.

* cited by examiner

| | Nucleotide | Amino Acids | Region |
|---|---|---|---|
| SAM001 | WT | WT | |
| SAM002 | C5830T | Pro to Ser | nsP2 |
| SAM003 | A5729T | Gln to Leu | nsP2 |

```
               T7-Pro                5UTR
Sam002:      TAATACGACTCACTATAGGATAGG
T7-VEE-GFP:  TAATACGACTCACTATAG-AT-GG
```

Fig. 4

19 nucleotides

Sam002: GGATTTTGTTTTTAATATTTC
Sam004: GGATTTTATTTTTAATATTTC
Sam005: AAATTTTGTTTTTAATATTTC
Sam006: AAATTTTATTTTTAATATTTC

| Puromycin (ug/ml) | Contigs | Nucleotide | Amino Acids | Region |
|---|---|---|---|---|
| 1 | 5 | G7663A | Glu to Lys | nsP4 |
| 10 | 2 | C4491A | Asp to Glu | nsP2 |
| 10 | 3 | T5177C | Met to Thr | nsP2 |
| 10 | 3 | A5361C | Glu to Asp | nsP2 |
| 10 | 3 | A5735G | Lys to Arg | nsP2 |
| 10 | 4 | A6452G | Lys to Arg | nsP3 |
| 10 | 5 | A7765G | Arg to Gly | nsP4 |

Fig. 28b

| Contigs | 2 | 3 | 4 | 5 |
|---|---|---|---|---|
| | WT | WT | WT | WT |
| | a1(4491A) | b1(T5177C) | c1(A6452G) | d1(A7765G) |
| | | b2(A5361C) | | |
| | | b3(A5735G) | | |
| Allele No | 2 | 4 | 2 | 2 |

Fig. 28c

SYNTHETIC SELF-AMPLIFYING MRNA MOLECULES WITH SECRETION ANTIGEN AND IMMUNOMODULATOR

CROSS-REFERENCE TO RELATED APPLICATIONS

This application claims priority to U.S. Provisional Application No. 63/341,018, filed on May 12, 2022, and U.S. Provisional Application No. 63/393,688, filed on Jul. 29, 2022, each of which is incorporated by reference herein in its entirety for all purposes.

SEQUENCE LISTING STATEMENT

The instant application contains a Sequence Listing in electronic format which has been submitted via EFS-Web. Said Sequence Listing, created on Jan. 18, 2024, is named "5292-102US2ST26.xml" and is 172,032 bytes in size. The information in the electronic format of the Sequence Listing is part of the present application and is incorporated herein by reference in its entirety.

TECHNICAL FIELD

The present disclosure provides novel self-amplifying mRNA (sa-mRNA) constructs, compositions comprising such constructs, and methods to deliver one or more biologically active agents to a subject in need thereof.

BACKGROUND mRNA vaccine platforms are able to stimulate humoral and cellular immune responses to foreign antigen that are encoded, and are an improvement to traditional vaccines because they allow for rapid, scalable, and cell free manufacturing. However, achieving adequate antigen expression for protection or immunomodulation is a medical challenge for existing mRNA vaccines because the number of mRNA transcripts available in vivo is proportional to the number of mRNA transcripts successfully delivered during vaccination, thus existing mRNA vaccines require large doses or repeated administrations. Large doses and repeated administrations of mRNA vaccines, circular mRNA, and sa-mRNA vaccines are undesirable because large doses of the mRNA, circular mRNA, or sa-mRNA can elicit undesirable immune responses and repeated administration can render subsequent administration of the same vaccine less effective.

Sa-mRNA is a kind of mRNA with the ability to replicate itself in a cell and amplify the expression of cargo genes, e.g., a gene of interest. However, achieving sufficient production of the molecules and interferon responses of sa-mRNA remain difficult due to the large size of sa-mRNA and the immunogenicity due to its origination from alphaviruses. Thus, there remains a need to increase intracellular mRNA transcripts in vivo, to produce better immune response at lower doses and avoid safety challenges.

Delivery of biologically active agents, including sa-mRNA, is also a medical challenge due to the inherent properties of RNA, including its highly negative charges and its size, which is much larger than modified mRNA and circular mRNA. In particular, the delivery of biologically active agents to cells is made difficult by the relative instability and low cell permeability of such molecules and safety concerns due to cytotoxicity. Ionizable lipids, one component of LNPs, are believed to play key role in uptake of LNPs by cells and the release of LNPs from the endosome. Thus, there exists a need to develop compounds, compositions, and methods for improved delivery of therapeutic, diagnostic and/or prophylactic molecules into cells or organs.

SUMMARY OF THE INVENTION

The present invention addresses these needs by providing novel ionizable lipids, nanoparticle compositions and sa-mRNA, which improve the delivery of biologically active agents into cells or organs while reducing safety concerns associated with incompatibly high transcript levels and/or rapid decay of the biologically active agent leading to increased administrations. The present disclosure provides novel sa-mRNA and compositions and methods involving the same.

In one aspect, the present disclosure provides a method of increasing transfection efficiency and decreasing cytotoxicity of a nanoparticle formulation by using a novel ionizable lipid in the LNP formulation. In some aspects, the method and compositions include the ionizable lipid Formula E6 (1,1',1"-(1,3,5-triazinane-1,3,5-triyl)tris(3-(ditridecylamino)propan-1-one)):

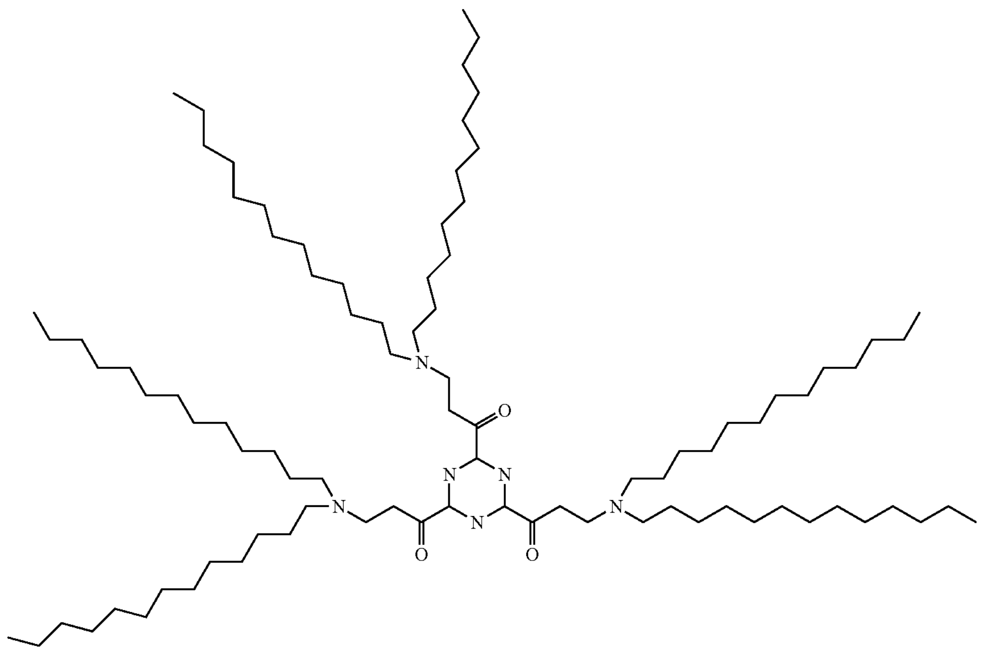 [SMILES: CCCCCCCCCCCCCN(CCCCCCCCCCCCC)CCC(=O)C1NC(C(=O)CCN(CCCCCCCCCCCCC)CCCCCCCCCCCCC)NC(C(=O)CCN(CCCCCCCCCCCCC)CCCCCCCCCCCCC)N1]
In some aspects, the method and compositions include the ionizable lipid Formula E2 (1,1',1"-(1,3,5-triazinane-1,3,5-triyl)tris(3-(dinonylamino)propan-1-one)):
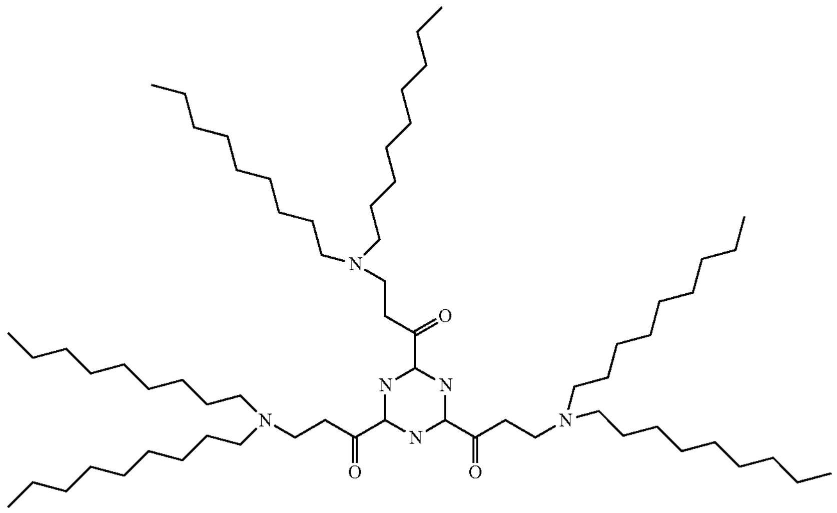 [SMILES: CCCCCCCCCN(CCCCCCCCC)CCC(=O)C1NC(C(=O)CCN(CCCCCCCCC)CCCCCCCCC)NC(C(=O)CCN(CCCCCCCCC)CCCCCCCCC)N1]

In some aspects, the method and compositions include the ionizable lipid Formula P6 (N-(2-(cyclohex-1-en-1-ylamino)-1-(1-ethylpiperidin-4-yl)-2-oxoethyl)-N-(heptadecan-9-yl)palmitamide):

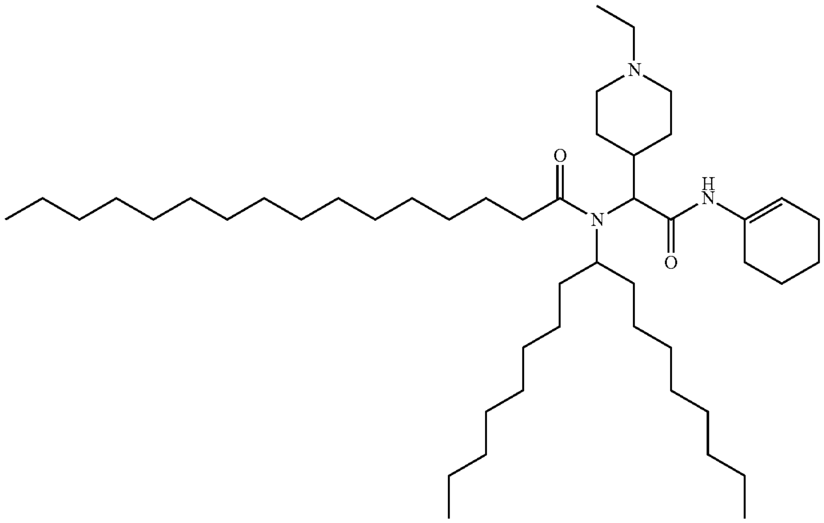

In one aspect, the sa-mRNA of the present disclosure is delivered to a host cell by an LNP formulated with an ionizable lipid, a helper lipid, a cholesterol, and/or a PEG-lipid. The present disclosure incorporates the ionizable lipid components of PCT Patent Application No. PCT/US2023/017777, which is fully incorporated herein. In one aspect, the LNP has a molar ratio of about 2-60% ionizable lipid, about 5-40% helper lipid, about 30-80% cholesterol and about 0.5-30% PEG-lipid. The present disclosure incorporates any integer or fraction thereof within the recited ranges as if expressly written herein. In one aspect, the LNP has a molar ratio of about 5-50% or 8 to 40% or 10 to 30% ionizable lipid, about 10-30% or 13 to 25% or 15 to 20% helper lipid, about 40-70% or 45 to 65% or 50 to 60% cholesterol and about 1-20% or 3-15% or 5 to 10% PEG-lipid. In one aspect, the LNP has a molar ratio of about 2-10% ionizable lipid, about 5-15% helper lipid, about 40-80% cholesterol and about 0.5-3% PEG-lipid. In one aspect, the ionizable lipid is E6. In one aspect, the helper lipid is independently selected from DOPE (2-dioleoyl-sn-glycero-3-phosphoethanolamine), DSPC (1,2-distearoyl-sn-glycero-3-phosphocholine), and POPE (1-palmitoyl-2-oleoyl-sn-glycero-3-phosphoethanolamine). In one aspect, the LNP of the present disclosure, the ionizable lipid is E6, the helper lipid is DOPE and the PEG-lipid is DMG-PEG2000. In one aspect of the disclosure, the LNP is composed of E6, DOPE, cholesterol, and DMG-PEG-2000. In one aspect, the LNP of the disclosure has a molar ratio of 50% ionizable lipid, 10% helper lipid, 38.5% cholesterol, and 1.5% PEG-lipid. In another aspect, the LNP of the disclosure has a molar ratio of 7.5% ionizable lipid, 15% helper lipid, 75% cholesterol, and 2.5% PEG-lipid. In another aspect, the LNP of the disclosure has a molar ratio of 5% ionizable lipid, 10% helper lipid, 50% cholesterol, and 1.5% PEG-lipid. In one aspect, the ionizable lipid is E6, the helper lipid is DOPE and the PEG-lipid is DMG-PEG2000.

In one aspect, the biologically active agent is a nucleic acid molecule, and the nucleic acid molecule is RNA or DNA. In one aspect, the biologically active agent is RNA and the RNA is mRNA, tRNA, rRNA, siRNA, or snRNA. In one aspect of the present disclosure, the biologically active agent is sa-mRNA. In one aspect, the mRNA is chemically modified. In one aspect, the chemically modified mRNA is composed of nucleotides selected from the group 1-methyl-pseudouridine, 5-methyl-uridine, and 5-methyl-cytidine. In one aspect, the biologically active agent is a sa-mRNA encoding one or more antigens and one or more immunomodulators. In one aspect, the encoded antigen is a viral antigen. In one aspect, the encoded antigen is a modified SARS-CoV-2 spike protein. In one aspect, the immunomodulator is a cytokine, a chemokine, or other immune stimulator or inhibitor.

In one aspect, the present disclosure provides a method of increasing the copy number of a nucleic acid encoding two expression units comprising: i) an origin of replication sequence (Ori); ii) a first expression unit encoding a first nucleotide sequence that is operably linked to a first promoter; and iii) a second expression unit encoding a second nucleotide sequence that is operably linked to a second promoter, wherein the first expression unit encodes a selectable marker and the second expression unit encodes a self-amplifying mRNA; b) selecting cells that express the selectable marker; c) subculturing the selected cells to obtain a population of cells that express the selectable marker; and d) propagating the population of cells to increase the copy number of the nucleic acid. In some aspects, the nucleic acid is an RNA molecule. In one aspect, the nucleic acid molecule of the present disclosure is a recombinant DNA molecule. In one aspect, the nucleic acid molecule of the present disclosure is a closed circular molecule or a linear molecule. In one aspect, said nucleic acid molecule is a plasmid. In one aspect, the initial nucleic acid encoding two expression units is synthesized using standard synthetic techniques, e.g., using an automated DNA synthesizer.

In one aspect, the nucleic acid includes a replication system allowing it to be maintained in the host for expression or for cloning and amplification. A nucleic acid may be present in the cell in either high or low copy number. Generally, about 5 to about 200 times of mRNA copies of house-keeping gene beta-Actins will be present within a host cell. A host cell containing a high copy number of mRNA transcripts will preferably contain at least about 10 to about 20 times mRNA copies of house-keeping gene beta-Actins. A host cell containing a low number of nucleic acid will preferably contain about 1 to 10, and usually about 1 to 4 times mRNA copies of house-keeping gene beta-Actins. The copy number of a nucleic acid including mRNA transcripts may be controlled by selection of different origins of replication according to methods known in the art. Sambrook and Russell, Molecular Cloning: A Laboratory Manual, 3rd edition (Jan. 15, 2001) Cold Spring Harbor Laboratory Press, ISBN: 0879695765.

In one aspect, the first expression unit comprises the following operably linked nucleic acid sequence in a 5' to 3' direction or in a 3' to 5' direction:

[Pr1]-[SM]

wherein, Pr1 is a first promoter sequence, and SM is a selectable marker. In some aspects, the first promoter is a promoter that is recognized by bacterial machinery and drives transcription of the encoded selective marker. In some aspects, the first expression unit encodes a selectable marker to allow for the selection of bacterial host cells that have been transformed. Selectable markers can be expressed in the bacterial host cell and may include genes which render bacteria resistant to drugs such as ampicillin, kanamycin (neomycin), chloramphenicol, erythromycin, and tetracycline (Davies et al., Ann. Rev. Microbiol., 32: 469 (1978)).

In one aspect, the second expression unit comprises the following operably linked nucleic acid sequence from 5' to 3':

Pr2-5'UTR-nsP-SGP-GOI-3'UTR-PolyA wherein, Pr2 is a second promoter sequence, 5'UTR is a 5' untranslated region, nsP is a plurality of non-structural replicase domain sequences, SGP is a subgenomic promoter, GOI is one or more gene or genes of interest, 3'UTR is a 3' untranslated region, and Poly-A is a 3' poly-adenylated tail (poly-A tail). In some aspects, when there is more than one GOI, each GOI is operably linked to its own SGP.

In some aspects, the second promoter is a promoter that drives transcription of the encoded self-amplifying mRNA using the second expression unit as a template for in vitro transcription of nucleic acid, e.g. mRNA. Suitable promoters include, for example, T7 promoter, T3 promoter, SV40 promoter, SP6 promoter, T5 promoter, β-lactamase promoter, *E. coli* galactose promoter, arabinose promoter, alkaline phosphatase promoter, tryptophan (trp) promoter, lactose operon (lac) promoter, lacUV5 promoter, trc promoter, tac promoter, and the like, or mutants of these promoters. A sa-mRNA can be prepared by transcribing (e.g., in vitro transcription) a DNA that encodes the sa-mRNA using a suitable DNA-dependent RNA polymerase, such as: T7 phage RNA polymerase, SP6 phage RNA polymerase, T3 phage RNA polymerase, T5 phage RNA polymerase, RNA polymerase III, RNA polymerase II, Taq polymerase, Vent polymerase, and the like, or mutants of these polymerases. The transcription reaction will contain nucleotides, including modified nucleotides in some aspects, and other components that support the activity of the selected polymerase, such as a suitable buffer, and suitable salts. In some aspects, nucleotide analogs will be incorporated into a sa-mRNA to, for example, alter the stability of such RNA molecules, to increase resistance against RNases, to establish replication after introduction into appropriate host cells ("infectivity" of the RNA), and/or to induce or reduce innate and adaptive immune responses.

In another aspect, the nucleic acid is engineered to express alphavirus nonstructural proteins. U.S. Pat. Nos. 7,045,335, 7,078,218, 7,425,337 and 7,442,381 describe numerous constructs for such alphavirus RNA replicons consisting of the 5' and 3' alphavirus replication recognition sequences, coding sequences for alphavirus nonstructural proteins, and a polyadenylation tract, and such constructs are incorporated herein by reference.

In some aspects, at least one non-structural replicase domain sequence comprise sequences selected from Group IV RNA viruses, including Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus. In yet another aspect, at least one non-structural replicase domain sequence is obtained from the TC-83 strain of Venezuelan Equine Encephalitis virus (VEE). In some aspects, the plurality of non-structural replicase domain sequences are alphavirus nonstructural proteins 1-4 (nsP1-4) and, in some aspects, the sa-mRNA of the present disclosure contains a subgenomic promoter that directs expression of said proteins.

In some aspects, a GOI can encode a therapeutic polypeptide, a prophylactic polypeptide, a diagnostic polypeptide, a reporter gene, an antigen, or a gene that encodes regulatory structures. In some aspects, a GOI can encode an infectious disease antigen, an allergic antigen or a tumor antigen. In some aspects, a GOI is a non-coding gene, which encodes regulatory structures such as small interfering RNA (siRNA), micro-RNA (miRNA), self-activating RNA (saRNA), transfer RNA (tRNA), guiding or guide RNA (gRNA) or long intergenic non-coding (lincRNA).

In some aspects, the nucleic acid of the disclosure comprise a sequence that is 90%, 91%, 92%, 93%, 94%, 95%, 96%, 97%, 98%, 99%, or 100% identical to SAM001 (SEQ ID NO: 35), SAM002 (SEQ ID NO: 36), SAM003 (SEQ ID NO: 37), SAM004 (SEQ ID NO: 38), SAM005 (SEQ ID NO: 39), SAM006 (SEQ ID NO: 40), MOD001 (SEQ ID NO: 41), or T7-VEE-GFP (SEQ ID NO: 42).

In some aspects, the nucleic acid molecule of the present disclosure is suitable, in particular after linearization, for in vitro transcription of RNA, in particular self-amplifying mRNA. Circular plasmids are generally linearized downstream of the poly-A tail of the second expression unit by type II restriction enzymes (recognition sequence corresponds to cleavage site), prior to in vitro transcription. The linearized plasmid can then be used as template for in vitro transcription, the resulting transcript ending in a poly-A sequence.

Accordingly, in one aspect, it is preferred that the nucleic acid molecule of the present disclosure can be cleaved, preferably enzymatically or in another biochemical way, within the nucleic acid sequence in such a way that said cleavage results in a nucleic acid molecule which comprises, in the 5'→3' direction of transcription:

L1-Ori-SM-Pr1-L2-Pr2-5'UTR-nsP-SGP-L3-GOI-L4-3'UTR-PolyA wherein, L1 is a first linker, Ori is an origin of replication sequence, SM is a selectable marker, Pr1 is a first promoter sequence, L2 is a second linker, Pr2 is a second promoter sequence, 5'UTR is a 5' untranslated region, nsP is a plurality of non-structural replicase domain sequences, SGP is a subgenomic promoter, L3 is a third linker, GOI is one or more gene or genes of interest, L4 is a fourth linker, 3'UTR is a 3' untranslated region, and Poly-A is a 3' poly-adenylated tail. The nucleic acid molecule of the present disclosure is preferably a closed circular molecule prior to cleavage and a linear molecule after cleavage. Preferably, cleavage is carried out with the aid of a restriction cleavage site which is preferably a restriction cleavage site for a type IIS restriction endonuclease. In one aspect, the recognition sequence for the type IIS restriction endonuclease is 5-26 base pairs. In aspect, restriction enzyme MluI is used at the end of the Poly A.

In one aspect, the nucleic acid contains one or more linkers wherein each linker is independently selected from a nucleic acid sequence comprising

```
CGCGTGATAACGCAGGAAAGAACATGTGAGCAAAAGGCCAGCAAAAGGCC
AGGAACCGTAAAAAGGCCGCGTTGCTGGCGTT (SEQ ID NO: 43),

CACATTTCCCCGAAAAGTGCCACCTGAGCTC (SEQ ID NO: 44),

TTCGAAGGCGCGCCTCTAGAGCCACC (SEQ ID NO: 45),
or

CATCGATGATATCGCGGCCGCATACAGCAGC (SEQ ID NO: 46).

In some aspects, L1 comprises SEQ ID NO: 43
(CGCGTGATAACGCAGGAAAGAACATGTGAGCAAAAGGCCAGCAAAAGGC
CAGGAACCGTAAAAAGGCCGCGTTGCTGGCGTT);

L2 comprises SEQ ID NO: 44
(CACATTTCCCCGAAAAGTGCCACCTGAGCTC);

L3 comprises SEQ ID NO: 45
(TTCGAAGGCGCGCCTCTAGAGCCACC);
and

L4 comprises SEQ ID NO: 46
(CATCGATGATATCGCGGCCGCATACAGCAGC).
```

In one aspect, the present disclosure relates to a method of obtaining self-amplifying mRNA comprising: a) performing an in vitro transcription reaction using an initial amount of a nucleic acid molecule of the present disclosure, and b) producing a sa-mRNA by in vitro transcription, using the nucleic acid molecule as a template and RNA polymerase (e.g., T7 polymerase).

In another aspect, the present disclosure relates to a nucleic acid molecule, preferably obtained by linearization of an above-described nucleic acid molecule by cleavage within the nucleic acid sequence, and to sa-mRNA obtainable by transcription, preferably in vitro transcription, with above-described nucleic acid molecules under the control of the second promoter.

Thus, in one aspect, the present disclosure relates to sa-mRNA comprising in the 5'→3' direction:

```
5'UTR-nsP-SGP-GOI-3'UTR-PolyA
```

wherein, 5'UTR is a 5' untranslated region, nsP is a plurality of non-structural replicase domain sequences, SGP is a subgenomic promoter, GOI is one or more gene or genes of interest, 3'UTR is a 3' untranslated region, and Poly-A is a 3' poly-adenylated tail. In some aspects, the RNA further comprises linkers before the nsP, and between the GOI and 3'UTR.

The methods of the present disclosure may be performed in vitro or in vivo. In one aspect of any of the methods of the present disclosure, transcription is carried out in vitro.

In one aspect, the present disclosure provides nucleic acids and modified regulatory elements, the use of which increases transcription efficiency while reducing the amount of truncated single-stranded ribonucleic acid (ssRNA) (e.g., sa-mRNA) transcript produced during an in vitro transcription (IVT) reaction. In a typical IVT reaction, greater than 50% (molarity) of the RNA transcripts produced are truncated abortive products (referred to herein as truncated ssRNA transcripts). Only a small fraction (e.g., 0.2-0.5%) of initiation events lead to full-length "run-off" ssRNA transcripts, which is inefficient and costly for large-scale IVT RNA synthesis systems. Sa-mRNA transcripts in particular are longer than conventional mRNA (larger than 7 kilo nucleotides) and are particularly susceptible to truncated abortive products. Thus, use of the IVT methods of the present disclosure (which include, for example, nucleic acids, modified promoters and/or modified 5'UTR), in some aspects, results in a sa-mRNA transcript yield that is at least 40% greater than the sa-mRNA transcript yield of an IVT method without the modified regulatory elements of the present disclosure.

In one aspect, the present disclosure provide nucleic acid templates that comprise a modified T7 promoter operably linked to nucleic acid comprising a sequence that encodes a modified 5' untranslated region (UTR) a plurality of non-structural replicase domain sequences, one or more gene or genes of interest (GOI), a 3' UTR, and a poly-A tail, wherein the sequence that encodes the T7 promoter and the sequence that encodes the 5' UTR is modified to enhance the binding strength of T7 polymerase to the T7 promoter to increase transcript yield.

In some aspects, a modified T7 promoter comprises at least one insertion at position at the 5' end of the wildtype T7 promoter nucleotide sequence. The modification may be, for example, insertion of a single guanine (G) at the 5' end of the wildtype T7 promoter. In some aspects, the modified T7 promoter comprises SEQ ID NO: 47 (TAATACGACTCACTATAGG).

In some aspects, a modified 5'UTR comprises at least one insertion at position 3 relative to the 5' end of the wildtype 5'UTR nucleotide sequence. The modification may be, for example, insertion of a single adenine (A) at position 3 of the wildtype 5'UTR of wildtype T7-VEE-GFP (SEQ ID NO: 42). In some aspects, the modified 5'UTR comprises ATAGG.

In one aspect, the present disclosure provides nucleic acids and modified regulatory elements, the use of which modulates, preferably decreases, the immunogenicity and/or immunostimulatory capacity of a mRNA (immune response against an mRNA), preferably a self-amplifying mRNA, which encodes at least one biologically active polypeptide or protein, by preferably increasing the adenine (A) content of the 3'UTR. In some aspects, use of the nucleic acids and modified regulatory elements of the present disclosure (which include, for example, nucleic acid constructs, and/or modified 3'UTR), results in interferon responses that are 2 times, 3 times, 4 times, or 5 times lower than the interferon response to self-amplifying mRNAs without the modified regulatory elements of the present disclosure after one day post-transfection. In one aspect, the nucleic acids and modified regulatory elements of the present disclosure is able to induce reduced interferon response without the use of modified nucleotides (e.g. $N^1$-Methylpseudouridine-5'-Triphosphate).

In some aspects, a modified 3'UTR comprises at least one modification at any one of positions 6, −1, or −2 relative to a conserved 19 nucleotide sequence SEQ ID NO: 49 (GGATTTTGTTTTTAATATTTC). The modification may be, for example, a mutant 3'UTR of an alphavirus comprising point mutations at position 6 relative to the conserved 19 nucleotide sequence, SEQ ID NO: 49, of the wild-type 3'UTR of an alphavirus. The modification may also be, for example, a mutant 3'UTR of an alphavirus comprising point mutations at positions −1 and −2 relative to the conserved 19 nucleotide sequence, SEQ ID NO: 49, of the wild-type 3'UTR of an alphavirus. The modification may also be, for example, a mutant 3'UTR of an alphavirus comprising point mutations at positions −1, −2 and 6 relative to the conserved 19 nucleotide sequence, SEQ ID NO: 49, of the wild-type 3'UTR of an alphavirus. In some aspects, the modified 3'UTR conserved sequence comprise GGATTTTATTTTTAATATTTC (SEQ ID NO: 50), AAATTTTGTTTTTAATATTTC (SEQ ID NO: 51), or AAATTTTATTTTTAATATTTC (SEQ ID NO: 52).

In one aspect, the biologically active agent comprises a sa-mRNA containing a polynucleotide sequence selected from:

a) a polynucleotide encoding a modified SARS-CoV-2 spike protein comprising the nucleic sequence set forth in SEQ ID NO: 1 (BA.1-1273);
b) a polynucleotide encoding a modified SARS-CoV-2 spike protein comprising the nucleic sequence set forth in SEQ ID NO: 2 (BA.1-1273-S2P);
c) a polynucleotide encoding a modified SARS-CoV-2 spike protein comprising the nucleic sequence set forth in SEQ ID NO: 3 (BA.2-1273);
d) a polynucleotide encoding a modified SARS-CoV-2 spike protein comprising the nucleic sequence set forth in SEQ ID NO: 4 (BA.2-1273-S2P);
e) a polynucleotide encoding a modified SARS-CoV-2 spike protein comprising the nucleic sequence set forth in SEQ ID NO: 5 (BA.1-1208); or
f) a polynucleotide encoding a modified SARS-CoV-2 spike protein comprising the nucleic sequence set forth in SEQ ID NO: 6 (BA.1-1208-S2P);
g) a polynucleotide encoding a modified SARS-CoV-2 spike protein comprising the nucleic sequence set forth in SEQ ID NO: 7 (BA.2-1208); or
h) a polynucleotide encoding a modified SARS-CoV-2 spike protein comprising the nucleic sequence set forth in SEQ ID NO: 8 (BA.2-1208-S2P).

In one aspect, the sa-mRNA of the present disclosure encodes two separated expression units, the nucleic acid comprising:

i) a first expression unit comprising a polynucleotide encoding a modified antigen, wherein the polynucleotide encoding the modified antigen is truncated to not include nucleotides encoding a transmembrane domain and short cytosolic domain amino acids of the antigen, operably linked to a first subgenomic promoter; and
ii) a second expression unit encoding immunomodulators (IM) that are operably linked to a second subgenomic promoter.

In one aspect, the polynucleotide sequence encoding the modified antigen comprises replacement of a transmembrane domain of the antigen with a secretion antigen. In one aspect, the antigen is a modified SARS-CoV-2 spike protein, wherein the polynucleotide has been truncated to not include nucleotides encoding a SARS-CoV-2 transmembrane domain and short cytosolic domain amino acids. In one aspect, the polynucleotide sequence encoding a coronavirus spike protein truncated to not include nucleotides encoding a SARS-CoV-2 transmembrane domain and short cytosolic domain amino acids corresponding to amino acids 1209-1273 of a polynucleotide is selected from the group SEQ ID NOs: 1 (BA.1-1273), and 3 (BA.2-1273).

In one aspect, the sa-mRNA comprises the following operably linked nucleic acid sequence from 5' to 3':

nsP-SGP1-Ag-SGP2-IM wherein nsP is a plurality of non-structural replicase domain sequences, SGP1 is the first subgenomic promoter, Ag is a nucleotide sequence selected from SEQ ID NO: 1 (BA.1-1273), 2 (BA.1-1273-S2P), 3 (BA.2-1273), and SEQ ID NO: 4 (BA.2-1273-S2P), SEQ ID NO: 5 (BA.1-1208), SEQ ID NO: 6 (BA.1-1208-S2P), SEQ ID NO: 7 (BA.2-1208), or SEQ ID NO: 8 (BA.2-1208-S2P).

SGP2 is the second subgenomic promoter, and

IM is the immunomodulator.

In one aspect, the sa-mRNA comprises the following operably linked nucleic acid sequence from 5' to 3':

nsP-SGP1-IM-SGP2-AG wherein nsP is a plurality of non-structural replicase domain sequences, SGP1 is the first subgenomic promoter, IM is the immunomodulatory, SGP2 is the second subgenomic promoter, and Ag is a nucleotide sequence selected from SEQ ID NO: 1 (BA.1-1273), 2 (BA.1-1273-S2P), 3 (BA.2-1273), and SEQ ID NO: 4 (BA.2-1273-S2P), SEQ ID NO: 5 (BA.1-1208), SEQ ID NO: 6 (BA.1-1208-S2P), SEQ ID NO: 7 (BA.2-1208), or SEQ ID NO: 8 (BA.2-1208-S2P).

In some aspects, the IM encodes one or more cytokines, chemokines, immune stimulators or inhibitors. In one aspect, the IM is selected from IL12 and IL21. In one aspect, the IM encodes one or more cytokines selected from SEQ ID NOs: 22 (hIL12-P40), 24 (hIL12-P35), 15 (mIL12 P40), 17 (mIL12-P35), and 19 (mIL21). In one aspect, SGP1 is SEQ ID NO: 9 (SGP1). In one aspect, SGP2 is SEQ ID NO: 11 (SGP2). In one aspect, IM is selected from SEQ ID NO: 13 (IM1), and SEQ ID NO: 20 (IM2).

In another aspect, the present disclosure includes a sa-mRNA comprising the following operably linked nucleic acid sequence from 5' to 3':

SP-IL12 P40-L1-IL12 P35-L2-IL21 wherein

SP is a signal peptide,

IL12-P40 is interleukin-12 comprising heavy chain p40,

L1 is linker 1,

IL12 P35 is interleukin-12 comprising light chain p35,

L2 is linker 2, and

IL21 is interleukin-21.

In some aspects, SP is selected from SEQ ID NO: 14 (MSP) and SEQ ID NO: 21 (HSP). In some aspects, IL12-P40 is selected from SEQ ID NO: 15 (mIL12-P40) and SEQ ID NO: 22 (hIL12-P40). In some aspects, L1 is selected from SEQ ID NO: 16 (L(a)) and SEQ ID NO: 23 (L(c)). In some aspects, IL12-P35 is selected from SEQ ID NO: 17 (mIL12-P35) and SEQ ID NO: 24 (hIL12-P35). In some aspects, L2 is selected from SEQ ID NO: 18 (L(b)) and SEQ ID NO: 25 (L(d)). In some aspects, IL12-P40 is selected from SEQ ID NO: 19 (mIL21) and SEQ ID NO: 26 (hIL21).

In some aspects, at least one non-structural replicase domain sequence comprise sequences selected from Group IV RNA viruses, selected from Picornaviridae, Togaviridae, Coronaviridae, Hepeviridae, Caliciviridae, Flaviviridae, and Astroviridae. In some aspects, at least one non-structural replicase domain sequence comprise sequences selected from Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus. In yet another aspect, at least one non-structural replicase domain sequence is obtained from the TC-83 strain of Venezuelan Equine Encephalitis virus (VEE). In some aspects, the plurality of non-structural replicase domain sequences are alphavirus nonstructural proteins 1-4 (nsP1-4).

In some aspects, SGP1 is a viral promoter recognized by viral RNA dependent RNA polymerase (RdRP). In some aspects, SGP2 is a viral promoter recognized by viral RNA dependent RNA polymerase (RdRP). In some aspects, SGP1 and SGP2 are different subgenomic promoters.

In some aspects, the sa-mRNA of the disclosure comprise one or more linkers. In some aspects, the linkers are selected from the group SEQ ID NOs: 13 (L(a)), 15 (L(b)), 20 (L(c)), and 22 (L(d)).

In some aspects, the sa-mRNA of the present disclosure comprise a polynucleotide encoding a modified SARS-CoV-2 spike protein. In some aspects, the polynucleotide encoding a modified SARS-CoV-2 spike protein comprising a nucleic sequence selected from SEQ ID NO: 1 (BA.1-1273), SEQ ID NO: 2 (BA.1-1273-S2P), SEQ ID NO: 3 (BA.2-1273), SEQ ID NO: 4 (BA.2-1273-S2P), SEQ ID NO: 5 (BA.1-1208), and SEQ ID NO: 6 (BA.1-1208-S2P), SEQ ID NO: 7 (BA.2-1208), or SEQ ID NO: 8 (BA.2-1208-S2P).

The molecules, platforms, methods and other aspects of the present disclosure may be utilized, for example, for increasing expression of certain biologically active proteins in cellular transcription and expression. In some aspects, the present disclosure may be used to induce expression of recombinant proteins. This includes, for example, recombinant antibodies, hormones, cytokines, enzymes, and the like.

It is also possible to use the nucleic acid molecules of the present disclosure for gene therapy applications. Accordingly, in some aspects, a nucleic acid molecule of the present disclosure may be a gene therapy vector and used for expression of a transgene. Preferably, alphavirus vector systems may be used.

It is also possible to use the nucleic acid molecules of the present disclosure for gene regulation applications. In some aspects, the present disclosure may be used to modulate, increase or decrease, transcription of certain genes for therapeutic purposes. This includes, for example, small interfering RNA (siRNA), guide RNA (gRNA), micro-RNA (miRNA), self-activating RNA (saRNA), transfer RNA (tRNA), long intergenic non-coding (lincRNA), and the like.

Cells can be transfected with these nucleic acid molecules in vitro, for example in lymphocytes or dendritic cells, or else in vivo by direct administration.

Sa-mRNA of the present disclosure (e.g. obtained using a nucleic acid molecule described herein as a transcription template) may be employed, for example, for transient expression or silencing of genes, with possible fields of application being self-amplifying mRNA-based vaccines which are transfected into cells in vitro or administered directly in vivo, transient expression of functional recombinant proteins in vitro, for example to study functions of proteins, and transient expression or silencing of functional proteins such as erythropoietin, hormones, coagulation inhibitors, etc., in vivo, in particular as pharmaceuticals.

Sa-mRNAs of the present disclosure may be used for transfecting antigen-presenting cells and thus as a tool for delivering the antigen to be presented with said antigen corresponding to the peptide, protein, or protein fragment expressed from said self-amplifying mRNA or being derived therefrom, in particular by way of intracellular processing such as cleavage. Such antigen-presenting cells may be used for stimulating T cells, in particular CD4+ and/or CD8+ T cells.

Accordingly, in a further aspect, the present disclosure relates to a use of the self-amplifying mRNAs of the present disclosure for transfecting a host cell. In one aspect, the host cell is an antigen-presenting cell, such as a dendritic cell, a monocyte or a macrophage.

In a further aspect, the present disclosure relates to a use of sa-mRNAs of the present disclosure for therapy, in particular for vaccination.

In a further aspect, the present disclosure relates to a pharmaceutical composition such as a vaccine composition comprising the sa-mRNAs of the present disclosure. In one aspect, the sa-mRNAs of the present disclosure is formulated within a pharmaceutically acceptable carrier. In some aspects, the pharmaceutically acceptable carrier is a sa-mRNA delivery system, preferably a nanoparticle composition. In some aspects, said nanoparticle composition comprises a cationic lipid, a PEG-modified lipid, a sterol and a non-cationic lipid.

In one aspect, the present disclosure provides a method of delivering a peptide to a subject, comprising administering a pharmaceutical composition containing one or more self-amplifying mRNAs of the present disclosure to the subject, wherein the sa-mRNA(s) of the present disclosure produces a detectable amount of peptide in a tissue of the subject.

In a further aspect, the present disclosure relates to a use of sa-mRNA of the present disclosure as a research tool, such transfecting a cell with the sa-mRNA of the present disclosure encoding a reporter gene, in particular a reporter gene encoding a Green fluorescent protein (GFP).

Also provided herein are methods for generating a library of sa-mRNA using the sa-mRNA of the present disclosure as a reference.

Each of the aspects of the present disclosure can encompass various elements of the present disclosure. It is, therefore, anticipated that each of the aspects of the present disclosure involving any one element or combinations of elements can be included in each aspect of the present disclosure. This disclosure is not limited in its application to the details of construction and the arrangement of components set forth in the following detailed description or illustrated in the drawings.

BRIEF DESCRIPTION OF THE DRAWINGS

FIG. 4 shows a comparison of the nucleotide sequence of the junction region of the T7-Promoter and 5' UTR in T7-VEE-GFP (nucleotides 1819-1840 of SEQ ID NO: 42) and SAM002 (SEQ ID NO: 53).

Omicron variant. Each group of mice were bled at day 0, and 2WP1, and 2WP2 (two week post second injection) to compare vaccine efficacy over time between different populations.

Figure 22:
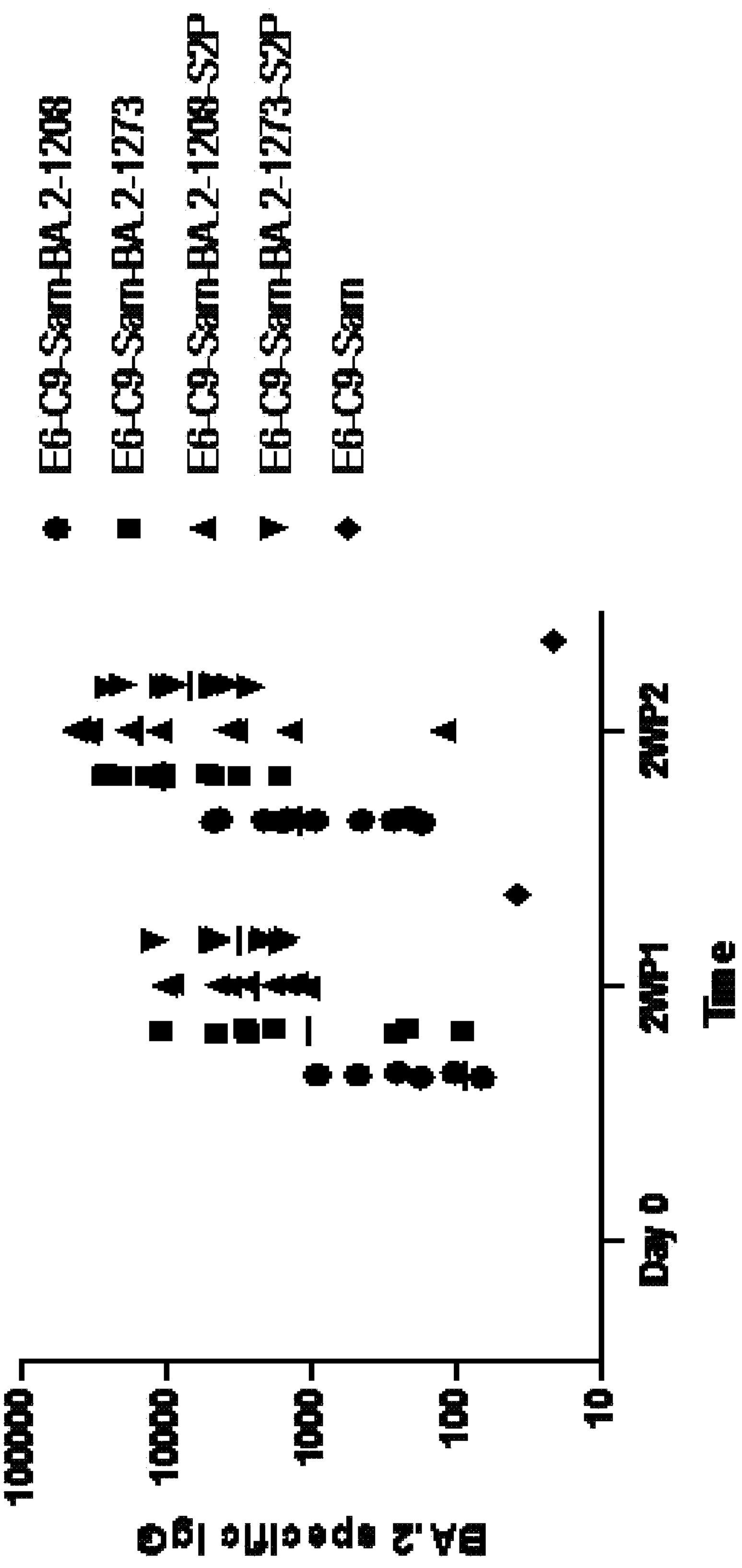

FIG. 22 shows the results of an assay of receptor-binding domain (RBD)-specific immunoglobulin G (IgG) binding titers against SARS-CoV-2 for a mouse experiment where Balb/c mice (10 mice per group) were injected at day 0 and 2WP1 (2 weeks post 1st injection) with E6-C9-LNP encapsulating 2 μg of sa-mRNA encoding a including BA.2-1208, BA.2-1273, BA.2-1208-S2P, BA.2-1273-S2P, or only sa-mRNA not encoding a SARS-CoV-2 Omicron variant. Each group of mice were bled at day 0, and 2WP1, and 2WP2 (two week post second injection) to compare vaccine efficacy over time between different populations.

Figure 23:
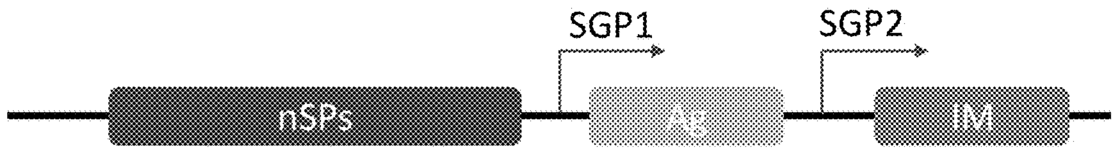

FIG. 23 shows a schematic representation of a dual subgenomic promoter sa-mRNA, with expression vectors encoding a SARS-CoV-2 antigen and immunomodulators (e.g. cytokines et al) under subgenomic promoter 1 and 2, respectively.

Figure 24:
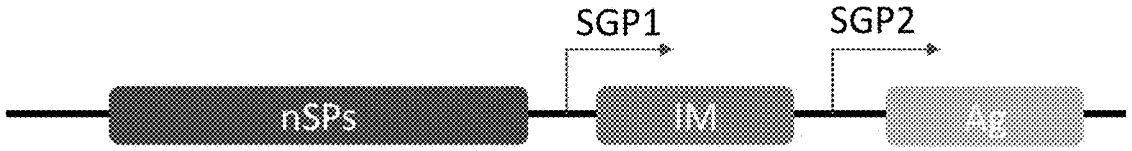

FIG. 24 shows a schematic representation of a dual subgenomic promoter sa-mRNA, with expression vectors encoding immunomodulators (e.g. cytokines et al) and a SARS-CoV-2 antigen under subgenomic promoter 1 and 2, respectively.

Figure 25:
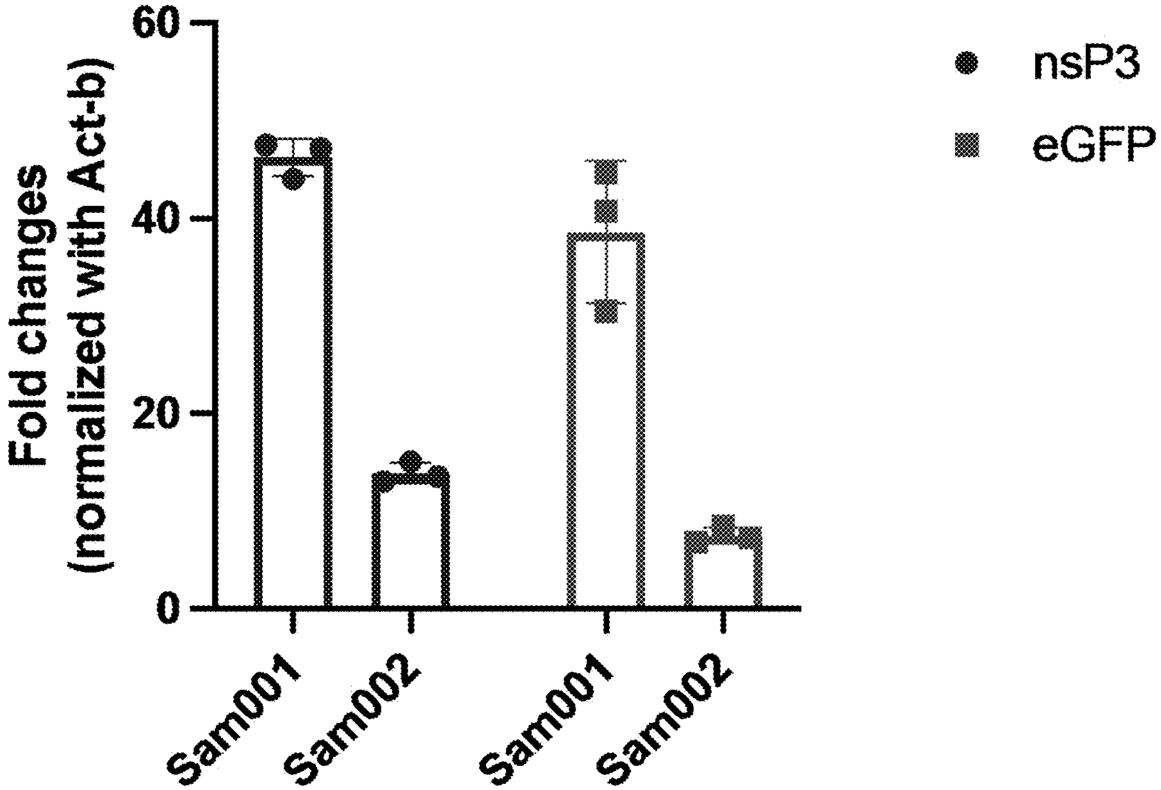

FIG. 25 shows transcripts of nsP3 and enhanced green fluorescent protein (eGFP) encoded by sa-mRNA and modified mRNA constructs SAM001, SAM002, SAM003, and modified mRNA from MOD001 normalized with mouse Actin beta (n=3). C2C12 cells were transfected with the P6-LNP encapsulated either SAM001 or SAM002 encoding with GFP. At day 1 post transfection, total RNAs were extracted, and reverse transcribed to cDNA. Then quantitively polymerase chain reactions (qPCR) were performed using the probes specifically targeting the nsP3 and eGFP. Shown are the fold changes of nsP3 and eGFP that normalized with mouse Actin beta (n=3).

Figure 26:
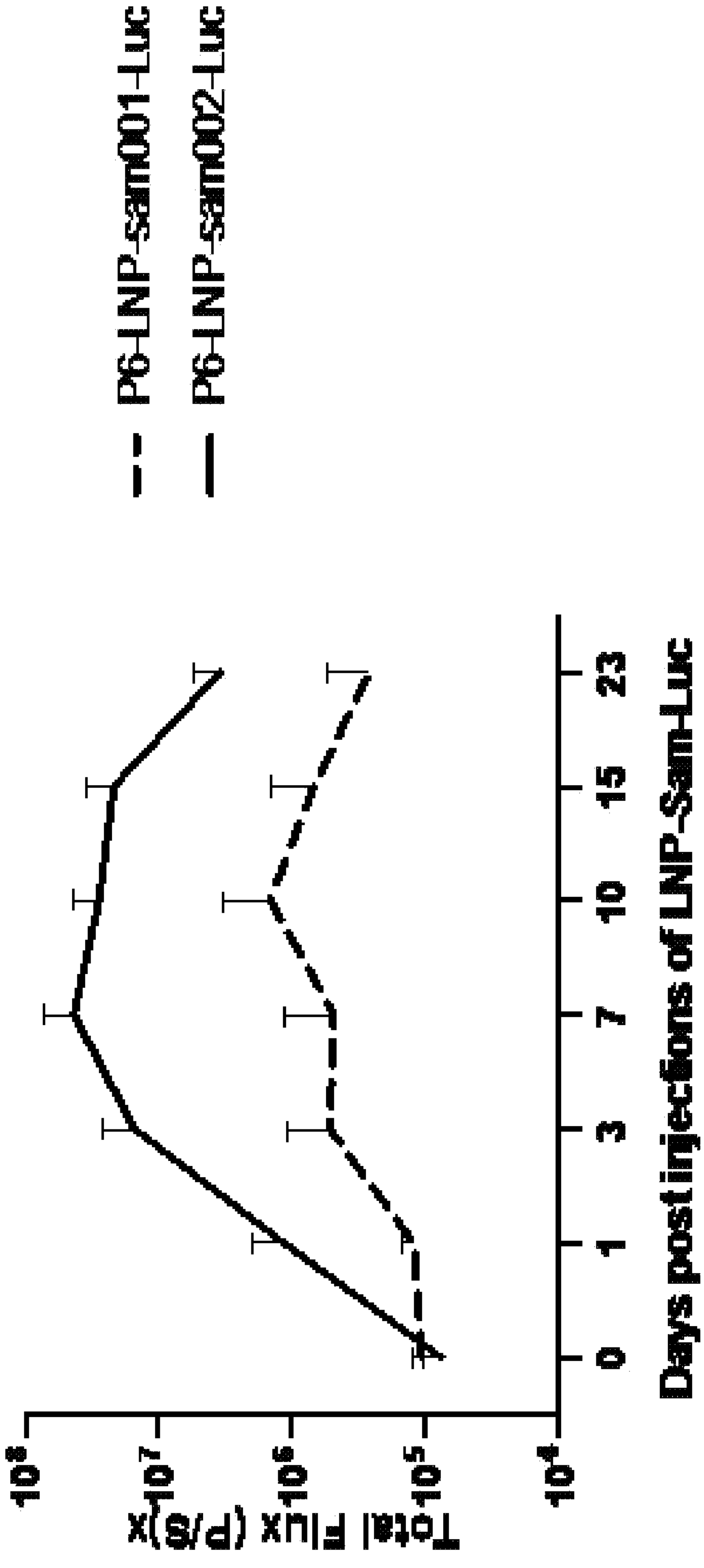

FIG. 26 shows a comparison of transcript expression between SAM001 and SAM002 sa-mRNA constructs encoding Luciferase in vivo. Balb-c mice at 6-8 weeks old were intramuscularly injected at both hind legs with the P6-LNP encapsulated either SAM001 or SAM002 encoding with Luciferase. The mice were intraperitoneally injected with 200 ul Luciferin (30 mg/ml) per mouse and imaged at 5 minutes after injections of Luciferin by in vitro imaging system (Perkin Elmer). Shown are the total flux (photon/second) at the time point indicated (n=10).

Figure 27:
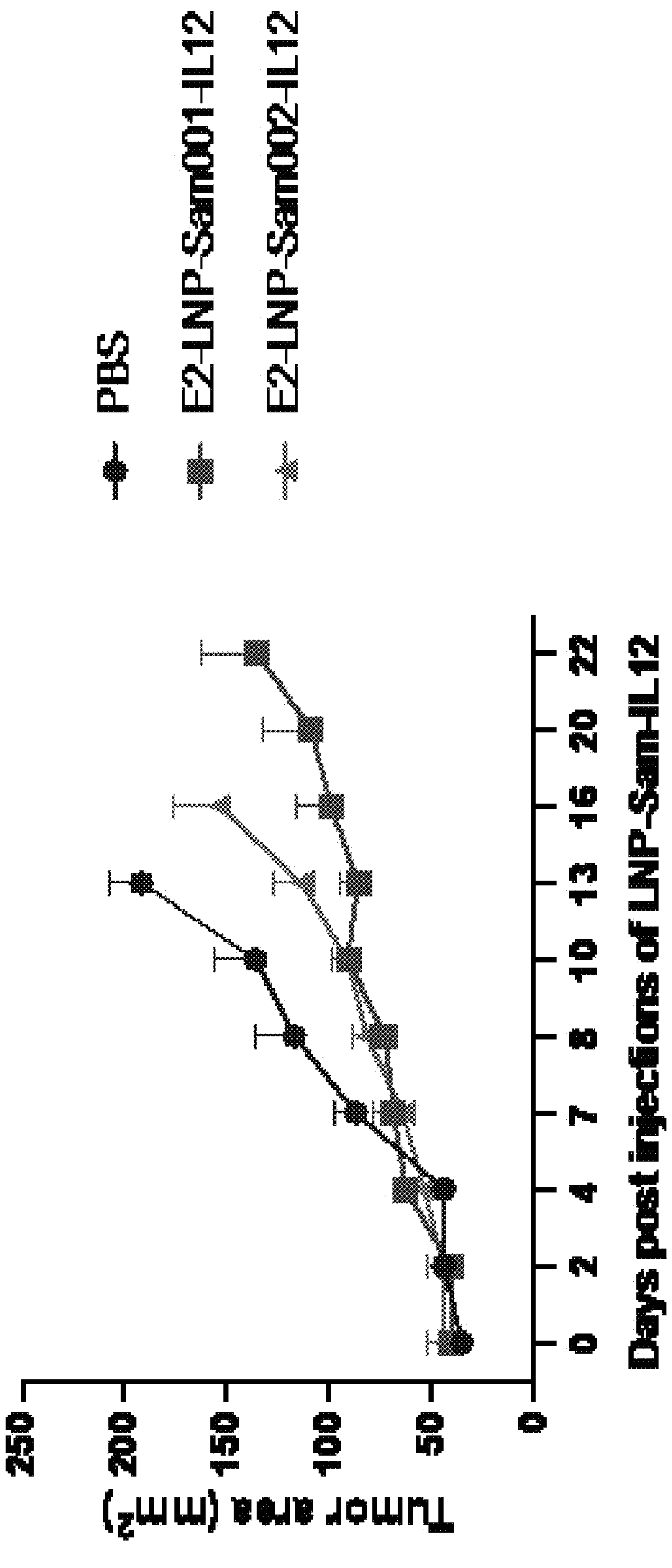

FIG. 27 shows a comparison of LLC1 tumor growth that was treated with E2-LNP-SAM001-IL12 and E2-LNP-SAM002-IL12. C57BL6/J mice (n=5) at 6-8 weeks old were subcutaneously injected with 1 million Lewis Lung Carcinoma (LLC1) cells. At day 7 post injections, the mice were intratumorally treated with PBS, E2-LNP-SAM001-IL12 and E2-LNP-SAM002-IL12. Shown are tumor area (Y-axis) versus time (X-axis).

Figure 28A:
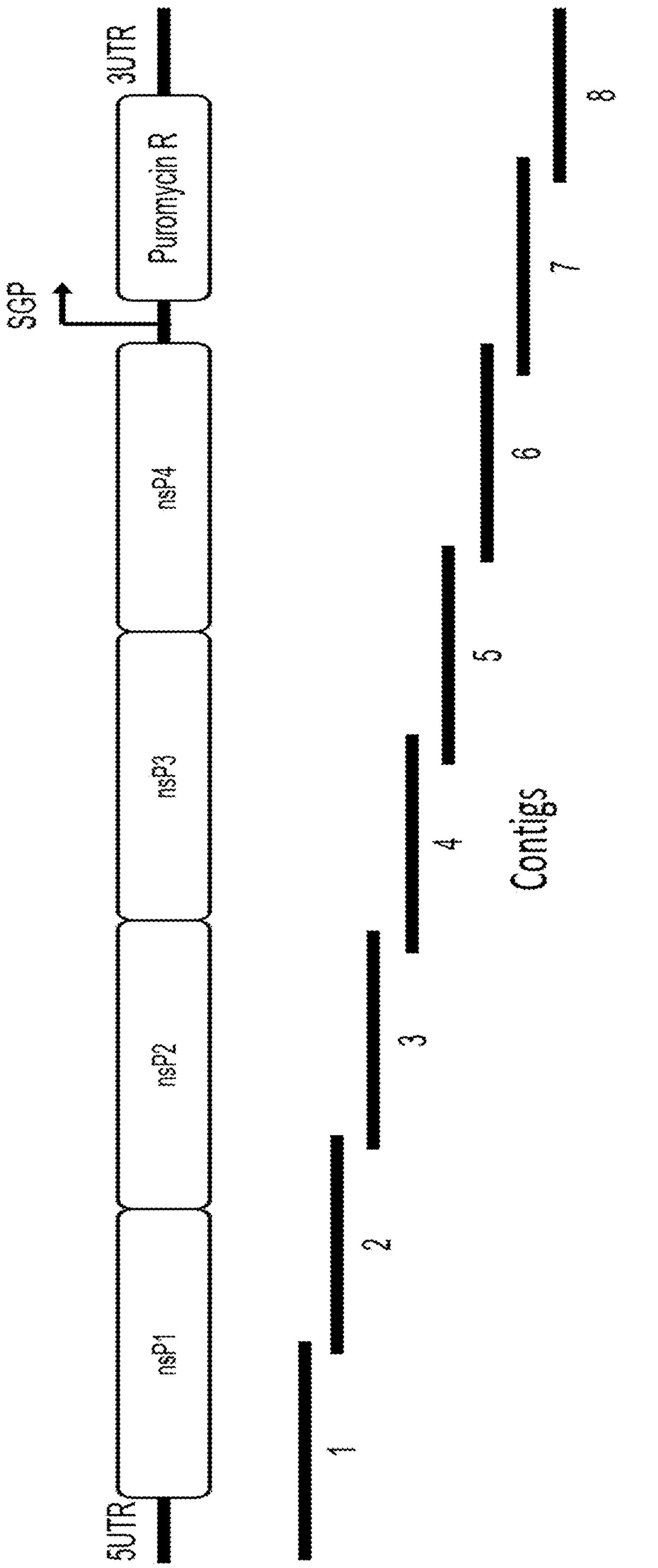

FIG. 28*a* shows a schematic representation of a linearized SAM002 that is used as a template for production of sa-mRNA. The definitions of the abbreviations in the nucleotide sequence map are as follows: 5UTR is a 5' untranslated region, nsP is a plurality of non-structural replicase domain sequences, SGP is a subgenomic promoter, Puromycin R is the puromycin resistance gene, 3UTR is a 3' untranslated region and contigs are subgenomic intervals generated as vectors to facilitate sequencing and numbered for the identification of mutations after directed evolution.

FIG. 28*b* shows the location of nucleotide and amino acid mutations in the non-structural proteins of the linearized nucleic acid after directed evolution. The contig numbers correspond to which region the mutations occurred on the linearized SAM002.

FIG. 28*c* shows where the mutations occur in the mutants with regards to the SAM002 contigs and the allele number of each mutant.

Note that any one of more of the illustrative components of the molecule are optional and the present disclosure includes aspects that contain fewer than all of the illustrated elements.

DETAILED DESCRIPTION

The disclosure relates to novel nucleic acid constructs and compositions, and methods to deliver one or more biologically active agents to subjects in need thereof and methods involving the same. The disclosure also provide methods of delivering biologically active agents to a cell, specifically delivering a therapeutic, diagnostic and/or prophylactic agent to an organ, producing a sa-mRNA of interest in the cell, and treating a disease or disorder in a subject in need thereof. For example, a method of producing a sa-mRNA of interest in a cell involves contacting a nanoparticle composition comprising a sa-mRNA with a cell, whereby the sa-mRNA may be translated to produce the polypeptide of interest. A method of delivering a biologically active agent to a mammalian cell or organ may involve administration of a nanoparticle composition including the biologically active agent to a subject, in which the administration involves contacting the cell or organ with the composition, whereby the biologically active agent is delivered to the cell or organ.

It is important to note that while many of the approaches described in this specification and the examples given are focused on vaccine development, they are equally applicable to sa-mRNA for other intended uses, such as for gene therapy or gene regulation.

Although the present disclosure is described in detail below, it is to be understood that this disclosure is not limited to the particular methodologies, protocols and reagents described herein as these may vary. It is also to be understood that the terminology used herein is for the purpose of describing particular aspects only, and is not intended to limit the scope of the present disclosure. Unless defined otherwise, all technical and scientific terms used herein have the same meanings as commonly understood by one of ordinary skill in the art.

The present disclosure includes constructs of the sa-mRNAs and variations thereof as shown and described, and methods of making and using the constructs. The present disclosure includes noncytopathic and cytopathic versions of the sa-mRNAs and variations thereof. The present disclosure includes sequences and engineering of conjugations between elements of the constructs as shown and described. The present disclosure includes self-amplifying mRNAs that reduce the transcription numbers of sa-mRNA (e.g., nsP3) and subgenome (e.g., eGFP) to make less-cytopathic versions of the sa-mRNA. The present disclosure includes methods and constructs for expressions of payload genes that encode various desired payloads for therapeutic, prophylactic, and/or diagnostic uses. The present disclosure includes methods and constructs including structure-based engineering to control replication rate and interferon responses of sa-mRNAs. The present disclosure includes methods for directed evolutions to identify mutations on sa-mRNA by encoding puromycin resistant genes in the subgenome. The present disclosure includes sa-mRNAs having identified mutations according to the present disclosure, including contigs having identified mutations and combinations thereof. The present disclosure includes designs of antigens in combinations of immunomodulators, such as cytokines and chemokine, in combination with antigens from infectious diseases and tumors.

Additionally, several documents are cited throughout the text of this specification. Each of the documents cited herein (including all patents, patent applications, scientific publications, manufacturer's specifications, instructions, etc.), whether supra or infra, are hereby incorporated by reference in their entirety.

Definitions

As used herein, the terms "gene of interest," "genes of interest," "gene or genes of interest," "GOI," or "coding region" refers to the nucleotide sequence which encode the amino acids found in polypeptides and proteins as a result of translation of a mRNA molecule, including from a sa-mRNA. A GOI, for the purposes of this disclosure, include, but is not limited to, polynucleotides encoding antigens (such as SARS-CoV2 Omicron variants) and immunomodulators (such as IL12 and IL21).

As used herein, "nucleotide" is a term of art that refers to a molecule that contains a nucleoside or deoxynucleoside, and at least one phosphate. A nucleoside or deoxynucleoside contains a single 5 carbon sugar moiety (e.g., ribose or deoxyribose) linked to a nitrogenous base, which is either a substituted pyrimidine (e.g., cytosine (C), thymine (T) or uracil (U)) or a substituted purine (e.g., adenine (A) or guanine (G)). A "polynucleotide" refers to a series or sequence of nucleotides.

As used herein, the terms "modified nucleotide" refers to a nucleotide that contains one or more chemical modifications (e.g. substitutions) in or on the nitrogenous base of the nucleoside (e.g., cytosine (C), thymine (T) or uracil (U)), adenine (A) or guanine (G)). A nucleotide analog can contain further chemical modifications in or on the sugar moiety of the nucleoside (e.g., ribose, deoxyribose, modified ribose, modified deoxyribose, six-membered sugar analog, or open-chain sugar analog), or the phosphate. There are more than 96 naturally occurring modified nucleosides found on mammalian RNA. See, e.g., Limbach et al, Nucleic Acids Research, 22(12):2183-2196 (1994). The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642 all of which are incorporated by reference in their entirety herein, and many modified nucleosides and modified nucleotides are commercially available.

As used herein, "nucleic acid" refers a nucleic acid molecule. According to the present disclosure, nucleic acids comprise genomic DNA, cDNA, RNA, recombinantly prepared and chemically synthesized molecules. According to the present disclosure, a nucleic acid may be in the form of a single-stranded or double stranded and linear or covalently closed circular molecule. The nucleic acid of the present disclosure may also containing non-natural nucleotides and modified nucleotides. "Nucleic acid" also refers to a consecutive list of abbreviations, letters, characters or words, which represent nucleotides. In some aspects, a "nucleic acid template" refers to a nucleic acid that is capable of transcription into RNA (e.g. self-amplifying mRNA).

As used herein, the term "contig" refers to contiguous regions of DNA sequence. "Contigs" can be determined by any number methods known in the art, such as, by comparing sequencing reads for overlapping sequences, and/or by comparing sequencing reads against databases of known sequences in order to identify which sequencing reads have a high probability of being contiguous. Contigs are often assembled from individual sequence reads or previously assembled sequence information in combination with sequence reads having overlapping end or edge sequence. Generally but not exclusively, contigs comprise overlapping sequence reads that assemble into a larger sequence grouping, in many cases without intervening gaps or regions of undetermined sequence, or alternately without regions of known sequence and unknown length.

The term "allele" refers to alternative forms of a gene, a reference nucleic acid or portions thereof. Alleles occupy the same locus or position on homologous chromosomes. Alleles of a specific gene or reference can differ from each other in a single nucleotide, or several nucleotides, and can include substitutions, deletions, and insertions of nucleotides. An allele can also be a form of a reference nucleic acid containing a mutation.

In one aspect, a library includes a collection of nucleic acid members, e.g., a collection of whole genomes, subgenomic fragments, cDNA, cDNA fragments, RNA (e.g., mRNA or sa-mRNA), RNA fragments, or a combination thereof. "Member" or "library member" or other similar term, as used herein, refers to a nucleic acid molecule, e.g., a DNA, RNA, or a combination thereof that is the member of a library. The data of each library member may comprise the number of each nucleoside in an amplicon that would be generated for each allele using each primer or the nucleotide sequence of each member. In this aspect of populating the database, a nucleic acid with a particular allele is selected and a primer pair is used to generate an amplicon. The amplicon's nucleotide sequence can be determined using a method known in the art, such as BAC clone sequencing, physical maps, and Sanger sequencing. An entry in the database is made to associate the base composition with the allele, contig or library member.

As used herein, the term "selectable marker" refers to a nucleotide sequence encoding a gene product that allow for the selection of bacterial cells that have been transformed. Selectable markers can be expressed in the bacterial host and may include genes which render bacteria resistant to drugs such as ampicillin, chloramphenicol, erythromycin, kanamycin (neomycin), and tetracycline (Davies et al., Ann. Rev. Microbiol., 32: 469 (1978)). Selectable markers may also include biosynthetic genes, such as those in the histidine, tryptophan, and leucine biosynthetic pathways.

As used herein, the term "regulatory element" refers to a nucleotide sequence that controls, at least in part, the transcription of a gene or genes of interest. Regulatory elements may include promoters, enhancers, and other nucleic acid sequences (e.g., polyadenylation signals) that control or help to control nucleic acid transcription or translation. Examples of transcription regulatory elements are described, for example, in Goeddel, Gene Expression Technology: Methods in Enzymology 185 (Academic Press, San Diego, Calif., 1990).

As used herein, the term "non-coding" refers to nucleotide sequences that do not encode a polypeptide or an expressed protein. Non-coding sequences include but are not limited to introns, enhancers, promoter regions, 3' untranslated regions, 5' untranslated regions, linkers and GOI which encode regulatory structures.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a GOI if the promoter modulates transcription of said GOI in a cell. Additionally, two portions of a transcription regulatory element are operably linked to one another if they are joined such that the transcription-activating functionality of one portion is not adversely affected by the presence of the other portion. Two transcription regulatory elements may be operably linked to one another by way of a linker nucleic acid (e.g., an intervening non-coding nucleic acid) or may be operably linked to one another with no intervening nucleotides present.

As used herein, the term "linker" refers to a nucleotide sequence added between two nucleotide sequences to connect said two nucleotide sequences. There is no particular limitation regarding the linker sequence.

As used herein, the term "subgenomic promoter," is a promoter that can be used to transcribe the subgenome of alphaviruses encoding structural proteins by RNA dependent RNA polymerase encoded by nsP. When two or more subgenomic promoters are present in a nucleic acid comprising multiple expression units, the promoters can be the same or different. In certain aspects, subgenomic promoters can be modified using techniques known in the art in order to increase or reduce viral transcription of the proteins, see e.g. U.S. Pat. No. 6,592,874, which is incorporated by reference in their entirety herein.

As used herein, the term "expression unit" as used herein mean a nucleotide sequence capable of directing expression of a particular GOI in an appropriate cell, comprising a promoter functional in said cell and a coding region. If translation is required, it also typically comprises sequences required for proper translation of the nucleotide sequence. The GOI may code for a protein or polypeptide of interest but may also code for a regulatory structure of interest, for example siRNA, or any other noncoding regulatory RNA. A nucleic acid may contain a plurality of expression units. The expression unit comprising the nucleotide sequence of interest may be chimeric, meaning that at least one of its components is heterologous with respect to at least one of its other components. The expression unit may also be one which is naturally occurring but has been obtained in a recombinant form useful for heterologous expression. Typically, however, the expression unit is heterologous with respect to the host, i.e., the particular DNA or RNA sequence of the expression unit does not occur naturally in the host cell and must have been introduced into the host cell or an ancestor of the host cell by a transformation event. The expression of the nucleotide sequence in the expression unit may be under the control of a constitutive promoter or of an inducible promoter, which initiates transcription only when the host cell is exposed to some particular external stimulus.

As used herein, the term "genomic DNA" is referring to the heritable genetic information of a host organism. Said genomic DNA comprises the DNA of the nucleus (also referred to as chromosomal DNA) but also the DNA of the other cellular organelles (e.g., mitochondria). In some aspects, the term genomic DNA refers to the chromosomal DNA of the nucleus.

As used herein, the terms "polypeptide," "peptide," "oligopeptide," "gene product," "expression product" and "protein" are used interchangeably herein to refer to a polymer or oligomer of consecutive amino acid residues. The terms "gene product" and "expression product" can also refer to regulatory structures.

As used herein, an "effective amount" of a sa-mRNA refers to an amount sufficient to elicit expression of a detectable amount of an antigen or protein, e.g., an amount suitable to produce a desired therapeutic, diagnostic or prophylactic effect.

As used herein, the term "naked" as used herein refers to nucleic acids that are substantially free of other macromolecules, such as lipids, polymers, and proteins. A "naked" nucleic acid, such as a plasmid or a sa-mRNA, is not formulated with other macromolecules to improve cellular uptake. Accordingly, a naked nucleic acid is not encapsulated in, absorbed on, or bound to a liposome, a microparticle or nanoparticle, a cationic emulsion, and the like.

As used herein, the term "transfection" or "transformation" refers to introducing one or more nucleic acids into an organism or into a host cell. Various methods may be employed in order to introduce nucleic acids into cells in vitro or in vivo. Such methods include transfection of nucleic acid-CaPO4 precipitates, transfection of nucleic acids associated with DEAE, transfection of infection with viruses carrying the nucleic acids of interest, liposome mediated transfection, lipid nanoparticle (LNP) mediated transfection, lipofectamine and the like.

As used herein, the term "reporter" relates to a molecule, typically a peptide or protein, which is encoded by a reporter gene and measured in a reporter assay. Existing systems usually employ an enzymatic reporter (e.g. GFP or Luciferase) and measure the activity of said reporter.

As used herein, "encapsulation efficiency" refers to the amount of a biological agent that becomes part of a nanoparticle composition, relative to the initial total amount of biologically active agent used in the preparation of a nanoparticle composition. For example, if 97 mg of biologically active agent are encapsulated in a nanoparticle composition out of a total 100 mg of biologically active agent initially provided to the composition, the encapsulation efficiency may be given as 97%. As used herein, "encapsulation" may refer to complete, substantial, or partial enclosure, confinement, surrounding, or encasement.

As used herein, a "nanoparticle composition" or "LNP formulation" is a composition comprising one or more lipids. Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less. For example, the lipid component of a nanoparticle composition may include one or more cationic/ionizable, PEGylated, structural, or other lipids, such as phospholipids.

As used herein, a "lipid component" is that component of a nanoparticle composition that includes one or more lipids. For example, the lipid component may include one or more cationic/ionizable, PEGylated, structural, or other lipids, such as phospholipids.

As used herein, the terms "PEG lipid" or "PEGylated lipid" refer to a lipid comprising a polyethylene glycol component. For example, a PEG lipid may be selected from the following non-limiting group: PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

As used herein, the terms "phospholipid" or "helper lipid" refer to a lipid that includes a phosphate moiety and one or more carbon chains, such as unsaturated fatty acid chains. A phospholipid may include one or more multiple (e.g., double or triple) bonds (e.g., one or more unsaturations). Particular phospholipids may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements of a lipid-containing composition to pass through the membrane permitting, e.g., delivery of the one or more elements to a cell. In general, phospholipids may include a phospholipid moiety and one or more fatty acid moieties.

Phospholipids useful in the compositions and methods of the present disclosure may be selected from the following non-limiting group: 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In some embodiments, a nanoparticle composition includes DSPC. In certain embodiments, a nanoparticle composition includes DOPE.

As used herein, "ionizable lipids" are lipids that may have a positive or partial positive charge at physiological pH in addition to a lipid according to Formula (E6) disclosed in PCT Patent Application No. PCT/US2023/017777, which is fully incorporated herein.

As used herein, the terms "stain" or "staining" include methods of detecting subpopulations of cells in a cell sample, and in particular, it relates to methods of detecting dead cells in a cell sample using a membrane permeable nucleic acid binding fluorescent label. The staining method can be used in combination with a cell capture system and/or an optical detection system for detecting the presence of live and or dead cells in a cell sample. For example, dead cells can be detected using fluorescent DNA binding dyes such as propidium iodide and 7-aminoactinomycin D (7-AAD) because they have compromised cell membrane integrity compared to live cells (Lecoeur et al., 2002; Gaforio et al., Cytometry 49:8, 2002; Ormerod et al., Cytometry 14:595, 1993; Schmid et al., J. Immunol. Methods 170:145, 1994; Philpott et al., Blood 87:2244, 1996).

As used herein, the terms "treat," "treating" or "treatment," may include alleviating, abating or ameliorating disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", may include, but are not limited to, prophylactic, diagnostic and/or therapeutic treatments.

As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions.

As used herein, the phrase "biologically active" refers to a characteristic of any substance that has activity in a biological system and/or organism. The term "biologically active agent" refers to any agent that, when administered to a subject, has a therapeutic, diagnostic, and/or prophylactic effect and/or elicits a desired biological and/or pharmacological effect. Such agents include, but are not limited to, cytotoxins, radioactive ions, chemotherapeutic agents, small molecule drugs, proteins, and nucleic acids.

As used herein, the term "payload" refers to a moiety whose biological activity is desired to be delivered (in)to and/or localize at a cell or tissue. Payloads include, but are not limited to biologically active agents, and the like. In some aspects, the payload may be a nucleic acid that encodes a protein or polypeptide. In some aspects, the payload may include or encode a cytokine, a chemokine, an antibody or antibody fragment, a receptor or receptor fragment, an enzyme, an enzyme inhibitor, a hormone, a lymphokine, a plasminogen activator, a natural or modified immunoglobulin or a fragment thereof, an antigen, a chimeric antibody receptor, variable or hypervariable regions of light and/or heavy chains of an antibody ($V_L$, $V_H$), variable fragments (Fv), Fab' fragments, F(ab') 2 fragments, Fab fragments, single chain antibodies (scAb), single chain variable regions (scFv), complementarity determining regions (CDR), domain antibodies (dAbs), single domain heavy chain immunoglobulins of the BHH or BNAR type, single domain light chain immunoglobulins, or other polypeptides known in the art containing an AB capable of binding target proteins or epitopes on target proteins, or any other desired biological macromolecule.

Cytokines of the present disclosure may include but are not limited to an interferon, an interleukin, GM-CSF, G-CSF, LIF, OSM, CD154, LT-β, TNF-α, TNF-β, 4-1BBL, APRIL, CD70, CD153, CD178, GITRL, LIGHT, OX40L, TALL-1, TRAIL, TWEAK, TRANCE, TGF-β1, TGF-β1, TGF-β3, Epo, Tpo, Flt-3L, SCF, M-CSF, and MSP, optionally wherein the CP1 and/or the CP2 is independently selected from IL-2, IL-7, IL-8, IL-10, IL-12, IL-15, IL-18, IL-17, IL-21, an IFN-alpha, an IFN beta, an IFN gamma, GM-CSF, TGF-beta, LIGHT, GITR-L, CD40L, CD27L, 4-1BB-L, OX40, and OX40L.

As used herein, the term "conserved" refers to a nucleic acid sequence that occur unaltered in the same position of two or more related sequences being compared. Nucleic acid sequences that are relatively conserved are those that are conserved amongst more related sequences than nucleic acid sequences appearing elsewhere in the sequences. In some aspects, two or more sequences are said to be conserved if they are 100% identical to one another. In some aspects, two or more sequences are said to be conserved if they are about 95% identical, about 98% identical, or about 99% identical to one another.

As used herein, the term "transcription" comprises "in vitro transcription" wherein the term "in vitro transcription" relates to a method in which RNA, in particular sa-mRNA, is synthesized in vitro in a cell-free manner.

As used herein, "expression" of a nucleic acid refers to one or more of the following events: (1) production of an RNA template from a DNA sequence (e.g., by transcription); and (2) translation of an RNA into a polypeptide or protein.

As used herein, two nucleic acids are substantially homologous when the nucleotide sequences have at least about 90%, 91%, 92%, 93%, 94%, 95%, 96%, 97%, 98%, or 99% identity. The percent identity between the two sequences is a function of the number of identical positions shared by the sequences, taking into account the number of gaps, and the length of each gap, which need to be introduced for optimal alignment of the two sequences. Sequence homology for nucleic acids, which can also be referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. A typical algorithm used comparing a molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997).

As used herein, the term "contacting" means establishing a physical connection between two or more entities. For example, contacting a cell with a nanoparticle composition comprising a sa-mRNA means that the mammalian cell and a nanoparticle are made to share a physical connection. Methods of contacting cells with external entities both in vivo and ex vivo are well known in the biological arts.

As used herein, the term "delivering" means providing an entity to a destination. For example, delivering a biologically active agent to a subject may involve administering a nanoparticle composition comprising sa-mRNA including the biologically active agent to the subject (e.g., by an intravenous, intranasal, intratracheal, intracerebral, intratumoral, intraperitoneal, intramuscular, intradermal, or subcutaneous route).

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe).

As used herein, the term "in situ" refers to events that occur in its original place, or in its natural context.

As used herein, the terms "isolated" refers to a substance or entity that has been (1) separated from at least some of the components with which it was associated when initially produced (whether in nature or in an experimental setting), and/or (2) produced, prepared, and/or manufactured in vitro. Isolated substances and/or entities may be separated from at least about 10%, about 20%, about 30%, about 40%, about 50%, about 60%, about 70%, about 80%, about 90%, or more of the other components with which they were initially associated. In some aspects, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, the term "substantially" refers to the qualitative condition of exhibiting total or near-total extent or degree of a characteristic or property of interest.

As used herein, the term "polypeptide" or "polypeptide of interest" refers to a polymer of amino acid residues typically joined by peptide bonds that can be produced naturally (e.g., isolated or purified) or synthetically.

As used herein, "size" or "mean size" in the context of nanoparticle composition refers to the mean diameter of a nanoparticle composition.

As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

As used herein, the term "therapeutically effective amount" means an amount of an agent to be delivered (e.g., nucleic acid, drug, composition, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, "methods of administration" may include intravenous, intranasal, intratracheal, intracerebral, intratumoral, intraperitoneal, intramuscular, intradermal, subcutaneous, or other methods of delivering a composition to a subject. A method of administration may be selected to target delivery (e.g., to specifically deliver) to a specific region or system of a body.

As used herein, "modified" means non-natural. For example, an RNA may be a modified RNA. That is, an RNA may include one or more nucleobases, nucleosides, nucleotides, or linkers that are non-naturally occurring. A "modified" species may also be referred to herein as an "altered" species. Species may be modified or altered chemically, structurally, or functionally. For example, a modified nucleobase species may include one or more substitutions that are not naturally occurring.

As used herein, "naturally occurring" means existing in nature without artificial aid.

As used herein, the terms "subgenomic" or "subgenome" refers to a nucleotide sequence (e.g. RNA or DNA) of a length or size which is smaller than the genomic nucleotide sequence from which it was derived. For example, a subgenome can be a region encoding VEE structural proteins, subgenomic RNA can be transcribed from the subgenome using an internal subgenomic promoter, whose sequences reside within the genomic viral RNA or its complement. Transcription of a subgenome may be mediated by viral-encoded polymerase(s) associated with host cell-encoded proteins (e.g. nsP1-4). In some aspects of the present disclosure, the subgenomic sa-mRNA is produced from a modified alphavirus replicon (e.g. a modified VEE replicon) as disclosed herein and encodes or expresses one or more gene or genes of interest (GOI).

The phrase "pharmaceutically acceptable" is used herein to refer to those compounds, materials, compositions, and/or dosage forms which are, reasonably suitable for use in contact with the tissues of human beings and animals without excessive toxicity, irritation, allergic response, or other problem or complication.

"Pharmaceutically acceptable compositions" may also include salts of one or more compounds. Salts may be pharmaceutically acceptable salts. As used herein, "pharmaceutically acceptable salts" refers to derivatives of the disclosed compounds wherein the parent compound is altered by converting an existing acid or base moiety to its salt form. Generally, such salts can be prepared by reacting the free acid or base forms of these compounds with a stoichiometric amount of the appropriate base or acid in water or in an organic solvent, or in a mixture of the two. In some aspects, a nonaqueous media like ether, ethyl acetate, ethanol, isopropanol, or acetonitrile may be used. Lists of suitable salts are found in Remington's Pharmaceutical Sciences, $17^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

As used herein, the term "innate immune response" includes a cellular response to exogenous single stranded nucleic acids, generally of viral or bacterial origin, which involves the induction of cytokine expression and release, particularly the interferons, and cell death. Protein synthesis is also reduced during the innate cellular immune response. The present disclosure provides modified self-amplifying mRNAs that substantially reduce the immune response, including interferon signaling. In some aspects, the immune response is the interferon response of a host cell is 2, 3, 4, 5 or 6 times lower as compared to the immune response induced by a corresponding unmodified nucleic acid. Such a reduction can be measured by expression or activity level of Type 1 interferons or the expression of interferon-regulated genes such as the toll-like receptors (e.g., TLR3, TLR7 and TLR8), and RIG-I like receptors (e.g., RIG1, MDA5, and LGP2). Reduction of innate immune response can also be measured by decreased cell death following one or more administrations of modified RNAs to a cell population; e.g., cell death is the interferon response of a host cell is 2, 3, 4, 5 or 6 times lower than the cell death frequency observed with a corresponding unmodified nucleic acid.

As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-18 and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor", erythropoietin, thrombopoietin, and the like.

A cytokine, for the purposes of this disclosure, include any cytokines including but not limited to IL-1, IL-2, IL-3, IL-6, IL-10, IL-12, IL-18, IL-21, interferon-α, interferon-β, and interferon-γ. It may also be a colony stimulating factor, such as GM-CSF, G-CSF, M-CSF, erythropoietin, thrombopoietin, and the like.

As used herein, the terms "approximately" and "about," as applied to one or more values of interest, refer to a value that is +/−20% of the recited value.

Self-Amplifying mRNA

In some aspects, the biologically active agent of the present disclosure is one or more sa-mRNA molecules.

Sa-mRNAs of the disclosure have the ability to self-replicate in cells and, thus, can be used to induce expression of encoded gene products, such as proteins (e.g., antigens) and regulatory structures (e.g. siRNA, miRNA, saRNA, tRNA, and lincRNA) encoded by the sa-mRNA. In addition, sa-mRNAs are generally based on the genome of an RNA virus (e.g. a Group IV positive single strand RNA virus), and therefore are foreign nucleic acids that can stimulate the innate immune system (e.g. induce an interferon response). This can lead to undesired consequences and safety concerns, such as rapid inactivation and clearance of the RNA, injection site irritation and/or inflammation and/or pain.

The sa-mRNAs of the present disclosure contain modified structures and have reduced capacity to stimulate the innate immune system, which will lead to rapid decay of the sa-mRNA and its associated gene products. Rapid decay of the sa-mRNA and its associated gene products will lead to increased frequency of administration, which is associated with safety concerns and reduced therapeutic efficacy. Thus one aspect of the invention is sa-mRNAs that have reduced cytotoxic effects on the host cell or subject. This provides for enhanced safety of the sa-mRNAs of the present disclosure and provides additional advantages. For example, an advantage of a sa-mRNA with low cytotoxicity allows for administration of a large dose of the sa-mRNAs to produce high expression levels of the encoded gene product with reduced risk of undesired effects, such as injection site irritation and or pain. In addition, because sa-mRNAs of the disclosure have reduced capacity to stimulate the innate immune system, they are well suited to use as vaccines to boost immunity.

One suitable system for producing a sa-mRNA of the present disclosure is to use an alphavirus-based RNA replicon. Alphavirus-based replicons are positive (+)-single stranded replicons that can be translated after delivery to a cell to give a replicase (or replicase-transcriptase). The replicase is translated as a polyprotein which auto-cleaves to provide a replication complex, comprising plurality of non-structural replicase domain sequences, which creates genomic (−)-strand copies of the (+)-strand delivered RNA. These (−)-strand transcripts can themselves be transcribed to give further copies of the (+)-stranded parent RNA and also to give an mRNA transcript which encodes the desired gene product. Translation of the subgenomic transcript thus leads to in situ expression of the desired gene product by the infected cell.

A sa-mRNA may encode (i) a RNA-dependent RNA polymerase which can replicate RNA from sa-mRNA and transcribe (ii) a GOI of the subgenome. The polymerase can be an alphavirus replicase e.g. comprising alphavirus non-structural proteins 1, 2, 3, and 4.

Whereas natural alphavirus genomes encode structural proteins in addition to the non-structural replicase, in one aspect, an alphavirus based sa-mRNA does not encode alphavirus structural proteins. Thus the sa-mRNA can lead to the production of RNA copies of itself in a cell, but not to the production of RNA-containing alphavirus virions. The inability to produce these virions means that, unlike a wild-type alphavirus, the sa-mRNA cannot perpetuate itself in infectious form. The alphavirus structural proteins which are necessary for perpetuation in wild-type viruses are absent from self-amplifying mRNAs and their place is taken by the GOI, such that the sa-mRNA transcript encodes the desired gene product rather than the structural alphavirus virion proteins.

Thus, the sa-mRNA of the present disclosure may have more than one coding region. The first (5') coding region encodes a plurality of non-structural replicase domain sequences; the second (3') coding region encodes a gene of interest operably linked to a subgenomic promoter. In some aspects the sa-mRNA may have additional (downstream) coding regions e.g. that encode other desired gene products. A coding region molecule can have a 5' sequence which is compatible with the encoded replicase.

The sa-mRNA of the present disclosure may be derived from or based on a virus other than an alphavirus, including but not limited to a Group IV positive-single stranded RNA virus, for example, picornaviridae, togaviridae, coronaviridae, hepeviridae, caliciviridae, flaviviridae, and astroviridae. Suitable wild-type alphavirus sequences are well-known and are available from sequence depositories, such as the American Type Culture Collection, Rockville, Md. Representative examples of suitable alphaviruses include Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus.

Sa-mRNAs as described herein can amplify themselves and initiate expression of heterologous gene products in the host cell. Sa-mRNAs of the present disclosure, unlike mRNA, use their own encoded viral polymerase to amplify itself. Particular sa-mRNA, such as those based on Group IV RNA viruses such as alphaviruses, generate large amounts of subgenomic mRNAs from which large amounts of proteins (or regulatory structures) can be expressed.

Advantageously, the host cell's own machinery is used by sa-mRNAs to generate an exponential increase of encoded gene products (such as proteins, antigens, or regulatory structures) which can accumulate in the cells or be secreted from the cells. Increased of proteins or antigens by self-amplifying mRNAs takes advantage of the immunostimulatory adjuvant effects, including stimulation of toll-like receptors (TLR) 3, 7 and 8 and non TLR pathways (e.g, RIG-I like receptor, RIG-I, MDA-5, LGP2) by the products of RNA replication and amplification, and translation which induces apoptosis of the transfected cell.

The sa-mRNA of the disclosure may encode any desired gene product, such as a regulatory structure, a polypeptide, a protein or a polypeptide or a fragment of a protein or polypeptide. Additionally, the sa-mRNA of the disclosure may encode a single polypeptide or, optionally, two or more of sequences linked together in a way that each of the sequences retains its identity (e.g., linked in series) when expressed as an amino acid sequence. The polypeptides generated from the sa-mRNAs of the disclosure may then be produced as a fusion protein or engineered in such a manner to result in separate polypeptide or peptide sequences.

The sa-mRNAs of the disclosure may encode one or more immunogenic polypeptides that contain a range of epitopes. In some aspects, such epitopes are capable of eliciting either a helper T-cell response or a cytotoxic T-cell response or both.

The sa-mRNAs described herein may be engineered to express multiple GOI, from two or more coding regions, thereby allowing co-expression of proteins and or regulatory structures, such as a two or more antigens together with cytokines or other immunomodulators, which can enhance the generation of an immune response. Such a sa-mRNA might be particularly useful, for example, in the production of various gene products (e.g., proteins) at the same time, for example, as a bivalent or multivalent vaccine, or in gene therapy applications.

Exemplary gene products that can be encoded by sa-mRNA of the disclosure include proteins and peptides from pathogens, such as bacteria, viruses, fungi and parasites, including any antigenic viral protein (e.g., proteins or peptides from coronavirus, cytomegalovirus, parvovirus, flaviviruses, picornaviruses, norovirus, influenza virus, rhinovirus, yellow fever virus, human immunodeficiency virus (HIV), and the like). Additional exemplary gene products that can be encoded by the sa-mRNAs of the disclosure include any desired eukaryotic polypeptide such as, for example, a mammalian polypeptide such as an enzyme, an enzyme inhibitor, a hormone, a lymphokine, a cytokine, a chemokine, a plasminogen activator, a natural or modified immunoglobulin or a fragment thereof, green fluorescence protein, or any desired combinations of the foregoing. Further exemplary gene products that can be encoded by the sa-mRNA of the disclosure include regulatory structures, such as siRNA, miRNA, gRNA, saRNA, tRNA, and lincRNA, which can be used to regulate expression of endogenous host genes.

The sa-mRNA may also comprise at least one modified nucleic acid and can be prepared using any suitable method. The modification may include a compound selected from the following non-limiting group: pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-m ethoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, N1-Methylpseudouridine-5'-Triphosphate, and N2,N2-dimethyl-6-thio-guanosine. In another aspect, the modifications are independently selected from: 5-methylcytosine, pseudouridine and 1-methylpseudouridine. In one aspect, a modification may be located on a nucleobase of the modified nucleic acid molecule. The modification on the nucleobase may be selected from the group consisting of cytosine, guanine, adenine, thymine and uracil. The modification on the nucleobase may be selected from the group consisting of deaza-adenosine and deaza-guanosine, and a linker may be attached at a C-7 or C-8 position of said deaza-adenosine or deaza-guanosine. The modified nucleobase may be selected from the group consisting of cytosine and uracil, and the linker may be attached to the modified nucleobase at an N-3 or C-5 position. The linker attached to the nucleobase may be selected from the group consisting of diethylene glycol, dipropylene glycol, triethylene glycol, tripropylene glycol, tetraethylene glycol, tetraethylene glycol, divalent alkyl, alkenyl, alkynyl moiety, ester, amide, and ether moiety. In one aspect, two modifications of the nucleic acid molecule may be located on nucleosides of the modified nucleic acid molecule. The modified nucleosides may be selected from 5-methylcytosine and pseudouridine.

Several suitable methods are known in the art for producing RNA molecules that contain modified nucleotides. For example, as described and exemplified herein, a sa-mRNA that contains modified nucleotides can be prepared by transcribing (e.g., in vitro transcription) a nucleic acid that encodes the sa-mRNA using a suitable DNA-dependent RNA polymerase, such as: T7 phage RNA polymerase, SP6 phage RNA polymerase, T3 phage RNA polymerase, T5 phage RNA polymerase, RNA polymerase III, RNA polymerase II, Taq polymerase, Vent polymerase, and the like, or mutants of these polymerases, which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of modified nucleotide into a sa-mRNA may be engineered, for example, to alter the stability of such RNA molecules, to increase resistance against RNases, to establish replication after introduction into appropriate host cells ("infectivity" of the RNA), and/or to induce or reduce innate and adaptive immune responses.

In one aspect, the sa-mRNA of the disclosure comprise a polynucleotide sequence selected from:

a) a polynucleotide encoding a modified SARS-CoV-2 spike protein comprising the nucleic sequence set forth in SEQ ID NO: 1 (BA.1-1273);
b) a polynucleotide encoding a modified SARS-CoV-2 spike protein comprising the nucleic sequence set forth in SEQ ID NO: 2 (BA.1-1273-S2P);
c) a polynucleotide encoding a modified SARS-CoV-2 spike protein comprising the nucleic sequence set forth in SEQ ID NO: 3 (BA.2-1273);
d) a polynucleotide encoding a modified SARS-CoV-2 spike protein comprising the nucleic sequence set forth in SEQ ID NO: 4 (BA.2-1273-S2P);
e) a polynucleotide encoding a modified SARS-CoV-2 spike protein comprising the nucleic sequence set forth in SEQ ID NO: 5 (BA.1-1208); or
f) a polynucleotide encoding a modified SARS-CoV-2 spike protein comprising the nucleic sequence set forth in SEQ ID NO: 6 (BA.1-1208-S2P).
g) a polynucleotide encoding a modified SARS-CoV-2 spike protein comprising the nucleic sequence set forth in SEQ ID NO: 7 (BA.2-1208); or
h) a polynucleotide encoding a modified SARS-CoV-2 spike protein comprising the nucleic sequence set forth in SEQ ID NO: 8 (BA.2-1208-S2P).

In one aspect of the present disclosure, the sa-mRNA comprises the following operably linked nucleic acid sequence from 5' to 3':

nsP-SGP1-Ag-SGP2-IM wherein nsP is a plurality of non-structural replicase domain sequences, SGP1 is the first subgenomic promoter, Ag is a nucleotide sequence selected from SEQ ID NO: 1 (BA.1-1273), 2 (BA.1-1273-S2P), 3 (BA.2-1273), and SEQ ID NO: 4 (BA.2-1273-S2P), SEQ ID NO: 5 (BA.1-1208), or SEQ ID NO: 6 (BA.1-1208-S2P), SEQ ID NO: 7 (BA.2-1208), or SEQ ID NO: 8 (BA.2-1208-S2P).

SGP2 is the second subgenomic promoter, and

IM is the immunomodulator.

In one aspect, the sa-mRNA comprises the following operably linked nucleic acid sequence from 5' to 3':

nsP-SGP1-IM-SGP2-AG wherein nsP is a plurality of non-structural replicase domain sequences, SGP1 is the first subgenomic promoter, IM is the immunomodulatory, SGP2 is the second subgenomic promoter, and Ag is a nucleotide sequence selected from SEQ ID NO: 1 (BA.1-1273), 2 (BA.1-1273-S2P), 3 (BA.2-1273), and SEQ ID NO: 4 (BA.2-1273-S2P), SEQ ID NO: 5 (BA.1-1208), or SEQ ID NO: 6 (BA.1-1208-S2P), SEQ ID NO: 7 (BA.2-1208), or SEQ ID NO: 8 (BA.2-1208-S2P).

In some aspects, the IM encodes one or more cytokines, chemokines, immune stimulators or inhibitors. In one aspect, the IM is selected from IL12 and IL21. In one aspect, the IM encodes one or more cytokines selected from SEQ ID NOs: 22 (hIL12-P40), 24 (hIL12-P35), 15 (mIL12 P40), 17 (mIL12-P35), and 21 (mIL21). In one aspect, SGP1 is SEQ ID NO: 9 (SGP1). In one aspect, SGP2 is SEQ ID NO: 11 (SGP2). In one aspect, IM is selected from SEQ ID NO: 13 (IM1), and SEQ ID NO: 20 (IM2).

In another aspect, the present disclosure includes sa-mRNA comprising the following operably linked nucleic acid sequence from 5' to 3':

SP-IL12 P40-L1-IL12 P35-L2-IL21 wherein

SP is a signal peptide,

IL12-P40 is interleukin-12 comprising heavy chain p40,

L1 is linker 1,

IL12 P35 is interleukin-12 comprising light chain p35,

L2 is linker 2, and

IL21 is interleukin-21.

In some aspects, SP is selected from SEQ ID NO: 14 (MSP) and SEQ ID NO: 21 HSP. In some aspects, IL12-P40 is selected from SEQ ID NO: 15 (mIL12-P40) and SEQ ID NO: 22 (hIL12-P40). In some aspects, L1 is selected from SEQ ID NO: 16 (L(a)) and SEQ ID NO: 23 (L(c)). In some aspects, IL12-P35 is selected from SEQ ID NO: 17 (mIL12-P35) and SEQ ID NO: 24 (hIL12-P35). In some aspects, L2 is selected from SEQ ID NO: 18 (L(b)) and SEQ ID NO: 25 (L(d)). In some aspects, IL12-P40 is selected from SEQ ID NO: 19 (mIL21) and SEQ ID NO: 26 (hIL21).

In some aspects, at least one non-structural replicase domain sequence comprise sequences selected from Group IV RNA viruses, selected from Picornaviridae, Togaviridae, Coronaviridae, Hepeviridae, Caliciviridae, Flaviviridae, and Astroviridae. In some aspects, at least one non-structural replicase domain sequence comprise sequences selected from Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus. In yet another aspect, at least one non-structural replicase domain sequence is obtained from the TC-83 strain of Venezuelan Equine Encephalitis virus (VEE). In some aspects, the plurality of non-structural replicase domain sequences are alphavirus nonstructural proteins 1-4 (nsP1-4).

In some aspects, SGP1 is a viral promoter that is recognized by viral RNA dependent RNA polymerase (RdRP). In some aspects, SGP2 is a viral promoter that is recognized by viral RNA dependent RNA polymerase (RdRP). In some aspects, SGP1 and SGP2 are different subgenomic promoters.

In some aspects, the sa-mRNA of the disclosure comprises one or more linkers. In some aspects, the linkers are selected from the group SEQ ID Nos: 16 (L(a)), 18 (L(b)), 23 (L(c)), and 25 (L(d)).

In some aspects, the sa-mRNA of the present disclosure comprises a polynucleotide encoding a modified SARS-CoV-2 spike protein. In some aspects, the polynucleotide encoding a modified SARS-CoV-2 spike protein comprise a nucleic sequence selected from the group SEQ ID NO: 1 (BA.1-1273), SEQ ID NO: 2 (BA.1-1273-S2P), SEQ ID NO: 3 (BA.2-1273), SEQ ID NO: 4 (BA.2-1273-S2P), SEQ ID NO: 5 (BA.1-1208), and SEQ ID NO: 6 (BA.1-1208-S2P), SEQ ID NO: 7 (BA.2-1208), and SEQ ID NO: 8 (BA.2-1208-S2P).

Sa-mRNAs of the present disclosure can be introduced into target cells or subjects using any suitable technique, e.g., by direct injection, microinjection, electroporation, lipofection, biolystics, and the like. The sa-mRNA may also be introduced into cells by way of receptor-mediated endocytosis. See e.g., U.S. Pat. No. 6,090,619; Wu and Wu, J. Biol. Chem., 263:14621 (1988); and Curiel et al, Proc. Natl. Acad. Sci. USA, 88:8850 (1991).

The sa-mRNAs of the present disclosure can be delivered into cells via amphiphiles. See e.g., U.S. Pat. No. 6,071,890. Typically, a nucleic acid molecule may form a complex with the cationic amphiphile. Mammalian cells contacted with the complex can readily take it up.

The sa-mRNAs of the present disclosure can be delivered as naked RNA (e.g. merely as an aqueous solution of RNA) but, to enhance entry into cells and also subsequent intercellular effects, the sa-mRNA may be administered in combination with a delivery system, such as a particulate or emulsion delivery system. A large number of delivery systems are well known to those of skill in the art. Such delivery systems include, for example lipid nanoparticle based delivery (Debs and Zhu (1993) WO 93/24640; Mannino and Gould-Fogerite (1988) BioTechniques 6(7): 682-691; Rose U.S. Pat. No. 5,279,833; Brigham (1991) WO 91/06309; and Feigner et al (1987) Proc. Natl. Acad. Sci. USA 84: 7413-7414), as well as use of viral vectors {e.g., adenoviral (see, e.g., Berns et al (1995) Ann. NY Acad. Sci. 772: 95-104; AIi et al (1994) Gene Ther. 1: 367-384; and Haddada et al. (1995) Curr. Top. Microbiol. Immunol. 199 (Pt 3): 297-306 for review), papillomaviral, retroviral (see, e.g., Buchscher et al. (1992) J. Virol. 66(5) 2731-2739; Johann et al. (1992) J. Virol. 66 (5): 1635-1640 (1992); Sommerfelt et al, (1990) Virol. 176:58-59; Wilson et al. (1989) J. Virol. 63:2374-2378; Miller et al, J. Virol. 65:2220-2224 (1991); Wong-Staal et al, PCT/US94/05700, and Rosenburg and Fauci (1993) in Fundamental Immunology, Third Edition Paul (ed) Raven Press, Ltd., New York and the references therein, and Yu et al, Gene Therapy (1994) supra.), and adeno-associated viral vectors (see, West et al (1987) Virology 160:38-47; Carter et al (1989) U.S. Pat. No. 4,797,368; Carter et al WO 93/24641 (1993); Kotin (1994) Human Gene Therapy 5:793-801; Muzyczka (1994) J. Clin. Invst. 94:1351 and Samulski (supra) for an overview of AAV vectors; see also, Lebkowski, U.S. Pat. No. 5,173,414; Tratschin et al (1985) MoI. Cell. Biol. 5(11):3251-3260; Tratschin, et al (1984) MoI. Cell. Biol, 4:2072-2081; Hermonat and Muzyczka (1984) Proc. Natl. Acad. Sci. USA, 81:6466-6470; McLaughlin et al (1988) and Samulski et al (1989) J. Virol, 63:03822-3828), and the like.

Three particularly useful delivery systems are (i) LNPs (ii) non-toxic and biodegradable polymer microparticles (iii) cationic submicron oil-in-water emulsions. In one aspect, the sa-mRNA of the present disclosure is delivered using LNPs.

In one aspect, a sa-mRNA of the disclosure encodes two separated expression units, the first expression unit comprising a polynucleotide encoding a modified antigen, wherein the polynucleotide encoding the modified antigen is truncated to not include nucleotides encoding a transmembrane domain and short cytosolic domain amino acids of the antigen, operably linked to a first subgenomic promoter; and the second expression unit encoding immunomodulators (IM) that are operably linked to a second subgenomic promoter. The polynucleotide encoding a modified antigen comprise a sequence that is 90%, 95%, 98%, 99% or 100% identical to SEQ ID NO: 1 (BA.1-1273), 2 (BA.1-1273-S2P), 3 (BA.2-1273), and SEQ ID NO: 4 (BA.2-1273-S2P), SEQ ID NO: 5 (BA.1-1208), SEQ ID NO: 6 (BA.1-1208-S2P), SEQ ID NO: 7 (BA.2-1208), SEQ ID NO: 8 (BA.2-1208-S2P). In addition, in some aspects, any of SEQ ID NO: 1, 3, or 5 wherein "T" is replaced by "U". Those of skill in the art will recognize that, due to the degenerate nature of the genetic code, a variety of codons differing in their nucleotide sequences can be used to encode a given amino acid. A particular nucleotide sequence encoding a polypeptide described herein are referenced merely to illustrate an aspect of the disclosure, and the disclosure includes nucleic acids of any sequence that encode a polypeptide comprising the same amino acid sequence of the polypeptides and proteins utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the RNA or DNA sequences shown herein merely illustrate aspects of the disclosure.

In one aspect, the sa-mRNA of the disclosure comprises, from 5' to 3', alphavirus nonstructural proteins 1-4 (nsP1-4) from the TC-83 strain of Venezuelan Equine Encephalitis virus (VEE); a first subgenomic promoter, a first expression unit encoding an antigen selected from SEQ ID NO: 1 (BA.1-1273), 2 (BA.1-1273-S2P), 3 (BA.2-1273), and SEQ ID NO: 4 (BA.2-1273-S2P), SEQ ID NO: 5 (BA.1-1208), SEQ ID NO: 6 (BA.1-1208-S2P), SEQ ID NO: 7 (BA.2-1208), SEQ ID NO: 8 (BA.2-1208-S2P), a second subgenomic promoter, and a second expression unit encoding one or more immunomodulator(s). In some aspects, the second expression unit encodes from 5' to 3: a signal peptide, interleukin-12 comprising heavy chain p40 (IL12-P40), linker 1 (L1), interleukin-12 comprising light chain p35 (IL12 P35), linker 2 (L2), and interleukin-21 (IL21).

In one aspect, the sa-mRNA of the disclosure comprises, alphavirus nonstructural proteins 1-4 (nsP1-4) from the TC-83 strain of Venezuelan Equine Encephalitis virus (VEE); a first subgenomic promoter, a first expression unit encoding one or more immunomodulator(s), a second subgenomic promoter, and a second expression unit encoding an antigen selected from SEQ ID NO: 1 (BA.1-1273), 2 (BA.1-1273-S2P), 3 (BA.2-1273), and SEQ ID NO: 4 (BA.2-1273-S2P), SEQ ID NO: 5 (BA.1-1208), SEQ ID NO: 6 (BA.1-1208-S2P), SEQ ID NO: 7 (BA.1-1208), SEQ ID NO: 8 (BA.1-1208-S2P). In some aspects, the second expression unit encodes from 5' to 3': a signal peptide, interleukin-12 comprising heavy chain p40 (IL12-P40), linker 1 (L1), interleukin-12 comprising light chain p35 (IL12 P35), linker 2 (L2), and interleukin-21 (IL21).

In one aspect, the sa-mRNA of the present disclosure can incorporate one or more custom GOI built by synthetic methods known in the art, or cloned from cDNA or a genomic library.

Sa-mRNA of the present disclosure can encode an antigen which can be tested for ability to induce humoral immune responses, as evidenced, for example, by induction of B cell production of antibodies specific for an antigen of interest. These assays can be conducted using, for example, peripheral B lymphocytes from immunized individuals. Such assay methods are known to those of skill in the art. Other assays that can be used to characterize the sa-mRNA of the present disclosure can involve detecting expression of the encoded antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

De Novo Synthesis of Self-Amplifying mRNA

The sa-mRNAs of the present disclosure may be produced from a nucleic acid template in the form of recombinant DNA expression vectors, RNA replicons or plasmids. The nucleic acid template of the present disclosure encodes two expression units comprising: i) an origin of replication sequence (Ori); ii) a first expression unit encoding a first nucleotide sequence that is operably linked to a first promoter; and iii) a second expression unit encoding a second nucleotide sequence that is operably linked to a second promoter, wherein the first expression unit encodes a selectable marker and the second expression unit encodes a sa-mRNA.

The nucleic acid template may be produced using a suitable synthetic method either alone or in combination with one or more other methods. Such methods are well known in the art, including chemical synthesis using suitable protecting groups such as CEM (Masuda et al., (2007) Nucleic Acids Symposium Series 57:3-4), the β-cyanoethyl phosphoramidite method (Beaucage S L et al. (1981) Tetrahedron Lett 22:1859); nucleoside H-phosphonate method (Garegg P et al. (1986) Tetrahedron Lett 27:4051-4; Froehler B C et al. (1986) Nucl Acid Res 14:5399-407; Garegg P et al. (1986) Tetrahedron Lett 27:4055-8; Gaffney B L et al. (1988) Tetrahedron Lett 29:2619-22). These chemistries can be performed or adapted for use with automated nucleic acid synthesizers that are commercially available. Additional suitable synthetic methods are disclosed in Uhlmann et al. (1990) Chem Rev 90:544-84, and Goodchild J (1990) Bioconjugate Chem 1: 165. Nucleic acid synthesis can also be performed using suitable recombinant methods that are well-known and conventional in the art, including cloning, processing, and/or expression of polynucleotides and gene products encoded by such polynucleotides. DNA shuffling by random fragmentation and PCR reassembly of gene fragments and synthetic polynucleotides are examples of known techniques that can be used to design and engineer polynucleotide sequences. Site-directed mutagenesis can be used to alter nucleic acids and the encoded proteins, for example, to insert new restriction sites, alter glycosylation patterns, change codon preference, produce splice variants, introduce mutations and the like. Suitable methods for transcription, translation and expression of nucleic acid sequences are known and conventional in the art. (See generally, Current Protocols in Molecular Biology, Vol. 2, Ed. Ausubel, et al., Greene Publish. Assoc. & Wiley Interscience, Ch. 13, 1988; Glover, DNA Cloning, Vol. II, IRL Press, Wash., D.C., Ch. 3, 1986; Bitter, et al., in Methods in Enzymology 153:516-544 (1987); The Molecular Biology of the Yeast *Saccharomyces*, Eds. Strathern et al., Cold Spring Harbor Press, Vols. I and II, 1982; and Sambrook et al., Molecular Cloning: A Laboratory Manual, Cold Spring Harbor Press, 1989.)

The present disclosure discloses a method of increasing the copy number of the nucleic acid template by transforming the nucleic acid into suitable host cells (e.g. *Escherichia coli* cells); selecting cells that express the selectable marker encoded by the first expression unit; subculturing the selected cells to obtain a population of host cells that express the selectable marker; and propagating the population of selected host cells to increase the copy number of the nucleic acid template.

In one aspect, a nucleic acid template of the disclosure comprise a sequence that is 90%, 95%, 98%, 99% or 100% identical to SAM001 (SEQ ID NO: 35), SAM002 (SEQ ID NO: 36), SAM003 (SEQ ID NO: 37), SAM004 (SEQ ID NO: 38), SAM005 (SEQ ID NO: 39), SAM006 (SEQ ID NO: 40), MOD001 (SEQ ID NO: 41), or T7-VEE-GFP (SEQ ID NO: 42). In addition, in some aspects, any of SEQ ID NOs: 35, 36, 37, 38, 39, 40, 41, or 42 wherein "T" is replaced by "U". Those of skill in the art will recognize that, due to the degenerate nature of the genetic code, a variety of codons differing in their nucleotide sequences can be used to encode a given amino acid. A particular nucleotide sequence encoding a polypeptide described herein are referenced merely to illustrate an aspect of the disclosure, and the disclosure includes nucleic acids of any sequence that encode a polypeptide comprising the same amino acid sequence of the polypeptides and proteins utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the RNA or DNA sequences shown herein merely illustrate aspects of the disclosure.

In one aspect, SEQ ID NO: 35 provides a nucleic acid of the disclosure. In another aspect the sequence of SEQ ID NO: 35 has "T" replaced with "U". The nucleic acid comprises, from 5' to 3', a first linker (SEQ ID NO: 43); a first promoter sequence comprising the ampicillin resistance (AmpR) promoter; a selectable marker comprising the ampicillin resistance gene (AmpR); a second linker (SEQ ID NO: 44); a second promoter sequence for in vitro transcription comprising the T7 promoter; a 5' untranslated region; a subgenomic promoter, alphavirus nonstructural proteins 1-4 (nsP1-4) from the TC-83 strain of Venezuelan Equine Encephalitis virus (VEE); a third linker (SEQ ID NO: 45); a subgenomic promoter; the gene of interest; a fourth linker (SEQ ID NO: 46); a 3' untranslated region; and a 3' poly-adenylated tail (poly-A tail).

In one aspect, SEQ ID NO: 36 provides a nucleic acid of the disclosure. In another aspect the sequence of SEQ ID NO: 36 has "T" replaced with "U". The nucleic acid comprises, from 5' to 3', a first linker (SEQ ID NO: 43); a first promoter sequence comprising the AmpR promoter; a selectable marker comprising AmpR; a second linker (SEQ ID NO: 44); a second promoter sequence for in vitro transcription comprising the T7 promoter; a 5' untranslated region; a subgenomic promoter; alphavirus nsP1-4 from the TC-83 strain of VEE; a third linker (SEQ ID NO: 45); a subgenomic promoter; the gene of interest; a fourth linker (SEQ ID NO: 46); a 3' untranslated region; and a 3' poly-adenylated tail (poly-A tail).

In one aspect, SEQ ID NO: 37 provides a nucleic acid of the disclosure. In another aspect the sequence of SEQ ID NO: 37 has "T" replaced with "U". The nucleic acid comprises, from 5' to 3', a first linker (SEQ ID NO: 43); a first promoter sequence comprising the AmpR promoter; a selectable marker comprising AmpR; a second linker (SEQ ID NO: 44); a second promoter sequence for in vitro transcription comprising the T7 promoter; a 5' untranslated region; a subgenomic promoter; alphavirus nsP1-4 from the TC-83 strain of VEE; a third linker (SEQ ID NO: 45); a subgenomic promoter; the gene of interest; a fourth linker (SEQ ID NO: 46); a 3' untranslated region; and a 3' poly-adenylated tail (poly-A tail).

In one aspect, SEQ ID NO: 38 provides a nucleic acid of the disclosure. In another aspect the sequence of SEQ ID NO: 104 has "T" replaced with "U". The nucleic acid comprises, from 5' to 3', a first linker (SEQ ID NO: 38); a first promoter sequence comprising the AmpR promoter; a selectable marker comprising AmpR; a second linker (SEQ ID NO: 44); a second promoter sequence for in vitro transcription comprising the T7 promoter; a 5' untranslated region; a subgenomic promoter; alphavirus nsP1-4 from the TC-83 strain of VEE; a third linker (SEQ ID NO: 45); a subgenomic promoter; the gene of interest; a fourth linker (SEQ ID NO: 46); a 3' untranslated region; and a 3' poly-adenylated tail (poly-A tail).

In one aspect, SEQ ID NO: 39 provides a nucleic acid of the disclosure. In another aspect the sequence of SEQ ID NO: 105 has "T" replaced with "U". The nucleic acid comprises, from 5' to 3', a first linker (SEQ ID NO: 39); a first promoter sequence comprising the AmpR promoter; a selectable marker comprising AmpR; a second linker (SEQ ID NO: 44); a second promoter sequence for in vitro transcription comprising the T7 promoter; a 5' untranslated region; a subgenomic promoter; alphavirus nsP1-4 from the TC-83 strain of VEE; a third linker (SEQ ID NO: 45); a subgenomic promoter; the gene of interest; a fourth linker (SEQ ID NO: 112); a 3' untranslated region; and a 3' poly-adenylated tail (poly-A tail).

In one aspect, SEQ ID NO: 40 provides a nucleic acid of the disclosure. In another aspect the sequence of SEQ ID NO: 40 has "T" replaced with "U". The nucleic acid comprises, from 5' to 3', a first linker (SEQ ID NO: 43); a first promoter sequence comprising the AmpR promoter; a selectable marker comprising AmpR; a second linker (SEQ ID NO: 44); a second promoter sequence for in vitro transcription comprising the T7 promoter; a 5' untranslated region; a subgenomic promoter; alphavirus nsP1-4 from the TC-83 strain of VEE; a third linker (SEQ ID NO: 45); a subgenomic promoter; the gene of interest; a fourth linker (SEQ ID NO: 46); a 3' untranslated region; and a 3' poly-adenylated tail (poly-A tail).

In one aspect, SEQ ID NO: 41 provides a nucleic acid of the disclosure. In another aspect the sequence of SEQ ID NO: 41 has "T" replaced with "U". The nucleic acid comprises, from 5' to 3', a first linker (SEQ ID NO: 43); a first promoter sequence comprising the AmpR promoter; a selectable marker comprising AmpR; a second linker (SEQ ID NO: 44); a second promoter sequence for in vitro transcription comprising the T7 promoter; a 5' untranslated region; a subgenomic promoter; alphavirus nsP1-4 from the TC-83 strain of VEE; a third linker (SEQ ID NO: 45); a subgenomic promoter; the gene of interest; a fourth linker (SEQ ID NO: 46); a 3' untranslated region; and a 3' poly-adenylated tail (poly-A tail).

In one aspect, SEQ ID NO: 42 provides a nucleic acid of the disclosure. In another aspect the sequence of SEQ ID NO: 42 has "T" replaced with "U". The nucleic acid comprises, from 5' to 3', a first linker (SEQ ID NO: 43); a first promoter sequence comprising the AmpR promoter; a selectable marker comprising AmpR; a second linker (SEQ ID NO: 44); a second promoter sequence for in vitro transcription comprising the T7 promoter; a 5' untranslated region; a subgenomic promoter; alphavirus nsP1-4 from the TC-83 strain of VEE; a third linker (SEQ ID NO: 45); a subgenomic promoter; the gene of interest comprising GFP; a fourth linker (SEQ ID NO: 46); a 3' untranslated region; and a 3' poly-adenylated tail (poly-A tail).

In one aspect, the sa-mRNA of the present disclosure can incorporate one or more custom GOI built by synthetic methods known in the art, or cloned from cDNA or a genomic library. The GOI, along with promoters, other regulatory elements, optionally one or more linkers, an origin of replication, and a selectable marker are incorporated into a nucleic acid template. Nucleic acid templates of essentially any length and sequence can be produced in high yield in *Escherichia coli*. Sa-mRNA of any desired sequence can be produced from nucleic acid templates by in vitro transcription.

In vitro transcription (IVT) methods permit template-directed synthesis of RNA molecules (including self-amplifying mRNA) of almost any sequence. The size of the RNA molecules that can be synthesized using IVT methods range from short oligonucleotides to long nucleic acid polymers of several thousand bases. IVT methods permit synthesis of large quantities of RNA transcript (e.g., from microgram to milligram quantities) (Beckert et al., Synthesis of RNA by in vitro transcription, Methods Mol Biol. 703:29-41(2011); Rio et al. RNA: A Laboratory Manual. Cold Spring Harbor: Cold Spring Harbor Laboratory Press, 2011, 205-220; Cooper, Geoffery M. The Cell: A Molecular Approach. 4th ed. Washington D.C.: ASM Press, 2007. 262-299). Generally, IVT utilizes a nucleic acid template featuring a promoter sequence upstream of a sequence of interest. The promoter sequence is most commonly a bacteriophage promoter (e.g. the T7, T3, SP6, or T5 promoter sequence) but many other promotor sequences can be tolerated (e.g SV40, β-lactamase promoter, *E. coli* galactose promoter, arabinose promoter, alkaline phosphatase promoter, trp promoter, lac promoter, lacUV5 promoter, trc promoter and tac promoter) including those designed de novo. Transcription of the DNA template is typically best achieved by using the RNA polymerase corresponding to the specific promoter sequence. Exemplary RNA polymerases include, but are not limited to T7 phage RNA polymerase, SP6 phage RNA polymerase, T3 phage RNA polymerase, T5 phage RNA polymerase, RNA polymerase III, RNA polymerase II, Taq polymerase, Vent polymerase, and the like, or mutants of these polymerases. IVT is generally initiated at a dsDNA but can proceed using RNA and/or on a single strand.

Self-Amplifying mRNA Library

One aspect of the present disclosure is a method of generating a sa-mRNA library. In one aspect, the invention is a method for preparing a library of sa-mRNA derived from a reference sa-mRNA comprising: (i) performing directed evolution of a reference sa-mRNA sample comprising the steps of:

(a) delivering a reference sa-mRNA sample encoding a selection marker into host cell(s),
(b) culturing said host cell(s) over a period of time under conditions that require replication of the reference sa-mRNA sample and permit expression of the selection marker, wherein mutations occur in the replicated sa-mRNA compared to the reference sa-mRNA,
(c) selecting cells that express the selectable marker;
(ii) extracting the replicated sa-mRNA from the host cell(s) and sequencing the replicated sa-mRNA; and thereby producing a library of sa-mRNA sequences.

In one aspect, the selection marker is an antibiotic resistance gene. In one aspect, the selection marker is a puromycin resistance gene. In one aspect, the reference sa-mRNA is delivered into a host cell using a delivery mechanism. In one aspect, the delivery system is a lipid nanoparticle. In one aspect, the reference sa-mRNA is selected from a group comprising SEQ ID NOs. 1-8 and SEQ ID NOs 35-42. In one aspect, the conditions that require replication of the reference sa-mRNA sample and permit expression of the selection marker is a culture environment containing an antibiotic. In one aspect, the concentration of the antibiotic affects the rate of mutation of the reference sa-mRNA.

In one aspect, the disclosure provides a method of evaluating mutations of the replicated self-amplifying mRNA, the method comprising: (i) obtaining a group of contig sequences comprising mutation(s) compared to a reference sa-mRNA sample, (ii) sequencing the contig sequences, and (iii) determining the number of mutations in the contig sequences compared to the reference sa-mRNA. In one aspect, the contig sequences are fragments of the replicated sa-mRNA. In certain aspects, the group of contig sequences comprise SEQ ID NOs. 27-34.

Increased In Vitro Transcription

One aspect of the present disclosure is a nucleic acid containing modified promoters and regulatory elements, such as a modified 5' UTR. Said nucleic acid shows an unexpected improvement in transcription efficiency while reducing the amount of truncated single-stranded ribonucleic acid (ssRNA) (e.g., sa-mRNA) transcript produced during an in vitro transcription (IVT) reaction. In a typical IVT reaction, greater than 50% (molarity) of the RNA transcripts produced are truncated abortive products (referred to herein as truncated ssRNA transcripts). Only a small fraction (e.g., 0.2-0.5%) of initiation events lead to full-length “run-off” ssRNA transcripts, which is inefficient and costly for large-scale IVT RNA synthesis systems. Sa-mRNA transcripts in particular are longer than conventional mRNA (larger than 7 kilo nucleotides) and are particularly susceptible to truncated abortive products. Thus, use of the IVT methods of the present disclosure (which include, for example, nucleic acid constructs, modified promoters and/or modified 5'UTR), in some aspects, results in a sa-mRNA transcript yield that is at least 40% greater than the sa-mRNA transcript yield of an IVT method without the modified regulatory elements of the present disclosure.

Preferably, the nucleic acid template of the present disclosure comprise a modified T7 promoter operably linked to nucleic acid comprising a sequence that encodes a modified 5' untranslated region (UTR) a plurality of non-structural replicase domain sequences, one or more gene or genes of interest (GOI), a 3' UTR, and a poly-A tail, wherein the sequence that encodes the T7 promoter and the sequence that encodes the 5' UTR is modified to enhance the binding strength of T7 polymerase to the T7 promoter to increase transcript yield.

In some aspects, a modified T7 promoter comprises at least one insertion at position at the 5' end of the wildtype T7 promoter nucleotide sequence. The modification may be, for example, insertion of a single guanine (G) at the 5' end of the wildtype T7 promoter. In some aspects, the modified T7 promoter comprises SEQ ID NO: 47 (TAATACGACTCACTATAGG).

In some aspects, a modified 5'UTR comprises at least one insertion at position 3 relative to the 5' end of the wildtype 5'UTR nucleotide sequence. The modification may be, for example, insertion of a single adenine (A) at position 3 of the wildtype 5'UTR of wildtype T7-VEE-GFP (SEQ ID NO: 42). In some aspects, the modified 5'UTR comprises ATAGG (repeating the last 5 nucleotides of T7 promoter).

In one aspect, a nucleic acid of the present disclosure consisting of a nucleotide sequence which is at least 90% identical to SEQ ID NO: 36.

Preferably, the nucleic acid template containing a modified T7 promoter and 5'UTR of the present disclosure will cause a host cell to produce more self-amplifying mRNA, which will translate an increased amount of gene product relative to the amount of gene product produced by the same cell type that contains the corresponding sa-mRNA that does not contain modified nucleotides. Methods of determining translation efficiency are well known in the art, and include, e.g. measuring the activity or amount of an encoded protein (e.g. luciferase and/or GFP), or measuring radioactive label incorporated into the translated protein (See, e.g., Ngosuwan J, Wang N M et al, J Biol Chem 2003; 278(9): 7034-42).

Immune Response Modulation

One aspect of the present disclosure is a nucleic acid containing regulatory elements, such as a modified 3' UTR. Said nucleic acid is capable of decreasing the immunogenicity and/or immunostimulatory capacity (immune response) of said nucleic acid. In one aspect, the nucleic acid of the present disclosure is a sa-mRNA. In another aspect, the nucleic acid of the present disclosure is a nucleic acid template (e.g. a DNA or RNA template), which encodes a sa-mRNA.

In general, exogenous nucleic acids, particularly of viral origin, induce an innate immune response when introduced into cells, resulting in interferon (IFN) production and cell death. However, it is of great interest for therapeutics, diagnostics, reagents and for biological assays to deliver a nucleic acid, e.g., a ribonucleic acid (RNA) inside a cell, either in vivo or ex vivo, such as to cause intracellular translation of the nucleic acid and production of the encoded protein. Of particular importance is the delivery and function of a non-integrative nucleic acid (e.g. RNA), as nucleic acids characterized by integration into a target cell are generally imprecise in their expression levels, deleteriously transferable to progeny and neighbor cells, and suffer from the substantial risk of mutation. Provided herein in are nucleic acids encoding useful gene products capable of modulating a cell's function and/or activity, and methods of making and using these nucleic acids and gene products. As described herein, these nucleic acids are capable of reducing the innate immune response of a population of cells into which they are introduced, thus increasing the efficiency of protein production in that cell population.

The sa-mRNA of the present disclosure encodes at least one gene product, by preferably increasing the adenine (A) content of the 3'UTR. In some aspects, use of the nucleic acid molecules and modified regulatory elements of the present disclosure (which include, for example, nucleic acid constructs, and/or modified 3'UTR), results in interferon responses that are 2 times, 3 times, 4 times, or 5 times lower than the interferon response to sa-mRNAs without the modified regulatory elements of the present disclosure after one day post-transfection.

In some aspects, a modified 3'UTR comprises at least one modification at any one of positions 6, −1, or −2 relative to a conserved 19 nucleotide sequence SEQ ID NO: 49 (GGATTTTGTTTTTAATATTTC). In another aspect the sequence of SEQ ID NO: 49 has "T" replaced with "U". The modification may be, for example, a mutant 3'UTR of an alphavirus comprising point mutations at position 6 relative to the conserved 19 nucleotide sequence, SEQ ID NO: 49, of the wild-type 3'UTR of an alphavirus. The modification may also be, for example, a mutant 3'UTR of an alphavirus comprising point mutations at positions −1 and −2 relative to the conserved 19 nucleotide sequence, SEQ ID NO: 49, of the wild-type 3'UTR of an alphavirus. The modification may also be, for example, a mutant 3'UTR of an alphavirus comprising point mutations at positions −1, −2 and 6 relative to the conserved 19 nucleotide sequence, SEQ ID NO: 49, of the wild-type 3'UTR of an alphavirus. In some aspects, the modified 3'UTR conserved sequence comprise GGATTTTATTTTTAATATTTC (SEQ ID NO: 50), AAATTTTGTTTTTAATATTTC (SEQ ID NO: 51), or AAATTTTATTTTTAATATTTC (SEQ ID NO: 52). In other aspects the sequence of SEQ ID NO: 50, SEQ ID NO: 51, and SEQ ID NO: 52 has "T" replaced with "U".

Sa-mRNA of the present disclosure can encode an antigen which can be tested for ability to induce humoral immune responses, as evidenced, for example, by induction of B cell production of antibodies specific for an antigen of interest. These assays can be conducted using, for example, peripheral B lymphocytes from immunized individuals. Such assay methods are known to those of skill in the art. Other assays that can be used to characterize the sa-mRNA of the present disclosure can involve detecting expression of the encoded antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

Antigens of SARS-CoV2 Omicron Variant BA.2

The disclosure also relates to polypeptides encoding a modified SARS-CoV2 antigen, wherein the polynucleotide encoding the modified antigen is truncated to not include nucleotides encoding a transmembrane domain and short cytosolic domain amino acids of the antigen. Since the SARS-Coronavirus 2 (SARS-CoV2) was firstly identified from Wuhan, China, there has been 526,808,553 cases and 6,280,679 deaths reported in global by May 25, 2022 (https://coronavirus.jhu.edu/map.html). Although the first generation of COVID vaccines (e.g. BNT162b2 (BioNTech-Pfizer), mRNA-1273 (Moderna)) are available and the temporary variants of SARS-Coronavirus 2 show gradually mild and lower death rate, the pandemic is still ongoing, giving rise to severe social and economic crisis. Therefore, while many people globally have been vaccinated with one or more shots of the first-generation COVID vaccines, there remains a need to develop COVID booster vaccines to address shortcomings of current COVID vaccines such as induction of hepatitis, and myocarditis; reduction efficiency in dealing with the rapid evolutions of SARS-CoV-2; inefficiency on preventing infection; and quick decrease of antibody titer.

In some aspects, the polypeptides of the present disclosure encode secreted versions of the SPIKE protein. The first generation of mRNA COVID vaccines, BNT162b2 and mRNA-1273, comprise 1273 amino acids including: S1 (RBD), S2, transmembrane domain and a short cytosolic domain. Since the transmembrane domain leads to the expression of SPIKE antigens on the cell surface of transfected cells, the transfected cells are targeted by immune system, this likely leads to side effects of hepatitis, and myocarditis that manifest in some individuals vaccinated using BNT162b2 and mRNA-1273. The polypeptides of the present disclosure encode a modified SPIKE protein that is secreted while retaining its native structure. This will prevent the expression of SPIKE antigens on the cell surfaces. The secreted version of the modified SPIKE antigen is able to trigger humoral immune responses and shows comparable BA.2 specific IgG compared to transmembrane SPIKE proteins.

Figure 18:
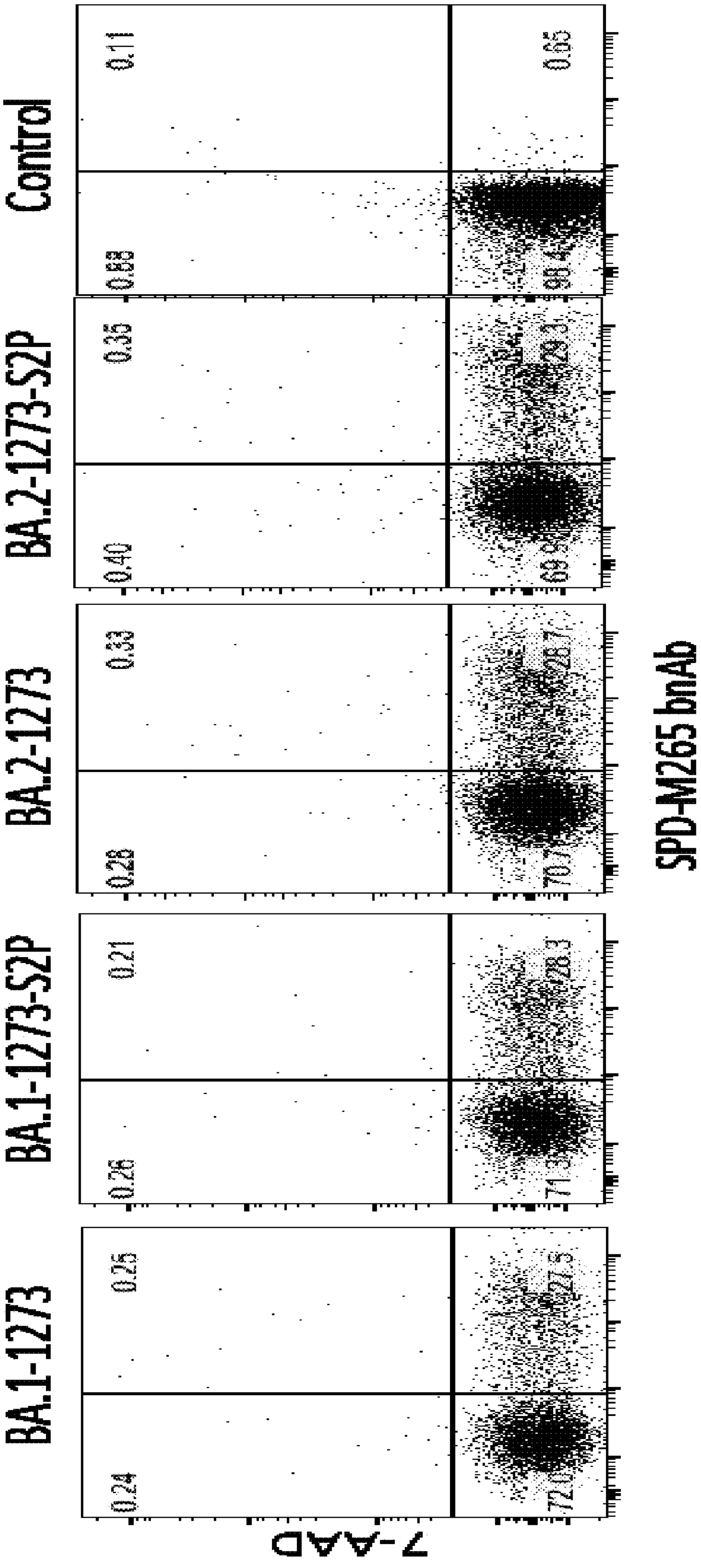
FIG. 18 shows FACS plots of GFP (a) expression (X-axis) versus live dead dye staining of 7-AAD (Y-axis) of E6-LNP encompassing a sa-mRNA encoding the SARS-CoV-2-BA.1-1273, SARS-CoV-2-BA.2-1273, SARS-CoV-2-BA.1-1273-S2P, and SARS-CoV-2-BA.2-1273-S2P transfected into 293 T-cells by lipofectamine. The cells were collected and the SPIKE of Omicron BA.1 and BA.2 were detected by the SPD-M265 bnAb (broad neutralization antibody) using flow cytometer. The results show that S2P is dispensable to stabilize the structure of SPIKE with transmembrane domain for recognition by SPD-M265 bnAb. The cells were analyzed by flow cytometer at day 1 post transfection.
Figure 19:
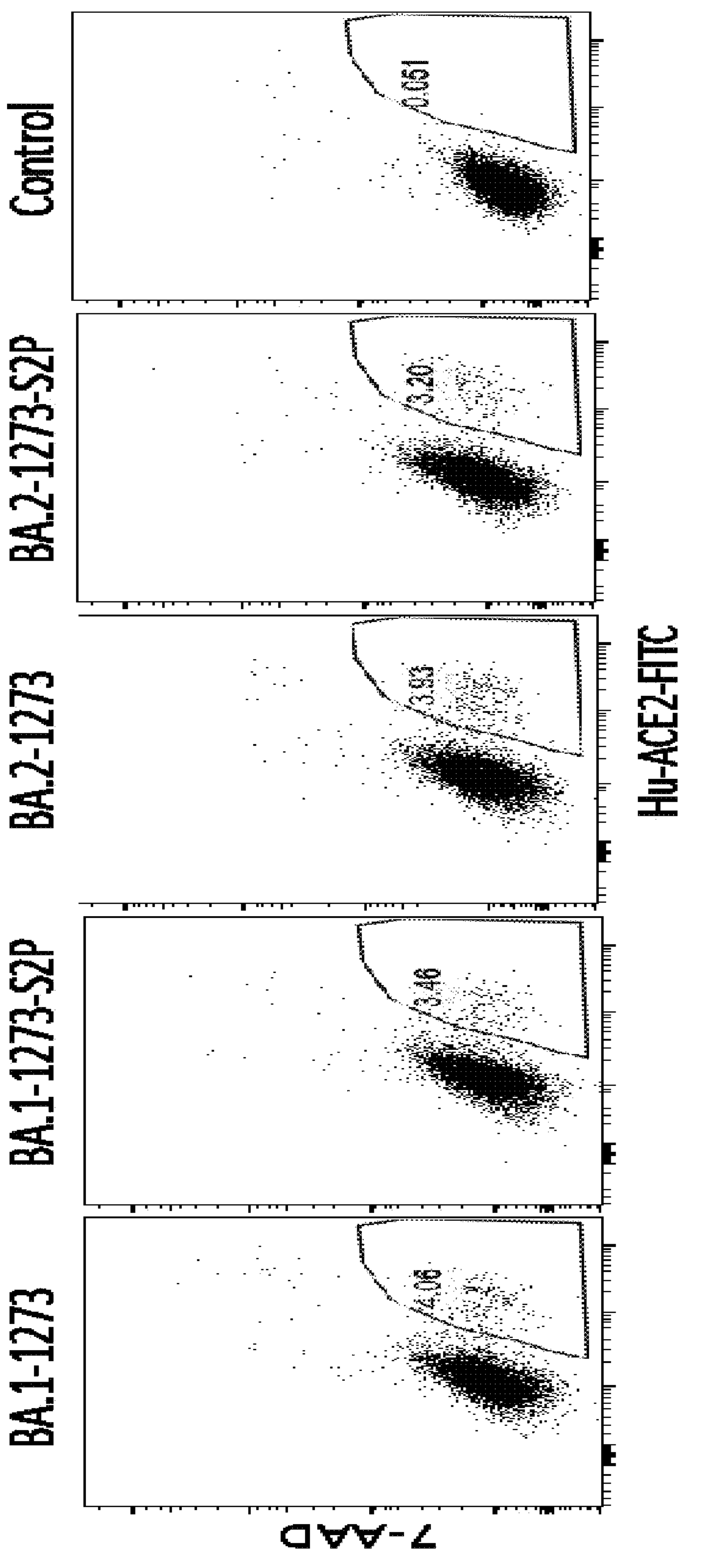
FIG. 19 shows FACS plots of binding of SPIKE expression with its receptor ACE2 versus live dead dye staining of 7-AAD (Y-axis) of E6-LNP encompassing a sa-mRNA encoding the SARS-CoV-2-BA.1-1273, SARS-CoV-2-BA.2-1273, SARS-CoV-2-BA.1-1273-S2P, and SARS-CoV-2-BA.2-1273-S2P transfected into 293 T-cells by lipofectamine. The treated cells were collected and the SPIKE of Omicron BA.1 and BA.2 were detected by the ACE2 conjugated with FITC using flow cytometer. The results show that S2P is dispensable to stabilize the structure of SPIKE with transmembrane domain for recognition by SPIKE receptor ACE2 conjugated with FITC. The cells were analyzed by flow cytometer at day 1 post transfection.
Figure 20:
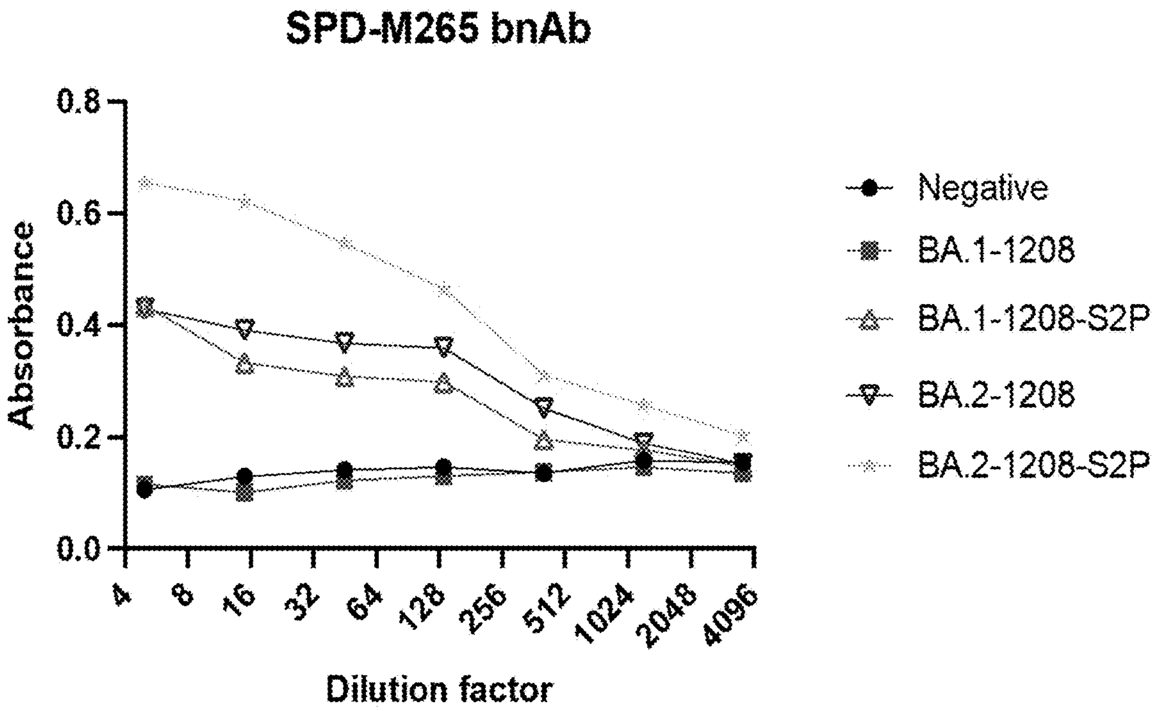
FIG. 20 shows ELISA data with absorbance on the Y-axis and dilution factor X-axis comparing S2P effects on secretion version of BA.1-1208, BA.1-1208-S2P, BA.2-1208, and BA.2-1208-S2P by transfecting 293 T cells with different sa-mRNA encoding with BA.1-1208, BA.1-1208-S2P, BA.2-1208, and BA.2-1208-S2P by lipofectamine and detecting absorbance using SPD-M265-bnAb. The data show that S2P is indispensable to stabilize the structure of the secretion SPIKE without transmembrane domain. The supernatants of transfected cells at day 1 post transfection were analyzed by ELISA.

In some aspects, the polypeptides of the present disclosure encode a modified SPIKE protein with 2 proline mutations on S2 (S2P). The S2P mutation keep the conformation of SPIKE protein for induction of neutralization antibodies stabilize the structure of SPIKE for recognition by broad neutralization antibody (bnAb) SPD-M265 and hACE2-FITC (FIG. 18-20).

Pharmaceutical Compositions

The disclosure also relates to pharmaceutical compositions comprising a sa-mRNA of the present disclosure (which optionally contains a modified 3' UTR of the present disclosure), a pharmaceutically acceptable carrier and a suitable delivery system of the present disclosure, as described herein, such as liposomes, lipid nanoparticles, nanoemulsions, PLG micro- and nanoparticles, lipoplexes, chitosan micro- and nanoparticles and other polyplexes. If desired other pharmaceutically acceptable components can be included, such as excipients and adjuvants.

Pharmaceutical Compositions

The disclosure also relates to pharmaceutical compositions comprising a self-amplifying mRNA (which optionally contains a modified 3' UTR of the present disclosure), a pharmaceutically acceptable carrier and a suitable delivery system as described herein, such as liposomes, nanoemulsions, PLG micro- and nanoparticles, lipoplexes, chitosan micro- and nanoparticles and other polyplexes. If desired other pharmaceutically acceptable components can be included, such as excipients and adjuvants.

Nanoparticle Composition

Preferably, the sa-mRNA of the present disclosure is delivered using a nanoparticle composition comprising one or more cationic and/or ionizable lipids (e.g., lipids that may have a positive or partial positive charge at physiological pH); one or more PEG or PEG-modified lipids (a lipid modified with polyethylene glycol); one or more structural lipids (e.g. cholesterol, fecosterol, sitosterol, ergosterol, campesterol, stigmasterol, brassicasterol, tomatidine, tomatine, ursolic acid, alpha-tocopherol, and mixtures thereof); and one or more phospholipids (e.g. (poly)unsaturated lipids).

Adjuvants

In some aspects, a pharmaceutical composition that includes one or more lipids described herein may further include one or more adjuvants, e.g., Glucopyranosyl Lipid Adjuvant (GLA), CpG oligodeoxynucleotides (e.g., Class A or B), poly(I:C), aluminum hydroxide, and Pam3CSK4.

Medical Uses

In some aspects, the sa-mRNA of the present disclosure optionally encodes messenger mRNA (mRNA), small interfering RNA (siRNA), micro-RNA (miRNA), guide RNA (gRNA), self-activating RNA (saRNA), transfer RNA (tRNA), long intergenic non-coding (lincRNA), etc.

In certain aspects, the biologically active sa-mRNA of the present disclosure encodes an mRNA. Said mRNA may encode any polypeptide of interest, including any naturally or non-naturally occurring or otherwise modified polypeptide. A polypeptide encoded by an mRNA may be of any size and may have any secondary structure or activity. In some aspects, a polypeptide encoded by an mRNA may have a therapeutic effect when expressed in a cell. In some aspects, the polypeptide encoded by the mRNA is a modified SPIKE antigen.

In other aspects, the biologically active sa-mRNA of the present disclosure encodes a siRNA or a miRNA. A siRNA or miRNA may be capable of selectively knocking down or down regulating expression of a gene of interest. For example, a siRNA could be selected to silence a gene associated with a particular disease, disorder, or condition upon administration to a subject in need thereof of a nanoparticle composition including the siRNA. A siRNA may comprise a sequence that is complementary to an mRNA sequence that encodes a gene or protein of interest. In some aspects, the siRNA may be an immunomodulatory siRNA.

Formulations

Pharmaceutical compositions may include a biologically active sa-mRNA and one or more additional components, such as a lipid component and one or more additional components. A nanoparticle composition may be designed for one or more specific applications or targets. The elements of a nanoparticle composition may be selected based on a particular application or target, and/or based on the efficacy, toxicity, expense, ease of use, availability, or other feature of one or more elements. Similarly, the particular formulation of a nanoparticle composition may be selected for a particular application or target according to, for example, the efficacy and toxicity of particular combinations of elements.

The sa-mRNA of a pharmaceutical composition may include, for example, a sa-mRNA comprising: an antigen selected from the group SEQ ID NO: 1 (BA.1-1273), 2 (BA.1-1273-S2P), 3 (BA.2-1273), and SEQ ID NO: 4 (BA.2-1273-S2P), SEQ ID NO: 5 (BA.1-1208), SEQ ID NO: 6 (BA.1-1208-S2P), SEQ ID NO: 7 (BA.2-1208), SEQ ID NO: 8 (BA.2-1208-S2P); immunomodulators selected from the group SEQ ID NO: 13 (IM1), and SEQ ID NO: 20 (IM2); SEQ ID NO: 9 (SGP1); SGP2 is SEQ ID NO: 11 (SGP2); and a nucleotide sequence encoding nsp1-4.

The amount of a biologically active sa-mRNA may depend on the size, composition, desired target and/or application, or other properties of the therapeutic, diagnostic and/or prophylactic. Generally, the size of sa-mRNA is always larger than 7 kilo nucleotides. The relative amounts of the sa-mRNA and other elements (e.g., lipids) in a pharmaceutical composition may also vary. In some aspects, the wt/wt ratio of the lipid component to a sa-mRNA in a nanoparticle composition may be from about 5:1 to about 60:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. For example, the wt/wt ratio of the lipid component to a sa-mRNA may be from about 1:1 to about 40:1. In certain aspects, the wt/wt ratio is about 20:1. The amount of a therapeutic, diagnostic and/or prophylactic in a nanoparticle composition may, for example, be measured using absorption spectroscopy (e.g., ultraviolet-visible spectroscopy).

Pharmaceutical compositions may include one or different therapeutic agents (e.g. sa-mRNA) and delivery systems. Pharmaceutical compositions may further include one or more pharmaceutically acceptable excipients or accessory ingredients such as those described herein. General guidelines for the formulation and manufacture of pharmaceutical compositions and agents are available, for example, in Remington's *The Science and Practice of Pharmacy*, 21$^{st}$ Edition, A. R. Gennaro; Lippincott, Williams & Wilkins, Baltimore, Md., 2006. Excipients and accessory ingredients may be used in any pharmaceutical composition, except insofar as any excipient or accessory ingredient may be incompatible with one or more components of a sa-mRNA delivery system. An excipient or accessory ingredient may be incompatible if its combination with the component may result in any undesirable biological effect or otherwise deleterious effect.

In some aspects, one or more excipients or accessory ingredients may make up greater than 50% of the total mass or volume of a pharmaceutical composition. For example, the one or more excipients or accessory ingredients may make up 50%, 60%, 70%, 80%, 90%, or more of a pharmaceutical composition. In some aspects, a pharmaceutically acceptable excipient is at least 95%, at least 96%, at least 97%, at least 98%, at least 99%, or 100% pure. In some aspects, an excipient is approved for use in humans and for veterinary use. In some aspects, an excipient is approved by United States Food and Drug Administration. In some aspects, an excipient is pharmaceutical grade. In some aspects, an excipient meets the standards of the United States Pharmacopoeia (USP), the European Pharmacopoeia (EP), the British Pharmacopoeia, and/or the International Pharmacopoeia.

Relative amounts of the one or more delivery systems, the one or more pharmaceutically acceptable excipients, and/or any additional ingredients in a pharmaceutical composition in accordance with the present disclosure will vary, depending upon the identity, size, and/or condition of the subject treated and further depending upon the route by which the composition is to be administered.

In certain aspects, the pharmaceutical compositions of the disclosure are refrigerated or frozen for storage and/or shipment (e.g., being stored at a temperature of 4° C. or lower, such as a temperature between about −150° C. and about 0° C. or between about −80° C. and about −20° C. For example, the pharmaceutical composition comprising the sa-mRNA of the present disclosure is a solution that is refrigerated for storage and/or shipment at, for example, about −20° C., −30° C., −40° C., −50° C., −60° C., −70° C., or −80° C. In certain aspects, the disclosure also relates to a method of increasing stability of pharmaceutical compositions comprising sa-mRNA and a delivery system by storing the pharmaceutical compositions at a temperature of 4° C. or lower, such as a temperature between about −150° C. and about 0° C. or between about −80° C. and about −20° C., e.g., about −5° C., −10° C., −15° C., −20° C., −25° C., −30° C., −40° C., −50° C., −60° C., −70° C., −80° C., −90° C., −130° C. or −150° C.). For example, the pharmaceutical compositions disclosed herein are stable for about at least 1 week, at least 2 weeks, at least 3 weeks, at least 4 weeks, at least 5 weeks, at least 6 weeks, at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months, e.g., at a temperature of 4° C. or lower (e.g., between about 4° C. and −20° C.). In one aspect, the formulation is stabilized for at least 4 weeks at about 4° C. In certain aspects, the pharmaceutical composition of the disclosure comprises a sa-mRNA disclosed herein, a nanoparticle composition delivery system, and a pharmaceutically acceptable carrier selected from one or more of Tris, an acetate (e.g., sodium acetate), an citrate (e.g., sodium citrate), saline, PBS, and sucrose. In certain aspects, the pharmaceutical composition of the disclosure has a pH value between about 5 and 8 (e.g., 5, 5.5, 6. 6.5, 6.8 6.9, 7.0, 7.1, 7.2, 7.3, 7.4, 7.5, 7.6, 7.7, 7.8, 7.9 or 8.0, or between 7.5 and 8 or between 7 and 7.8). For example, a pharmaceutical composition of the disclosure comprises a sa-mRNA disclosed herein, a nanoparticle composition delivery system, Tris, saline and sucrose, and has a pH of about 7.5-8, which is suitable for storage and/or shipment at, for example, about −20° C. For example, a pharmaceutical composition of the disclosure comprises a sa-mRNA disclosed herein, a nanoparticle composition delivery system, and PBS and has a pH of about 7-7.8, suitable for storage and/or shipment at, for example, about 4° C. or lower. "Stability," "stabilized," and "stable" in the context of the present disclosure refers to the resistance of pharmaceutical compositions disclosed herein to chemical or physical changes (e.g., degradation, particle size change, aggregation, change in encapsulation, etc.) under given manufacturing, preparation, transportation, storage and/or in-use conditions, e.g., when stress is applied such as shear force, freeze/thaw stress, etc.

Pharmaceutical compositions of the disclosure may be administered to any patient or subject, including those patients or subjects that may benefit from a therapeutic effect provided by the delivery of a biologically active agent to one or more particular cells, tissues, organs, or systems or groups thereof, such as the renal system. Although the descriptions provided herein of pharmaceutical compositions are principally directed to compositions which are suitable for administration to humans, it will be understood by the skilled artisan that such compositions are generally suitable for administration to any other mammal. Modification of compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the compositions is contemplated include, but are not limited to, humans, other primates, and other mammals, including commercially relevant mammals such as cattle, pigs, hoses, sheep, cats, dogs, mice, and/or rats.

A pharmaceutical composition of the present disclosure may be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., sa-mRNA). The amount of the active ingredient is generally equal to the dosage of the active ingredient which would be administered to a subject and/or a convenient fraction of such a dosage such as, for example, one-half or one-third of such a dosage.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils may be employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

Methods of Producing Polypeptides in Cells

The present disclosure provides methods of producing a sa-mRNA of interest in a mammalian cell. Methods of producing sa-mRNA in a cell involve contacting a cell with sa-mRNA (either as naked RNA, or in combination with a delivery system), encoding one or more gene or genes of interest. Upon contacting the cell, the sa-mRNA may be taken up and translated in the cell to produce the gene product.

In general, the step of contacting a cell with a sa-mRNA encoding a gene or genes of interest may be performed in vivo, ex vivo, in culture, or in vitro. The amount of sa-mRNA, may depend on the type of cell or tissue being contacted, the means of administration, the physiochemical characteristics of the sa-mRNA and delivery system (e.g., size, charge, and chemical composition), and other factors. In general, an effective amount of the sa-mRNA will allow for efficient polypeptide production in the cell. Metrics for efficiency may include polypeptide translation (indicated by polypeptide expression), level of sa-mRNA degradation, and immune response indicators.

The step of contacting a nanoparticle composition containing a sa-mRNA with a cell may involve or cause transfection. A phospholipid including in the lipid component of a nanoparticle composition may facilitate transfection and/or increase transfection efficiency, for example, by interacting and/or fusing with a cellular or intracellular membrane. Transfection may allow for the transcription and translation of the sa-mRNA within the cell.

Methods of Delivering Therapeutic Agents to Cells and Organs

The present disclosure provides methods of delivering a biologically active agent to a cell or organ. Delivery of a biologically active agent to a cell involves administering a delivery system including the biologically active agent to a subject, where administration of the composition involves contacting the cell with the composition. In the instance that a biologically active agent is a sa-mRNA, upon contacting a cell, a translatable sa-mRNA may be translated in the cell to produce a polypeptide of interest. However, sa-mRNA of the present disclosure may encode gene products that are substantially not translatable (e.g. regulatory structures) may also be delivered to cells. Regulatory structures may be useful as vaccines and/or may sequester translational components of a cell to reduce expression of other species in the cell.

In some aspects, a delivery system such as a nanoparticle composition may target a particular type or class of cells (e.g., cells of a particular organ or system thereof). For example, a nanoparticle composition delivering a biologically active agent of interest may be specifically delivered to a mammalian liver, kidney, spleen, femur, or lung. Specific delivery to a particular class of cells, an organ, or a system or group thereof implies that a higher proportion of the therapeutic, diagnostic and/or prophylactic are delivered to the destination (e.g., tissue) of interest relative to other destinations. In some aspects, specific delivery may result in a greater than 2 fold, 5 fold, 10 fold, 15 fold, or 20 fold increase in the amount of therapeutic and/or prophylactic per 1 g of tissue of the targeted destination (e.g., tissue of interest, such as a liver) as compared to another destination (e.g., the spleen). In some aspects, the tissue of interest is selected from the group consisting of a liver, kidney, a lung, a spleen, a femur, an ocular tissue (e.g., via intraocular, subretinal, or intravitreal injection), vascular endothelium in vessels (e.g., intra-coronary or intra-femoral) or kidney, and tumor tissue (e.g., via intratumoral injection).

As another example of targeted or specific delivery, a sa-mRNA of the present disclosure may encode a protein-binding partner (e.g., an antibody or functional fragment thereof, a scaffold protein, or a peptide) or a receptor on a cell surface. A sa-mRNA may additionally or instead be used to direct the synthesis and extracellular localization of lipids, carbohydrates, or other biological moieties. Alternatively, other biologically active agents (e.g., lipids or ligands) of a delivery system may be selected based on their affinity for particular receptors (e.g., low density lipoprotein receptors) such that a delivery system may more readily interact with a target cell population including the receptors. For example, ligands may include, but are not limited to, members of a specific binding pair, antibodies, monoclonal antibodies, Fv fragments, single chain Fv (scFv) fragments, Fab' fragments, $F(ab')_2$ fragments, single domain antibodies, camelized antibodies and fragments thereof, humanized antibodies and fragments thereof, and multivalent versions thereof; multivalent binding reagents including mono- or bi-specific antibodies such as disulfide stabilized Fv fragments, scFv tandems, diabodies, tribodies, or tetrabodies; and aptamers, receptors, and fusion proteins.

In some aspects, a ligand may be a surface-bound antibody, which can permit tuning of cell targeting specificity. This is especially useful since highly specific antibodies can be raised against an epitope of interest for the desired targeting site. In one aspect, multiple antibodies are expressed on the surface of a cell, and each antibody can have a different specificity for a desired target. Such approaches can increase the avidity and specificity of targeting interactions.

In certain aspects, compositions in accordance with the present disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.05 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.05 mg/kg to about 5 mg/kg, from about 0.1 mg/kg to about 5 mg/kg, from about 1 mg/kg to about 5 mg/kg, from about 2 mg/kg to about 5 mg/kg, from about 0.0001 mg/kg to about 2.5 mg/kg, from about 0.001 mg/kg to about 2.5 mg/kg, from about 0.005 mg/kg to about 2.5 mg/kg, from about 0.01 mg/kg to about 2.5 mg/kg, from about 0.05 mg/kg to about 2.5 mg/kg, from about 0.1 mg/kg to about 2.5 mg/kg, from about 1 mg/kg to about 2.5 mg/kg, from about 2 mg/kg to about 2.5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, from about 0.05 mg/kg to about 1 mg/kg, from about 0.1 mg/kg to about 1 mg/kg, from about 0.0001 mg/kg to about 0.25 mg/kg, from about 0.001 mg/kg to about 0.25 mg/kg, from about 0.005 mg/kg to about 0.25 mg/kg, from about 0.01 mg/kg to about 0.25 mg/kg, from about 0.05 mg/kg to about 0.25 mg/kg, or from about 0.1 mg/kg to about 0.25 mg/kg of a therapeutic, diagnostic and/or prophylactic (e.g., a self-amplifying mRNA) in a given dose, where a dose of 1 mg/kg (mpk) provides 1 mg of a biologically active agent per 1 kg of subject body weight. In some aspects, a dose of about 0.001 mg/kg to about 10 mg/kg of a biologically active agent (e.g., self-amplifying mRNA) may be administered. In other aspects, a dose of about 0.005 mg/kg to about 2.5 mg/kg of a biologically active agent may be administered. In certain aspects, a dose of about 0.1 mg/kg to about 1 mg/kg may be administered. In other aspects, a dose of about 0.05 mg/kg to about 0.25 mg/kg may be administered. A dose may be administered one or more times per day, in the same or a different amount, to obtain a desired level of sa-mRNA expression and/or biologically active agent, or imaging effect.

The desired dosage may be delivered, for example, three times a day, two times a day, once a day, every other day, every third day, every week, every two weeks, every three weeks, or every four weeks. In certain aspects, the desired dosage may be delivered using multiple administrations (e.g., two, three, four, five, six, seven, eight, nine, ten, eleven, twelve, thirteen, fourteen, or more administrations). In some aspects, a single dose may be administered, for example, prior to or after a surgical procedure or in the instance of an acute disease, disorder, or condition.

Pharmaceutical compositions including one or more biologically active agents may be used in combination with one or more other biologically active or imaging agents. By "in combination with," it is not intended to imply that the agents must be administered at the same time and/or formulated for delivery together, although these methods of delivery are within the scope of the present disclosure. For example, one or more pharmaceutical compositions including one or more different biologically active agents may be administered in combination. Compositions can be administered concurrently with, prior to, or subsequent to, one or more other desired therapeutics or medical procedures. In general, each agent will be administered at a dose and/or on a time schedule determined for that agent. In some aspects, the present disclosure encompasses the delivery of compositions, or imaging, therapeutic, diagnostic, or prophylactic compositions thereof in combination with agents that improve their bioavailability, reduce and/or modify their metabolism, inhibit their excretion, and/or modify their distribution within the body.

It will further be appreciated that biologically active or imaging active agents utilized in combination may be administered together in a single composition or administered separately in different compositions. In general, it is expected that agents utilized in combination will be utilized at levels that do not exceed the levels at which they are utilized individually. In some aspects, the levels utilized in combination may be lower than those utilized individually.

The particular combination of therapies to employ in a combination regimen will take into account compatibility of the desired therapeutic, diagnostic and/or prophylactic procedure and the desired biological effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects, such as infusion related reactions).

This disclosure includes the following non-limiting items:

1. A method of increasing the copy number of a nucleic acid comprising:
    a) contacting cells with a nucleic acid encoding two expression units, the nucleic acid comprising:
        i) an origin of replication sequence (Ori);
        ii) a first expression unit encoding a first nucleotide sequence that is operably linked to a first promoter; and
        iii) a second expression unit encoding a second nucleotide sequence that is operably linked to a second promoter, wherein the first expression unit encodes a selectable marker and the second expression unit encodes a self-amplifying mRNA (sa-mRNA);
    b) selecting cells that express the selectable marker;
    c) subculturing the selected cells to obtain a population of cells that express the selectable marker; and
    d) propagating the population of cells to increase the copy number of the nucleic acid.
2. The method item 1, wherein the nucleic acid is a recombinant DNA molecule.
3. The method of item 2, wherein the recombinant DNA molecule is a plasmid.
4. The method of item 1, wherein the nucleic acid is a closed circular molecule or a linear molecule.
5. The method of any one of items 1-4, wherein the nucleic acid is suitable for in vitro transcription of RNA after linearization using the nucleic acid as a template.
6. The method of any one of items 1-5, wherein the cell is a bacterium.
7. The method of item 6, wherein the bacterium is *Escherichia coli.*
8. The method of any one of items 1-7, wherein the nucleic acid comprises SAM001 (SEQ ID NO: 35), SAM002 (SEQ ID NO: 36), SAM003 (SEQ ID NO: 37), SAM004 (SEQ ID NO: 38), SAM005 (SEQ ID NO: 39), SAM006 (SEQ ID NO: 40), MOD001 (SEQ ID NO: 41), or T7-VEE-GFP (SEQ ID NO: 42).
9. The method of any one of items 1-8, wherein the nucleic acid sequence has at least 90% sequence identity to SAM001 (SEQ ID NO: 35), SAM002 (SEQ ID NO: 36), SAM003 (SEQ ID NO: 37), SAM004 (SEQ ID NO: 38), SAM005 (SEQ ID NO: 39), SAM006 (SEQ ID NO: 40), MOD001 (SEQ ID NO: 41), or T7-VEE-GFP (SEQ ID NO: 42).
10. The method of any one of items 1-9, wherein the first expression unit comprises the following operably linked nucleic acid sequence in a 5' to 3' direction or in a 3' to 5' direction:

Pr1-SM wherein

Pr1 is the first promoter sequence, and

SM is the selectable marker.
11. The method of any one of items 1-10, wherein the first promoter is an ampicillin resistance (AmpR) promoter, a kanamycin resistance (KanR) promoter, a chloramphenicol resistance (CamR) promoter, an erythromycin resistance (ErmR) promoter, and a tetracycline resistance (TetR) promoter.
12. The method of any one of items 1-11, wherein the selectable marker is AmpR, KanR, CamR, ErmR, or TetR.
13. The method of any one of items 1-12, wherein the second expression unit comprises the following operably linked nucleic acid sequence from 5' to 3':

Pr2-5'UTR-nsP-SGP-GOI-3'UTR-PolyA wherein

Pr2 is the second promoter sequence for in vitro transcription,

5'UTR is a 5' untranslated region, nsP is a plurality of non-structural replicase domain sequences, SGP is a subgenomic promoter, GOI is one or more genes of interest, 3'UTR is a 3' untranslated region, and Poly-A is a 3' poly-adenylated tail (poly-A tail).
14. The method of item 13, wherein at least one gene of interest (GOI), encodes a therapeutic polypeptide, a prophylactic polypeptide, a diagnostic polypeptide, an antigen, or a non-coding gene that encodes regulatory structures.
15. The method of any one of items 13-14, wherein the regulatory structures are selected from a group comprising small interfering RNA (siRNA), micro-RNA (miRNA), guide RNA (gRNA), self-activating RNA (saRNA), transfer RNA (tRNA), or long intergenic non-coding (lincRNA).
16. The method of any one of items 13-14, wherein at least one GOI encodes an infectious disease antigen, an allergic antigen, or a tumor antigen.
17. The method of item 13, wherein at least one GOI encodes a reporter gene.
18. The method of item 17, wherein the reporter gene is green fluorescent protein (GFP).
19. The method of any one of items 13-18, wherein the plurality of non-structural replicase domain sequences are obtained from a Group IV positive single strand RNA virus selected from the group comprising Picornaviridae, Togaviridae, Coronaviridae, Hepeviridae, Caliciviridae, Flaviviridae, and Astroviridae.
20. The method of any one of items 13-19, wherein the plurality of non-structural replicase domain sequences are obtained from an alphavirus selected from the group comprising Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus.

21. The method of any one of items 13-20, wherein the plurality of non-structural replicase domain sequences are alphavirus nonstructural proteins 1-4 (nsP1-4).
22. The method of any one of items 13-21, wherein the plurality of non-structural replicase domain sequences are obtained from the TC-83 strain of Venezuelan Equine Encephalitis virus (VEE).
23. The method of any one of items 1-22, wherein the second promoter is selected from the group consisting of T7, T3, SV40, SP6, T5, β-lactamase promoter, *E. coli* galactose promoter, arabinose promoter, alkaline phosphatase promoter, tryptophan (trp) promoter, lactose operon (lac) promoter, lacUV5 promoter, trc promoter and tac promoter.
24. The method of any one of items 1-23, wherein the nucleic acid further comprises one or more linkers.
25. The method of item 24, wherein the nucleic acid sequence comprises from 5' to 3':
   a) Ori-SM-Pr1-L2-Pr2-5'UTR-nsP-L3-GOI-L4-3'UTR-PolyA;
   b) L1-Ori-SM-Pr1-Pr2-5'UTR-nsP-L3-GOI-L4-3'UTR-PolyA
   c) L1-Ori-SM-Pr1-L2-Pr2-5'UTR-nsP-GOI-L4-3'UTR-PolyA;
   d) L1-Ori-SM-Pr1-L2-Pr2-5'UTR-nsP-L3-GOI-3'UTR-PolyA; or
   e) L1-Ori-SM-Pr1-L2-Pr2-5'UTR-nsP-SGP-L3-GOI-L4-3'UTR-PolyA, wherein
   L1 is a first linker,
   Ori is an origin of replication sequence,
   SM is a selectable marker,
   Pr1 is a first promoter sequence,
   L2 is a second linker,
   Pr2 is a second promoter sequence,
   5'UTR is a 5' untranslated region,
   nsP is a plurality of non-structural replicase domain sequences,
   L3 is a third linker,
   SGP is a subgenomic promoter,
   GOI is one or more genes of interest,
   L4 is a fourth linker,
   3'UTR is a 3' untranslated region, and
   Poly-A is a 3' poly-adenylated tail (poly-A tail).
26. The method of item 25, wherein each of L1, L2, L3, and L4 is independently selected from a nucleic acid a sequence comprising

```
CGCGTGATAACGCAGGAAAGAACATGTGAGCAAAAGGCCAGCAAAAGGCC
AGGAACCGTAAAAAGGCCGCGTTGCTGGCGTT (SEQ ID NO: 43),

CACATTTCCCCGAAAAGTGCCACCTGAGCTC (SEQ ID NO: 44),

TTCGAAGGCGCGCCTCTAGAGCCACC (SEQ ID NO: 45),
or

CATCGATGATATCGCGGCCGCATACAGCAGC (SEQ ID NO: 46),
or

wherein L1 comprises SEQ ID NO: 43
(CGCGTGATAACGCAGGAAAGAACATGTGAGCAAAAGGCCAGCAAAAGGC
CAGGAACCGTAAAAAGGCCGCGTTGCTGGCGTT);

L2 comprises SEQ ID NO: 44
(CACATTTCCCCGAAAAGTGCCACCTGAGCTC);
```

-continued

```
L3 comprises SEQ ID NO: 45
(TTCGAAGGCGCGCCTCTAGAGCCACC);
and

L4 comprises SEQ ID NO: 46
(CATCGATGATATCGCGGCCGCATACAGCAGC).
```

27. A self-amplifying mRNA comprising a nucleic acid sequence from 5' to 3':
   a) 5'UTR-nsP-L-GOI-L-3'UTR-PolyA
   b) 5'UTR-nsP-GOI-L-3'UTR-PolyA;
   c) 5'UTR-nsP-L-GOI-3'UTR-PolyA; or wherein
   5'UTR is a 5' untranslated region,
   nsP is a plurality of non-structural replicase domain sequences,
   L is a linker,
   SGP is a subgenomic promoter,
   GOI is one or more genes of interest,
   3'UTR is a 3' untranslated region, and
   Poly-A is a 3' poly-adenylated tail (poly-A tail).
28. The self-amplifying mRNA of item 27, wherein the GOI is an antigen or antigen receptor.
29. The self-amplifying mRNA of any one of items 27-28, wherein the GOI is a viral antigen.
30. The self-amplifying mRNA of any one of items 27-29, wherein the GOI is a modified SARS-CoV-2 spike protein.
31. The self-amplifying mRNA of any one of items 27-30, wherein the immunomodulator is a cytokine, a chemokine, or other immune stimulator or inhibitor.
32. The self-amplifying mRNA of any one of items 27-31, comprising a polynucleotide sequence selected from:
   a) a polynucleotide encoding a modified SARS-CoV-2 spike protein comprising the nucleic sequence set forth in SEQ ID NO: 1 (BA.1-1273);
   b) a polynucleotide encoding a modified SARS-CoV-2 spike protein comprising the nucleic sequence set forth in SEQ ID NO: 2 (BA.1-1273-S2P);
   c) a polynucleotide encoding a modified SARS-CoV-2 spike protein comprising the nucleic sequence set forth in SEQ ID NO: 3 (BA.2-1273);
   d) a polynucleotide encoding a modified SARS-CoV-2 spike protein comprising the nucleic sequence set forth in SEQ ID NO: 4 (BA.2-1273-S2P);
   e) a polynucleotide encoding a modified SARS-CoV-2 spike protein comprising the nucleic sequence set forth in SEQ ID NO: 5 (BA.1-1208); or
   f) a polynucleotide encoding a modified SARS-CoV-2 spike protein comprising the nucleic sequence set forth in SEQ ID NO: 6 (BA.1-1208-S2P);
   g) a polynucleotide encoding a modified SARS-CoV-2 spike protein comprising the nucleic sequence set forth in SEQ ID NO: 7 (BA.2-1208); or
   h) a polynucleotide encoding a modified SARS-CoV-2 spike protein comprising the nucleic sequence set forth in SEQ ID NO: 8 (BA.2-1208-S2P).
33. A self-amplifying mRNA encoding two separated expression units, the nucleic acid comprising:
   i) a first expression unit comprising a polynucleotide encoding a modified antigen, wherein the polynucleotide encoding the modified antigen is truncated to not include nucleotides encoding a transmembrane domain and short cytosolic domain amino acids of the antigen, operably linked to a first subgenomic promoter; and ii) a second expression unit encoding immunomodulators (IM) that are operably linked to a second subgenomic promoter.

34. The self-amplifying mRNA of item 33, wherein the polynucleotide sequence encoding the modified antigen comprises replacement of a transmembrane domain of the antigen with a secretion antigen.

35. The self-amplifying mRNA of item 33 or item 34, wherein the antigen is a modified SARS-CoV-2 spike protein, wherein the polynucleotide has been truncated to not include nucleotides encoding a SARS-CoV-2 transmembrane domain and short cytosolic domain amino acids.

36. The self-amplifying mRNA of any one of items 33-35, wherein the polynucleotide sequence encoding a coronavirus spike protein truncated to not include nucleotides encoding a SARS-CoV-2 transmembrane domain and short cytosolic domain amino acids corresponding to amino acids 1209-1273 of a nucleotide sequence is SEQ ID NOs: 1 (BA.1-1273) or 3 (BA.2-1273).

37. The self-amplifying mRNA of any one of items 33-36, wherein the sa-mRNA comprises the following operably linked nucleic acid sequence from 5' to 3':

nsP-SGP1-Ag-SGP2-IM wherein nsP is a plurality of non-structural replicase domain sequences, SGP1 is the first subgenomic promoter, Ag is a nucleotide sequence selected from SEQ ID NO: 1 (BA.1-1273), 2 (BA.1-1273-S2P), 3 (BA.2-1273), and SEQ ID NO: 4 (BA.2-1273-S2P), SEQ ID NO: 5 (BA.1-1208), or SEQ ID NO: 6 (BA.1-1208-S2P), SEQ ID NO: 7 (BA.2-1208), or SEQ ID NO: 8 (BA.2-1208-S2P), SGP2 is the second subgenomic promoter, and IM is the immunomodulator.

38. The self-amplifying mRNA of any one of items 33-36, wherein the sa-mRNA comprises the following operably linked nucleic acid sequence from 5' to 3':

nsP-SGP1-IM-SGP2-AG wherein nsP is a plurality of non-structural replicase domain sequences, SGP1 is the first subgenomic promoter, IM is the immunomodulator, SGP2 is the second subgenomic promoter, and Ag is a nucleotide sequence selected from SEQ ID NO: 1 (BA.1-1273), 2 (BA.1-1273-S2P), 3 (BA.2-1273), and SEQ ID NO: 4 (BA.2-1273-S2P), SEQ ID NO: 5 (BA.1-1208), or SEQ ID NO: 6 (BA.1-1208-S2P), SEQ ID NO: 7 (BA.2-1208), or SEQ ID NO: 8 (BA.2-1208-S2P).

39. The self-amplifying mRNA of any one of items 33-38, wherein the IM encodes one or more cytokines, chemokines, immune stimulators or inhibitors.

40. The self-amplifying mRNA of any one of items 33-39, wherein the IM is IL12 or IL21.

41. The self-amplifying mRNA of any one of items 33-40, wherein the IM encodes one or more cytokines selected from SEQ ID NOs: 22 (hIL12-P40), 24 (hIL12-P35), 26 (hL21), 15 (mIL12 P40), 17 (mIL12-P35), and 19 (mL21).

42. The self-amplifying mRNA of any one of items 33-41, wherein SGP1 is SEQ ID NO: 9

(SGP1) (TAACCTGAATGGACTACGACATAGTCTAGTCCGCCAAG).

43. The self-amplifying mRNA of any one of items 33-42, wherein SGP2 is SEQ ID NO: 11

(SGP2)
(GAACTTCCATCATAGTTATGGCCATGACTACTCTAGCTAGCAGTGTTAA
ATCATTCAGCTACCTGAGAGGGGCCCCTATAACTCTCTACGGC).

44. The self-amplifying mRNA of any one of items 33-43, wherein IM is selected from SEQ ID NO: 13 (IM1), and SEQ ID NO: 20 (IM2).

45. The self-amplifying mRNA of any one of items 33-44, comprising the following operably linked nucleic acid sequence from 5' to 3':

SP-IL12 P40-L1-IL12 P35-L2-IL21

Wherein

SP is a signal peptide,

IL12-P40 is interleukin-12 comprising heavy chain p40,

L1 is linker 1,

IL12 P35 is interleukin-12 comprising light chain p35,

L2 is linker 2, and

IL21 is interleukin-21.

46. The self-amplifying mRNA of any one of 33-45, wherein SP is selected from SEQ ID NO: 14 (MSP) (ATGACCTCCCGGCTTGT-GAGGGTACTGGCTGCTGC-TATGCTGGTGGCTGCTG CTGTGAGTGTGGC) and SEQ ID NO: 21 (HSP) (ATGGACTGGACCTGGCGAATACTGTTCTTGGT TGCCGCCGCTACAGGGACTC ACGCA).

47. The self-amplifying mRNA of any one of items 33-46, wherein IL12-P40 is selected from SEQ ID NO: 15 (mIL12-P40) and SEQ ID NO: 22 (hIL12-P40).

48. The self-amplifying mRNA of any one of items 33-47, wherein L1 is selected from SEQ ID NO: 16 (L(a)) and SEQ ID NO: 23 (L(c)).

49. The self-amplifying mRNA of any one of items 33-48, wherein IL12-P35 is selected from SEQ ID NO: 17 (mIL12-P35) and SEQ ID NO: 24 (hIL12-P35).

50. The self-amplifying mRNA of any one of items 33-49, wherein L2 is selected from SEQ ID NO: 18 (L(b)) and SEQ ID NO: 25 (L(d)).

51. The self-amplifying mRNA of any one of items 33-50, wherein IL12-P40 is selected from SEQ ID NO: 19 (mIL21) and SEQ ID NO: 26 (hIL21).

52. The self-amplifying mRNA of any one of items 33-51, wherein the plurality of non-structural replicase domain sequences is obtained from a Group IV RNA virus selected from Picornaviridae, Togaviridae, Coronaviridae, Hepeviridae, Caliciviridae, Flaviviridae, or Astroviridae.

53. The self-amplifying mRNA of any one of items 33-52, wherein the plurality of non-structural replicase domain sequences are obtained from an alphavirus selected from Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, or Buggy Creek virus.

54. The self-amplifying mRNA of any one of items 33-53, wherein the plurality of non-structural replicase domain sequences are alphavirus nonstructural proteins 1-4 (nsP1-4).

55. The self-amplifying mRNA of any one of items 33-54, wherein the plurality of non-structural replicase domain sequences are obtained from the TC-83 strain of Venezuelan Equine Encephalitis virus (VEE).

56. The self-amplifying mRNA of any one of items 33-55, wherein SGP1 is a viral promoter that is recognized by viral RNA dependent RNA polymerase.

57. The self-amplifying mRNA of any one of items 33-56, wherein SGP2 is a viral promoter that is recognized by viral RNA dependent RNA polymerase.

58. The self-amplifying mRNA of any one of items 33-57, wherein SGP1 and SGP2 are different subgenomic promoters.

59. The self-amplifying mRNA of any one of items 33-58, wherein the sa-mRNA further comprises one or more linkers.

60. The self-amplifying mRNA of any one of items 33-59, wherein the linkers are selected from the group SEQ ID NOs: 16 (L(a)), 18 (L(b)), 23 (L(c)), and 25 (L(d)).

61. A composition comprising the self-amplifying mRNA of any one of items 33-60 and a pharmaceutically acceptable carrier.

62. The composition of item 61, further comprising a self-amplifying mRNA delivery system.

63. The composition of item 62, wherein the self-amplifying mRNA delivery system is a lipid nanoparticle.

64. A method of expressing a gene in a cell, comprising delivering the self-amplifying mRNA of any one of items 33-60 to the cell, and maintaining the cell under conditions suitable for expression of the gene encoded by the GOI.

65. The method of item 64, wherein the cell is in an animal cell.

66. A method for producing a self-amplifying mRNA, the method comprising:
  a) performing an in vitro transcription reaction using an initial amount of the nucleic acid produced by the method of any one of items 1-27; and
  b) producing a self-amplifying mRNA by in vitro transcription, using the nucleic acid as a template.

67. A method of inducing an immune response in an individual, comprising administering to the individual a sa-mRNA produced from the method of item 66.

68. A nucleic acid encoding a self-amplifying mRNA comprising a mutant T7 promoter comprising the nucleotide sequence of SEQ ID NO: 47 (TAATACGACTCACTATAGG) operably linked to a 5' UTR, a plurality of non-structural replicase domain sequences, one or more gene or genes of interest (GOI), a 3' UTR, and a poly-A tail.

69. The nucleic acid of item 68, wherein the 5'UTR comprises the nucleotide sequence ATAGG.

70. The nucleic acid of any one of items 68-69, comprising SAM002 (SEQ ID NO: 36).

71. The nucleic acid of any one of items 68-70, wherein the nucleic acid further comprises one or more linkers.

72. The nucleic acid of any one of items 68-71 comprising the following nucleic acid sequence from 5' to 3':
  a) Ori-SM-Pr1-L2-Pr2-5'UTR-nsP-L3-GOI-L4-3'UTR-PolyA;
  b) L1-Ori-SM-Pr1-Pr2-5'UTR-nsP-L3-GOI-L4-3'UTR-PolyA
  c) L1-Ori-SM-Pr1-L2-Pr2-5'UTR-nsP-GOI-L4-3'UTR-PolyA;
  d) L1-Ori-SM-Pr1-L2-Pr2-5'UTR-nsP-L3-GOI-3'UTR-PolyA; or
  e) L1-Ori-SM-Pr1-L2-Pr2-5'UTR-nsP-SGP-L3-GOI-L4-3'UTR-PolyA, wherein
  L1 is a first linker,
  Ori is an origin of replication sequence,
  SM is a selectable marker,
  Pr1 is a first promoter sequence,
  L2 is a second linker,
  T7' is a mutant T7 promoter of SEQ ID NO: 47 (TAATACGACTCACTATAGG),
  5'UTR' is a mutant 5' untranslated region of ATAGG,
  nsP is a plurality of non-structural replicase domain sequences,
  L3 is a first linker,
  SGP is a subgenomic promoter,
  GOI is one or more gene or genes of interest,
  L4 is a second linker,
  3'UTR is a 3' untranslated region, and
  Poly-A is a 3' poly-adenylated tail (poly-A tail).

73. The nucleic acid of any one of items 68-72, wherein each of L1, L2, L3, and L4 is independently selected from a nucleic acid a sequence comprising

```
CGCGTGATAACGCAGGAAAGAACATGTGAGCAAAAGGCCAGCAAAAGGCC
AGGAACCGTAAAAAGGCCGCGTTGCTGGCGTT (SEQ ID NO: 43),

CACATTTCCCCGAAAAGTGCCACCTGAGCTC (SEQ ID NO: 44),

TTCGAAGGCGCGCCTCTAGAGCCACC (SEQ ID NO: 45),
or

CATCGATGATATCGCGGCCGCATACAGCAGC (SEQ ID NO: 46),
or

wherein L1 comprises SEQ ID NO: 43
(CGCGTGATAACGCAGGAAAGAACATGTGAGCAAAAGGCCAGCAAAAGGC
CAGGAACCGTAAAAAGGCCGCGTTGCTGGCGTT);

L2 comprises SEQ ID NO: 44
(CACATTTCCCCGAAAAGTGCCACCTGAGCTC);

L3 comprises SEQ ID NO: 45
(TTCGAAGGCGCGCCTCTAGAGCCACC);
and

L4 comprises SEQ ID NO: 46
(CATCGATGATATCGCGGCCGCATACAGCAGC).
```

74. The nucleic acid of any one of items 68-73, wherein the first promoter is an ampicillin resistance (AmpR) promoter, a kanamycin resistance (KanR) promoter, a chloramphenicol resistance (CamR) promoter, an erythromycin resistance (ErmR) promoter, or a tetracycline resistance (TetR) promoter.

75. The nucleic acid of any one of items 68-74, wherein the selectable marker is AmpR, KanR, CamR, ErmR, or TetR.

76. The nucleic acid of any one of items 68-75, wherein at least one gene of interest (GOI) encodes a therapeutic polypeptide, a prophylactic polypeptide, a diagnostic polypeptide, an antigen, an antigen receptor, or a non-coding gene that encodes regulatory structures.

77. The nucleic acid of item 76, wherein the regulatory structures are selected from a group comprising small interfering RNA (siRNA), micro-RNA (miRNA), self-activating RNA (saRNA), transfer RNA (tRNA), long intergenic non-coding (lincRNA).

78. The nucleic acid of any one of items 68-77, wherein at least one GOI encodes an infectious disease antigen, an allergic antigen, or a tumor antigen.

79. The nucleic acid of any one of items 68-78, wherein at least one GOI encodes a reporter gene.

80. The nucleic acid of item 79, wherein the reporter gene is green fluorescent protein (GFP).

81. The nucleic acid of any one of items 68-80, wherein the plurality of non-structural replicase domain sequences are obtained from a Group IV RNA virus selected from the group comprising Picornaviridae, Togaviridae, Coronaviridae, Hepeviridae, Caliciviridae, Flaviviridae, and Astroviridae.

82. The nucleic acid of any one of items 68-81, wherein the plurality of non-structural replicase domain sequences are obtained from an alphavirus selected from the group comprising Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus.

83. The nucleic acid of any one of items 68-82, wherein the plurality of non-structural replicase domain sequences are alphavirus nonstructural proteins 1-4 (nsP1-4).

84. The nucleic acid of any one of items 68-83, wherein the plurality of non-structural replicase domain sequences are obtained from the TC-83 strain of Venezuelan Equine Encephalitis virus (VEE).

85. A method for producing a self-amplifying mRNA, the method comprising:
  a) performing an in vitro transcription reaction using an initial amount of the nucleic acid of any one of items 68-84; and
  b) producing a self-amplifying mRNA by in vitro transcription, using the nucleic acid as a template.

86. The method of item 85, wherein the amount of self-amplifying mRNAs containing a mutant T7 promoter of SEQ ID NO: 47 (TAATACGACTCACTATAGG) and a mutant 5' untranslated region of ATAGG produced is at least 40% greater compared to the amount of the self-amplifying mRNAs produced from a nucleic acid template with wildtype T7 promoter and 5' UTR.

87. A composition comprising the self-amplifying mRNA produced from the method of item 85 and a pharmaceutically acceptable carrier.

88. The composition of item 87, further comprising a self-amplifying mRNA delivery system.

89. The composition of item 88, wherein the self-amplifying mRNA delivery system is a nanoparticle composition.

90. A method of expressing a gene encoded by a GOI in a cell, comprising delivering the self-amplifying mRNA produced from the method of item 85 or item 86 to a cell, and causing the cell to express the gene encoded by the GOI.

91. The method of item 90, wherein the cell is in an animal cell.

92. A method of inducing an immune response in an individual, comprising administering to the individual a self-amplifying mRNA produced from the method of item 85 or item 86.

93. A nucleic acid encoding a self-amplifying mRNA comprising:
  a) a mutant 3'UTR of an alphavirus comprising point mutations at position 6 relative to a conserved 19 nucleotide sequence GGATTTTGTTTTTAATATTTC (SEQ ID NO: 49) of the wild-type 3'UTR of an alphavirus;
  b) a mutant 3'UTR of an alphavirus comprising point mutations at positions −1, and −2 relative to a conserved 19 nucleotide sequence GGATTTTGTTTTTAATATTTC (SEQ ID NO: 49) of the wild-type 3'UTR of an alphavirus;
  c) a mutant 3'UTR of an alphavirus comprising point mutations at positions −1, −2 and 6 relative to a conserved 19 nucleotide sequence GGATTTTGTTTTTAATATTTC (SEQ ID NO: 49) of the wild-type 3'UTR of an alphavirus;
  d) a mutant 3'UTR of an alphavirus comprising a sequence selected from a group comprising GGATTTTATTTTTAATATTTC (SEQ ID NO: 50), AAATTTTGTTTTTAATATTTC (SEQ ID NO: 51), or AAATTTTATTTTTAATATTTC (SEQ ID NO: 52); or
  e) a promoter operably linked to a 5' UTR, a plurality of non-structural replicase domain sequences, one or more gene or genes of interest (GOI), the mutant 3'UTR of any one of SEQ ID NOs: 49-52, and a poly-A tail.

94. The nucleic acid of item 93 comprising a sequence selected from a group comprising SAM004 (SEQ ID NO: 38), SAM005 (SEQ ID NO: 39), SAM006 (SEQ ID NO: 40).

95. The nucleic acid of item 94, wherein the nucleic acid further comprises one or more linkers.

96. The nucleic acid of any one of items 93-95, wherein the nucleic acid sequence comprises from 5' to 3':
  a) Ori-SM-Pr1-L2-Pr2-5'UTR-nsP-L3-GOI-L4-3'UTR-PolyA;
  b) L1-Ori-SM-Pr1-Pr2-5'UTR-nsP-L3-GOI-L4-3'UTR-PolyA
  c) L1-Ori-SM-Pr1-L2-Pr2-5'UTR-nsP-GOI-L4-3'UTR-PolyA;
  d) L1-Ori-SM-Pr1-L2-Pr2-5'UTR-nsP-L3-GOI-3'UTR-PolyA; or
  e) L1-Ori-SM-Pr1-L2-Pr2-5'UTR-nsP-SGP-L3-GOI-L4-3'UTR-PolyA, wherein,
L1 is a first linker,
Ori is an origin of replication sequence,
SM is a selectable marker,
Pr1 is a first promoter sequence,
L2 is a second linker,
Pr2 is a second promoter sequence,
5'UTR is a 5' untranslated region,
nsP is a plurality of non-structural replicase domain sequences,
SGP is a subgenomic promoter,
L3 is a first linker, GOI is one or more gene or genes of interest,
L4 is a second linker,
3'UTR' is a mutant 3' untranslated region, and
Poly-A is a 3' poly-adenylated tail (poly-A tail),
wherein the 3'UTR' is:
a) a mutant 3'UTR of an alphavirus comprising GGATTTTATTTTTAATATTTC (SEQ ID NO: 50);
b) a mutant 3'UTR of an alphavirus comprising AAATTTTGTTTTTAATATTTC (SEQ ID NO: 51); or
c) a mutant 3'UTR of an alphavirus comprising AAATTTTATTTTTAATATTTC (SEQ ID NO: 52).

97. The nucleic acid of item 96, wherein each of L1, L2, L3, and L4 is independently selected from a nucleic acid a sequence comprising

```
CGCGTGATAACGCAGGAAAGAACATGTGAGCAAAAGGCCAGCAAAAGGCC
AGGAACCGTAAAAAGGCCGCGTTGCTGGCGTT (SEQ ID NO: 43),

CACATTTCCCCGAAAAGTGCCACCTGAGCTC (SEQ ID NO: 44),

TTCGAAGGCGCGCCTCTAGAGCCACC (SEQ ID NO: 45),
or

CATCGATGATATCGCGGCCGCATACAGCAGC (SEQ ID NO: 46),
or

wherein L1 comprises SEQ ID NO: 43
(CGCGTGATAACGCAGGAAAGAACATGTGAGCAAAAGGCCAGCAAAAGGC
CAGGAACCGTAAAAAGGCCGCGTTGCTGGCGTT);

L2 comprises SEQ ID NO: 44
(CACATTTCCCCGAAAAGTGCCACCTGAGCTC);

L3 comprises SEQ ID NO: 45
(TTCGAAGGCGCGCCTCTAGAGCCACC);
and

L4 comprises SEQ ID NO: 46
(CATCGATGATATCGCGGCCGCATACAGCAGC).
```

98. The nucleic acid of any one of items 96-97, wherein the first promoter is an ampicillin resistance (AmpR) promoter, a kanamycin resistance (KanR) promoter, a chloramphenicol resistance (CamR) promoter, an erythromycin resistance (ErmR) promoter, and a tetracycline resistance (TetR) promoter.

99. The nucleic acid of any one of items 96-98, wherein the selectable marker is AmpR, KanR, CamR, ErmR, or TetR.

100. The nucleic acid of any one of items 96-99, wherein at least one gene of interest (GOI), encodes a therapeutic polypeptide, a prophylactic polypeptide, a diagnostic polypeptide, an antigen, or a non-coding gene that encodes regulatory structures.

101. The nucleic acid of item 100, wherein the regulatory structures are selected from a group comprising small interfering RNA (siRNA), micro-RNA (miRNA), self-activating RNA (saRNA), transfer RNA (tRNA), long intergenic non-coding (lincRNA).

102. The nucleic acid of item 101, wherein at least one GOI encodes an infectious disease antigen, an allergic antigen, or a tumor antigen.

103. The nucleic acid of any one of items 96-102, wherein at least one GOI encodes a reporter gene.

104. The nucleic acid of item 103, wherein the reporter gene is green fluorescent protein (GFP).

105. The nucleic acid of any one of items 96-104, wherein the plurality of non-structural replicase domain sequences are obtained from a Group IV RNA virus selected from the group comprising Picornaviridae, Togaviridae, Coronaviridae, Hepeviridae, Caliciviridae, Flaviviridae, and Astroviridae.

106. The nucleic acid of any one of items 96-105, wherein the plurality of non-structural replicase domain sequences are obtained from an alphavirus selected from the group comprising Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus.

107. The nucleic acid of any one of items 96-106, wherein the plurality of non-structural replicase domain sequences are alphavirus nonstructural proteins 1-4 (nsP1-4).

108. The nucleic acid of any one of items 96-107, wherein the plurality of non-structural replicase domain sequences are obtained from the TC-83 strain of Venezuelan Equine Encephalitis virus (VEE).

109. A method for producing a self-amplifying mRNA, the method comprising:
a) performing an in vitro transcription reaction using an initial amount of the nucleic acid of any one of items 96-108; and
b) producing a self-amplifying mRNA by in vitro transcription, using the nucleic acid as a template.

110. A composition comprising the self-amplifying mRNA produced from the method of item 109 and a pharmaceutically acceptable carrier.

111. The composition of item 110, further comprising a self-amplifying mRNA delivery system.

112. The composition of item 111, wherein the self-amplifying mRNA delivery system is a lipid nanoparticle.

113. A method of expressing a gene encoded by a GOI in a cell, comprising delivering the self-amplifying mRNA produced from the method of item 109, and maintaining the cell under conditions suitable for expression of the gene encoded by the GOI.

114. The method of item 113, wherein the cell is in an animal cell.

115. A method of inducing an immune response in an individual, comprising administering to the individual a self-amplifying mRNA produced from the method of item 109.

116. A method for decreasing the interferon response of a host cell compared to the interferon response of the host cell where a self-amplifying mRNA containing a wild-type 3'UTR of an alphavirus is introduced, comprising introducing the self-amplifying mRNA produced from the method of item 109 into the host cell.

117. The method according to item 116, wherein the interferon response of a host cell is 2, 3, 4, 5 or 6 times lower than the amount of interferon response of the host cell to the introduction of a self-amplifying mRNA containing a wild-type 3'UTR of an alphavirus.

118. A method of de novo synthesizing a construct for making a self-amplifying nucleic acid comprising:
  a) contacting *Escherichia coli* cells with a nucleic acid encoding two expression units, the nucleic acid comprising:
    i) an origin of replication sequence (Ori);
    ii) a first expression unit encoding a first nucleotide sequence that is operably linked to a first promoter that for expressing selectable marker; and
    iii) a second expression unit encoding a second nucleotide sequence that is operably linked to a second promoter for in vitro transcriptions of self-amplifying nucleic acids,
    wherein the first expression unit encodes a selectable marker and the second expression unit encodes a self-amplifying nucleic acid;
  b) selecting *Escherichia coli* cells that express the selectable marker; and
  c) subculturing the selected *Escherichia coli* cells to obtain a population of *Escherichia coli* cells that express the selectable marker;
  d) propagating the population of cells; and
  e) performing in vitro transcription of the second expression unit to produce the self-amplifying nucleic acid.

119. A polynucleotide encoding:
  a) a modified SARS-CoV-2 spike protein comprising the nucleic sequence set forth in SEQ ID NO: 1 (BA.1-1273);
  b) a modified SARS-CoV-2 spike protein comprising the nucleic sequence set forth in SEQ ID NO: 2 (BA.1-1273-S2P);
  c) a modified SARS-CoV-2 spike protein comprising the nucleic sequence set forth in SEQ ID NO: 3 (BA.2-1273);
  d) a modified SARS-CoV-2 spike protein comprising the nucleic sequence set forth in SEQ ID NO: 4 (BA.2-1273-S2P);
  e) a modified SARS-CoV-2 spike protein comprising the nucleic sequence set forth in SEQ ID NO: 5 (BA.1-1208);
  f) a modified SARS-CoV-2 spike protein comprising the nucleic sequence set forth in SEQ ID NO: 6 (BA.1-1208-S2P);
  g) a modified SARS-CoV-2 spike protein comprising the nucleic sequence set forth in SEQ ID NO: 7 (BA.2-1208); or
  h) a modified SARS-CoV-2 spike protein comprising the nucleic sequence set forth in SEQ ID NO: 8 (BA.2-1208-S2P).

120. A method for preparing a library of self-amplifying mRNA derived from a reference self-amplifying mRNA comprising:
  (i) performing directed evolution of a reference self-amplifying mRNA sample comprising the steps of:
    (a) delivering a reference self-amplifying mRNA sample encoding a selection marker into host cell(s),
    (b) culturing said host cell(s) over a period of time under conditions that require replication of the reference self-amplifying mRNA sample and permit expression of the selection marker, wherein mutations occur in the replicated self-amplifying mRNA compared to the reference self-amplifying mRNA,
    (c) selecting cells that express the selectable marker; and
  (ii) extracting the replicated self-amplifying mRNA from the host cell(s) and sequencing the replicated self-amplifying mRNA;
  thereby producing a library of self-amplifying mRNA sequences.

121. The method of item 120, wherein the selection marker is an antibiotic resistance gene.

122. The method of any one of items 120-121, wherein the selection marker is a puromycin resistance gene.

123. The method of any one of items 120-122, wherein the reference self-amplifying mRNA is delivered into a host cell using a delivery mechanism.

124. The method of item 123, wherein the delivery system is a lipid nanoparticle.

125. The method of any one of items 120-124, wherein the reference self-amplifying mRNA is selected from a group comprising SEQ ID Nos. 1-8 and SEQ ID NOs 35-42.

126. The method of any one of items 120-125, wherein the conditions that require replication of the reference self-amplifying mRNA sample and permit expression of the selection marker is a culture environment containing an antibiotic.

127. The method of any one of items 120-126, wherein the concentration of the antibiotic affects the rate of mutation of the reference self-amplifying mRNA.

128. A method of evaluating mutations of the replicated self-amplifying mRNA produced from the method of any one of items 120-127, the method comprising:
  (i) obtaining a group of contig sequences comprising mutation(s) compared to a reference self-amplifying mRNA sample;
  (ii) sequencing the contig sequences; and
  (iii) determining the number of mutations in the contig sequences compared to the reference self-amplifying mRNA.

129. The method of item 128, wherein the contig sequences are fragments of the replicated self-amplifying mRNA.

130. The method of item 128, wherein the contig sequence is SEQ ID NO: 27.

131. The method of item 128, wherein the contig sequence is SEQ ID NO: 28.

132. The method of item 128, wherein the contig sequence is SEQ ID NO: 29.

133. The method of item 128, wherein the contig sequence is SEQ ID NO: 30.

134. The method of item 128, wherein the contig sequence is SEQ ID NO: 31.

135. The method of item 128, wherein the contig sequence is SEQ ID NO: 32.

136. The method of item 128, wherein the contig sequence is SEQ ID NO: 33.
137. The method of item 128, wherein the contig sequence is SEQ ID NO: 34.
138. A method of identifying self-amplifying mRNA with reduced cytotoxic effects as part of a therapeutic product comprising:
   (i) obtaining a group comprising a plurality of self-amplifying mRNA;
   (ii) quantifying the relative gene product expression of each self-amplifying mRNA over a period of time; and
   (iii) identifying self-amplifying mRNA(s) showing stable gene product expression over the period of time compared to other self-amplifying mRNA of the group;

wherein the self-amplifying mRNA(s) that show sustained gene product expression over the period of time show reduced cytotoxic effects as part of a therapeutic product compared to the other self-amplifying mRNA of the group.
139. The method of item 138, wherein the period of time is between 12 hours to 10 days.
140. The method of any one of items 138-139, wherein the period of time is 1 day.
141. The method of any one of items 138-140, wherein the self-amplifying mRNA(s) that show sustained gene product expression over the period of time show a change in expression of less than 20 fold.
142. A therapeutic product comprising SAM002 (SEQ ID NO: 36), wherein the therapeutic product shows reduced cytotoxic effects as part of a therapeutic product compared to a therapeutic product comprising SAM001 (SEQ ID NO: 35).

EXAMPLES

The biologically active agent of the disclosure may be delivered using a nanoparticle composition comprising a ionizable lipid; one or more PEG lipids; one or more structural lipids (e.g. cholesterol, fecosterol, sitosterol, ergosterol, campesterol, stigmasterol, brassicasterol, tomatidine, tomatine, ursolic acid, alpha-tocopherol, and mixtures thereof); and one or more phospholipids.

Example 1: LNP Delivery System

One suitable system for delivering the sa-mRNA of the disclosure is using a lipid nanoparticle (LNP) delivery system. A method of increasing transfection efficiency and decreasing cytotoxicity of a LNP formulation is by using a novel ionizable lipid described in PCT Patent Application No. PCT/US2023/017777, which is fully incorporated herein. The ionizable lipid in an LNP formulation play a key role in the uptake of LNP by cells and the release of LNP from the endosome. Formula E6 (1,1',1"-(1,3,5-triazinane-1,3,5-triyl)tris(3-(ditridecylamino)propan-1-one)) is a novel ionizable lipid described in PCT Patent Application No. PCT/US2023/017777 and shown below:

E6

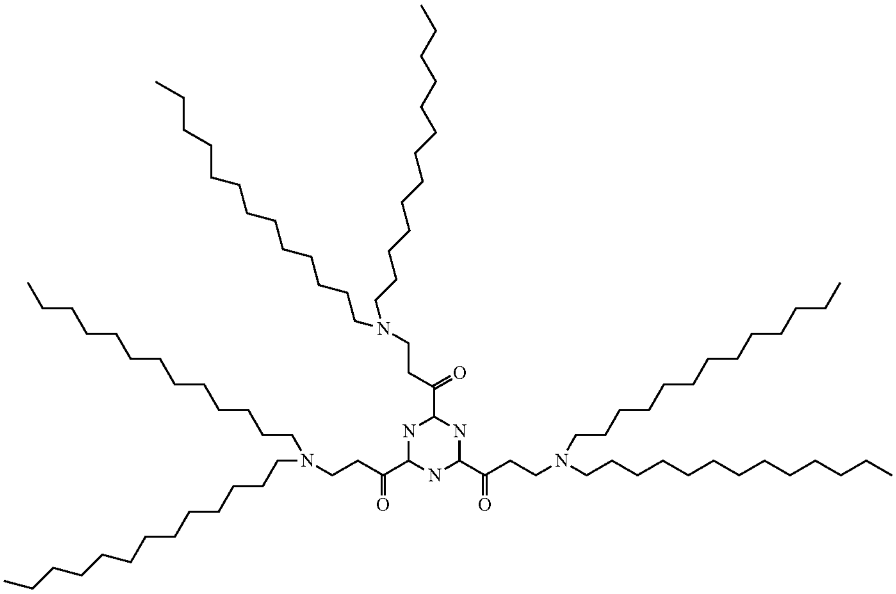

The structure of E6 was confirmed by 1H NMR spectroscopy and mass spectrometry. $^{1}$H_NMR (400 MHz, CDCl3, δ) 0.88 (t, J=0.8 Hz, 18H), 1.23-1.32 (m, 132H), 1.42-1.44 (m, 12H), 2.43 (s, 12H), 2.67 (s, 6H), 2.81 (s, 6H), 5.26 (s, 6H). MS (m/z): $[M+2H]^{2+}$ calcd. for $C_{90}H_{182}N_6O_3$, 697.7; found, 697.9.

E2 (1,1',1"-(1,3,5-triazinane-1,3,5-triyl)tris(3-(dinonylamino)propan-1-one)) and P6 (N-(2-(cyclohex-1-en-1-ylamino)-1-(1-ethylpiperidin-4-yl)-2-oxoethyl)-N-(heptadecan-9-yl)palmitamide) are novel ionizable lipids described in PCT Patent Application No. PCT/US2023/017777 and shown below:

E2

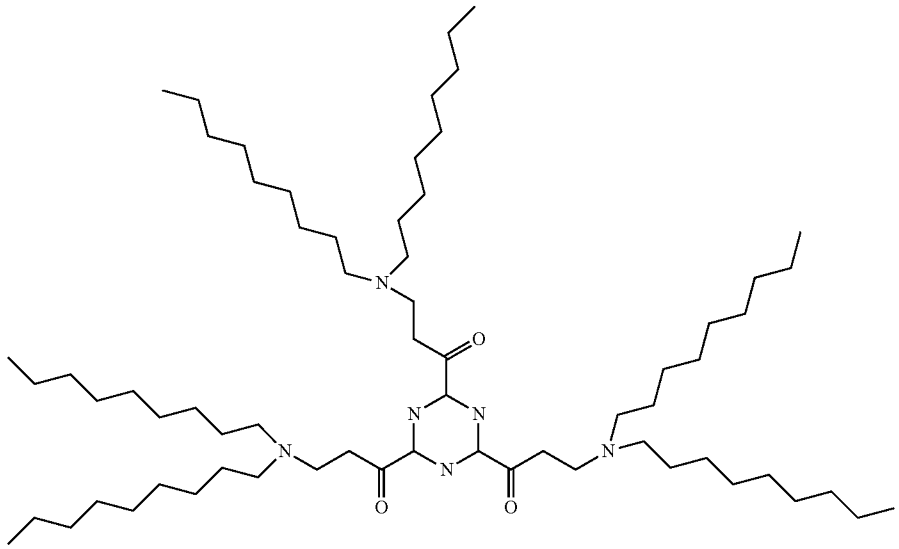

P6

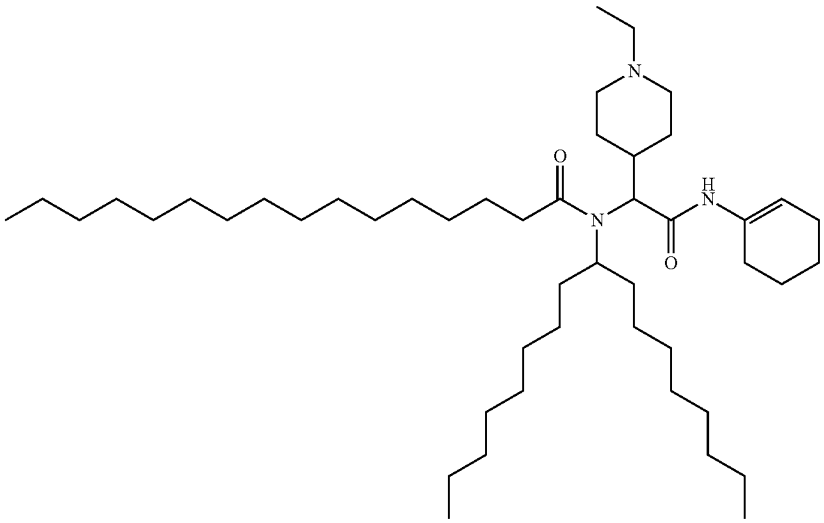 [SMILES: CCCCCCCCCCCCCCCC(=O)N(C(CCCCCCCC)CCCCCCCC)C(C(=O)NC1=CCCCC1)C1CCN(CC)CC1]

The structure of E2 was confirmed by 1H NMR spectroscopy and mass spectrometry. $^{1}$H-NMR (400 MHz, CDCl3, δ) 5.26 (s, 6H), 2.79 (t, J=8 Hz, 6H), 2.65 (t, J=8 Hz, 6H), 2.41 (t, J=8 Hz, 12H), 1.42-1.26 (m, 84H), 0.88 (t, J=8 Hz, 18H). MS (ESI) m/z 529.6 $[M+2H]^{2+}$.

The structure of P6 was confirmed by 1H NMR spectroscopy and mass spectrometry. $^{1}$H-NMR (400 MHz, Me-OD, δ) 6.05 (t, J=8 Hz, 1H), 4.26 (s, 1H), 3.26-3.17 (m, 3H), 2.49-2.42 (m, 5H), 2.19-2.01 (m, 6H), 1.67-1.57 (m, 14H), 1.31-1.16 (m, 48H), 0.92-0.87 (m, 12H). MS (APCI) m/z 742.7 $[M+H]^{+}$.

The nucleic acids of the present disclosure may be delivered using a LNP delivery system wherein the LNP is formulated with ionizable lipid, helper lipid, cholesterol, and PEG-lipid. In one aspect, the LNP of the disclosure has a molar ratio of about 2-60% ionizable lipid, about 5-40% helper lipid, about 30-80% cholesterol and about 0.5-30% PEG-lipid. In one aspect, the LNP of the disclosure has a molar ratio of about 2-10% ionizable lipid, about 5-15% helper lipid, about 40-80% cholesterol and about 0.5-3% PEG-lipid. In one aspect of the disclosure, the ionizable lipid is E6. In one aspect of the disclosure, the helper lipid is independently selected from DOPE (2-dioleoyl-sn-glycero-3-phosphoethanolamine), DSPC (1,2-distearoyl-sn-glycero-3-phosphocholine), and POPE (1-palmitoyl-2-oleoyl-sn-glycero-3-phosphoethanolamine). In one aspect, nucleic acids of the present disclosure may be delivered using a LNP delivery system wherein the ionizable lipid is E6, the helper lipid is DOPE and the PEG-lipid is DMG-PEG2000. In one aspect of the present disclosure, the LNP is composed of E6, DOPE, cholesterol, and DMG-PEG-2000. In one aspect, the LNP has a molar ratio of 50% ionizable lipid, 10% helper lipid, 38.5% cholesterol, and 1.5% PEG-lipid. In another aspect, the LNP has a molar ratio of 7.5% ionizable lipid, 15% helper lipid, 75% cholesterol, and 2.5% PEG-lipid. In another aspect, the LNP of the disclosure has a molar ratio of 5% ionizable lipid, 10% helper lipid, 50% cholesterol, and 1.5% PEG-lipid. In some aspects, the ionizable lipid may include E6, the helper lipid may include DOPE and the PEG-lipid may include DMG-PEG2000.

E6, was synthesized and formulated into LNPs with DOPE, cholesterol and DMG-PEG2000. Transfection efficacy and cell cytotoxicity of the LNPs were assayed in 293T cells using a self-amplifying mRNA encoding GFP. The LNPs of the present disclosure were found to effectively transfect each type of cell in vitro and demonstrated comparable or increased encapsulation efficiency and comparable or decreased cytotoxicity between the secreted version of the modified SPIKE protein of the present disclosure and the SPIKE protein encoded by mRNA currently approved by FDA.

Example 2: Self-Amplifying mRNA

Figure 16:
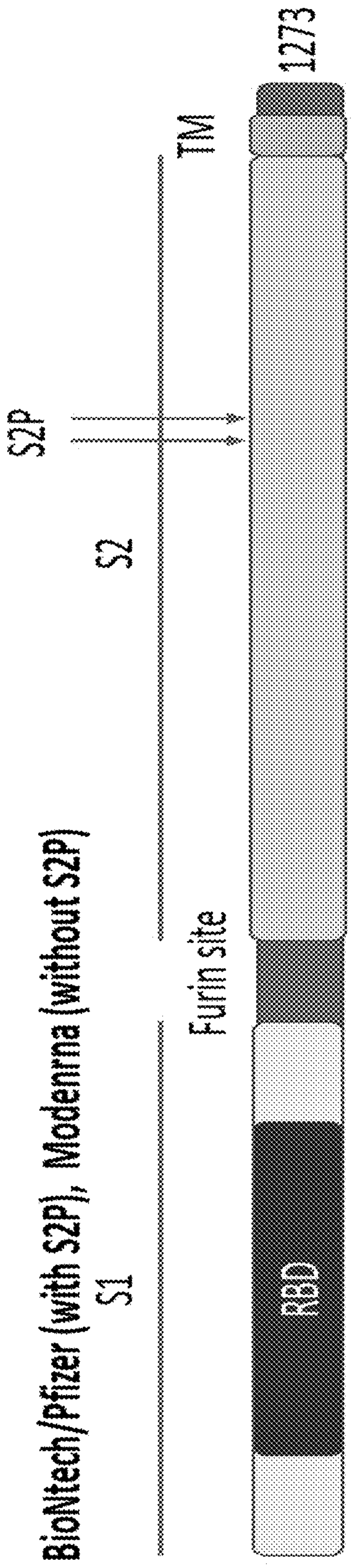
FIG. 16 shows a schematic representation of released mRNA sequences of BioNTech-Pfizer (BNT162b2) and Moderna vaccine (mRNA-1273) the antigens are 1273 amino acids, including S1 (RBD), S2, transmembrane domain and short cytosolic domain. Since the transmembrane domain leads to the expression of SPIKE antigens on the cell surfaces, the transfected cells could be targeted by immune system, which likely results in hepatitis and myocarditis induced by BNT162b2 and mRNA-1273. This schematic representation also shows the location of 2 proline mutations on S2 (S2P), which are found in the mRNA of covid vaccine BNT162b2, but not in the mRNA of mRNA-1273. This version of the mRNA polypeptide sequence encoding the SPIKE protein is hereinafter referred to as “1273.”
Figure 17:
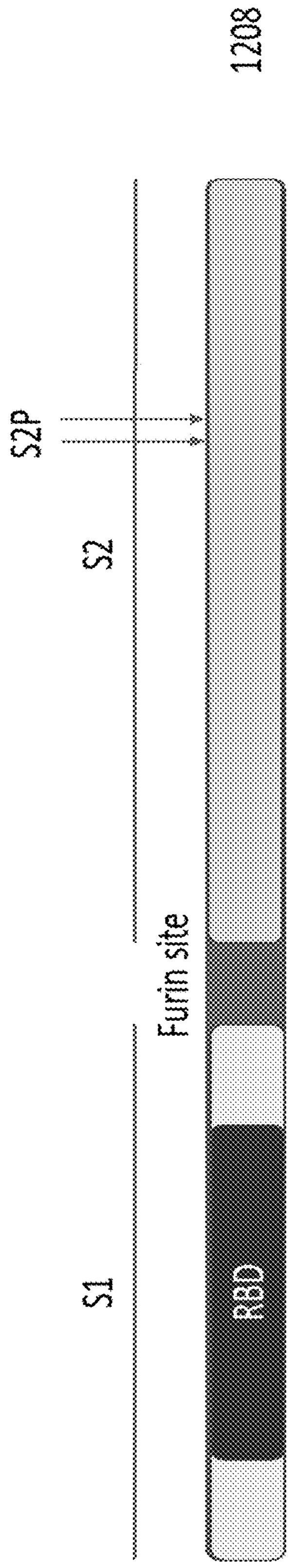
FIG. 17 shows a schematic representation of a truncated, secretion version (1-1208) of the SPIKE protein. As the 1-1208 amino acids were used for structural studies of the SPIKE protein the truncated protein (“1028”). This schematic representation also shows the location of 2 proline mutations on S2 (S2P), which is found in the mRNA of covid vaccine BNT162b2, but not in the mRNA of mRNA-1273.

The sa-mRNA of the present disclosure were synthesized using the TC-83 strain of VEE, a subclass of alphavirus, wherein the sa-mRNA of the present disclosure is derived from wildtype TC-83 replicon without the alphavirus structural proteins; SEQ ID NO: 1 (BA.1-1273), 2 (BA.1-1273-S2P), 3 (BA.2-1273), 4 (BA.2-1273-S2P), 5 (BA.1-1208), SEQ ID NO: 6 (BA.1-1208-S2P), 7 (BA.2-1208), SEQ ID NO: 8 (BA.2-1208-S2P) are modified variants of the SPIKE antigen as shown in FIGS. 16-17; SEQ ID NO: 13 (IM1) and SEQ ID NO: 20 (IM2) encode immunomodulators SEQ ID NO: 15 (mIL12 P40), SEQ ID NO 17. (mIL12-P35) and SEQ ID NO 19 (mIL21); SEQ ID NO: 9 encodes subgenomic promotor 1; and SEQ ID NO: 11 encodes subgenomic promotor 2 as shown in FIGS. 23-24.

The modified SPIKE proteins encoded by the sa-mRNAs of the present disclosure form correct conformation of SPIKE protein for vaccinations and can be recognized by the broad neutralization antibodies when transfected into 293 T cells using lipofectamine as shown in FIGS. 18-19. Data show that 293 T cells transfected with SEQ ID NO: 1 (BA.1-1273), 2 (BA.1-1273-S2P), 3 (BA.2-1273), 4 (BA.2-1273-S2P) can be recognized by broad neutralization antibody (bnAb) SPD-M265 and hACE2-FITC measured using FACS plots of GFP (FIG. 18) or ACE2 (FIG. 19) expression on the X-axis and live dead dye staining of 7-AAD on the Y-axis. The modified SPIKE protein encoded by the sa-mRNA of the present disclosure can trigger humoral immune responses.

Example 3: Sa-mRNA Encoding a Modified SPIKE Protein

Figure 21:
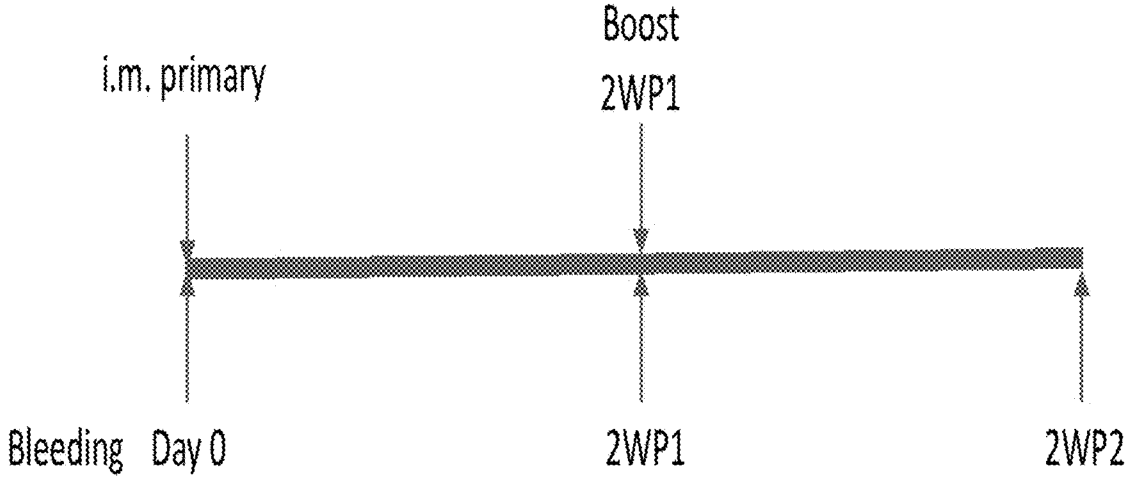
FIG. 21 shows a schematic representation of a mouse experiment where Balb/c mice (10 mice per group) were injected at day 0 and 2WP1 (2 weeks post 1st injection) with E6-C9-LNP encapsulating 2 μg of sa-mRNA encoding a including BA.2-1208, BA.2-1273, BA.2-1208-S2P, BA.2-1273-S2P, or only sa-mRNA not encoding a SARS-CoV-2

As shown in FIG. 20, sa-mRNA encoding a modified SPIKE protein containing a S2P modification stabilizes the structure of secretion SPIKE. In this study, 293 T cells transfected with sa-mRNAs with and without the S2P modification and absorbance was measured on the Y-axis using SPD-M265 bnAb and dilution factor was measured on the X-axis. Furthermore, the secreted version of the modified SPIKE antigen (SEQ ID NO: 6 (BA.1-1208-S2P)) show comparable BA.2 specific IgG as SEQ ID Nos: 1 (BA.1-1273) and 2 (BA.1-1273-S2P), which are more similar to the transmembrane SPIKE proteins encoded by the mRNA of the first generation COVID vaccines, as shown in FIG. 22. The serum of the mice injected with sa-mRNA encoding 3 (BA.2-1273), 4 (BA.2-1273-S2P), 7 (BA.2-1208), and 8 (BA.2-1208-S2P) delivered using the LNP of the present disclosure were collected at day 0, day 14 (2WP1, 2 weeks post 1st injection), and day 28 (2WP2, 2 weeks post 2nd injection) and assayed for titer of antigen specific IgG. As shown in FIGS. 21-22, the data demonstrated comparable immune responses between the secreted version of the modified SPIKE protein of the present disclosure and the SPIKE protein encoded by mRNA currently approved by FDA.

Example 4: Characterization of the sa-mRNA of the Disclosure

A study was conducted to compare the cytotoxicity of different sa-mRNA constructs of the disclosure (SAM001, SAM002, and SAM003, and modified mRNA from MOD001) in HEK293 cells. While sa-mRNA advantageously produce an increased number of mRNA transcripts and/or higher expression of gene products, these characteristics could have cytotoxic effects on the host cell or organism. Therefore, it is important for a therapeutic sa-mRNA construct to sustain increased intracellular mRNA transcripts compared to conventional mRNA, while not increasing the transcript and gene product expression levels so much as to harm the host cell. Sustained intracellular mRNA transcript levels allow for a higher initial delivery of the therapeutic sa-mRNA payload with less cytopathic effects because the transcript and gene product expression levels will not increase dramatically or decay rapidly over time. The results of this study show that SAM001 is a cytopathic construct and SAM002 is a non-cytopathic construct.

Figure 1A:
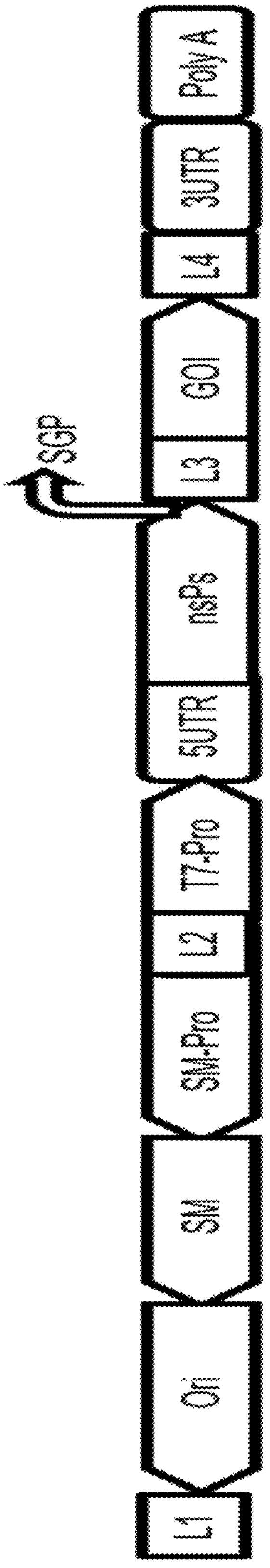
FIG. 1*a* shows a schematic representation of a linearized nucleic acid that is used as a template for production of sa-mRNA. The definitions of the abbreviations in the nucleotide sequence map are as follows: L1 is a first linker, Ori is an origin of replication sequence, SM is a selectable marker, Pr1 is a first promoter sequence, L2 is a second linker, Pr2 is a second promoter sequence, 5'UTR is a 5' untranslated region, nsP is a plurality of non-structural replicase domain sequences, SGP is a subgenomic promoter, L3 is a third linker, GOI is one or more gene or genes of interest, L4 is a fourth linker, 3'UTR is a 3' untranslated region, and Poly-A is a 3' poly-adenylated tail. Note that any one of more of the illustrative components of the molecule are optional and the present disclosure includes aspects that contain fewer than all of the illustrated elements.
Figures 1B, 2:
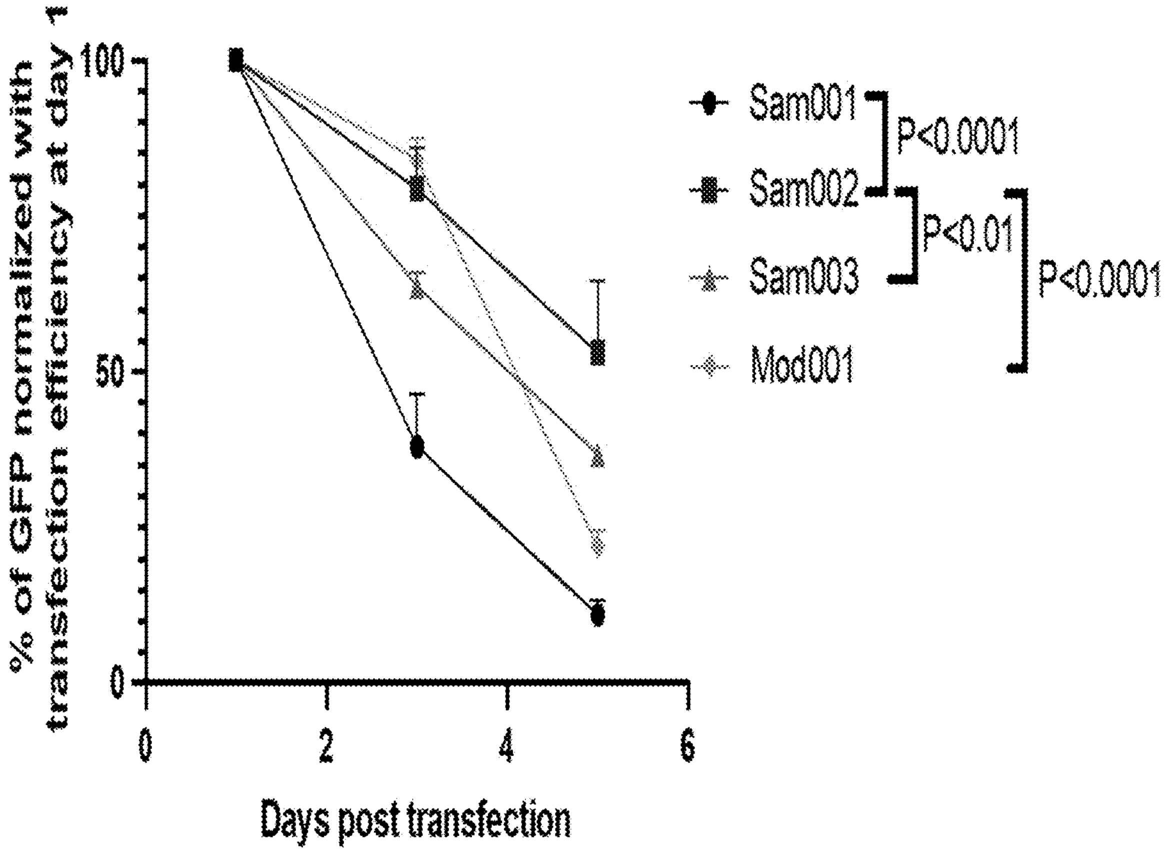
FIG. 1*b* shows the engineered sa-mRNA constructs of the disclosure (SAM001, SAM002, and SAM003) and the nucleotide and amino acid sequences changed in the nsP region compared to the wildtype SAM001.
FIG. 2 shows FACS of 4 individual sa-mRNA in 293T cells over time.
Figure 3:
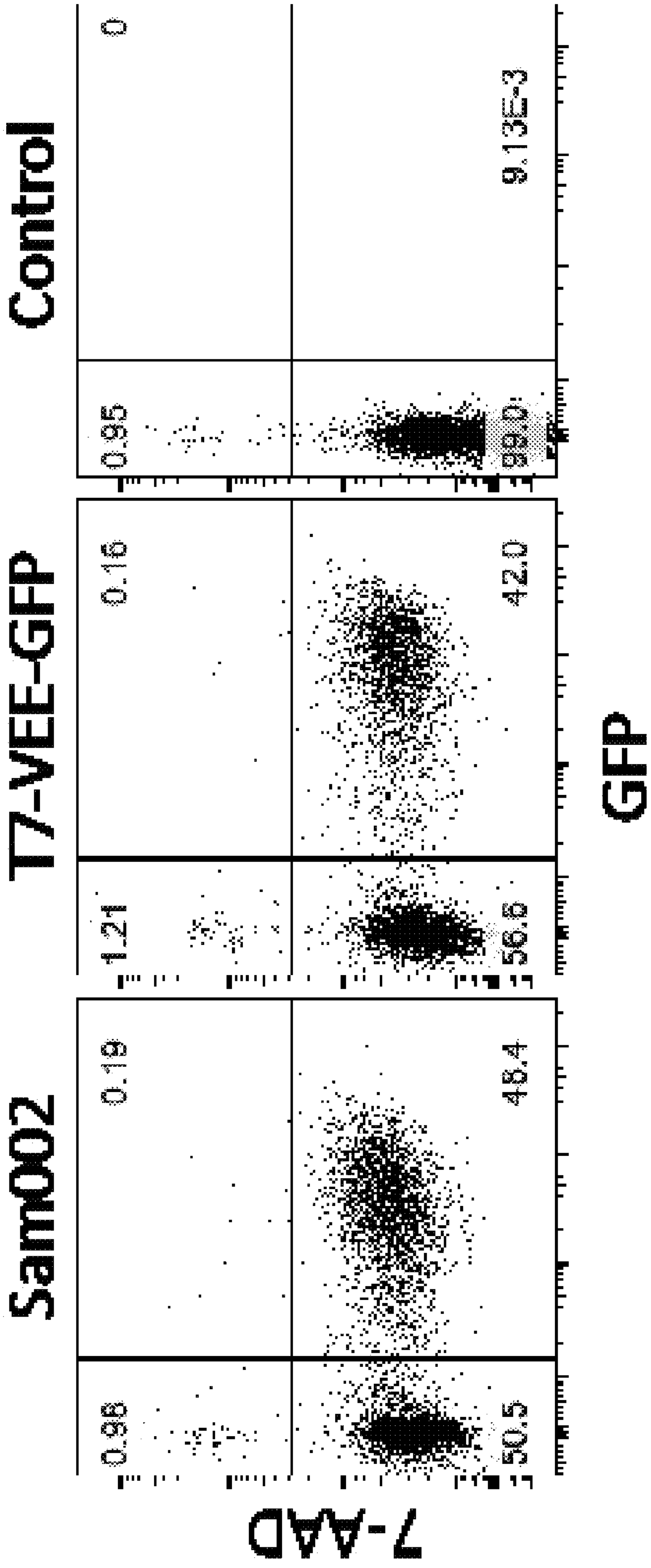
FIG. 3 shows FACS of SAM002 and T7-VEE-GFP sa-mRNA expressing GFP-mRNA in 293T cells at day 1 post transfection.

As shown in FIG. 2, SAM002 showed the most stable reporter gene expression compared to the other tested sa-mRNA constructs, which suggests that it would be more suitable for vaccinations against infectious diseases or gene replacement therapies. In comparison, SAM001 reporter gene expression decreased dramatically, which suggests that it would be more suitable for cancer therapies requiring increased release of tumor associated antigens.

A study was also conducted to characterize the replication rate of each sa-mRNA construct of the disclosure SAM001, SAM002, and SAM003, and modified mRNA from MOD001). As shown in FIG. 25, the relative expression of nsP3 and eGFP indicate the copies of sa-mRNA and subgenomic transcripts, respectively. SAM002 showed approximately 3 times lower transcript copies of both nsP3 or eGFP compared to SAM001. This result indicates that there is a higher rate of replication of sa-mRNA and transcription of the subgenomic eGFP reporter of SAM001 compared to SAM002, which indicates that there is an increased rate of decay of SAM001 and its transcripts.

As shown in FIG. 26, the expression of the SAM001 encoding Luciferase consistently showed much lower in vivo expression compared to SAM002 when each construct is delivered intramuscularly using a P6-LNP delivery method. This result suggest that SAM002 is more suitable for delivery of therapeutic payloads in higher levels with less cytopathic effects compared to the SAM001 construct. Though the more cytopathic of SAM001 showed shorter and lower expressions of payload genes in FIGS. 2 and 26, those cytopathic effects can be helpful to increase therapeutic efficacy in cancer therapies that function through a release of tumor associated antigens, as demonstrated in FIG. 27. Thus, each of SAM001 and SAM002 has utility as a result of its unique biological activity.

Example 5: Directed Evolution of sa-mRNA

A study was conducted to produce sa-mRNA constructs. Directed evolution of sa-mRNA was performed on SAM002 at different concentrations (1 ug/ml or 10 ug/ml) of puromycin in C2C12 cells for 60 days. RNA dependent RNA polymerases are known to have a high error rate, which will cause mutants of SAM002 to appear over time. The SAM002 construct as shown in FIG. 28*a* was divided into 8 contigs, marked 1-8 on FIG. 28*a*, comprising SEQ ID NOs. 27-34. The 8 overlapping contigs facilitate cloning to a vector form suitable for Sanger DNA sequencing. As shown in FIG. 28*b*, only 1 mutation was found at nsP4 in 1 ug/ml puromycin. In contrast, there were 6 mutations found in nsP2, nsP3, and nsP4 at 10 ug/ml puromycin. The 6 mutations were in the 2nd, 3rd, 4th, 5th contigs. The 6 mutations of SAM002 is numbered as alleles 2, 4, 2, 2 respectively, which could form 32 variants, Shown in Tables 2-13 below:

TABLE 1

| No. | | % of GFP normalized at day 3 | | |
|---|---|---|---|---|
| 1 | a1BCD-Sam002 | 93.60967 | 85.55008 | 92.43697479 |
| 2 | a1BCD-Sam001 | 26.3245 | 26.94064 | 24.56418384 |
| 3 | Ab1CD-Sam002 | 84.06015 | 83.50669 | 80.09049774 |
| 4 | Ab1CD-Sam001 | 20.36517 | 21.08844 | 21.40921409 |
| 5 | Ab2CD-Sam002 | 88.83792 | 89.1369 | 91.12781955 |
| 6 | Ab2CD-Sam001 | 35.46667 | 36.71875 | 32.23593964 |
| 7 | Ab3CD-Sam002 | 42.59259 | 41.76991 | 40.625 |
| 8 | Ab3CD-Sam001 | 7.362637 | 10.01764 | 8.549747049 |
| 9 | ABc1D-Sam002 | 75.67568 | 74.12224 | 72.98701299 |
| 10 | ABc1D-Sam001 | 25.06739 | 19.02174 | 21.32253711 |
| 11 | ABCd1-Sam002 | 88.4273 | 84.55657 | 85.80246914 |
| 12 | ABCd1-Sam001 | 34.73282 | 31.71355 | 36.14609572 |
| 13 | a1b1CD-Sam002 | 82.53968 | 75.84803 | 83.81962865 |
| 14 | a1b1CD-Sam001 | 24.43325 | 22.82472 | 18.86075949 |
| 15 | a1b2CD-Sam002 | 90.82707 | 85.01441 | 85.89928058 |
| 16 | a1b2CD-Sam001 | 43.10345 | 43 | 41.4004914 |
| 17 | a1b3CD-Sam002 | 47.98808 | 51.11441 | 51.30674003 |
| 18 | a1b3CD-Sam001 | 13.7415 | 11.36182 | 14.97975709 |
| 19 | a1Bc1D-Sam002 | 68.26265 | 70.17544 | 73.82550336 |
| 20 | a1Bc1D-Sam001 | 24.86842 | 26.52005 | 24.66843501 |
| 21 | a1BCd1-Sam002 | 81.64557 | 85.66929 | 87.59936407 |
| 22 | a1BCd1-Sam001 | 23.58621 | 28.09587 | 30.1759134 |

TABLE 2

| No. | | % of MFI normalized at day 3 | | |
|---|---|---|---|---|
| 1 | a1BCD-Sam002 | 26.70408 | 24.86716 | 28.17502279 |
| 2 | a1BCD-Sam001 | 92.66064 | 71.8318 | 69.01040305 |
| 3 | Ab1CD-Sam002 | 29.60338 | 27.95987 | 28.80892183 |
| 4 | Ab1CD-Sam001 | 54.84388 | 72.12059 | 59.69650342 |
| 5 | Ab2CD-Sam002 | 25.2417 | 22.28458 | 24.65648054 |
| 6 | Ab2CD-Sam001 | 79.93834 | 75.08098 | 69.93131997 |
| 7 | Ab3CD-Sam002 | 62.02842 | 59.2609 | 53.425 |
| 8 | Ab3CD-Sam001 | 72.97279 | 46.89674 | 60.26471613 |
| 9 | ABc1D-Sam002 | 44.37571 | 45.86502 | 40.95282024 |
| 10 | ABc1D-Sam001 | 80.15279 | 73.20619 | 82.89277065 |
| 11 | ABCd1-Sam002 | 19.66246 | 19.21909 | 18.82683057 |
| 12 | ABCd1-Sam001 | 64.61213 | 70.72639 | 68.27440117 |
| 13 | a1b1CD-Sam002 | 26.06985 | 28.32976 | 26.02497234 |
| 14 | a1b1CD-Sam001 | 63.195 | 56.67116 | 53.00767428 |
| 15 | a1b2CD-Sam002 | 21.32604 | 21.28533 | 21.99453112 |
| 16 | a1b2CD-Sam001 | 69.66121 | 71.22326 | 72.73373474 |
| 17 | a1b3CD-Sam002 | 60.85935 | 58.26164 | 56.95274307 |
| 18 | a1b3CD-Sam001 | 61.42157 | 45.29323 | 38.56780888 |
| 19 | a1Bc1D-Sam002 | 49.57803 | 46.91416 | 44.24096222 |

TABLE 2-continued

| No. | | % of MFI normalized at day 3 | | |
|---|---|---|---|---|
| 20 | a1Bc1D-Sam001 | 68.03935 | 78.72531 | 75.14674158 |
| 21 | a1BCd1-Sam002 | 18.37446 | 19.01418 | 19.03699816 |
| 22 | a1BCd1-Sam001 | 61.15648 | 70.99497 | 64.04494382 |

TABLE 3

| No. | | nsP3 transcripts normalized with Actin | | |
|---|---|---|---|---|
| 1 | a1BCD-Sam002 | 9.447941 | 12.38052 | 10.056107 |
| 2 | a1BCD-Sam001 | 51.62507 | 58.08123 | 49.8665331 |
| 3 | Ab1CD-Sam002 | 14.42001 | 24.59 | 25.4571675 |
| 4 | Ab1CD-Sam001 | 84.44851 | 119.4282 | 119.428223 |
| 5 | Ab2CD-Sam002 | 14.92853 | 16.91229 | 14.825409 |
| 6 | Ab2CD-Sam001 | 63.11889 | 64.89341 | 62.682899 |
| 7 | Ab3CD-Sam002 | 36.75835 | 41.35529 | 41.9325889 |
| 8 | Ab3CD-Sam001 | 177.294 | 199.4661 | 160.897712 |
| 9 | ABc1D-Sam002 | 19.42712 | 17.5087 | 16.336194 |
| 10 | ABc1D-Sam001 | 66.71781 | 57.68003 | 72.5045687 |
| 11 | ABCd1-Sam002 | 11.71269 | 10.48315 | 13.4543426 |
| 12 | ABCd1-Sam001 | 60.96883 | 58.89201 | 85.6273635 |
| 13 | a1b1CD-Sam002 | 17.75311 | 17.02992 | 24.7610399 |
| 14 | a1b1CD-Sam001 | 148.0561 | 121.9377 | 150.122874 |
| 15 | a1b2CD-Sam002 | 8.75435 | 8.815241 | 11.1579493 |
| 16 | a1b2CD-Sam001 | 7.568461 | 6.453134 | 9.44794129 |
| 17 | a1b3CD-Sam002 | 56.88593 | 47.83518 | 61.3929036 |
| 18 | a1b3CD-Sam001 | 182.2784 | 178.5272 | 163.14376 |
| 19 | a1Bc1D-Sam002 | 36.50444 | 37.27147 | 36.0018715 |
| 20 | a1Bc1D-Sam001 | 120.2589 | 124.4998 | 119.428223 |
| 21 | a1BCd1-Sam002 | 10.77787 | 11.47164 | 13.6421583 |
| 22 | a1BCd1-Sam001 | 27.09585 | 22.3159 | 27.09585 |

TABLE 4

| No. | | eGFP transcripts normalized with Actin | | |
|---|---|---|---|---|
| 1 | a1BCD-Sam002 | 5.133704 | 4.958831 | 4.40762046 |
| 2 | a1BCD-Sam001 | 37.79177 | 40.50421 | 30.4844159 |
| 3 | Ab1CD-Sam002 | 7.110741 | 10.05611 | 11.1579493 |
| 4 | Ab1CD-Sam001 | 62.6829 | 72.50457 | 66.7178087 |
| 5 | Ab2CD-Sam002 | 6.062866 | 5.61778 | 5.46416103 |
| 6 | Ab2CD-Sam001 | 41.64294 | 49.86653 | 44.323503 |
| 7 | Ab3CD-Sam002 | 21.55574 | 22.47112 | 24.2514651 |
| 8 | Ab3CD-Sam001 | 90.50967 | 92.41147 | 81.5718801 |
| 9 | ABc1D-Sam002 | 8.514961 | 6.868523 | 8.63382589 |
| 10 | ABc1D-Sam001 | 67.64915 | 56.49299 | 67.1818678 |
| 11 | ABCd1-Sam002 | 3.41054 | 3.24901 | 3.58010028 |
| 12 | ABCd1-Sam001 | 24.93327 | 26.72281 | 34.7755156 |
| 13 | a1b1CD-Sam002 | 6.543216 | 6.147501 | 7.3615012 |
| 14 | a1b1CD-Sam001 | 86.82268 | 76.10926 | 74.5429495 |
| 15 | a1b2CD-Sam002 | 3.116658 | 2.8481 | 3.07375036 |
| 16 | a1b2CD-Sam001 | 2.789487 | 2.584706 | 3.07375036 |
| 17 | a1b3CD-Sam002 | 25.81254 | 23.91759 | 25.281322 |
| 18 | a1b3CD-Sam001 | 51.62507 | 33.3589 | 41.3552906 |
| 19 | a1Bc1D-Sam002 | 12.81712 | 11.15795 | 10.5560633 |
| 20 | a1Bc1D-Sam001 | 50.21338 | 50.91434 | 47.176615 |
| 21 | a1BCd1-Sam002 | 2.694467 | 3.052518 | 3.97236998 |
| 22 | a1BCd1-Sam001 | 3.97237 | 3.917681 | 4.72397065 |

TABLE 5

| No. | | % of GFP normalized at day 3 | | |
|---|---|---|---|---|
| 23 | Ab1c1D-Sam002 | 57.94271 | 55.04711 | 58.37696335 |
| 24 | Ab1c1D-Sam001 | 14.20749 | 14.68531 | 12.45390071 |
| 25 | Ab2c1D-Sam002 | 70.09736 | 68.3844 | 68.66096866 |
| 26 | Ab2c1D-Sam001 | 20.82067 | 23.27965 | 21.19309262 |
| 27 | Ab3c1D-Sam002 | 34.7651 | 33.24397 | 35.53162853 |
| 28 | Ab3c1D-Sam001 | 13.96648 | 20.9589 | 13.76404494 |
| 29 | Ab1Cd1-Sam002 | 74.92308 | 76.68232 | 80.26101142 |
| 30 | Ab1Cd1-Sam001 | 15.24476 | 20.0569 | 13.22727273 |
| 31 | Ab2Cd1-Sam002 | 84.28571 | 82.7957 | 84.78964401 |

TABLE 5-continued

| No. | | % of GFP normalized at day 3 | | |
|---|---|---|---|---|
| 32 | Ab2Cd1-Sam001 | 33.70474 | 30.24251 | 27.28592163 |
| 33 | Ab3Cd1-Sam002 | 44.31138 | 39.58333 | 44.50704225 |
| 34 | Ab3Cd1-Sam001 | 19.94498 | 10.28037 | 10.68181818 |
| 35 | ABc1d1-Sam002 | 65.26868 | 67.29798 | 67.59847522 |
| 36 | ABc1d1-Sam001 | 22.30483 | 21.73397 | 23.50791717 |
| 37 | a1b1c1D-Sam002 | 51.07731 | 52.57069 | 51.30890052 |
| 38 | a1b1c1D-Sam001 | 18.37769 | 16.13723 | 15.2866242 |
| 39 | a1b2c1D-Sam002 | 63.92496 | 56.13772 | 57.55725191 |
| 40 | a1b2c1D-Sam001 | 18.06167 | 17.48148 | 16.79389313 |
| 41 | a1b3c1D-Sam002 | 18.5 | 19.86755 | 21.06109325 |
| 42 | a1b3c1D-Sam001 | 7.973761 | 10.42735 | 9.677891654 |
| 43 | a1b1Cd1-Sam002 | 73.34315 | 73.23308 | 75.65485362 |
| 44 | a1b1Cd1-Sam001 | 14.30536 | 13.49501 | 15.88652482 |

TABLE 6

| No. | | % of MFI normalized at day 3 | | |
|---|---|---|---|---|
| 23 | Ab1c1D-Sam002 | 50.962 | 48.41584 | 49.06840699 |
| 24 | Ab1c1D-Sam001 | 45.2422 | 52.21293 | 80.05868412 |
| 25 | Ab2c1D-Sam002 | 40.1987 | 36.34074 | 41.85967826 |
| 26 | Ab2c1D-Sam001 | 77.60194 | 64.59525 | 72.00743858 |
| 27 | Ab3c1D-Sam002 | 75.13296 | 69.43731 | 88.85059056 |
| 28 | Ab3c1D-Sam001 | 82.07372 | 41.10864 | 70.3764424 |
| 29 | Ab1Cd1-Sam002 | 21.75325 | 22.44224 | 21.7947142 |
| 30 | Ab1Cd1-Sam001 | 56.84459 | 57.05329 | 47.73401939 |
| 31 | Ab2Cd1-Sam002 | 16.99651 | 16.89642 | 15.9159919 |
| 32 | Ab2Cd1-Sam001 | 54.45878 | 52.79225 | 51.64851339 |
| 33 | Ab3Cd1-Sam002 | 47.26541 | 48.89045 | 41.55331882 |
| 34 | Ab3Cd1-Sam001 | 57.46982 | 80.52686 | 74.81101512 |
| 35 | ABc1d1-Sam002 | 38.89447 | 36.95033 | 39.74566762 |
| 36 | ABc1d1-Sam001 | 73.61894 | 61.88906 | 78.83554648 |
| 37 | a1blc1D-Sam002 | 48.99976 | 52.12974 | 55.4643059 |
| 38 | a1b1c1D-Sam001 | 36.22922 | 41.67375 | 47.0700924 |
| 39 | a1b2c1D-Sam002 | 40.58023 | 43.91632 | 45.09061489 |
| 40 | a1b2c1D-Sam001 | 77.31859 | 68.19837 | 66.24362946 |
| 41 | a1b3c1D-Sam002 | 83.91999 | 67.79338 | 66.58917612 |
| 42 | a1b3c1D-Sam001 | 47.01905 | 34.42404 | 37.22906315 |
| 43 | a1b1Cd1-Sam002 | 25.29739 | 23.40211 | 23.24178645 |
| 44 | a1b1Cd1-Sam001 | 83.93086 | 70.15867 | 53.45713157 |

TABLE 7

| No. | | nsP3 transcripts normalized with Actin | | |
|---|---|---|---|---|
| 23 | Ab1c1D-Sam002 | 50.21338 | 43.71329 | 46.5271206 |
| 24 | Ab1c1D-Sam001 | 79.89316 | 81.57188 | 79.3412928 |
| 25 | Ab2c1D-Sam002 | 36.50444 | 35.0174 | 37.5307184 |
| 26 | Ab2c1D-Sam001 | 115.3601 | 106.8913 | 107.634741 |
| 27 | Ab3c1D-Sam002 | 37.27147 | 41.06963 | 41.6429394 |
| 28 | Ab3c1D-Sam001 | 69.55103 | 77.1717 | 62.2499166 |
| 29 | Ab1Cd1-Sam002 | 27.85762 | 29.65082 | 27.09585 |
| 30 | Ab1Cd1-Sam001 | 163.1438 | 172.4459 | 178.527189 |
| 31 | Ab2Cd1-Sam002 | 34.29675 | 32.89964 | 33.1284776 |
| 32 | Ab2Cd1-Sam001 | 166.5718 | 155.4169 | 148.056088 |
| 33 | Ab3Cd1-Sam002 | 0.752623 | 0.779165 | 0.83508792 |
| 34 | Ab3Cd1-Sam001 | 1.536875 | 1.231144 | 1.26575659 |
| 35 | ABc1d1-Sam002 | 2.770219 | 2.496661 | 2.37841423 |
| 36 | ABc1d1-Sam001 | 147.0334 | 132.5139 | 142.024892 |
| 37 | a1b1c1D-Sam002 | 91.13921 | 96.33579 | 95.0095085 |
| 38 | a1b1c1D-Sam001 | 191.3407 | 207.9366 | 196.720023 |
| 39 | a1b2c1D-Sam002 | 15.45498 | 14.6213 | 19.6983106 |
| 40 | a1b2c1D-Sam001 | 101.1253 | 101.8287 | 113.771863 |
| 41 | a1b3c1D-Sam002 | 0.447513 | 0.397768 | 0.42337266 |
| 42 | a1b3c1D-Sam001 | 116.1625 | 124.4998 | 133.435617 |
| 43 | a1b1Cd1-Sam002 | 22.7848 | 22.62742 | 24.5900029 |
| 44 | a1b1Cd1-Sam001 | 210.8393 | 210.8393 | 207.936613 |

TABLE 8

| No. | | eGFP transcripts normalized with Actin | | |
|---|---|---|---|---|
| 23 | Ab1c1D-Sam002 | 16.44982 | 16 | 16.2233517 |
| 24 | Ab1c1D-Sam001 | 38.05463 | 41.64294 | 44.323503 |
| 25 | Ab2c1D-Sam002 | 11.47164 | 12.90627 | 14.5203065 |
| 26 | Ab2c1D-Sam001 | 49.86653 | 48.50293 | 51.9841534 |
| 27 | Ab3c1D-Sam002 | 9.063071 | 6.19026 | 6.58872814 |
| 28 | Ab3c1D-Sam001 | 21.55574 | 20.39297 | 19.0273138 |
| 29 | Ab1Cd1-Sam002 | 3.41054 | 3.5801 | 2.65737163 |
| 30 | Ab1Cd1-Sam001 | 26.72281 | 32.89964 | 37.7917652 |
| 31 | Ab2Cd1-Sam002 | 3.340352 | 3.530812 | 3.36358566 |
| 32 | Ab2Cd1-Sam001 | 21.40684 | 17.75311 | 18.5070109 |
| 33 | Ab3Cd1-Sam002 | 0.005486 | 0.005839 | 0.03564887 |
| 34 | Ab3Cd1-Sam001 | 0.00982 | 0.008729 | 0.00872881 |
| 35 | ABc1d1-Sam002 | 0.011438 | 0.010167 | 0.01045256 |
| 36 | ABc1d1-Sam001 | 10.41073 | 7.727491 | 10.6294865 |
| 37 | a1b1c1D-Sam002 | 24.42015 | 20.39297 | 35.2609637 |
| 38 | a1b1c1D-Sam001 | 86.22295 | 89.88447 | 72.5045687 |
| 39 | a1b2c1D-Sam002 | 0.406126 | 0.539614 | 0.70710678 |
| 40 | a1b2c1D-Sam001 | 68.11969 | 76.10926 | 69.0706071 |
| 41 | a1b3c1D-Sam002 | 0.004944 | 0.004072 | 0.00315094 |
| 42 | a1b3c1D-Sam001 | 134.3637 | 140.0696 | 138.141214 |
| 43 | a1b1Cd1-Sam002 | 4.890561 | 4.563055 | 5.16941132 |
| 44 | a1b1Cd1-Sam001 | 50.21338 | 49.18001 | 46.5271206 |

TABLE 9

| No. | | % of GFP normalized at day 3 | | |
|---|---|---|---|---|
| 45 | a1b2Cd1-Sam002 | 86.72087 | 85.7337 | 85.2367688 |
| 46 | a1b2Cd1-Sam001 | 29.46429 | 27.00922 | 31.53846154 |
| 47 | a1b3Cd1-Sam002 | 37.07025 | 36.80124 | 37.57668712 |
| 48 | a1b3Cd1-Sam001 | 5.844828 | 6.109091 | 6.763110307 |
| 49 | Ab1c1d1-Sam002 | 42.32633 | 37.85124 | 41.06870229 |
| 50 | Ab1c1d1-Sam001 | 9.556314 | 5.738832 | 7.123966942 |
| 51 | Ab2c1d1-Sam002 | 60.93294 | 60 | 60.34732272 |
| 52 | Ab2c1d1-Sam001 | 22.2964 | 16.52893 | 20.51282051 |
| 53 | Ab3c1d1-Sam002 | 30.11583 | 30.46272 | 22.75132275 |
| 54 | Ab3c1d1-Sam001 | 9.871959 | 9.257362 | 9.638242894 |
| 55 | a1Bc1d1-Sam002 | 53.46535 | 49.91334 | 58.52842809 |
| 56 | a1Bc1d1-Sam001 | 11.69697 | 11.47692 | 13.87442573 |
| 57 | a1b1c1d1-Sam002 | 45.08929 | 40.68554 | 38.14102564 |
| 58 | a1b1c1d1-Sam001 | 12.20979 | 12.54795 | 21.51724138 |
| 59 | a1b2c1d1-Sam002 | 68.81579 | 70.96774 | 67.578125 |
| 60 | a1b2c1d1-Sam001 | 21.31783 | 21.50259 | 25.89641434 |
| 61 | a1b3c1d1-Sam002 | 26.46675 | 24.3807 | 29.17214192 |
| 62 | a1b3c1d1-Sam001 | 9.371795 | 10.38119 | 17.31984829 |
| 63 | ABCD-Sam001 | 42.87516 | 41.27182 | 47.11779449 |
| 64 | ABCD-Sam002 | 88.08777 | 85.36585 | 87.59231905 |
| 65 | ABCd2-Sam002 | 76.58897 | 82.50433 | 90.74117236 |
| 66 | ABCd2-Sam001 | 25.07269 | 23.83486 | 27.81926965 |

TABLE 10

| No. | | % of MFI normalized at day 3 | | |
|---|---|---|---|---|
| 45 | a1b2Cd1-Sam002 | 21.59581 | 21.38896 | 21.2904946 |
| 46 | a1b2Cd1-Sam001 | 80.67199 | 62.76361 | 60.79245886 |
| 47 | a1b3Cd1-Sam002 | 59.51047 | 50.75597 | 49.29017604 |
| 48 | a1b3Cd1-Sam001 | 37.66094 | 100.0263 | 53.2477737 |
| 49 | Ab1c1d1-Sam002 | 46.83513 | 47.13787 | 50.37907506 |
| 50 | Ab1c1d1-Sam001 | 59.35291 | 51.54369 | 51.29244805 |
| 51 | Ab2c1d1-Sam002 | 49.5077 | 41.19688 | 43.92891221 |
| 52 | Ab2c1d1-Sam001 | 54.3385 | 71.99053 | 72.05443699 |
| 53 | Ab3c1d1-Sam002 | 68.90104 | 77.1418 | 86.83062969 |
| 54 | Ab3c1d1-Sam001 | 97.9473 | 55.35554 | 49.14956012 |
| 55 | a1Bc1d1-Sam002 | 47.22042 | 38.97181 | 40.27795818 |
| 56 | a1Bc1d1-Sam001 | 55.91852 | 77.0978 | 55.41929666 |
| 57 | a1b1c1d1-Sam002 | 45.95797 | 40.88739 | 55.26597644 |
| 58 | a1b1c1d1-Sam001 | 39.12734 | 47.70419 | 30.85771948 |
| 59 | a1b2c1d1-Sam002 | 36.97674 | 36.20338 | 35.07727652 |
| 60 | a1b2c1d1-Sam001 | 61.17269 | 58.38926 | 53.09734513 |
| 61 | a1b3c1d1-Sam002 | 77.3002 | 69.05956 | 44.25943546 |
| 62 | a1b3c1d1-Sam001 | 54.34123 | 134.8006 | 109.557945 |
| 63 | ABCD-Sam001 | 75.08005 | 63.53236 | 58.12901796 |

TABLE 10-continued

| No. | | % of MFI normalized at day 3 | | |
|---|---|---|---|---|
| 64 | ABCD-Sam002 | 25.37244 | 25.65748 | 24.13470845 |
| 65 | ABCd2-Sam002 | 22.24231 | 25.40835 | 20.73913043 |
| 66 | ABCd2-Sam001 | 87.19298 | 79.77941 | 87.31617647 |

TABLE 11

| No. | | nsP3 transcripts normalized with Actin | | |
|---|---|---|---|---|
| 45 | a1b2Cd1-Sam002 | 41.06963 | 36.75835 | 35.2609637 |
| 46 | a1b2Cd1-Sam001 | 128 | 137.187 | 121.937664 |
| 47 | a1b3Cd1-Sam002 | 49.18001 | 51.98415 | 48.8402947 |
| 48 | a1b3Cd1-Sam001 | 136.2394 | 146.0178 | 165.421162 |
| 49 | Ab1c1d1-Sam002 | 60.54769 | 63.55792 | 70.5219274 |
| 50 | Ab1c1d1-Sam001 | 257.7806 | 243.8753 | 266.871235 |
| 51 | Ab2c1d1-Sam002 | 38.58585 | 43.71329 | 42.2242531 |
| 52 | Ab2c1d1-Sam001 | 62.24992 | 69.55103 | 71.5063768 |
| 53 | Ab3c1d1-Sam002 | 56.49299 | 60.96883 | 60.5476894 |
| 54 | Ab3c1d1-Sam001 | 139.1021 | 141.0439 | 141.043855 |
| 55 | a1Bc1d1-Sam002 | 26.90869 | 31.55945 | 31.3414495 |
| 56 | a1Bc1d1-Sam001 | 58.48521 | 64 | 62.682899 |
| 57 | a1b1c1d1-Sam002 | 29.04061 | 34.29675 | 39.3966212 |
| 58 | a1b1c1d1-Sam001 | 103.2501 | 109.1373 | 135.298309 |
| 59 | a1b2c1d1-Sam002 | 27.47409 | 26.53823 | 28.0513831 |
| 60 | a1b2c1d1-Sam001 | 60.12946 | 74.02804 | 66.2569551 |
| 61 | a1b3c1d1-Sam002 | 51.26847 | 55.71524 | 58.4852128 |
| 62 | a1b3c1d1-Sam001 | 128.8903 | 129.7868 | 132.51391 |
| 63 | ABCD-Sam001 | 69.07061 | 61.3929 | 63.1188931 |
| 64 | ABCD-Sam002 | 13.92881 | 13.8326 | 9.64646262 |
| 65 | ABCd2-Sam002 | 47.17662 | 47.50475 | 44.0173382 |
| 66 | ABCd2-Sam001 | 13.08643 | 13.64216 | 15.1369223 |

TABLE 12

| No. | | eGFP transcripts normalized with Actin | | |
|---|---|---|---|---|
| 45 | a1b2Cd1-Sam002 | 1.931873 | 1.292353 | 1.86606598 |
| 46 | a1b2Cd1-Sam001 | 30.90996 | 28.44297 | 23.7523771 |
| 47 | a1b3Cd1-Sam002 | 16.56424 | 17.14838 | 13.3614067 |
| 48 | a1b3Cd1-Sam001 | 48.50293 | 56.49299 | 61.8199251 |
| 49 | Ab1c1d1-Sam002 | 14.3204 | 15.24221 | 15.5624792 |
| 50 | Ab1c1d1-Sam001 | 80.44886 | 81.57188 | 75.5835303 |
| 51 | Ab2c1d1-Sam002 | 9.189587 | 10.05611 | 8.9382971 |
| 52 | Ab2c1d1-Sam001 | 32 | 35.50622 | 35.0173984 |
| 53 | Ab3c1d1-Sam002 | 28.05138 | 26.17287 | 28.6408023 |
| 54 | Ab3c1d1-Sam001 | 49.18001 | 36.50444 | 48.1678959 |
| 55 | a1bc1d1-Sam002 | 14.22148 | 12.04197 | 11.7941537 |
| 56 | a1Bc1d1-Sam001 | 37.01402 | 36.25228 | 30.6964518 |
| 57 | a1b1c1d1-Sam002 | 13.36141 | 14.52031 | 18.6357374 |
| 58 | a1b1c1d1-Sam001 | 61.3929 | 64 | 75.0614368 |
| 59 | a1b2c1d1-Sam002 | 9.646463 | 8.815241 | 8.6938789 |
| 60 | a1b2c1d1-Sam001 | 32.89964 | 34.77552 | 33.8245773 |
| 61 | a1b3c1d1-Sam002 | 22.16175 | 23.75238 | 25.281322 |
| 62 | a1b3c1d1-Sam001 | 71.01245 | 64.89341 | 71.0124462 |
| 63 | ABCD-Sam001 | 35.50622 | 22.94328 | 27.857618 |
| 64 | ABCD-Sam002 | 14.22148 | 5.897077 | 6.45313407 |
| 65 | ABCd2-Sam002 | 44.6318 | 40.78594 | 30.4844159 |
| 66 | ABCd2-Sam001 | 6.868523 | 7.310652 | 8.45614432 |

Tables 1-12 show characterizations of 66 sa-mRNA mutants. To generate these mutants, C2C12 cells were transfected with SAM002 encoding with puromycin by P6-LNP. The transfected cells were cultured for 2 months at 1 or 10 ug/ml puromycin. At 2 months post transfection, the total RNA of selected cells was extracted and reverse transcribed. The specific primers covering contigs from 1 to 6 were for amplicons and sub-cloning. For each contig, 8 clones were cultured and isolated using a Mini-Prep procedure to isolate small plasmid DNA from bacteria while limiting contaminating proteins and genomic DNA for Sanger Sequencing. The contig sequences comprise SEQ ID NOs. 27-34, which correspond to contigs 1-8, respectively.

The identified mutations could make 66 combinations and were further engineered into SAM001 or SAM002 at the specified location for each mutation. Thus, this study identified 67 constructs of cytopathic and non-cytopathic sa-mRNA, including the mutation at 1 ug/ml puromycin and the 66 mutants shown in Tables 1-12.

A characterization study was conducted to study the expression level of the 66 sa-mRNA variants identified using the method described above. The 66 sa-mRNA variants were transcribed in vitro and transfected to C2C12 cells using a LNP comprising an ionizable lipid P6 as defined in PCT Patent Application No. PCT/US2023/017777 (P6-LNP), which is fully incorporated herein. The transfected cells were performed by fluorescence-activated cell sorting (FACS) at day 1 and 3 post transfection. The percentages of GFP and mean fluorescent intensities (MFI), representing gene product expression of each variant, were analyzed. The percentage and MFI of GFP at day 3 were normalized compared to the data from day 1. Total RNA of the transfected cells was extracted and reverse transcribed as complementary DNA for quantification polymerase chain reaction (qPCR) by specific probes nsP3 and eGFP.

To characterize the identified variants over time, the variants were transfected using P6-LNP into mouse myoblast C2C12 cells, analyzed by flow cytometer at day 1 and 3 post transfection, and quantified the transcript number of each sa-mRNA construct using nsP3 specific probes. The subgenomic transcripts were quantified using GFP specific probes. The decrease of GFP cells and intensity of GFP ranged broadly between the tested variants.

Thus, the present disclosure includes a sa-mRNA library that is useful for various specialized indications, such as mRNA medicines against infectious diseases, cancers, autoimmune diseases, and rare diseases.

Example 4: Characterization of De Novo Synthesized Sa-mRNA of the Disclosure

The nucleic acids of the present disclosure were synthesized using the TC-83 strain of VEE, a subclass of alphavirus, wherein SAM001 (SEQ ID NO: 35) is derived from wildtype TC-83 replicon without the alphavirus structural proteins, and SAM002 (SEQ ID NO: 36), SAM003 (SEQ ID NO: 37), SAM004 (SEQ ID NO: 38), SAM005 (SEQ ID NO: 39), SAM006 (SEQ ID NO: 40), and MOD001 (SEQ ID NO: 41) are modified according to the present disclosure. T7-VEE-GFP (SEQ ID NO: 42) was derived from wildtype TC-83 replicon and comprised a wildtype T7 promoter and a GOI encoding GFP. In vitro transcription efficacy of the nucleic acid template into sa-mRNAs and immune response to the sa-mRNAs were assayed in Raw-ISG-Lucia, and 293T cells. The nucleic acid templates of the present disclosure were found to effectively transcribe into sa-mRNAs. The data demonstrated better or comparable in vitro transcription yields and decreased immune responses than therapeutic mRNA currently approved by FDA.

DNA fragments of sa-mRNA (sa-mRNA) were de novo synthesized using a strain of Venezuelan equine encephalitis (VEE) virus TC-83, which is a subclass of alphavirus, with deletions of genes encoding structural proteins. The DNA fragments were assembled under T7 promoter as shown in FIG. 1 with other components including linker 1, origin of replication sequences (Ori), Ampicillin resistance gene (SM), Promoter of SM (SM-Pro), linker 2, 5UTR, nsp1-4, linker 3, reporter genes or genes of interests (GOI), linker 4, 3'UTR, polyadenine (polyA). Based on the wild-type version SAM001, mutations for non-cytopathic versions of SAM002 (C5830T, Pro to Ser) and SAM003 (A5729T, Gln to Leu) were engineered.

A comparison of the stability of different sa-mRNA versions from SAM001, SAM002, and SAM003, and modified mRNA from MOD001 as seen in as shown in FIG. 2 show that SAM002 is more stable compared to the other tested sa-mRNAs, including the modified mRNA. This data indicates that SAM002 is more suitable for vaccinations against infectious diseases or gene replacements of gene editing.

As can be seen in FIG. 2, expression of SAM001 decreased dramatically over time, which indicates that SAM001 be suitable for transient expressions or cancer immunotherapy as well as therapeutic cancer vaccines.

Comparisons of different versions of sa-mRNA and modified mRNA were conducted. 293 T cells were transfected with different sa-mRNA (sa-mRNA) from SAM001, SAM002, SAM003, and modified mRNA from MOD001 encoding GFP by lipofectamine. The cells were analyzed by flow cytometer at day 1, 3, and 5. Decrease of GFP expression were normalized with the percentage of GFP at day 1. Statistical analyses were performed by one-way ANOVA. The modified sa-mRNA of the disclosure showed better GFP expression over time compared to SAM001 (SEQ ID NO: 35) as shown in FIG. 2.

Figure 5:
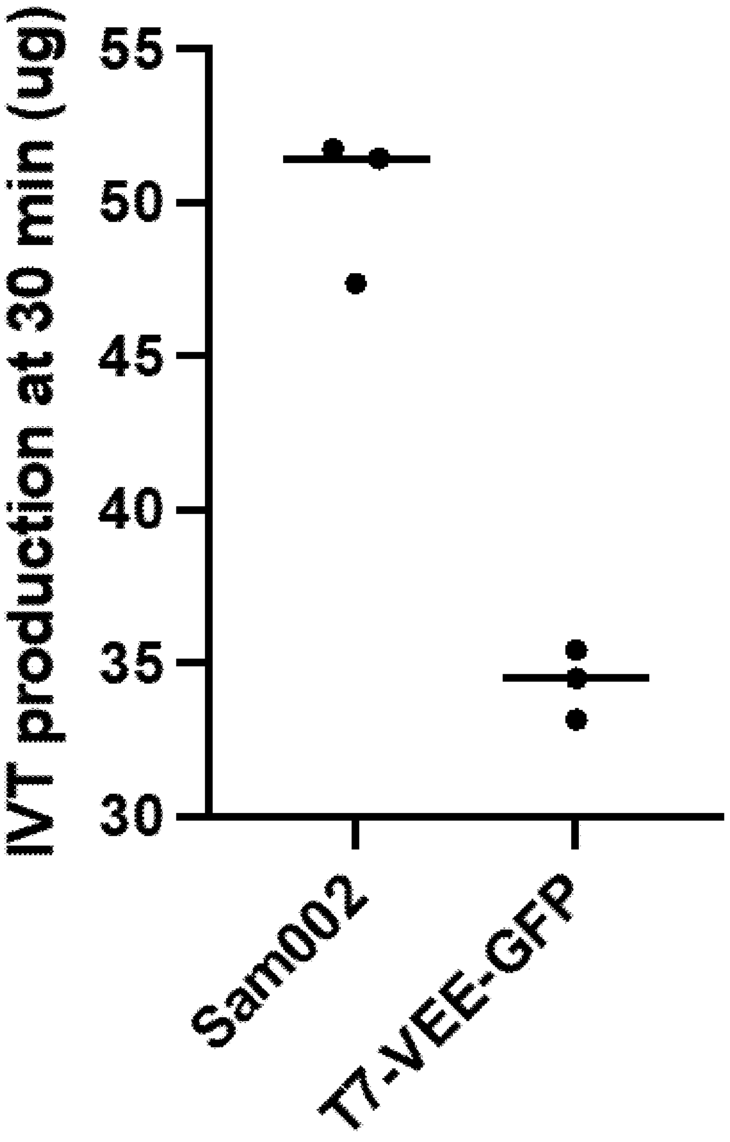
FIG. 5 shows sa-mRNA production by in vitro transcription using a microgram template within 30 minutes of in vitro transcription using T7 polymerase.

As the size of sa-mRNA is always larger than 7 kilo nucleotides, it is one of the challenges for mRNA production in limited time by in vitro transcription. As shown in FIG. 4, SAM002 (TAATACGACTCACTATAGGATAGG) (SEQ ID NO: 53) has unique repeating sequences of ATAGG. mRNA productions of SAM002 increased 46% than the T7-VEE-GFP as shown in FIG. 5. Thus, the sa-mRNA of the present disclosure has increased ability for transcription and higher yields, suitable for transcription of large fragments of mRNA and manufacture of high amount of mRNA. In a related experiment, the modified sa-mRNA comprising modified T7 and 5' UTR (SAM002 (SEQ ID NO: 36)) of FIG. 4 showed a higher yield at 30 minutes of in vitro transcription compared to the control (T7-VEE-GFP), as can be seen in FIG. 5.

Figure 6:
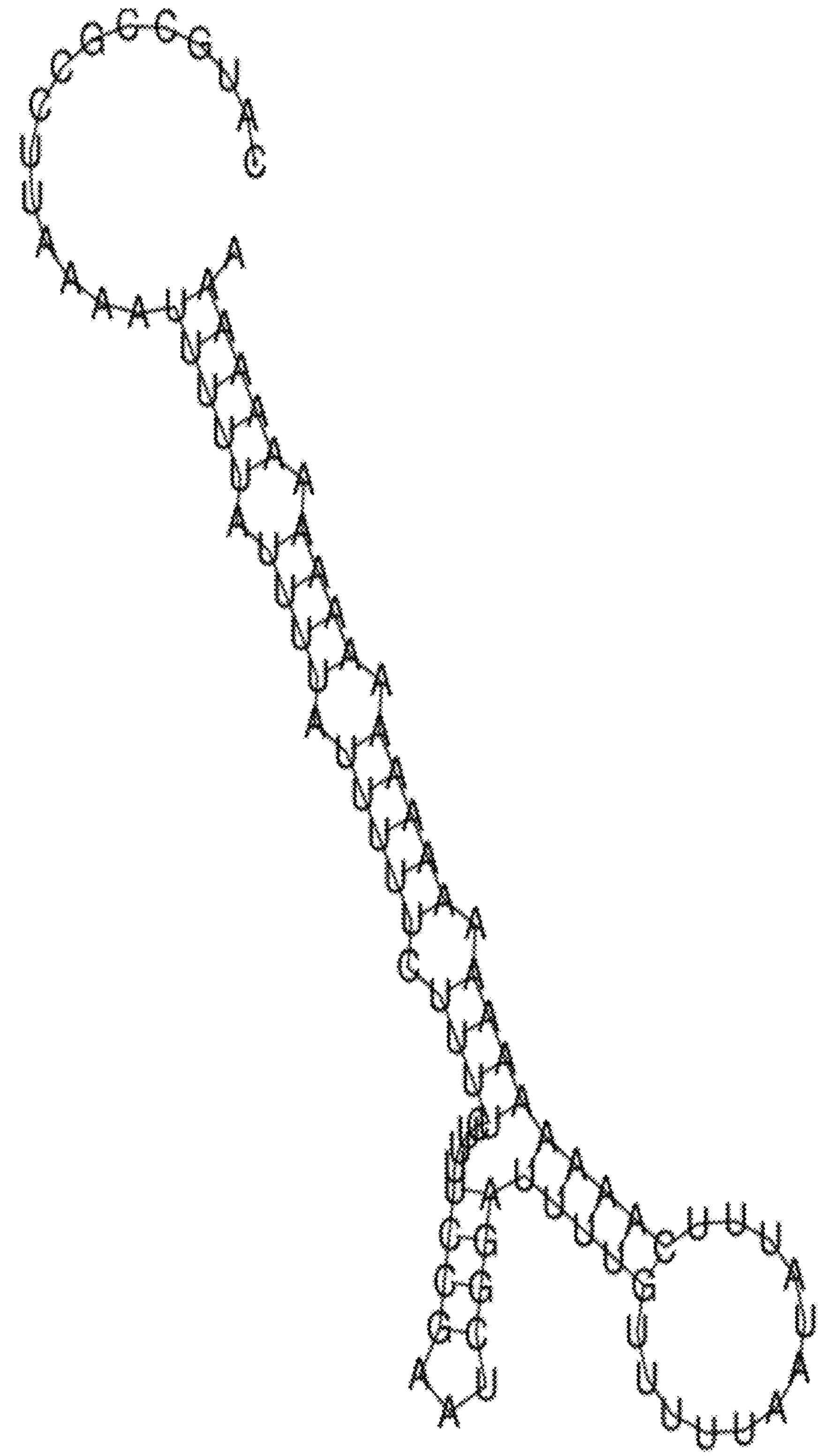
FIG. 6 shows the structure prediction of the 3' UTR of wildtype VEE (SEQ ID NO: 54).

Interferon responses are innate reactions of host cells to exotic RNAs and materials as well as pathogens, which significantly restrict the half-life of mRNA in cells and give rise to side effects, such as fever. It is a medical challenge to manipulate interferon responses using mRNA. Sequencing and functional analysis showed that a conserved 19 nucleotides fragment in the 3'UTR of alphavirus is critical to the repair of alphavirus. FIG. 6 shows the structure prediction of 3'UTR of wildtype VEE with the probability of the structure indicated according to the scale. The modified 3'UTR of the disclosure (SAM004 (SEQ ID NO: 38), SAM005 (SEQ ID NO: 39), and SAM006 (SEQ ID NO: 40)) showed reduced or comparable interferon responses than self-amplified mRNA transcribed from nucleic acid templates containing 3'UTR of wildtype VEE (SAM002 (SEQ ID NO: 36) and MOD001 (SEQ ID NO: 41)). Based on the model shown in FIG. 6 of the 3'UTR and Poly-A of the VEE, the G at position 6 and the C at position 19 form a G::C pair to lock a loop, two GG at position minus 1 and 2 form GG::CC pair to build up a stem. A mutation of G to A at position 6, GG to AA at position minus 1, and 2, or both generated SAM004, SAM005, and SAM006 based on SAM002 as shown in FIG. 7.

The sa-mRNA from SAM004, SAM005, and SAM006, and modified mRNA from MOD001 were transfected to Raw-ISG-Lucia cells, an interferon reporter cell developed by Invivogen. As shown in FIG. 8, at day 1 post transfection, SAM004 showed more than 5.1- and 2.1-times lower interferon responses than SAM002 and modified mRNA MOD001 in an interferon simulation assay.

Figures 7, 8:
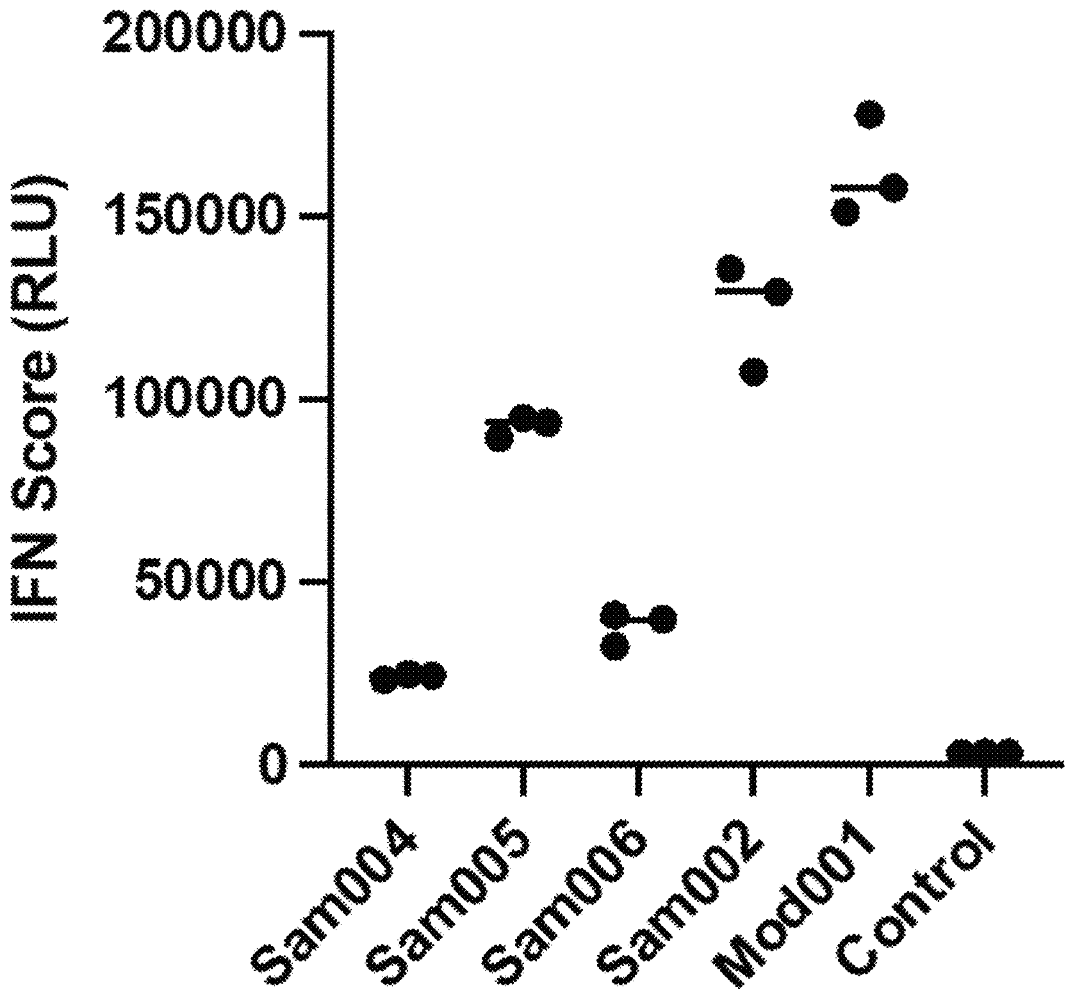
FIG. 7 shows a comparison of the nucleotide sequence of a conserved 19 nucleotide sequence of the 3' UTR of wildtype VEE and modified sequences of the present disclosure, which sequences are labeled as Sam002 (SEQ ID NO: 49), Sam004 (SEQ ID NO: 50), Sam005 (SEQ ID NO: 51), and Sam006 (SEQ ID NO: 52).
FIG. 8 shows a reporter assay of 5 individual sa-mRNA in Raw-ISG-Lucia cells at day 1 post transfection.

FIG. 8 shows a reporter assay of 5 individual self-amplifying mRNAs produced from nucleic acid templates SAM002 (SEQ ID NO: 36), SAM004 (SEQ ID NO: 38), SAM005 (SEQ ID NO: 39), SAM006 (SEQ ID NO: 40), and MOD001 (SEQ ID NO: 41) expressing GFP in Raw-ISG-Lucia cells at day 1 post-transfection. The modified 3'UTR of the disclosure (SAM004 (SEQ ID NO: 38), SAM005 (SEQ ID NO: 39), and SAM006 (SEQ ID NO: 40)) showed reduced or comparable interferon responses than self-amplified mRNA transcribed from nucleic acid templates containing 3'UTR of wildtype VEE (SAM002 (SEQ ID NO: 36) and MOD001 (SEQ ID NO: 41)).

Figure 9:
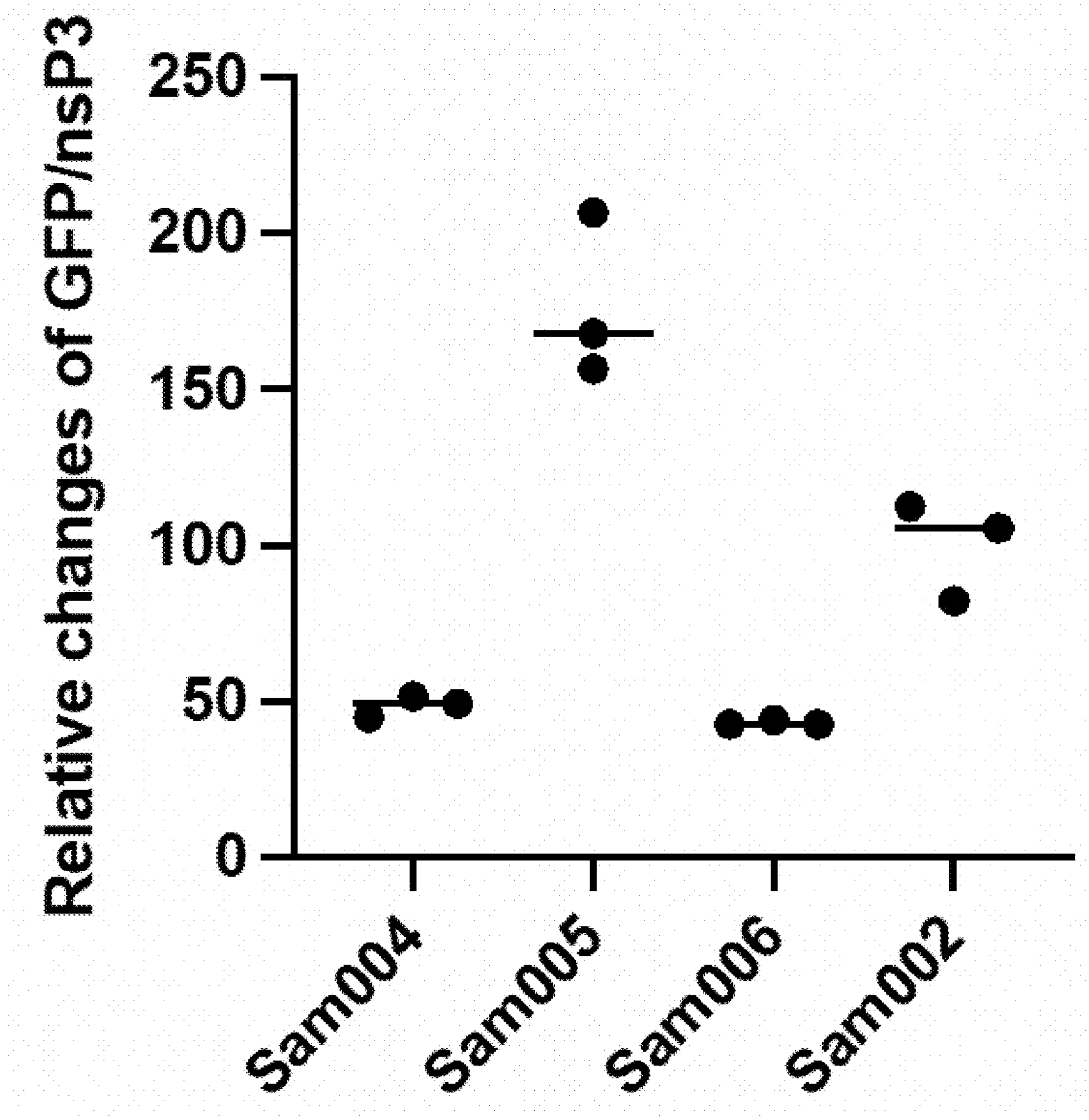
FIG. 9 shows a reporter assay of 4 individual sa-mRNA in Raw-ISG-Lucia cells at day 1 post-transfection, where GFP expression is normalized with nsP3 in comparison to SAM002.
Figure 10:
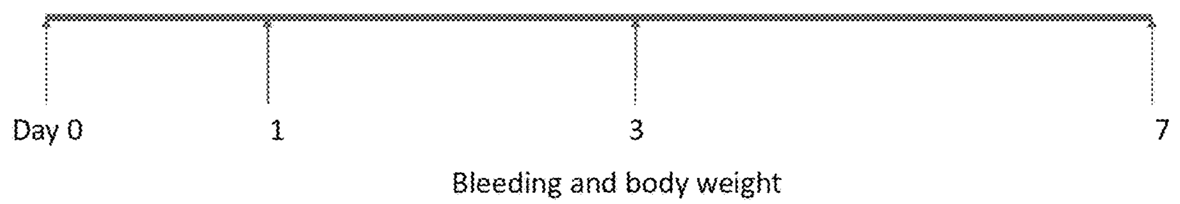
FIG. 10 shows a schematic representation of a in vivo experiment, which tested the toxicity the E6-C9 LNP formulation by examining changes in bleeding and body weight of Balb/C mice injected intramuscularly with dosage of 10, 5, 2.5, 1.25 μg mRNA (5 mice/group). At the day 0, 1, 3, and 7 days post injection, the mice were bled and the body weight of the mice were measured.
Figure 11:
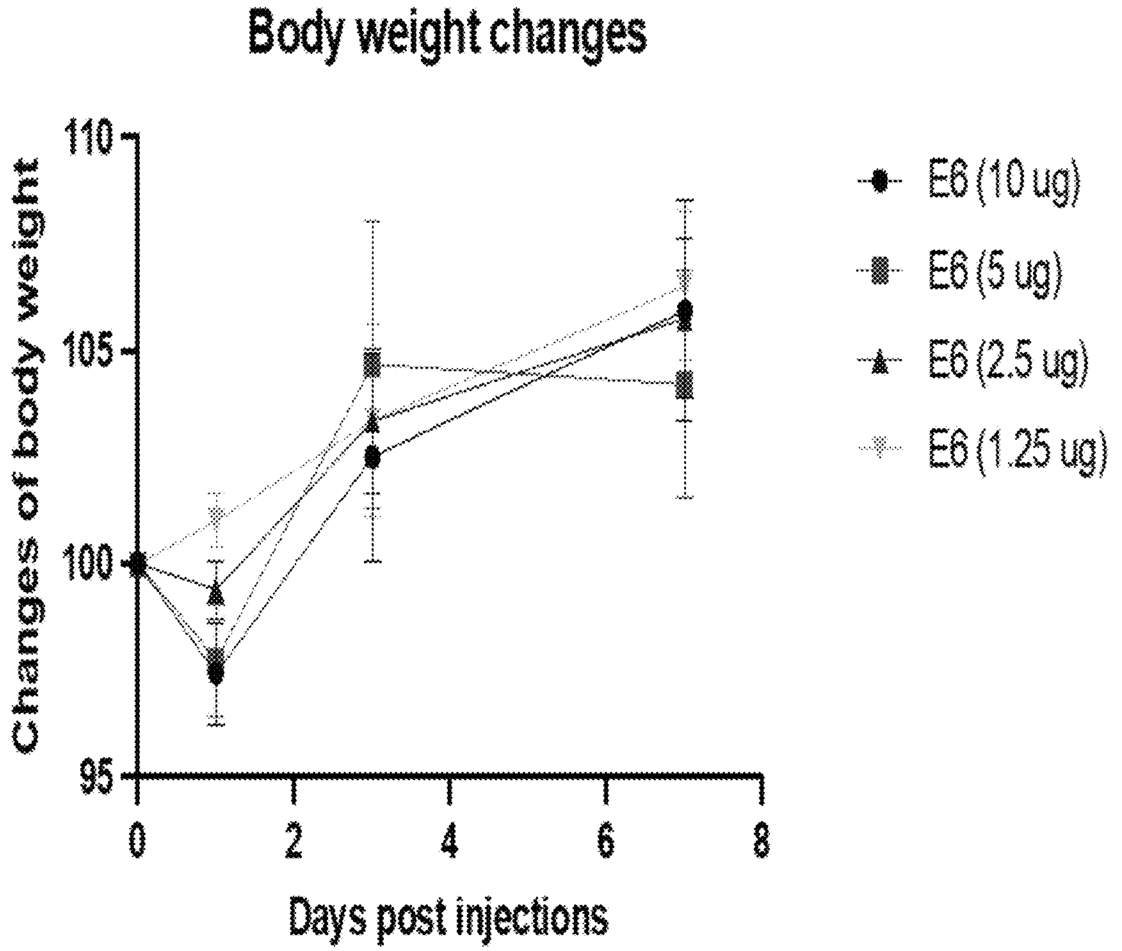
FIG. 11 shows body weight changes of Balb/C mice injected intramuscularly with dosage of 10, 5, 2.5, 1.25 μg mRNA (5 mice/group). At the day 0, 1, 3, and 7 days post injection.
Figure 12:
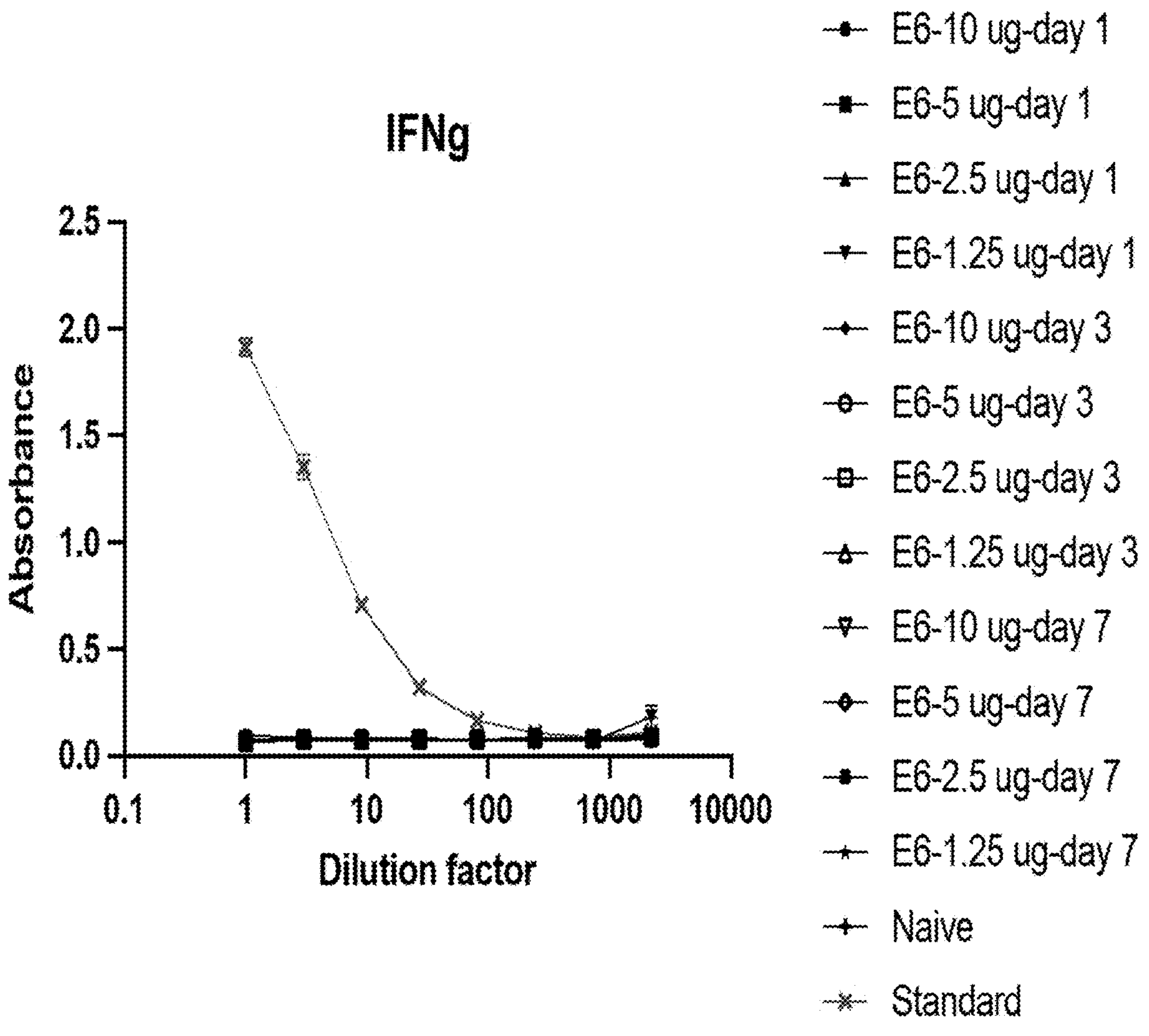
FIG. 12 shows changes in pro-inflammatory cytokine IFNg in mice injected intramuscularly with dosage of 10, 5, 2.5, 1.25 μg mRNA (5 mice/group) at day 0, 1, 3, and 7 post injection as the indicated. The positive control (standard) was labeled as red. Shown are Elisa plots of absorbance (Y-axis) versus dilution factors (X-axis).
Figure 13:
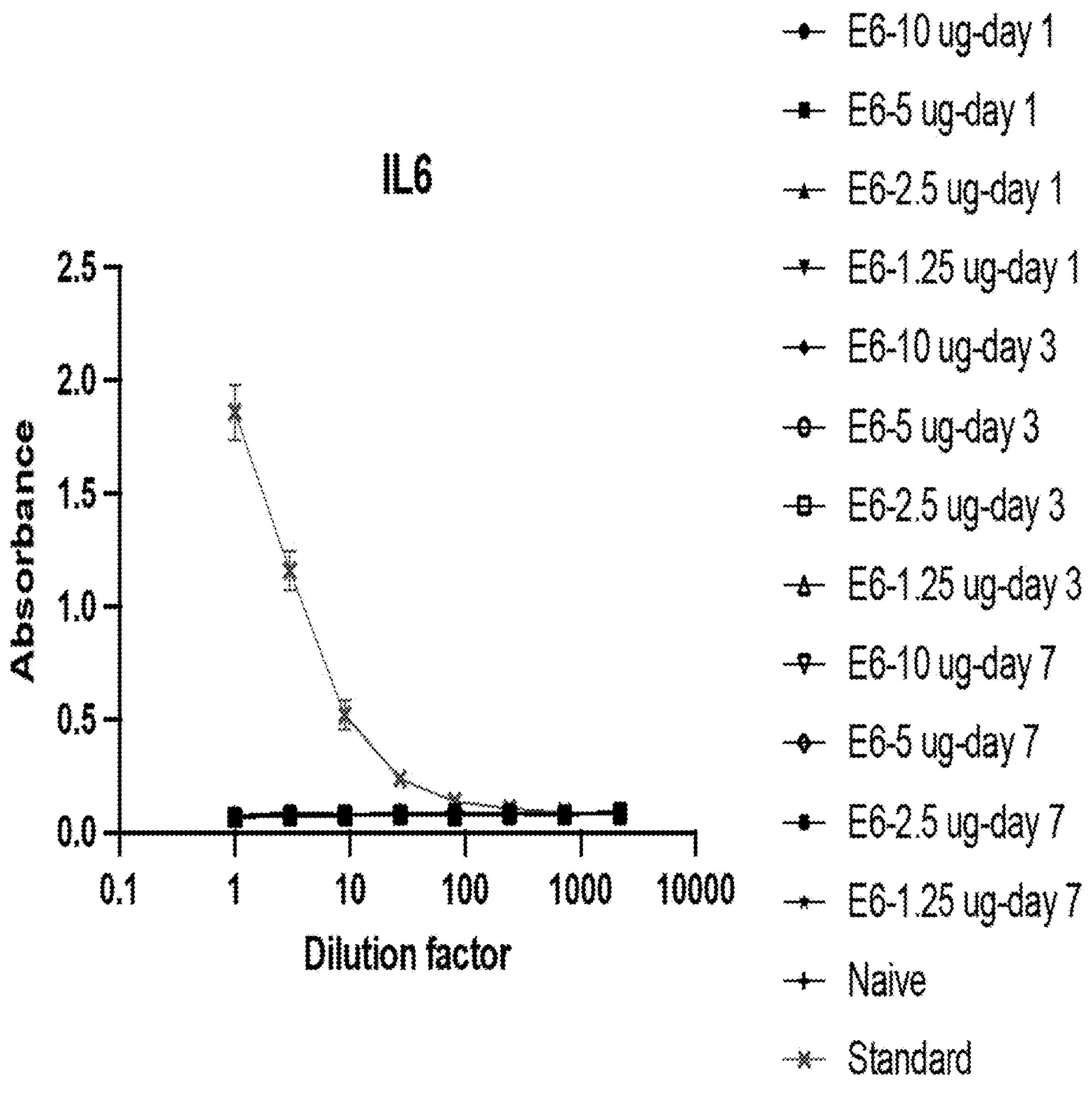
FIG. 13 shows changes in pro-inflammatory cytokine IL6 in mice injected intramuscularly with dosage of 10, 5, 2.5, 1.25 μg mRNA (5 mice/group) at day 0, 1, 3, and 7 post injection as the indicated. The positive control (standard) was labeled as red. Shown are Elisa plots of absorbance (Y-axis) versus dilution factors (X-axis).
Figure 14:
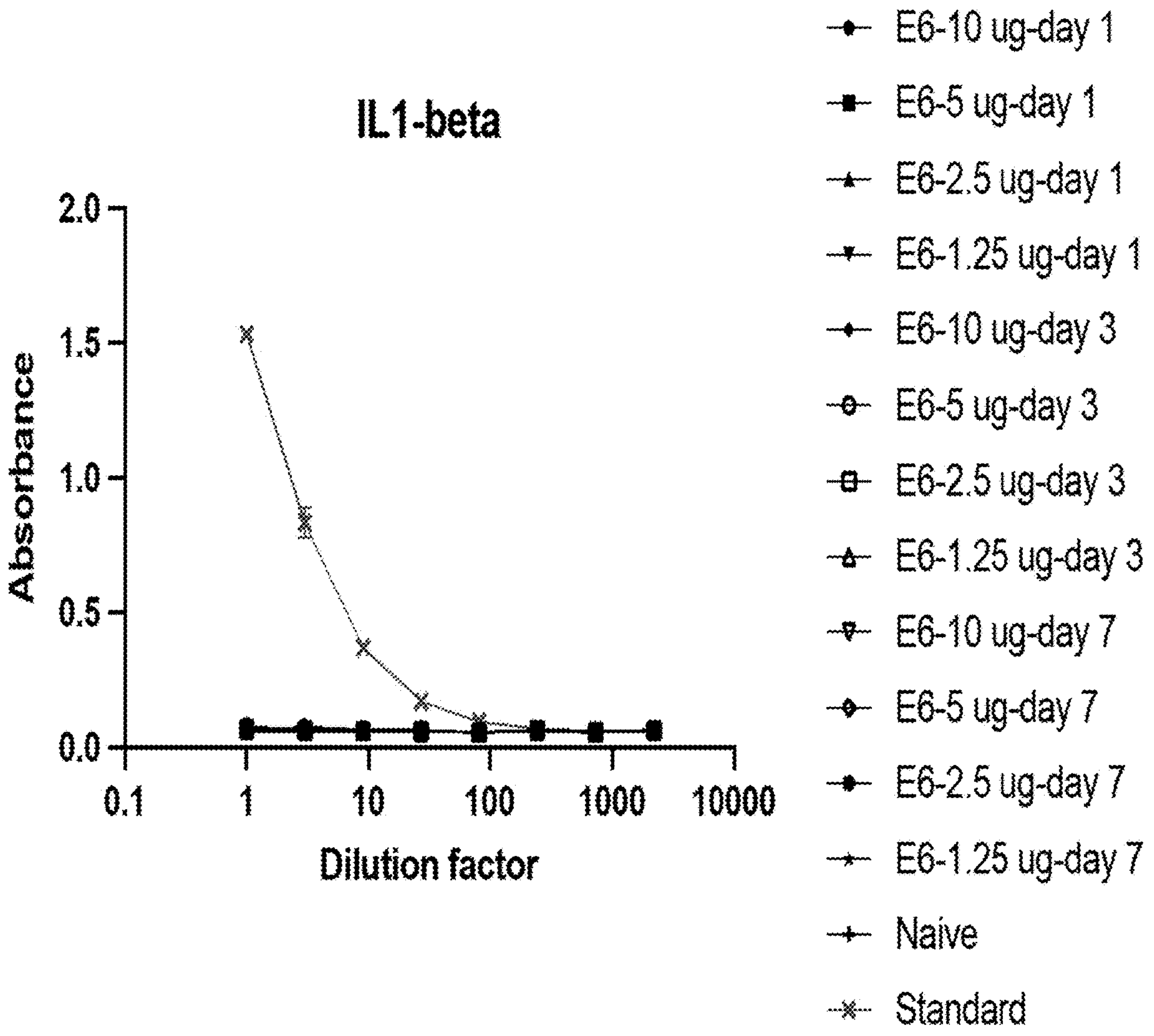
FIG. 14 shows changes in pro-inflammatory cytokine IL1-beta in mice injected intramuscularly with dosage of 10, 5, 2.5, 1.25 μg mRNA (5 mice/group) at day 0, 1, 3, and 7 post injection as the indicated. The positive control (standard) was labeled as red. Shown are Elisa plots of absorbance (Y-axis) versus dilution factors (X-axis).
Figure 15:
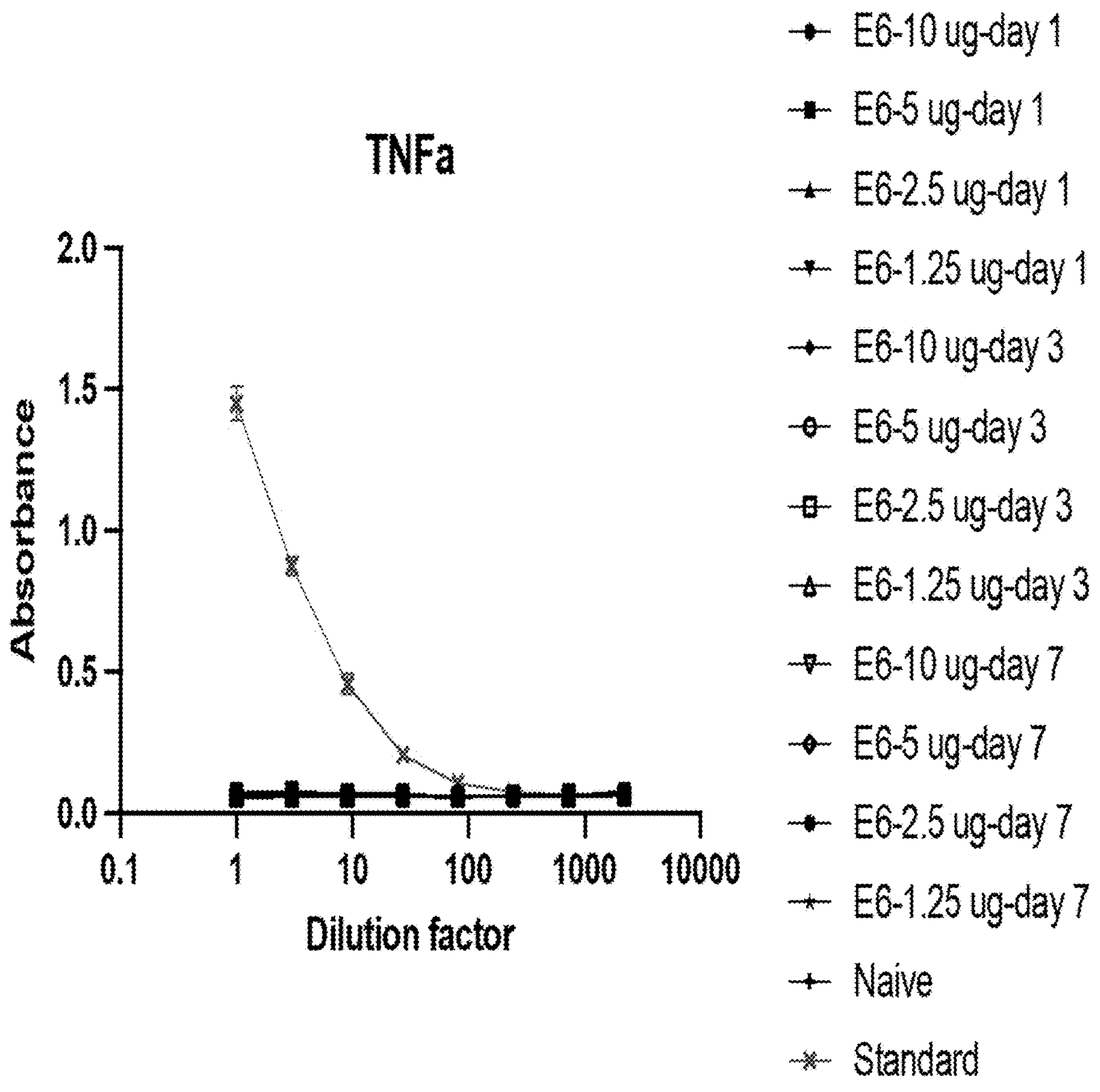
FIG. 15 shows changes in pro-inflammatory cytokine TNFa in mice injected intramuscularly with dosage of 10, 5, 2.5, 1.25 μg mRNA (5 mice/group) at day 0, 1, 3, and 7 post injection as the indicated. The positive control (standard) was labeled as red. Shown are Elisa plots of absorbance (Y-axis) versus dilution factors (X-axis).

FIG. 9 shows a reporter assay of 4 individual sa-mRNAs produced from nucleic acid templates SAM002 (SEQ ID NO: 36), SAM004 (SEQ ID NO: 38), SAM005 (SEQ ID NO: 39), and SAM006 (SEQ ID NO: 40) expressing GFP in Raw-ISG-Lucia cells at day 1 post-transfection where GFP expression is normalized with nsP3 in comparison to SAM002. In the GFP mRNA transcripts in SAM004, SAM005, SAM006, and SAM002, GFP level is 2 times lower in SAM004 and even 1.8 times higher in SAM005, than it in SAM002.

Nucleic Acid Sequences

In the following exemplary sequences, represent exemplary GOI that may be replaced with any other GOI. Persons skilled in the art will recognize that these sequences are exemplary and not limiting disclosures that support and serve as proof of the concepts disclosed and claimed herein.

TABLE 13

| Description | SEQ ID NO. | Sequence |
|---|---|---|
| Subgenomic promoter 1 (SGP1) | SEQ ID NO: 9 | TAACCTGAATGGACTACGACATAGTCTAGTC CGCCAAG |
| Cloning site for SGP1 | SEQ ID NO: 10 | TTCGAAGGCGCGCCTCTA |
| Subgenomic promoter 2 (SGP2) | SEQ ID NO: 11 | GAACTTCCATCATAGTTATGGCCATGACTACT CTAGCTAGCAGTGTTAAATCATTCAGCTACCT GAGAGGGGCCCCTATAACTCTCTACGGC |

TABLE 13-continued

| Description | SEQ ID NO. | Sequence |
| --- | --- | --- |
| Cloning site for SGP2 | SEQ ID NO: 12 | ATCGATGATATCGCGGCCGCATACAGCAGC |
| Murine signal peptide (MSP) | SEQ ID NO: 14 | ATGACCTCCCGGCTTGTGAGGGTACTGGCTG CTGCTATGCTGGTGGCTGCTGCTGTGAGTGTG GC |
| Murine interleukin-12 comprising heavy chain p40 (mIL12 P40) | SEQ ID NO: 15 | ATGTGGGAGCTTGAAAAAGACGTCTATGTAG TAGAAGTGGACTGGACACCTGATGCTCCTGG CGAGACAGTTAACCTCACATGCGATACCCCT GAGGAAGATGATATCACCTGGACTTCTGACC AGAGACACGGGGTGATTGGGAGCGGCAAAA CCCTGACGATCACTGTGAAGGAGTTTCTGGA CGCCGGCCAGTATACCTGTCACAAGGGGGGG GAGACCCTGAGTCATAGCCACCTGTTGCTGC ACAAGAAGGAGAATGGCATCTGGTCTACAGA GATCCTGAAGAACTTTAAGAACAAGACCTTC CTGAAGTGTGAAGCACCAAACTACAGTGGTC GCTTTACCTGCAGCTGGCTGGTCCAAAGAAA CATGGACCTGAAATTTAATATAAAGAGTAGC TCTTCGAGTCCTGATTCCAGGGCCGTGACGT GCGGCATGGCAAGCCTTTCAGCCGAAAAAGT CACGCTGGATCAGCGAGACTATGAGAAGTAC AGCGTTAGCTGTCAGGAGGACGTAACTTGCC CGACTGCCGAGGAGACTCTGCCCATAGAGCT CGCTCTGGAGGCCAGGCAGCAGAACAAATAT GAGAATTACAGCACTAGTTTCTTTATTAGAG ACATCATCAAACCCGACCCACCCAAGAATCT GCAGATGAAGCCGCTGAAGAATAGTCAGGTC GAGGTTTCCTGGGAATATCCAGATTCATGGT CCACTCCGCATTCTTATTTTTCCTTAAAATTC TTTGTTAGGATTCAGCGGAAAAAAGAAAAGA TGAAAGAGACGGAGGAAGGGTGCAACCAGA AGGGGGCCTTCCTGGTGGAAAAGACAAGCAC TGAGGTCCAATGTAAGGGTGGGAACGTTTGC GTGCAGGCTCAGGATCGCTACTACAACAGCA GTTGCTCTAAGTGGGCCTGCGTACCTTGTCGC GTCAGGAGT |
| Linker (L(a)) | SEQ ID NO: 16 | GGAGGGGGGTCAGGGGGTGGCTCAGGCGGC GGCAGTGGGGGCAGC |
| Murine interleukin-12 comprising light chain p35 (mIL12-P35) | SEQ ID NO: 17 | AGGGTGATCCCAGTGTCTGGGCCGGCCCGTT GCTTGTCTCAATCCAGAAACCTCCTCAAGAC CACTGACGATATGGTAAAGACTGCCCGAGAG AAGCTAAAACACTACTCTTGTACAGCTGAAG ATATAGACCATGAGGATATAACACGGGACCA GACCTCTACTCTGAAAACCTGTCTGCCTCTTG AGCTGCACAAGAACGAGTCCTGTCTGGCTAC CCGCGAAACCTCAAGCACAACCAGAGGTAGT TGCCTGCCCCCACAAAAGACATCGCTTATGA TGACCTTGTGTCTGGGATCTATTTATGAGGAC CTGAAGATGTACCAAACTGAGTTCCAGGCAA TAAATGCTGCTCTCCAGAATCACAATCATCA ACAAATCATCCTTGATAAGGGGATGCTGGTC GCAATCGACGAGCTCATGCAATCGCTGAACC ACAATGGGGAAACCCTCAGGCAGAAACCAC CGGTGGGAGAGGCCGACCCCTACCGTGTTAA AATGAAGTTGTGTATTCTTTTGCATGCATTCT CTACAAGAGTCGTTACCATCAATCGCGTCAT GGGGTACCTGTCATCAGCC |
| Linker (L(b)) | SEQ ID NO: 18 | GGCGGTAGTGGTGGTGGGAGC |
| Murine interleukin-21 (mIL21) | SEQ ID NO: 19 | GGGTACCTGTCATCAGCCGGCGGTAGTGGTG GTGGGAGCCACAAGTCCTCCCCCCAGGGTCC GGATCGGCTCTTGATCAGACTGAGACATCTG ATTGATATTGTCGAGCAGTTGAAGATCTATG AGAATGACCTCGATCCTGAGTTACTGAGTGC CCCACAGGACGTTAAAGGGCACTGTGAACAC GCCGCATTTGCTTGTTTTCAGAAGGCCAAGCT GAAACCTTCTAATCCCGGGAATAACAAAACT |

TABLE 13-continued

| Description | SEQ ID NO. | Sequence |
|---|---|---|
| | | TTCATTATCGATCTCGTCGCGCAGCTGAGGC GGCGACTTCCTGCACGGCGGGGGGGAAAA AGCAAAAGCACATCGCAAAGTGTCCCTCATG CGACTCTTACGAGAAACGTACCCCTAAGGAG TTCCTTGAAAGACTCAAATGGCTGCTGCAAA AGATGATCCACCAGCATCTCAGC |
| Human signal peptide (HSP) | SEQ ID NO: 21 | ATGGACTGGACCTGGCGAATACTGTTCTTGG TTGCCGCCGCTACAGGGACTCACGCA |
| Human interleukin-12 comprising heavy chain p40 (hIL12 P40) | SEQ ID NO: 22 | ATATGGGAGCTGAAGAAGGACGTGTATGTCG TGGAGCTGGACTGGTACCCAGATGCTCCTGG CGAAATGGTGGTTTTAACATGTGATACCCCC GAGGAGGACGGCATCACATGGACTCTGGACC AGAGTTCTGAGGTGCTGGGGTCCGGCAAGAC TCTGACAATCCAGGTTAAGGAGTTCGGCGAC GCAGGACAGTACACTTGTCACAAGGGAGGTG AGGTGCTTTCTCACAGCCTGTTGCTGCTCCAT AAGAAGGAAGACGGTATTTGGTCAACCGACA TCCTCAAGGACCAGAAGGAGCCCAAAAACA AGACCTTTCTGAGATGTGAGGCCAAGAATTA CAGCGGTAGATTCACTTGTTGGTGGCTCACC ACCATATCCACAGACTTGACCTTCAGTGTCA AAAGTTCACGAGGGAGCTCAGATCCTCAAGG CGTTACCTGTGGCGCAGCGACGCTGTCCGCA GAAAGAGTCAGGGGAGACAACAAGGAATAC GAGTACTCTGTCGAGTGCCAGGAGGATTCCG CCTGTCCGGCCGCAGAGGAGTCTTTACCTATT GAGGTGATGGTCGATGCCGTGCACAAGCTTA AGTACGAGAATTACACATCAAGTTTTTTCATC CGCGACATCATTAAACCTGATCCACCAAAGA ACCTGCAGCTCAAGCCTCTGAAGAATAGCAG GCAGGTCGAGGTAAGCTGGGAGTATCCTGAT ACCTGGTCCACCCCCCACAGTTATTTCAGCCT CACCTTCTGCGTCCAAGTCCAGGGAAAGAGC AAGAGAGAGAAGAAGGATAGGGTGTTCACA GATAAGACTTCAGCTACTGTGATCTGCAGAA AGAAtGCGTCTATCTCTGTGCGAGCACAAGAC AGGTACTACAGTTCTAGCTGGAGCGAGTGGG CATCAGTCCCCTGCAGT |
| Linker (L(c)) | SEQ ID NO: 23 | GGTGGCGGAAGCGGAGGGGGCAGCGGAGGT GGGAGCGGAGGGAGC |
| Human interleukin-12 comprising light chain p35 (hIL12-P35) | SEQ ID NO 24 | AGGAACCTCCCAGTTGCTACACCTGACCCGG GAATGTTTCCATGCCTCCACCATTCCCAGAAT CTCCTCCGAGCCGTGTCCAATATGCTGCAAA AGGCTCGGCAGACCTTGGAGTTTTACCCTTG CACCTCAGAAGAAATCGATCATGAGGATATC ACAAAGGATAAGACGAGCACTGTTGAGGCAT GCCTGCCCCTGGAGCTAACTAAGAATGAGTC TTGCCTGAACAGCAGGGAGACTTCCTTCATT ACCAACGGTAGCTGTCTTGCCAGCAGGAAGA CATCTTTTATGATGGCCCTGTGTCTATCTAGC ATATATGAAGACCTGAAGATGTACCAGGTGG AATTCAAAACCATGAATGCTAAGCTTCTCAT GGATCCCAAGAGGCAAATCTTCCTGGACCAG AATATGCTTGCTGTCATAGATGAACTGATGC AGGCGTTGAATTTTAACAGCGAGACGGTGCC TCAAAAAAGCTCACTGGAAGAACCTGATTTT TATAAAACGAAGATCAAGCTGTGTATTTTAC TACACGCCTTTAGAATCCGCGCTGTTACCATC GACAGAGTAATGTCCTACCTAAATGCTTCA |
| Linker (L(d)) | SEQ ID NO 25 | GGAGGGTCAGGAGGAGGATCC |
| Human interleukin-21 (hIL21) | SEQ ID NO 26 | CAGGACAGGCATATGATCCGGATGCGGCAGC TGATCGATATTGTAGACCAGTTGAAGAATTA TGTGAACGACTTAGTGCCGGAATTCCTCCCC GCCCCCGAGGACGTGGAGACTAATTGTGAGT GGTCTGCATTCTCATGCTTCCAAAAAGCACA GCTGAAGAGTGCCAATACCGGCAATAACGAA AGGATCATCAATGTAAGTATAAAGAAGTTAA AACGCAAACCGCCCAGTACCAACGCTGGACG |

TABLE 13-continued

| Description | SEQ ID NO. | Sequence |
|---|---|---|
| | | CAGGCAAAAACACAGGCTGACATGCCCCTCG TGTGATTCGTACGAAAAAAAACCTCCAAAGG AATTCCTGGAAAGGTTCAAGTCCTTATTACA GAAAATGATTCACCAGCACCTGAGTAGTAGG ACCCACGGATCCGAAGACTCC |
| Linker 1 | SEQ ID NO: 43 | CGCGTGATAACGCAGGAAAGAACATGTGAG CAAAAGGCCAGCAAAAGGCCAGGAACCGTA AAAAGGCCGCGTTGCTGGCGTT |
| Linker 2 | SEQ ID NO: 44 | CACATTTCCCCGAAAAGTGCCACCTGAGCTC |
| Linker 3 | SEQ ID NO: 45 | TTCGAAGGCGCGCCTCTAGAGCCACC |
| Linker 4 | SEQ ID NO: 46 | CATCGATGATATCGCGGCCGCATACAGCAGC |
| T7' | SEQ ID NO: 47 | TAATACGACTCACTATAGG |
| 5'UTR' | intentionally skipped sequence | ATAGG |
| 3'UTR conserved sequence | SEQ ID NO: 49 | GGATTTTGTTTTTAATATTTC |
| 3'UTR' | SEQ ID NO: 50 | GGATTTTATTTTTAATATTTC |
| 3'UTR' | SEQ ID NO: 51 | AAATTTTGTTTTTAATATTTC |
| 3'UTR' | SEQ ID NO: 52 | AAATTTTATTTTTAATATTTC |

SARS-COV-2, Omicron BA.1-1273

(SEQ ID NO: 1)

ATGTTTGTGTTCTTGGTGTTGCTTCCACTGGTCAGTTCCCAATGCGTTAATCTCACCA
CCCGAACTCAACTCCCACCCGCATATACAAATTCCTTCACCAGAGGAGTGTACTATC
CTGACAAAGTGTTTCGGTCAAGTGTCCTCCACTCTACTCAGGACCTCTTTCTGCCTTT
CTTTTCTAACGTTACATGGTTTCATGTGATCTCTGGGACAAACGGCACCAAACGCTT
CGACAACCCTGTATTGCCATTCAATGATGGGGTGTACTTTGCCTCCATCGAGAAATC
CAACATCATTCGAGGATGGATTTTCGGGACTACTCTGGACTCAAAGACACAGAGCCT
GCTGATCGTTAACAACGCCACAAACGTTGTCATCAAAGTGTGCGAATTCCAGTTTTG
CAATGATCCCTTCCTGGACCACAAGAATAACAAGTCCTGGATGGAGAGCGAATTTC
GGGTCTACAGCAGCGCAAACAACTGCACCTTCGAGTACGTGAGTCAACCCTTTCTGA
TGGACCTGGAAGGGAAACAGGGAAACTTCAAGAACCTGAGAGAGTTTGTCTTTAAG
AACATCGACGGCTATTTTAAGATCTATAGTAAGCATACGCCTATCATTGTAAGGGAG
CCCGAGGATCTTCCCCAGGGCTTTTCAGCCCTGGAACCTTTGGTTGACTTGCCTATTG
GTATCAATATCACCAGATTTCAGACCCTTCTGGCATTGCATCGGTCTTATCTTACTCC
AGGTGATTCCTCCTCCGGGTGGACTGCCGGCGCCGCTGCCTACTATGTCGGCTATCT
GCAACCAAGAACGTTCCTGCTCAAGTACAACGAAAACGGCACTATTACGGATGCTG
TTGATTGTGCCCTGGACCCTCTGTCTGAGACTAAATGCACCCTCAAGAGCTTTACCG
TTGAGAAGGGGATTTACCAAACCAGTAATTTCCGGGTCCAACCCACCGAAAGCATT
GTGCGGTTCCCAAATATCACCAATCTGTGTCCCTTTGATGAAGTGTTCAATGCTACA
AGGTTTGCTTCTGTGTACGCATGGAATAGGAAACGCATCTCCAATTGTGTCGCTGAT
TACTCCGTGCTGTACAATCTGGCCCCATTCTTCACCTTCAAGTGTTATGGCGTTTCAC
CTACCAAACTTAACGACCTGTGCTTCACTAATGTGTATGCCGACTCTTTTGTGATACG
AGGCGATGAAGTGAGACAGATTGCACCAGGGCAGACCGGCAACATTGCCGACTACA
ACTACAAGCTTCCAGATGACTTTACCGGATGTGTTATTGCATGGAACTCAAACAAGC
TGGATTCCAAGGTGAGCGGCAACTATAACTACCTGTATAGACTGTTCAGGAAATCCA
ACCTGAAACCATTCGAGCGAGATATAAGCACAGAAATCTACCAGGCTGGAAACAAA
CCCTGCAACGGCGTGGCTGGGTTCAACTGCTACTTCCCATTGCGCAGTTACAGCTTC
AGACCTACATACGGGGTGGGTCACCAACCCTATCGTGTCGTAGTCCTGAGTTTTGAG
CTCCTCCATGCCCCAGCCACAGTCTGTGGCCCCAAGAAAAGCACCAATCTGGTGAA
GAACAAATGCGTGAACTTTAACTTTAACGGACTCAAGGGAACCGGCGTATTGACGG
AGAGTAACAAGAAGTTCCTGCCATTCCAGCAGTTCGGTCGCGATATTGCCGACACTA
CCGACGCTGTCCGAGATCCCCAGACATTGGAGATTCTTGATATCACACCCTGTAGTT
TCGGCGGAGTGAGCGTGATTACGCCCGGAACCAATACCAGCAATCAGGTTGCCGTC
CTGTATCAGGGCGTGAATTGCACCGAGGTACCTGTCGCCATCCACGCTGACCAACTT
ACACCCACATGGCGAGTATATTCCACCGGCTCCAACGTCTTTCAGACACGTGCTGGA
TGTCTGATCGGTGCAGAATATGTTAATAATAGCTACGAGTGTGATATCCCCATCGGT
GCTGGAATATGCGCCTCTTATCAAACTCAAACCAAATCTCACAGGCGGGCACGTAGT
GTAGCATCCCAAAGTATCATTGCCTACACAATGAGCCTCGGTGCTGAGAATTCTGTC
GCCTACAGCAACAACTCCATTGCTATCCCTACTAACTTCACAATCAGTGTGACAACT
GAAATTCTGCCCGTATCTATGACCAAAACAAGCGTTGACTGCACCATGTACATCTGT
GGCGATTCTACCGAATGTAGCAATCTCCTCCTGCAATACGGATCATTCTGCACTCAG
CTGAAGCGTGCCCTCACAGGTATTGCAGTTGAGCAGGACAAGAATACGCAGGAAGT
GTTTGCCCAGGTGAAGCAAATCTACAAAACTCCACCCATAAAATACTTTGGCGGATT

-continued

CAATTTCTCACAGATCCTGCCCGATCCCTCAAAACCCTCCAAGCGTAGCTTTATCGA
GGATCTGCTCTTCAACAAGGTAACCCTCGCAGATGCCGGTTTCATCAAGCAGTATGG
CGATTGTCTGGGAGACATCGCCGCTCGGGACCTGATCTGTGCACAGAAGTTCAAAG
GACTGACCGTGCTGCCTCCCTTGCTGACCGACGAGATGATAGCCCAATACACTAGCG
CCCTGCTGGCCGGCACCATCACTTCTGGGTGGACATTCGGAGCTGGCGCTGCCCTTC
AGATTCCTTTTGCTATGCAGATGGCCTACCGCTTTAACGGCATCGGTGTGACACAAA
ACGTTCTGTATGAAAACCAGAAACTCATCGCCAACCAGTTCAACAGTGCTATCGGTA
AGATACAGGATAGCCTGTCATCCACTGCCAGCGCATTGGGAAAGTTGCAGGATGTA
GTGAACCACAATGCCCAGGCACTTAACACCCTGGTGAAACAGCTCTCTTCAAAGTTT
GGTGCCATTTCTAGCGTGCTGAATGACATATTTAGCCGGTTGGACAAGGTGGAGGCT
GAAGTGCAGATTGATAGGCTGATAACTGGGCGCCTTCAGTCTCTTCAGACCTATGTG
ACCCAGCAGCTCATCCGCGCTGCTGAAATTCGCGCATCCGCTAACCTGGCAGCAACC
AAAATGTCCGAGTGTGTGCTGGGTCAGTCTAAGAGAGTGGACTTTTGCGGGAAGGG
GTATCACCTGATGTCTTTTCCTCAGTCTGCACCCCATGGTGTGGTCTTTCTGCACGTG
ACTTATGTCCCAGCTCAGGAAAAGAACTTCACTACAGCCCCAGCCATCTGCCACGAT
GGGAAAGCCCACTTTCCCAGGGAAGGCGTATTCGTGTCCAATGGTACTCATTGGTTC
GTCACTCAGAGAAATTTCTACGAGCCCCAGATTATAACCACTGACAATACATTTGTA
TCCGGCAATTGTGATGTGGTTATCGGGATTGTGAATAATACTGTTTACGATCCTTTGC
AGCCAGAGCTGGACTCCTTCAAGGAGGAGCTTGACAAATATTTTAAGAATCACACA
TCACCTGACGTCGACCTCGGAGATATTTCAGGAATCAATGCTTCCGTGGTCAATATT
CAGAAGGAGATAGACAGGCTGAATGAGGTTGCCAAGAACCTCAACGAGTCTCTGAT
CGATCTGCAGGAGTTGGGCAAGTACGAACAGTATATCAAATGGCCTTGGTACATTTG
GCTTGGGTTCATTGCTGGGCTGATAGCTATCGTCATGGTGACAATTATGTTGTGTTGC
ATGACATCCTGCTGTAGTTGTCTGAAGGGCTGCTGCTCATGCGGCAGCTGTTGCAAG
TTCGACGAGGACGATTCTGAGCCCGTGCTGAAGGGCGTGAAACTGCACTACACATG
A

SARS-COV-2, Omicron BA.1-1273-S2P (SEQ ID NO: 2)

ATGTTTGTGTTCTTGGTGTTGCTTCCACTGGTCAGTTCCCAATGCGTTAATCTCACCA
CCCGAACTCAACTCCCACCCGCATATACAAATTCCTTCACCAGAGGAGTGTACTATC
CTGACAAAGTGTTTCGGTCAAGTGTCCTCCACTCTACTCAGGACCTCTTTCTGCCTTT
CTTTTCTAACGTTACATGGTTTCATGTGATCTCTGGGACAAACGGCACCAAACGCTT
CGACAACCCTGTATTGCCATTCAATGATGGGGTGTACTTTGCCTCCATCGAGAAATC
CAACATCATTCGAGGATGGATTTTCGGGACTACTCTGGACTCAAAGACACAGAGCCT
GCTGATCGTTAACAACGCCACAAACGTTGTCATCAAAGTGTGCGAATTCCAGTTTTG
CAATGATCCCTTCCTGGACCACAAGAATAACAAGTCCTGGATGGAGAGCGAATTTC
GGGTCTACAGCAGCGCAAACAACTGCACCTTCGAGTACGTGAGTCAACCCTTTCTGA
TGGACCTGGAAGGGAAACAGGGAAACTTCAAGAACCTGAGAGAGTTTGTCTTTAAG
AACATCGACGGCTATTTTAAGATCTATAGTAAGCATACGCCTATCATTGTAAGGGAG
CCCGAGGATCTTCCCCAGGGCTTTTCAGCCCTGGAACCTTTGGTTGACTTGCCTATTG
GTATCAATATCACCAGATTTCAGACCCTTCTGGCATTGCATCGGTCTTATCTTACTCC
AGGTGATTCCTCCTCCGGGTGGACTGCCGGCGCCGCTGCCTACTATGTCGGCTATCT
GCAACCAAGAACGTTCCTGCTCAAGTACAACGAAAACGGCACTATTACGGATGCTG
TTGATTGTGCCCTGGACCCTCTGTCTGAGACTAAATGCACCCTCAAGAGCTTTACCG
TTGAGAAGGGGATTTACCAAACCAGTAATTTCCGGGTCCAACCCACCGAAAGCATT
GTGCGGTTCCCAAATATCACCAATCTGTGTCCCTTTGATGAAGTGTTCAATGCTACA
AGGTTTGCTTCTGTGTACGCATGGAATAGGAAACGCATCTCCAATTGTGTCGCTGAT
TACTCCGTGCTGTACAATCTGGCCCCATTCTTCACCTTCAAGTGTTATGGCGTTTCAC
CTACCAAACTTAACGACCTGTGCTTCACTAATGTGTATGCCGACTCTTTTGTGATACG
AGGCGATGAAGTGAGACAGATTGCACCAGGGCAGACCGGCAACATTGCCGACTACA
ACTACAAGCTTCCAGATGACTTTACCGGATGTGTTATTGCATGGAACTCAAACAAGC
TGGATTCCAAGGTGAGCGGCAACTATAACTACCTGTATAGACTGTTCAGGAAATCCA
ACCTGAAACCATTCGAGCGAGATATAAGCACAGAAATCTACCAGGCTGGAAACAAA
CCCTGCAACGGCGTGGCTGGGTTCAACTGCTACTTCCCATTGCGCAGTTACAGCTTC
AGACCTACATACGGGGTGGGTCACCAACCCTATCGTGTCGTAGTCCTGAGTTTTGAG
CTCCTCCATGCCCCAGCCACAGTCTGTGGCCCCAAGAAAAGCACCAATCTGGTGAA
GAACAAATGCGTGAACTTTAACTTTAACGGACTCAAGGGAACCGGCGTATTGACGG
AGAGTAACAAGAAGTTCCTGCCATTCCAGCAGTTCGGTCGCGATATTGCCGACACTA
CCGACGCTGTCCGAGATCCCCAGACATTGGAGATTCTTGATATCACACCCTGTAGTT
TCGGCGGAGTGAGCGTGATTACGCCCGGAACCAATACCAGCAATCAGGTTGCCGTC
CTGTATCAGGGCGTGAATTGCACCGAGGTACCTGTCGCCATCCACGCTGACCAACTT
ACACCCACATGGCGAGTATATTCCACCGGCTCCAACGTCTTTCAGACACGTGCTGGA
TGTCTGATCGGTGCAGAATATGTTAATAATAGCTACGAGTGTGATATCCCCATCGGT
GCTGGAATATGCGCCTCTTATCAAACTCAAACCAAATCTCACAGGCGGGCACGTAGT
GTAGCATCCCAAAGTATCATTGCCTACACAATGAGCCTCGGTGCTGAGAATTCTGTC
GCCTACAGCAACAACTCCATTGCTATCCCTACTAACTTCACAATCAGTGTGACAACT
GAAATTCTGCCCGTATCTATGACCAAAACAAGCGTTGACTGCACCATGTACATCTGT
GGCGATTCTACCGAATGTAGCAATCTCCTCCTGCAATACGGATCATTCTGCACTCAG
CTGAAGCGTGCCCTCACAGGTATTGCAGTTGAGCAGGACAAGAATACGCAGGAAGT
GTTTGCCCAGGTGAAGCAAATCTACAAAACTCCACCCATAAAATACTTTGGCGGATT
CAATTTCTCACAGATCCTGCCCGATCCCTCAAAACCCTCCAAGCGTAGCTTTATCGA
GGATCTGCTCTTCAACAAGGTAACCCTCGCAGATGCCGGTTTCATCAAGCAGTATGG
CGATTGTCTGGGAGACATCGCCGCTCGGGACCTGATCTGTGCACAGAAGTTCAAAG
GACTGACCGTGCTGCCTCCCTTGCTGACCGACGAGATGATAGCCCAATACACTAGCG
CCCTGCTGGCCGGCACCATCACTTCTGGGTGGACATTCGGAGCTGGCGCTGCCCTTC
AGATTCCTTTTGCTATGCAGATGGCCTACCGCTTTAACGGCATCGGTGTGACACAAA
ACGTTCTGTATGAAAACCAGAAACTCATCGCCAACCAGTTCAACAGTGCTATCGGTA
AGATACAGGATAGCCTGTCATCCACTGCCAGCGCATTGGGAAAGTTGCAGGATGTA
GTGAACCACAATGCCCAGGCACTTAACACCCTGGTGAAACAGCTCTCTTCAAAGTTT
GGTGCCATTTCTAGCGTGCTGAATGACATATTTAGCCGGTTGGACcctccgGAGGCTGA -continued AGTGCAGATTGATAGGCTGATAACTGGGCGCCTTCAGTCTCTTCAGACCTATGTGAC
CCAGCAGCTCATCCGCGCTGCTGAAATTCGCGCATCCGCTAACCTGGCAGCAACCAA
AATGTCCGAGTGTGTGCTGGGTCAGTCTAAGAGAGTGGACTTTTGCGGGAAGGGGT
ATCACCTGATGTCTTTTCCTCAGTCTGCACCCCATGGTGTGGTCTTTCTGCACGTGAC
TTATGTCCCAGCTCAGGAAAAGAACTTCACTACAGCCCCAGCCATCTGCCACGATGG
GAAAGCCCACTTTCCCAGGGAAGGCGTATTCGTGTCCAATGGTACTCATTGGTTCGT
CACTCAGAGAAATTTCTACGAGCCCCAGATTATAACCACTGACAATACATTTGTATC
CGGCAATTGTGATGTGGTTATCGGGATTGTGAATAATACTGTTTACGATCCTTTGCA
GCCAGAGCTGGACTCCTTCAAGGAGGAGCTTGACAAATATTTTAAGAATCACACATC
ACCTGACGTCGACCTCGGAGATATTTCAGGAATCAATGCTTCCGTGGTCAATATTCA
GAAGGAGATAGACAGGCTGAATGAGGTTGCCAAGAACCTCAACGAGTCTCTGATCG
ATCTGCAGGAGTTGGGCAAGTACGAACAGTATATCAAATGGCCTTGGTACATTTGGC
TTGGGTTCATTGCTGGGCTGATAGCTATCGTCATGGTGACAATTATGTTGTGTTGCAT
GACATCCTGCTGTAGTTGTCTGAAGGGCTGCTGCTCATGCGGCAGCTGTTGCAAGTT
CGACGAGGACGATTCTGAGCCCGTGCTGAAGGGCGTGAAACTGCACTACACATGA SARS-COV-2, Omicron BA.2-1273

(SEQ ID NO: 3)

ATGTTTGTGTTCTTGGTGTTGCTTCCACTGGTCAGTTCCCAATGCGTTAATCTCATCA
CCCGAACTCAATCCTATACAAATTCCTTCACCAGAGGAGTGTACTATCCTGACAAAG
TGTTTCGGTCAAGTGTCCTCCACTCTACTCAGGACCTCTTTCTGCCTTTCTTTTCTAAC
GTTACATGGTTTCATGCAATCCATGTGTCTGGGACAAACGGCACCAAACGCTTCGAC
AACCCTGTATTGCCATTCAATGATGGGGTGTACTTTGCCTCCACAGAGAAATCCAAC
ATCATTCGAGGATGGATTTTCGGGACTACTCTGGACTCAAAGACACAGAGCCTGCTG
ATCGTTAACAACGCCACAAACGTTGTCATCAAAGTGTGCGAATTCCAGTTTTGCAAT
GATCCCTTCCTGGACGTGTACTATCACAAGAATAACAAGTCCTGGATGGAGAGCGA
ATTTCGGGTCTACAGCAGCGCAAACAACTGCACCTTCGAGTACGTGAGTCAACCCTT
TCTGATGGACCTGGAAGGGAAACAGGGAAACTTCAAGAACCTGAGAGAGTTTGTCT
TTAAGAACATCGACGGCTATTTTAAGATCTATAGTAAGCATACGCCTATCAACCTGG
GAAGGGATCTTCCCCAGGGCTTTTCAGCCCTGGAACCTTTGGTTGACTTGCCTATTG
GTATCAATATCACCAGATTTCAGACCCTTCTGGCATTGCATCGGTCTTATCTTACTCC
AGGTGATTCCTCCTCCGGGTGGACTGCCGGCGCCGCTGCCTACTATGTCGGCTATCT
GCAACCAAGAACGTTCCTGCTCAAGTACAACGAAAACGGCACTATTACGGATGCTG
TTGATTGTGCCCTGGACCCTCTGTCTGAGACTAAATGCACCCTCAAGAGCTTTACCG
TTGAGAAGGGGATTTACCAAACCAGTAATTTCCGGGTCCAACCCACCGAAAGCATT
GTGCGGTTCCCAAATATCACCAATCTGTGTCCCTTTGATGAAGTGTTCAATGCTACA
AGGTTTGCTTCTGTGTACGCATGGAATAGGAAACGCATCTCCAATTGTGTCGCTGAT
TACTCCGTGCTGTACAATTTTGCCCCATTCTTCGCTTTCAAGTGTTATGGCGTTTCAC
CTACCAAACTTAACGACCTGTGCTTCACTAATGTGTATGCCGACTCTTTTGTGATACG
AGGCAATGAAGTGAGCCAGATTGCACCAGGGCAGACCGGCAACATTGCCGACTACA
ACTACAAGCTTCCAGATGACTTTACCGGATGTGTTATTGCATGGAACTCAAACAAGC
TGGATTCCAAGGTGGGTGGCAACTATAACTACCTGTATAGACTGTTCAGGAAATCCA
ACCTGAAACCATTCGAGCGAGATATAAGCACAGAAATCTACCAGGCTGGAAACAAA
CCCTGCAACGGCGTGGCTGGGTTCAACTGCTACTTCCCATTGCGCAGTTACGGATTC
AGACCTACATACGGGGTGGGTCACCAACCCTATCGTGTCGTAGTCCTGAGTTTTGAG
CTCCTCCATGCCCCAGCCACAGTCTGTGGCCCCAAGAAAAGCACCAATCTGGTGAA
GAACAAATGCGTGAACTTTAACTTTAACGGACTCACAGGAACCGGCGTATTGACGG
AGAGTAACAAGAAGTTCCTGCCATTCCAGCAGTTCGGTCGCGATATTGCCGACACTA
CCGACGCTGTCCGAGATCCCCAGACATTGGAGATTCTTGATATCACACCCTGTAGTT
TCGGCGGAGTGAGCGTGATTACGCCCGGAACCAATACCAGCAATCAGGTTGCCGTC
CTGTATCAGGGCGTGAATTGCACCGAGGTACCTGTCGCCATCCACGCTGACCAACTT
ACACCCACATGGCGAGTATATTCCACCGGCTCCAACGTCTTTCAGACACGTGCTGGA
TGTCTGATCGGTGCAGAATATGTTAATAATAGCTACGAGTGTGATATCCCCATCGGT
GCTGGAATATGCGCCTCTTATCAAACTCAAACCAAATCTCACAGGCGGGCACGTAGT
GTAGCATCCCAAAGTATCATTGCCTACACAATGAGCCTCGGTGCTGAGAATTCTGTC
GCCTACAGCAACAACTCCATTGCTATCCCTACTAACTTCACAATCAGTGTGACAACT
GAAATTCTGCCCGTATCTATGACCAAAACAAGCGTTGACTGCACCATGTACATCTGT
GGCGATTCTACCGAATGTAGCAATCTCCTCCTGCAATACGGATCATTCTGCACTCAG
CTGAAGCGTGCCCTCACAGGTATTGCAGTTGAGCAGGACAAGAATACGCAGGAAGT
GTTTGCCCAGGTGAAGCAAATCTACAAAACTCCACCCATAAAATACTTTGGCGGATT
CAATTTCTCACAGATCCTGCCCGATCCCTCAAAACCCTCCAAGCGTAGCTTTATCGA
GGATCTGCTCTTCAACAAGGTAACCCTCGCAGATGCCGGTTTCATCAAGCAGTATGG
CGATTGTCTGGGAGACATCGCCGCTCGGGACCTGATCTGTGCACAGAAGTTCAATGG
ACTGACCGTGCTGCCTCCCTTGCTGACCGACGAGATGATAGCCCAATACACTAGCGC
CCTGCTGGCCGGCACCATCACTTCTGGGTGGACATTCGGAGCTGGCGCTGCCCTTCA
GATTCCTTTTGCTATGCAGATGGCCTACCGCTTTAACGGCATCGGTGTGACACAAAA
CGTTCTGTATGAAAACCAGAAACTCATCGCCAACCAGTTCAACAGTGCTATCGGTAA
GATACAGGATAGCCTGTCATCCACTGCCAGCGCATTGGGAAAGTTGCAGGATGTAG
TGAACCACAATGCCCAGGCACTTAACACCCTGGTGAAACAGCTCTCTTCAAAGTTTG
GTGCCATTTCTAGCGTGCTGAATGACATACTGAGCCGGTTGGACAAGGTGGAGGCTG
AAGTGCAGATTGATAGGCTGATAACTGGGCGCCTTCAGTCTCTTCAGACCTATGTGA
CCCAGCAGCTCATCCGCGCTGCTGAAATTCGCGCATCCGCTAACCTGGCAGCAACCA
AAATGTCCGAGTGTGTGCTGGGTCAGTCTAAGAGAGTGGACTTTTGCGGGAAGGGG
TATCACCTGATGTCTTTTCCTCAGTCTGCACCCCATGGTGTGGTCTTTCTGCACGTGA
CTTATGTCCCAGCTCAGGAAAAGAACTTCACTACAGCCCCAGCCATCTGCCACGATG
GGAAAGCCCACTTTCCCAGGGAAGGCGTATTCGTGTCCAATGGTACTCATTGGTTCG
TCACTCAGAGAAATTTCTACGAGCCCCAGATTATAACCACTGACAATACATTTGTAT
CCGGCAATTGTGATGTGGTTATCGGGATTGTGAATAATACTGTTTACGATCCTTTGC
AGCCAGAGCTGGACTCCTTCAAGGAGGAGCTTGACAAATATTTTAAGAATCACACA
TCACCTGACGTCGACCTCGGAGATATTTCAGGAATCAATGCTTCCGTGGTCAATATT
CAGAAGGAGATAGACAGGCTGAATGAGGTTGCCAAGAACCTCAACGAGTCTCTGAT

-continued

CGATCTGCAGGAGTTGGGCAAGTACGAACAGTATATCAAATGGCCTTGGTACATTTG
GCTTGGGTTCATTGCTGGGCTGATAGCTATCGTCATGGTGACAATTATGTTGTGTTGC
ATGACATCCTGCTGTAGTTGTCTGAAGGGCTGCTGCTCATGCGGCAGCTGTTGCAAG
TTCGACGAGGACGATTCTGAGCCCGTGCTGAAGGGCGTGAAACTGCACTACACATG
A

SARS-COV-2, Omicron BA.2-1273-S2P (SEQ ID NO: 4)

ATGTTTGTGTTCTTGGTGTTGCTTCCACTGGTCAGTTCCCAATGCGTTAATCTCATCA
CCCGAACTCAATCCTATACAAATTCCTTCACCAGAGGAGTGTACTATCCTGACAAAG
TGTTTCGGTCAAGTGTCCTCCACTCTACTCAGGACCTCTTTCTGCCTTTCTTTTCTAAC
GTTACATGGTTTCATGCAATCCATGTGTCTGGGACAAACGGCACCAAACGCTTCGAC
AACCCTGTATTGCCATTCAATGATGGGGTGTACTTTGCCTCCACAGAGAAATCCAAC
ATCATTCGAGGATGGATTTTCGGGACTACTCTGGACTCAAAGACACAGAGCCTGCTG
ATCGTTAACAACGCCACAAACGTTGTCATCAAAGTGTGCGAATTCCAGTTTTGCAAT
GATCCCTTCCTGGACGTGTACTATCACAAGAATAACAAGTCCTGGATGGAGAGCGA
ATTTCGGGTCTACAGCAGCGCAAACAACTGCACCTTCGAGTACGTGAGTCAACCCTT
TCTGATGGACCTGGAAGGGAAACAGGGAAACTTCAAGAACCTGAGAGAGTTTGTCT
TTAAGAACATCGACGGCTATTTTAAGATCTATAGTAAGCATACGCCTATCAACCTGG
GAAGGGATCTTCCCCAGGGCTTTTCAGCCCTGGAACCTTTGGTTGACTTGCCTATTG
GTATCAATATCACCAGATTTCAGACCCTTCTGGCATTGCATCGGTCTTATCTTACTCC
AGGTGATTCCTCCTCCGGGTGGACTGCCGGCGCCGCTGCCTACTATGTCGGCTATCT
GCAACCAAGAACGTTCCTGCTCAAGTACAACGAAAACGGCACTATTACGGATGCTG
TTGATTGTGCCCTGGACCCTCTGTCTGAGACTAAATGCACCCTCAAGAGCTTTACCG
TTGAGAAGGGGATTTACCAAACCAGTAATTTCCGGGTCCAACCCACCGAAAGCATT
GTGCGGTTCCCAAATATCACCAATCTGTGTCCCTTTGATGAAGTGTTCAATGCTACA
AGGTTTGCTTCTGTGTACGCATGGAATAGGAAACGCATCTCCAATTGTGTCGCTGAT
TACTCCGTGCTGTACAATTTTGCCCCATTCTTCGCTTTCAAGTGTTATGGCGTTTCAC
CTACCAAACTTAACGACCTGTGCTTCACTAATGTGTATGCCGACTCTTTTGTGATACG
AGGCAATGAAGTGAGCCAGATTGCACCAGGGCAGACCGGCAACATTGCCGACTACA
ACTACAAGCTTCCAGATGACTTTACCGGATGTGTTATTGCATGGAACTCAAACAAGC
TGGATTCCAAGGTGGGTGGCAACTATAACTACCTGTATAGACTGTTCAGGAAATCCA
ACCTGAAACCATTCGAGCGAGATATAAGCACAGAAATCTACCAGGCTGGAAACAAA
CCCTGCAACGGCGTGGCTGGGTTCAACTGCTACTTCCCATTGCGCAGTTACGGATTC
AGACCTACATACGGGGTGGGTCACCAACCCTATCGTGTCGTAGTCCTGAGTTTTGAG
CTCCTCCATGCCCCAGCCACAGTCTGTGGCCCCAAGAAAAGCACCAATCTGGTGAA
GAACAAATGCGTGAACTTTAACTTTAACGGACTCACAGGAACCGGCGTATTGACGG
AGAGTAACAAGAAGTTCCTGCCATTCCAGCAGTTCGGTCGCGATATTGCCGACACTA
CCGACGCTGTCCGAGATCCCCAGACATTGGAGATTCTTGATATCACACCCTGTAGTT
TCGGCGGAGTGAGCGTGATTACGCCCGGAACCAATACCAGCAATCAGGTTGCCGTC
CTGTATCAGGGCGTGAATTGCACCGAGGTACCTGTCGCCATCCACGCTGACCAACTT
ACACCCACATGGCGAGTATATTCCACCGGCTCCAACGTCTTTCAGACACGTGCTGGA
TGTCTGATCGGTGCAGAATATGTTAATAATAGCTACGAGTGTGATATCCCCATCGGT
GCTGGAATATGCGCCTCTTATCAAACTCAAACCAAATCTCACAGGCGGGCACGTAGT
GTAGCATCCCAAAGTATCATTGCCTACACAATGAGCCTCGGTGCTGAGAATTCTGTC
GCCTACAGCAACAACTCCATTGCTATCCCTACTAACTTCACAATCAGTGTGACAACT
GAAATTCTGCCCGTATCTATGACCAAAACAAGCGTTGACTGCACCATGTACATCTGT
GGCGATTCTACCGAATGTAGCAATCTCCTCCTGCAATACGGATCATTCTGCACTCAG
CTGAAGCGTGCCCTCACAGGTATTGCAGTTGAGCAGGACAAGAATACGCAGGAAGT
GTTTGCCCAGGTGAAGCAAATCTACAAAACTCCACCCATAAAATACTTTGGCGGATT
CAATTTCTCACAGATCCTGCCCGATCCCTCAAAACCCTCCAAGCGTAGCTTTATCGA
GGATCTGCTCTTCAACAAGGTAACCCTCGCAGATGCCGGTTTCATCAAGCAGTATGG
CGATTGTCTGGGAGACATCGCCGCTCGGGACCTGATCTGTGCACAGAAGTTCAATGG
ACTGACCGTGCTGCCTCCCTTGCTGACCGACGAGATGATAGCCCAATACACTAGCGC
CCTGCTGGCCGGCACCATCACTTCTGGGTGGACATTCGGAGCTGGCGCTGCCCTTCA
GATTCCTTTTGCTATGCAGATGGCCTACCGCTTTAACGGCATCGGTGTGACACAAAA
CGTTCTGTATGAAAACCAGAAACTCATCGCCAACCAGTTCAACAGTGCTATCGGTAA
GATACAGGATAGCCTGTCATCCACTGCCAGCGCATTGGGAAAGTTGCAGGATGTAG
TGAACCACAATGCCCAGGCACTTAACACCCTGGTGAAACAGCTCTCTTCAAAGTTTG
GTGCCATTTCTAGCGTGCTGAATGACATACTGAGCCGGTTGGACcctccgGAGGCTGAA
GTGCAGATTGATAGGCTGATAACTGGGCGCCTTCAGTCTCTTCAGACCTATGTGACC
CAGCAGCTCATCCGCGCTGCTGAAATTCGCGCATCCGCTAACCTGGCAGCAACCAA
AATGTCCGAGTGTGTGCTGGGTCAGTCTAAGAGAGTGGACTTTTGCGGGAAGGGGT
ATCACCTGATGTCTTTTCCTCAGTCTGCACCCCATGGTGTGGTCTTTCTGCACGTGAC
TTATGTCCCAGCTCAGGAAAAGAACTTCACTACAGCCCCAGCCATCTGCCACGATGG
GAAAGCCCACTTTCCCAGGGAAGGCGTATTCGTGTCCAATGGTACTCATTGGTTCGT
CACTCAGAGAAATTTCTACGAGCCCCAGATTATAACCACTGACAATACATTTGTATC
CGGCAATTGTGATGTGGTTATCGGGATTGTGAATAATACTGTTTACGATCCTTTGCA
GCCAGAGCTGGACTCCTTCAAGGAGGAGCTTGACAAATATTTTAAGAATCACACATC
ACCTGACGTCGACCTCGGAGATATTTCAGGAATCAATGCTTCCGTGGTCAATATTCA
GAAGGAGATAGACAGGCTGAATGAGGTTGCCAAGAACCTCAACGAGTCTCTGATCG
ATCTGCAGGAGTTGGGCAAGTACGAACAGTATATCAAATGGCCTTGGTACATTTGGC
TTGGGTTCATTGCTGGGCTGATAGCTATCGTCATGGTGACAATTATGTTGTGTTGCAT
GACATCCTGCTGTAGTTGTCTGAAGGGCTGCTGCTCATGCGGCAGCTGTTGCAAGTT
CGACGAGGACGATTCTGAGCCCGTGCTGAAGGGCGTGAAACTGCACTACACATGA SARS-COV-2, Omicron BA.1-1208

(SEQ ID NO: 5)

ATGTTTGTGTTCTTGGTGTTGCTTCCACTGGTCAGTTCCCAATGCGTTAATCTCACCA
CCCGAACTCAACTCCCACCCGCATATACAAATTCCTTCACCAGAGGAGTGTACTATC
CTGACAAAGTGTTTCGGTCAAGTGTCCTCCACTCTACTCAGGACCTCTTTCTGCCTTT

-continued

CTTTTCTAACGTTACATGGTTTCATGTGATCTCTGGGACAAACGGCACCAAACGCTT
CGACAACCCTGTATTGCCATTCAATGATGGGGTGTACTTTGCCTCCATCGAGAAATC
CAACATCATTCGAGGATGGATTTTCGGGACTACTCTGGACTCAAAGACACAGAGCCT
GCTGATCGTTAACAACGCCACAAACGTTGTCATCAAAGTGTGCGAATTCCAGTTTTG
CAATGATCCCTTCCTGGACCACAAGAATAACAAGTCCTGGATGGAGAGCGAATTTC
GGGTCTACAGCAGCGCAAACAACTGCACCTTCGAGTACGTGAGTCAACCCTTTCTGA
TGGACCTGGAAGGGAAACAGGGAAACTTCAAGAACCTGAGAGAGTTTGTCTTTAAG
AACATCGACGGCTATTTTAAGATCTATAGTAAGCATACGCCTATCATTGTAAGGGAG
CCCGAGGATCTTCCCCAGGGCTTTTCAGCCCTGGAACCTTTGGTTGACTTGCCTATTG
GTATCAATATCACCAGATTTCAGACCCTTCTGGCATTGCATCGGTCTTATCTTACTCC
AGGTGATTCCTCCTCCGGGTGGACTGCCGGCGCCGCTGCCTACTATGTCGGCTATCT
GCAACCAAGAACGTTCCTGCTCAAGTACAACGAAAACGGCACTATTACGGATGCTG
TTGATTGTGCCCTGGACCCTCTGTCTGAGACTAAATGCACCCTCAAGAGCTTTACCG
TTGAGAAGGGGATTTACCAAACCAGTAATTTCCGGGTCCAACCCACCGAAAGCATT
GTGCGGTTCCCAAATATCACCAATCTGTGTCCCTTTGATGAAGTGTTCAATGCTACA
AGGTTTGCTTCTGTGTACGCATGGAATAGGAAACGCATCTCCAATTGTGTCGCTGAT
TACTCCGTGCTGTACAATCTGGCCCCATTCTTCACCTTCAAGTGTTATGGCGTTTCAC
CTACCAAACTTAACGACCTGTGCTTCACTAATGTGTATGCCGACTCTTTTGTGATACG
AGGCGATGAAGTGAGACAGATTGCACCAGGGCAGACCGGCAACATTGCCGACTACA
ACTACAAGCTTCCAGATGACTTTACCGGATGTGTTATTGCATGGAACTCAAACAAGC
TGGATTCCAAGGTGAGCGGCAACTATAACTACCTGTATAGACTGTTCAGGAAATCCA
ACCTGAAACCATTCGAGCGAGATATAAGCACAGAAATCTACCAGGCTGGAAACAAA
CCCTGCAACGGCGTGGCTGGGTTCAACTGCTACTTCCCATTGCGCAGTTACAGCTTC
AGACCTACATACGGGGTGGGTCACCAACCCTATCGTGTCGTAGTCCTGAGTTTTGAG
CTCCTCCATGCCCCAGCCACAGTCTGTGGCCCCAAGAAAAGCACCAATCTGGTGAA
GAACAAATGCGTGAACTTTAACTTTAACGGACTCAAGGGAACCGGCGTATTGACGG
AGAGTAACAAGAAGTTCCTGCCATTCCAGCAGTTCGGTCGCGATATTGCCGACACTA
CCGACGCTGTCCGAGATCCCCAGACATTGGAGATTCTTGATATCACACCCTGTAGTT
TCGGCGGAGTGAGCGTGATTACGCCCGGAACCAATACCAGCAATCAGGTTGCCGTC
CTGTATCAGGGCGTGAATTGCACCGAGGTACCTGTCGCCATCCACGCTGACCAACTT
ACACCCACATGGCGAGTATATTCCACCGGCTCCAACGTCTTTCAGACACGTGCTGGA
TGTCTGATCGGTGCAGAATATGTTAATAATAGCTACGAGTGTGATATCCCCATCGGT
GCTGGAATATGCGCCTCTTATCAAACTCAAACCAAATCTCACAGGCGGGCACGTAGT
GTAGCATCCCAAAGTATCATTGCCTACACAATGAGCCTCGGTGCTGAGAATTCTGTC
GCCTACAGCAACAACTCCATTGCTATCCCTACTAACTTCACAATCAGTGTGACAACT
GAAATTCTGCCCGTATCTATGACCAAAACAAGCGTTGACTGCACCATGTACATCTGT
GGCGATTCTACCGAATGTAGCAATCTCCTCCTGCAATACGGATCATTCTGCACTCAG
CTGAAGCGTGCCCTCACAGGTATTGCAGTTGAGCAGGACAAGAATACGCAGGAAGT
GTTTGCCCAGGTGAAGCAAATCTACAAAACTCCACCCATAAAATACTTTGGCGGATT
CAATTTCTCACAGATCCTGCCCGATCCCTCAAAACCCTCCAAGCGTAGCTTTATCGA
GGATCTGCTCTTCAACAAGGTAACCCTCGCAGATGCCGGTTTCATCAAGCAGTATGG
CGATTGTCTGGGAGACATCGCCGCTCGGGACCTGATCTGTGCACAGAAGTTCAAAG
GACTGACCGTGCTGCCTCCCTTGCTGACCGACGAGATGATAGCCCAATACACTAGCG
CCCTGCTGGCCGGCACCATCACTTCTGGGTGGACATTCGGAGCTGGCGCTGCCCTTC
AGATTCCTTTTGCTATGCAGATGGCCTACCGCTTTAACGGCATCGGTGTGACACAAA
ACGTTCTGTATGAAAACCAGAAACTCATCGCCAACCAGTTCAACAGTGCTATCGGTA
AGATACAGGATAGCCTGTCATCCACTGCCAGCGCATTGGGAAAGTTGCAGGATGTA
GTGAACCACAATGCCCAGGCACTTAACACCCTGGTGAAACAGCTCTCTTCAAAGTTT
GGTGCCATTTCTAGCGTGCTGAATGACATATTTAGCCGGTTGGACAAGGTGGAGGCT
GAAGTGCAGATTGATAGGCTGATAACTGGGCGCCTTCAGTCTCTTCAGACCTATGTG
ACCCAGCAGCTCATCCGCGCTGCTGAAATTCGCGCATCCGCTAACCTGGCAGCAACC
AAAATGTCCGAGTGTGTGCTGGGTCAGTCTAAGAGAGTGGACTTTTGCGGGAAGGG
GTATCACCTGATGTCTTTTCCTCAGTCTGCACCCCATGGTGTGGTCTTTCTGCACGTG
ACTTATGTCCCAGCTCAGGAAAAGAACTTCACTACAGCCCCAGCCATCTGCCACGAT
GGGAAAGCCCACTTTCCCAGGGAAGGCGTATTCGTGTCCAATGGTACTCATTGGTTC
GTCACTCAGAGAAATTTCTACGAGCCCCAGATTATAACCACTGACAATACATTTGTA
TCCGGCAATTGTGATGTGGTTATCGGGATTGTGAATAATACTGTTTACGATCCTTTGC
AGCCAGAGCTGGACTCCTTCAAGGAGGAGCTTGACAAATATTTTAAGAATCACACA
TCACCTGACGTCGACCTCGGAGATATTTCAGGAATCAATGCTTCCGTGGTCAATATT
CAGAAGGAGATAGACAGGCTGAATGAGGTTGCCAAGAACCTCAACGAGTCTCTGAT
CGATCTGCAGGAGTTGGGCAAGTACGAACAGTAA

SARS-COV-2, Omicron BA.1-1208-S2P (SEQ ID NO: 6)

ATGTTTGTGTTCTTGGTGTTGCTTCCACTGGTCAGTTCCCAATGCGTTAATCTCACCA
CCCGAACTCAACTCCCACCCGCATATACAAATTCCTTCACCAGAGGAGTGTACTATC
CTGACAAAGTGTTTCGGTCAAGTGTCCTCCACTCTACTCAGGACCTCTTTCTGCCTTT
CTTTTCTAACGTTACATGGTTTCATGTGATCTCTGGGACAAACGGCACCAAACGCTT
CGACAACCCTGTATTGCCATTCAATGATGGGGTGTACTTTGCCTCCATCGAGAAATC
CAACATCATTCGAGGATGGATTTTCGGGACTACTCTGGACTCAAAGACACAGAGCCT
GCTGATCGTTAACAACGCCACAAACGTTGTCATCAAAGTGTGCGAATTCCAGTTTTG
CAATGATCCCTTCCTGGACCACAAGAATAACAAGTCCTGGATGGAGAGCGAATTTC
GGGTCTACAGCAGCGCAAACAACTGCACCTTCGAGTACGTGAGTCAACCCTTTCTGA
TGGACCTGGAAGGGAAACAGGGAAACTTCAAGAACCTGAGAGAGTTTGTCTTTAAG
AACATCGACGGCTATTTTAAGATCTATAGTAAGCATACGCCTATCATTGTAAGGGAG
CCCGAGGATCTTCCCCAGGGCTTTTCAGCCCTGGAACCTTTGGTTGACTTGCCTATTG
GTATCAATATCACCAGATTTCAGACCCTTCTGGCATTGCATCGGTCTTATCTTACTCC
AGGTGATTCCTCCTCCGGGTGGACTGCCGGCGCCGCTGCCTACTATGTCGGCTATCT
GCAACCAAGAACGTTCCTGCTCAAGTACAACGAAAACGGCACTATTACGGATGCTG
TTGATTGTGCCCTGGACCCTCTGTCTGAGACTAAATGCACCCTCAAGAGCTTTACCG
TTGAGAAGGGGATTTACCAAACCAGTAATTTCCGGGTCCAACCCACCGAAAGCATT

-continued

GTGCGGTTCCCAAATATCACCAATCTGTGTCCCTTTGATGAAGTGTTCAATGCTACA
AGGTTTGCTTCTGTGTACGCATGGAATAGGAAACGCATCTCCAATTGTGTCGCTGAT
TACTCCGTGCTGTACAATCTGGCCCCATTCTTCACCTTCAAGTGTTATGGCGTTTCAC
CTACCAAACTTAACGACCTGTGCTTCACTAATGTGTATGCCGACTCTTTTGTGATACG
AGGCGATGAAGTGAGACAGATTGCACCAGGGCAGACCGGCAACATTGCCGACTACA
ACTACAAGCTTCCAGATGACTTTACCGGATGTGTTATTGCATGGAACTCAAACAAGC
TGGATTCCAAGGTGAGCGGCAACTATAACTACCTGTATAGACTGTTCAGGAAATCCA
ACCTGAAACCATTCGAGCGAGATATAAGCACAGAAATCTACCAGGCTGGAAACAAA
CCCTGCAACGGCGTGGCTGGGTTCAACTGCTACTTCCCATTGCGCAGTTACAGCTTC
AGACCTACATACGGGGTGGGTCACCAACCCTATCGTGTCGTAGTCCTGAGTTTTGAG
CTCCTCCATGCCCCAGCCACAGTCTGTGGCCCCAAGAAAAGCACCAATCTGGTGAA
GAACAAATGCGTGAACTTTAACTTTAACGGACTCAAGGGAACCGGCGTATTGACGG
AGAGTAACAAGAAGTTCCTGCCATTCCAGCAGTTCGGTCGCGATATTGCCGACACTA
CCGACGCTGTCCGAGATCCCCAGACATTGGAGATTCTTGATATCACACCCTGTAGTT
TCGGCGGAGTGAGCGTGATTACGCCCGGAACCAATACCAGCAATCAGGTTGCCGTC
CTGTATCAGGGCGTGAATTGCACCGAGGTACCTGTCGCCATCCACGCTGACCAACTT
ACACCCACATGGCGAGTATATTCCACCGGCTCCAACGTCTTTCAGACACGTGCTGGA
TGTCTGATCGGTGCAGAATATGTTAATAATAGCTACGAGTGTGATATCCCCATCGGT
GCTGGAATATGCGCCTCTTATCAAACTCAAACCAAATCTCACAGGCGGGCACGTAGT
GTAGCATCCCAAAGTATCATTGCCTACACAATGAGCCTCGGTGCTGAGAATTCTGTC
GCCTACAGCAACAACTCCATTGCTATCCCTACTAACTTCACAATCAGTGTGACAACT
GAAATTCTGCCCGTATCTATGACCAAAACAAGCGTTGACTGCACCATGTACATCTGT
GGCGATTCTACCGAATGTAGCAATCTCCTCCTGCAATACGGATCATTCTGCACTCAG
CTGAAGCGTGCCCTCACAGGTATTGCAGTTGAGCAGGACAAGAATACGCAGGAAGT
GTTTGCCCAGGTGAAGCAAATCTACAAAACTCCACCCATAAAATACTTTGGCGGATT
CAATTTCTCACAGATCCTGCCCGATCCCTCAAAACCCTCCAAGCGTAGCTTTATCGA
GGATCTGCTCTTCAACAAGGTAACCCTCGCAGATGCCGGTTTCATCAAGCAGTATGG
CGATTGTCTGGGAGACATCGCCGCTCGGGACCTGATCTGTGCACAGAAGTTCAAAG
GACTGACCGTGCTGCCTCCCTTGCTGACCGACGAGATGATAGCCCAATACACTAGCG
CCCTGCTGGCCGGCACCATCACTTCTGGGTGGACATTCGGAGCTGGCGCTGCCCTTC
AGATTCCTTTTGCTATGCAGATGGCCTACCGCTTTAACGGCATCGGTGTGACACAAA
ACGTTCTGTATGAAAACCAGAAACTCATCGCCAACCAGTTCAACAGTGCTATCGGTA
AGATACAGGATAGCCTGTCATCCACTGCCAGCGCATTGGGAAAGTTGCAGGATGTA
GTGAACCACAATGCCCAGGCACTTAACACCCTGGTGAAACAGCTCTCTTCAAAGTTT
GGTGCCATTTCTAGCGTGCTGAATGACATATTTAGCCGGTTGGACcctccgGAGGCTGA
AGTGCAGATTGATAGGCTGATAACTGGGCGCCTTCAGTCTCTTCAGACCTATGTGAC
CCAGCAGCTCATCCGCGCTGCTGAAATTCGCGCATCCGCTAACCTGGCAGCAACCAA
AATGTCCGAGTGTGTGCTGGGTCAGTCTAAGAGAGTGGACTTTTGCGGGAAGGGGT
ATCACCTGATGTCTTTTCCTCAGTCTGCACCCCATGGTGTGGTCTTTCTGCACGTGAC
TTATGTCCCAGCTCAGGAAAAGAACTTCACTACAGCCCCAGCCATCTGCCACGATGG
GAAAGCCCACTTTCCCAGGGAAGGCGTATTCGTGTCCAATGGTACTCATTGGTTCGT
CACTCAGAGAAATTTCTACGAGCCCCAGATTATAACCACTGACAATACATTTGTATC
CGGCAATTGTGATGTGGTTATCGGGATTGTGAATAATACTGTTTACGATCCTTTGCA
GCCAGAGCTGGACTCCTTCAAGGAGGAGCTTGACAAATATTTTAAGAATCACACATC
ACCTGACGTCGACCTCGGAGATATTTCAGGAATCAATGCTTCCGTGGTCAATATTCA
GAAGGAGATAGACAGGCTGAATGAGGTTGCCAAGAACCTCAACGAGTCTCTGATCG
ATCTGCAGGAGTTGGGCAAGTACGAACAGTAA SARS-COV-2, Omicron BA.2-1208

(SEQ ID NO: 7)

ATGTTTGTGTTCTTGGTGTTGCTTCCACTGGTCAGTTCCCAATGCGTTAATCTCATCA
CCCGAACTCAATCCTATACAAATTCCTTCACCAGAGGAGTGTACTATCCTGACAAAG
TGTTTCGGTCAAGTGTCCTCCACTCTACTCAGGACCTCTTTCTGCCTTTCTTTTCTAAC
GTTACATGGTTTCATGCAATCCATGTGTCTGGGACAAACGGCACCAAACGCTTCGAC
AACCCTGTATTGCCATTCAATGATGGGGTGTACTTTGCCTCCACAGAGAAATCCAAC
ATCATTCGAGGATGGATTTTCGGGACTACTCTGGACTCAAAGACACAGAGCCTGCTG
ATCGTTAACAACGCCACAAACGTTGTCATCAAAGTGTGCGAATTCCAGTTTTGCAAT
GATCCCTTCCTGGACGTGTACTATCACAAGAATAACAAGTCCTGGATGGAGAGCGA
ATTTCGGGTCTACAGCAGCGCAAACAACTGCACCTTCGAGTACGTGAGTCAACCCTT
TCTGATGGACCTGGAAGGGAAACAGGGAAACTTCAAGAACCTGAGAGAGTTTGTCT
TTAAGAACATCGACGGCTATTTTAAGATCTATAGTAAGCATACGCCTATCAACCTGG
GAAGGGATCTTCCCCAGGGCTTTTCAGCCCTGGAACCTTTGGTTGACTTGCCTATTG
GTATCAATATCACCAGATTTCAGACCCTTCTGGCATTGCATCGGTCTTATCTTACTCC
AGGTGATTCCTCCTCCGGGTGGACTGCCGGCGCCGCTGCCTACTATGTCGGCTATCT
GCAACCAAGAACGTTCCTGCTCAAGTACAACGAAAACGGCACTATTACGGATGCTG
TTGATTGTGCCCTGGACCCTCTGTCTGAGACTAAATGCACCCTCAAGAGCTTTACCG
TTGAGAAGGGGATTTACCAAACCAGTAATTTCCGGGTCCAACCCACCGAAAGCATT
GTGCGGTTCCCAAATATCACCAATCTGTGTCCCTTTGATGAAGTGTTCAATGCTACA
AGGTTTGCTTCTGTGTACGCATGGAATAGGAAACGCATCTCCAATTGTGTCGCTGAT
TACTCCGTGCTGTACAATTTTGCCCCATTCTTCGCTTTCAAGTGTTATGGCGTTTCAC
CTACCAAACTTAACGACCTGTGCTTCACTAATGTGTATGCCGACTCTTTTGTGATACG
AGGCAATGAAGTGAGCCAGATTGCACCAGGGCAGACCGGCAACATTGCCGACTACA
ACTACAAGCTTCCAGATGACTTTACCGGATGTGTTATTGCATGGAACTCAAACAAGC
TGGATTCCAAGGTGGGTGGCAACTATAACTACCTGTATAGACTGTTCAGGAAATCCA
ACCTGAAACCATTCGAGCGAGATATAAGCACAGAAATCTACCAGGCTGGAAACAAA
CCCTGCAACGGCGTGGCTGGGTTCAACTGCTACTTCCCATTGCGCAGTTACGGATTC
AGACCTACATACGGGGTGGGTCACCAACCCTATCGTGTCGTAGTCCTGAGTTTTGAG
CTCCTCCATGCCCCAGCCACAGTCTGTGGCCCCAAGAAAAGCACCAATCTGGTGAA
GAACAAATGCGTGAACTTTAACTTTAACGGACTCACAGGAACCGGCGTATTGACGG
AGAGTAACAAGAAGTTCCTGCCATTCCAGCAGTTCGGTCGCGATATTGCCGACACTA
CCGACGCTGTCCGAGATCCCCAGACATTGGAGATTCTTGATATCACACCCTGTAGTT

-continued

TCGGCGGAGTGAGCGTGATTACGCCCGGAACCAATACCAGCAATCAGGTTGCCGTC
CTGTATCAGGGCGTGAATTGCACCGAGGTACCTGTCGCCATCCACGCTGACCAACTT
ACACCCACATGGCGAGTATATTCCACCGGCTCCAACGTCTTTCAGACACGTGCTGGA
TGTCTGATCGGTGCAGAATATGTTAATAATAGCTACGAGTGTGATATCCCCATCGGT
GCTGGAATATGCGCCTCTTATCAAACTCAAACCAAATCTCACAGGCGGGCACGTAGT
GTAGCATCCCAAAGTATCATTGCCTACACAATGAGCCTCGGTGCTGAGAATTCTGTC
GCCTACAGCAACAACTCCATTGCTATCCCTACTAACTTCACAATCAGTGTGACAACT
GAAATTCTGCCCGTATCTATGACCAAAACAAGCGTTGACTGCACCATGTACATCTGT
GGCGATTCTACCGAATGTAGCAATCTCCTCCTGCAATACGGATCATTCTGCACTCAG
CTGAAGCGTGCCCTCACAGGTATTGCAGTTGAGCAGGACAAGAATACGCAGGAAGT
GTTTGCCCAGGTGAAGCAAATCTACAAAACTCCACCCATAAAATACTTTGGCGGATT
CAATTTCTCACAGATCCTGCCCGATCCCTCAAAACCCTCCAAGCGTAGCTTTATCGA
GGATCTGCTCTTCAACAAGGTAACCCTCGCAGATGCCGGTTTCATCAAGCAGTATGG
CGATTGTCTGGGAGACATCGCCGCTCGGGACCTGATCTGTGCACAGAAGTTCAATGG
ACTGACCGTGCTGCCTCCCTTGCTGACCGACGAGATGATAGCCCAATACACTAGCGC
CCTGCTGGCCGGCACCATCACTTCTGGGTGGACATTCGGAGCTGGCGCTGCCCTTCA
GATTCCTTTTGCTATGCAGATGGCCTACCGCTTTAACGGCATCGGTGTGACACAAAA
CGTTCTGTATGAAAACCAGAAACTCATCGCCAACCAGTTCAACAGTGCTATCGGTAA
GATACAGGATAGCCTGTCATCCACTGCCAGCGCATTGGGAAAGTTGCAGGATGTAG
TGAACCACAATGCCCAGGCACTTAACACCCTGGTGAAACAGCTCTCTTCAAAGTTTG
GTGCCATTTCTAGCGTGCTGAATGACATACTGAGCCGGTTGGACAAGGTGGAGGCTG
AAGTGCAGATTGATAGGCTGATAACTGGGCGCCTTCAGTCTCTTCAGACCTATGTGA
CCCAGCAGCTCATCCGCGCTGCTGAAATTCGCGCATCCGCTAACCTGGCAGCAACCA
AAATGTCCGAGTGTGTGCTGGGTCAGTCTAAGAGAGTGGACTTTTGCGGGAAGGGG
TATCACCTGATGTCTTTTCCTCAGTCTGCACCCCATGGTGTGGTCTTTCTGCACGTGA
CTTATGTCCCAGCTCAGGAAAAGAACTTCACTACAGCCCCAGCCATCTGCCACGATG
GGAAAGCCCACTTTCCCAGGGAAGGCGTATTCGTGTCCAATGGTACTCATTGGTTCG
TCACTCAGAGAAATTTCTACGAGCCCCAGATTATAACCACTGACAATACATTTGTAT
CCGGCAATTGTGATGTGGTTATCGGGATTGTGAATAATACTGTTTACGATCCTTTGC
AGCCAGAGCTGGACTCCTTCAAGGAGGAGCTTGACAAATATTTTAAGAATCACACA
TCACCTGACGTCGACCTCGGAGATATTTCAGGAATCAATGCTTCCGTGGTCAATATT
CAGAAGGAGATAGACAGGCTGAATGAGGTTGCCAAGAACCTCAACGAGTCTCTGAT
CGATCTGCAGGAGTTGGGCAAGTACGAACAGTAA

SARS-COV-2, Omicron BA.2-1208-S2P (SEQ ID NO: 8)

ATGTTTGTGTTCTTGGTGTTGCTTCCACTGGTCAGTTCCCAATGCGTTAATCTCATCA
CCCGAACTCAATCCTATACAAATTCCTTCACCAGAGGAGTGTACTATCCTGACAAAG
TGTTTCGGTCAAGTGTCCTCCACTCTACTCAGGACCTCTTTCTGCCTTTCTTTTCTAAC
GTTACATGGTTTCATGCAATCCATGTGTCTGGGACAAACGGCACCAAACGCTTCGAC
AACCCTGTATTGCCATTCAATGATGGGGTGTACTTTGCCTCCACAGAGAAATCCAAC
ATCATTCGAGGATGGATTTTCGGGACTACTCTGGACTCAAAGACACAGAGCCTGCTG
ATCGTTAACAACGCCACAAACGTTGTCATCAAAGTGTGCGAATTCCAGTTTTGCAAT
GATCCCTTCCTGGACGTGTACTATCACAAGAATAACAAGTCCTGGATGGAGAGCGA
ATTTCGGGTCTACAGCAGCGCAAACAACTGCACCTTCGAGTACGTGAGTCAACCCTT
TCTGATGGACCTGGAAGGGAAACAGGGAAACTTCAAGAACCTGAGAGAGTTTGTCT
TTAAGAACATCGACGGCTATTTTAAGATCTATAGTAAGCATACGCCTATCAACCTGG
GAAGGGATCTTCCCCAGGGCTTTTCAGCCCTGGAACCTTTGGTTGACTTGCCTATTG
GTATCAATATCACCAGATTTCAGACCCTTCTGGCATTGCATCGGTCTTATCTTACTCC
AGGTGATTCCTCCTCCGGGTGGACTGCCGGCGCCGCTGCCTACTATGTCGGCTATCT
GCAACCAAGAACGTTCCTGCTCAAGTACAACGAAAACGGCACTATTACGGATGCTG
TTGATTGTGCCCTGGACCCTCTGTCTGAGACTAAATGCACCCTCAAGAGCTTTACCG
TTGAGAAGGGGATTTACCAAACCAGTAATTTCCGGGTCCAACCCACCGAAAGCATT
GTGCGGTTCCCAAATATCACCAATCTGTGTCCCTTTGATGAAGTGTTCAATGCTACA
AGGTTTGCTTCTGTGTACGCATGGAATAGGAAACGCATCTCCAATTGTGTCGCTGAT
TACTCCGTGCTGTACAATTTTGCCCCATTCTTCGCTTTCAAGTGTTATGGCGTTTCAC
CTACCAAACTTAACGACCTGTGCTTCACTAATGTGTATGCCGACTCTTTTGTGATACG
AGGCAATGAAGTGAGCCAGATTGCACCAGGGCAGACCGGCAACATTGCCGACTACA
ACTACAAGCTTCCAGATGACTTTACCGGATGTGTTATTGCATGGAACTCAAACAAGC
TGGATTCCAAGGTGGGTGGCAACTATAACTACCTGTATAGACTGTTCAGGAAATCCA
ACCTGAAACCATTCGAGCGAGATATAAGCACAGAAATCTACCAGGCTGGAAACAAA
CCCTGCAACGGCGTGGCTGGGTTCAACTGCTACTTCCCATTGCGCAGTTACGGATTC
AGACCTACATACGGGGTGGGTCACCAACCCTATCGTGTCGTAGTCCTGAGTTTTGAG
CTCCTCCATGCCCCAGCCACAGTCTGTGGCCCCAAGAAAAGCACCAATCTGGTGAA
GAACAAATGCGTGAACTTTAACTTTAACGGACTCACAGGAACCGGCGTATTGACGG
AGAGTAACAAGAAGTTCCTGCCATTCCAGCAGTTCGGTCGCGATATTGCCGACACTA
CCGACGCTGTCCGAGATCCCCAGACATTGGAGATTCTTGATATCACACCCTGTAGTT
TCGGCGGAGTGAGCGTGATTACGCCCGGAACCAATACCAGCAATCAGGTTGCCGTC
CTGTATCAGGGCGTGAATTGCACCGAGGTACCTGTCGCCATCCACGCTGACCAACTT
ACACCCACATGGCGAGTATATTCCACCGGCTCCAACGTCTTTCAGACACGTGCTGGA
TGTCTGATCGGTGCAGAATATGTTAATAATAGCTACGAGTGTGATATCCCCATCGGT
GCTGGAATATGCGCCTCTTATCAAACTCAAACCAAATCTCACAGGCGGGCACGTAGT
GTAGCATCCCAAAGTATCATTGCCTACACAATGAGCCTCGGTGCTGAGAATTCTGTC
GCCTACAGCAACAACTCCATTGCTATCCCTACTAACTTCACAATCAGTGTGACAACT
GAAATTCTGCCCGTATCTATGACCAAAACAAGCGTTGACTGCACCATGTACATCTGT
GGCGATTCTACCGAATGTAGCAATCTCCTCCTGCAATACGGATCATTCTGCACTCAG
CTGAAGCGTGCCCTCACAGGTATTGCAGTTGAGCAGGACAAGAATACGCAGGAAGT
GTTTGCCCAGGTGAAGCAAATCTACAAAACTCCACCCATAAAATACTTTGGCGGATT
CAATTTCTCACAGATCCTGCCCGATCCCTCAAAACCCTCCAAGCGTAGCTTTATCGA
GGATCTGCTCTTCAACAAGGTAACCCTCGCAGATGCCGGTTTCATCAAGCAGTATGG
CGATTGTCTGGGAGACATCGCCGCTCGGGACCTGATCTGTGCACAGAAGTTCAATGG

-continued

ACTGACCGTGCTGCCTCCCTTGCTGACCGACGAGATGATAGCCCAATACACTAGCGC
CCTGCTGGCCGGCACCATCACTTCTGGGTGGACATTCGGAGCTGGCGCTGCCCTTCA
GATTCCTTTTGCTATGCAGATGGCCTACCGCTTTAACGGCATCGGTGTGACACAAAA
CGTTCTGTATGAAAACCAGAAACTCATCGCCAACCAGTTCAACAGTGCTATCGGTAA
GATACAGGATAGCCTGTCATCCACTGCCAGCGCATTGGGAAAGTTGCAGGATGTAG
TGAACCACAATGCCCAGGCACTTAACACCCTGGTGAAACAGCTCTCTTCAAAGTTTG
GTGCCATTTCTAGCGTGCTGAATGACATACTGAGCCGGTTGGACcctccgGAGGCTGAA
GTGCAGATTGATAGGCTGATAACTGGGCGCCTTCAGTCTCTTCAGACCTATGTGACC
CAGCAGCTCATCCGCGCTGCTGAAATTCGCGCATCCGCTAACCTGGCAGCAACCAA
AATGTCCGAGTGTGTGCTGGGTCAGTCTAAGAGAGTGGACTTTTGCGGGAAGGGGT
ATCACCTGATGTCTTTTCCTCAGTCTGCACCCCATGGTGTGGTCTTTCTGCACGTGAC
TTATGTCCCAGCTCAGGAAAAGAACTTCACTACAGCCCCAGCCATCTGCCACGATGG
GAAAGCCCACTTTCCCAGGGAAGGCGTATTCGTGTCCAATGGTACTCATTGGTTCGT
CACTCAGAGAAATTTCTACGAGCCCCAGATTATAACCACTGACAATACATTTGTATC
CGGCAATTGTGATGTGGTTATCGGGATTGTGAATAATACTGTTTACGATCCTTTGCA
GCCAGAGCTGGACTCCTTCAAGGAGGAGCTTGACAAATATTTTAAGAATCACACATC
ACCTGACGTCGACCTCGGAGATATTTCAGGAATCAATGCTTCCGTGGTCAATATTCA
GAAGGAGATAGACAGGCTGAATGAGGTTGCCAAGAACCTCAACGAGTCTCTGATCG
ATCTGCAGGAGTTGGGCAAGTACGAACAGTAA Immunomodulator (IM1)(murine signal peptide-mIL12 P40-linker-mIL12-P35-linker-mIl21)

(SEQ ID NO 13)

ATGACCTCCCGGCTTGTGAGGGTACTGGCTGCTGCTATGCTGGTGGCTGCTGCTGTG
AGTGTGGCAATGTGGGAGCTTGAAAAAGACGTCTATGTAGTAGAAGTGGACTGGAC
ACCTGATGCTCCTGGCGAGACAGTTAACCTCACATGCGATACCCCTGAGGAAGATG
ATATCACCTGGACTTCTGACCAGAGACACGGGGTGATTGGGAGCGGCAAAACCCTG
ACGATCACTGTGAAGGAGTTTCTGGACGCCGGCCAGTATACCTGTCACAAGGGGGG
GGAGACCCTGAGTCATAGCCACCTGTTGCTGCACAAGAAGGAGAATGGCATCTGGT
CTACAGAGATCCTGAAGAACTTTAAGAACAAGACCTTCCTGAAGTGTGAAGCACCA
AACTACAGTGGTCGCTTTACCTGCAGCTGGCTGGTCCAAAGAAACATGGACCTGAA
ATTTAATATAAAGAGTAGCTCTTCGAGTCCTGATTCCAGGGCCGTGACGTGCGGCAT
GGCAAGCCTTTCAGCCGAAAAAGTCACGCTGGATCAGCGAGACTATGAGAAGTACA
GCGTTAGCTGTCAGGAGGACGTAACTTGCCCGACTGCCGAGGAGACTCTGCCCATA
GAGCTCGCTCTGGAGGCCAGGCAGCAGAACAAATATGAGAATTACAGCACTAGTTT
CTTTATTAGAGACATCATCAAACCCGACCCACCCAAGAATCTGCAGATGAAGCCGCT
GAAGAATAGTCAGGTCGAGGTTTCCTGGGAATATCCAGATTCATGGTCCACTCCGCA
TTCTTATTTTTCCTTAAAATTCTTTGTTAGGATTCAGCGGAAAAAAGAAAAGATGAA
AGAGACGGAGGAAGGGTGCAACCAGAAGGGGGCCTTCCTGGTGGAAAAGACAAGC
ACTGAGGTCCAATGTAAGGGTGGGAACGTTTGCGTGCAGGCTCAGGATCGCTACTA
CAACAGCAGTTGCTCTAAGTGGGCCTGCGTACCTTGTCGCGTCAGGAGTGGAGGGG
GGTCAGGGGGTGGCTCAGGCGGCGGCAGTGGGGGCAGCAGGGTGATCCCAGTGTCT
GGGCCGGCCCGTTGCTTGTCTCAATCCAGAAACCTCCTCAAGACCACTGACGATATG
GTAAAGACTGCCCGAGAGAAGCTAAAACACTACTCTTGTACAGCTGAAGATATAGA
CCATGAGGATATAACACGGGACCAGACCTCTACTCTGAAAACCTGTCTGCCTCTTGA
GCTGCACAAGAACGAGTCCTGTCTGGCTACCCGCGAAACCTCAAGCACAACCAGAG
GTAGTTGCCTGCCCCCACAAAAGACATCGCTTATGATGACCTTGTGTCTGGGATCTA
TTTATGAGGACCTGAAGATGTACCAAACTGAGTTCCAGGCAATAAATGCTGCTCTCC
AGAATCACAATCATCAACAAATCATCCTTGATAAGGGGATGCTGGTCGCAATCGAC
GAGCTCATGCAATCGCTGAACCACAATGGGGAAACCCTCAGGCAGAAACCACCGGT
GGGAGAGGCCGACCCCTACCGTGTTAAAATGAAGTTGTGTATTCTTTTGCATGCATT
CTCTACAAGAGTCGTTACCATCAATCGCGTCATGGGGTACCTGTCATCAGCCGGCGG
TAGTGGTGGTGGGAGCCACAAGTCCTCCCCCCAGGGTCCGGATCGGCTCTTGATCAG
ACTGAGACATCTGATTGATATTGTCGAGCAGTTGAAGATCTATGAGAATGACCTCGA
TCCTGAGTTACTGAGTGCCCCACAGGACGTTAAAGGGCACTGTGAACACGCCGCATT
TGCTTGTTTTCAGAAGGCCAAGCTGAAACCTTCTAATCCCGGGAATAACAAAACTTT
CATTATCGATCTCGTCGCGCAGCTGAGGCGGCGACTTCCTGCACGGCGGGGGGGGA
AAAAGCAAAAGCACATCGCAAAGTGTCCCTCATGCGACTCTTACGAGAAACGTACC
CCTAAGGAGTTCCTTGAAAGACTCAAATGGCTGCTGCAAAAGATGATCCACCAGCA
TCTCAGCTAG

Immunomodulator (IM2)(human signal peptide-huIL12 P40-linker-huIL12-P35-linker-huIl21)

(SEQ ID NO: 20)

ATGACGTCTCGACTGGTCCGTGTTCTTGCGGCAGCTATGCTGGTGGCAGCTGCCGTT
AGCGTAGCCATATGGGAACTGAAGAAGGATGTCTATGTAGTTGAGCTGGACTGGTA
CCCCGACGCGCCAGGCGAAATGGTGGTGCTCACATGCGACACACCAGAGGAGGACG
GAATCACTTGGACCCTGGACCAGTCTTCAGAGGTGCTTGGGTCCGGTAAAACCTTGA
CCATACAGGTAAAGGAGTTCGGTGACGCAGGCCAGTACACATGTCACAAGGGCGGG
GAAGTGCTCTCACATTCACTCCTTTTGCTCCACAAGAAGGAGGATGGGATATGGTCG
ACTGACATTTTGAAAGACCAGAAGGAGCCTAAGAATAAAACCTTCCTGCGGTGCGA
GGCAAAAAATTATTCAGGGCGATTTACATGTTGGTGGCTTACCACCATTTCGACCGA
TTTAACATTTTCCGTGAAGTCTTCAAGAGGCAGCTCAGATCCACAGGGTGTCACATG
CGGGGCCGCAACCCTGTCCGCAGAAAGGGTGCGGGGGGATAATAAGGAATACGAAT
ACTCCGTGGAATGCCAAGAGGATTCTGCATGCCCTGCCGCCGAGGAAAGTCTGCCC
ATTGAAGTAATGGTGGACGCTGTGCATAAGCTTAAGTACGAGAATTACACCTCCTCA
TTCTTCATAAGGGATATCATTAAACCTGATCCACCAAAGAACCTGCAGCTCAAGCCT
CTGAAGAATAGCAGGCAGGTCGAGGTAAGCTGGGAGTATCCTGATACCTGGTCCAC
CCCCCACAGTTATTTCAGCCTCACCTTCTGCGTCCAAGTCCAGGGAAAGAGCAAGAG
AGAGAAGAAGGATAGGGTGTTCACAGATAAGACTTCAGCTACTGTGATCTGCAGAA
AGAAtGCGTCTATCTCTGTGCGAGCACAAGACAGGTACTACAGTTCTAGCTGGAGCG

-continued

AGTGGGCATCAGTCCCCTGCAGTGGTGGCGGAAGCGGAGGGGGCAGCGGAGGTGG
GAGCGGAGGGGAGCAGGAACCTCCCAGTTGCTACACCTGACCCGGGAATGTTTCCAT
GCCTCCACCATTCCCAGAATCTCCTCCGAGCCGTGTCCAATATGCTGCAAAAGGCTC
GGCAGACCTTGGAGTTTTACCCTTGCACCTCAGAAGAAATCGATCATGAGGATATCA
CAAAGGATAAGACGAGCACTGTTGAGGCATGCCTGCCCCTGGAGCTAACTAAGAAT
GAGTCTTGCCTGAACAGCAGGGAGACTTCCTTCATTACCAACGGTAGCTGTCTTGCC
AGCAGGAAGACATCTTTTATGATGGCCCTGTGTCTATCTAGCATATATGAAGACCTG
AAGATGTACCAGGTGGAATTCAAAACCATGAATGCTAAGCTTCTCATGGATCCCAA
GAGGCAAATCTTCCTGGACCAGAATATGCTTGCTGTCATAGATGAACTGATGCAGGC
GTTGAATTTTAACAGCGAGACGGTGCCTCAAAAAAGCTCACTGGAAGAACCTGATTT
TTATAAAACGAAGATCAAGCTGTGTATTTTACTACACGCCTTTAGAATCCGCGCTGT
TACCATCGACAGAGTAATGTCCTACCTAAATGCTTCAGGAGGGTCAGGAGGAGGAT
CCCAGGACAGGCATATGATCCGGATGCGGCAGCTGATCGATATTGTAGACCAGTTG
AAGAATTATGTGAACGACTTAGTGCCGGAATTCCTCCCCGCCCCCGAGGACGTGGA
GACTAATTGTGAGTGGTCTGCATTCTCATGCTTCCAAAAAGCACAGCTGAAGAGTGC
CAATACCGGCAATAACGAAAGGATCATCAATGTAAGTATAAAGAAGTTAAAACGCA
AACCGCCCAGTACCAACGCTGGACGCAGGCAAAAACACAGGCTGACATGCCCCTCG
TGTGATTCGTACGAAAAAAAACCTCCAAAGGAATTCCTGGAAAGGTTCAAGTCCTTA
TTACAGAAAATGATTCACCAGCACCTGAGTAGTAGGACCCACGGATCCGAAGACTC
CTAG

SAM001

(SEQ ID NO: 35)

AAAAAAAAAACGCGTGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTGGCGCTTT
CTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATC
GTCTTGAGTCCAACCCGGTAAGACACGACTTATCGCCACTGGCAGCAGCCACTGGTA
ACAGGATTAGCAGAGCGAGGTATGTAGGCGGTGCTACAGAGTTCTTGAAGTGGTGG
CCTAACTACGGCTACACTAGAAGAACAGTATTTGGTATCTGCGCTCTGCTGAAGCCA
GTTACCTTCGGAAAAAGAGTTGGTAGCTCTTGATCCGGCAAACAAACCACCGCTGGT
AGCGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGTTA
CCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGC
CCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAG
TTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAG
AATAGTGTATGCGGCGACCGAGTTGCTCTTGCCCGGCGTCAATACGGGATAATACCG
CGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCAC
CCAACTGATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGC
GGATACATATTTGAATGTATTTAGAAAAATAAACAAATAGGGGTTCCGCGCACATTT
CCCCGAAAAGTGCCACCTGAGCTCTAATACGACTCACTATAGgATaGGCGGCGCATG
AGAGAAGCCCAGACCAATTACCTACCCAAAATGGAGAAAGTTCACGTTGACATCGA
GGAAGACAGCCCATTCCTCAGAGCTTTGCAGCGGAGCTTCCCGCAGTTTGAGGTAGA
AGCCAAGCAGGTCACTGATAATGACCATGCTAATGCCAGAGCGTTTTCGCATCTGGC
TTCAAAACTGATCGAAACGGAGGTGGACCCATCCGACACGATCCTTGACATTGGAA
GTGCGCCCGCCCGCAGAATGTATTCTAAGCACAAGTATCATTGTATCTGTCCGATGA
GATGTGCGGAAGATCCGGACAGATTGTATAAGTATGCAACTAAGCTGAAGAAAAAC
TGTAAGGAAATAACTGATAAGGAATTGGACAAGAAAATGAAGGAGCTGGCCGCCGT
CATGAGCGACCCTGACCTGGAAACTGAGACTATGTGCCTCCACGACGACGAGTCGT
GTCGCTACGAAGGGCAAGTCGCTGTTTACCAGGATGTATACGCGGTTGACGGACCG
ACAAGTCTCTATCACCAAGCCAATAAGGGAGTTAGAGTCGCCTACTGGATAGGCTTT
GACACCACCCCTTTTATGTTTAAGAACTTGGCTGGAGCATATCCATCATACTCTACC
AACTGGGCCGACGAAACCGTGTTAACGGCTCGTAACATAGGCCTATGCAGCTCTGA
CGTTATGGAGCGGTCACGTAGAGGGATGTCCATTCTTAGAAAGAAGTATTTGAAACC
ATCCAACAATGTTCTATTCTCTGTTGGCTCGACCATCTACCACGAGAAGAGGGACTT
ACTGAGGAGCTGGCACCTGCCGTCTGTATTTCACTTACGTGGCAAGCAAAATTACAC
ATGTCGGTGTGAGACTATAGTTAGTTGCGACGGGTACGTCGTTAAAAGAATAGCTAT
CAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCG
TGTGCACGTATGTGCCAGCTACATTGTGTGACCAAATGACTGGCATACTGGCAACAG
ATGTCAGTGCGGACGACGCGCAAAAACTGCTGGTTGGGCTCAACCAGCGTATAGTC
GTCAACGGTCGCACCCAGAGAAACACCAATACCATGAAAAATTACCTTTTGCCCGT
AGTGGCCCAGGCATTTGCTAGGTGGGCAAAGGAATATAAGGAAGATCAAGAAGATG
AAAGGCCACTAGGACTACGAGATAGACAGTTAGTCATGGGGTGTTGTTGGGCTTTTA
GAAGGCACAAGATAACATCTATTTATAAGCGCCCGGATACCCAAACCATCATCAAA
GTGAACAGCGATTTCCACTCATTCGTGCTGCCCAGGATAGGCAGTAACACATTGGAG

-continued

ATCGGGCTGAGAACAAGAATCAGGAAAATGTTAGAGGAGCACAAGGAGCCGTCAC
CTCTCATTACCGCCGAGGACGTACAAGAAGCTAAGTGCGCAGCCGATGAGGCTAAG
GAGGTGCGTGAAGCCGAGGAGTTGCGCGCAGCTCTACCACCTTTGGCAGCTGATGTT
GAGGAGCCCACTCTGGAAGCCGATGTCGACTTGATGTTACAAGAGGCTGGGGCCGG
CTCAGTGGAGACACCTCGTGGCTTGATAAAGGTTACCAGCTACGATGGCGAGGACA
AGATCGGCTCTTACGCTGTGCTTTCTCCGCAGGCTGTACTCAAGAGTGAAAAATTAT
CTTGCATCCACCCTCTCGCTGAACAAGTCATAGTGATAACACACTCTGGCCGAAAAG
GGCGTTATGCCGTGGAACCATACCATGGTAAAGTAGTGGTGCCAGAGGGACATGCA
ATACCCGTCCAGGACTTTCAAGCTCTGAGTGAAAGTGCCACCATTGTGTACAACGAA
CGTGAGTTCGTAAACAGGTACCTGCACCATATTGCCACACATGGAGGAGCGCTGAA
CACTGATGAAGAATATTACAAAACTGTCAAGCCCAGCGAGCACGACGGCGAATACC
TGTACGACATCGACAGGAAACAGTGCGTCAAGAAAGAACTAGTCACTGGGCTAGGG
CTCACAGGCGAGCTGGTGGATCCTCCCTTCCATGAATTCGCCTACGAGAGTCTGAGA
ACACGACCAGCCGCTCCTTACCAAGTACCAACCATAGGGGTGTATGGCGTGCCAGG
ATCAGGCAAGTCTGGCATCATTAAAAGCGCAGTCACCAAAAAAGATCTAGTGGTGA
GCGCCAAGAAAGAAAACTGTGCAGAAATTATAAGGGACGTCAAGAAAATGAAAGG
GCTGGACGTCAATGCCAGAACTGTGGACTCAGTGCTCTTGAATGGATGCAAACACCC
CGTAGAGACCCTGTATATTGACGAAGCTTTTGCTTGTCATGCAGGTACTCTCAGAGC
GCTCATAGCCATTATAAGACCTAAAAAGGCAGTGCTCTGCGGGGATCCCAAACAGT
GCGGTTTTTTTAACATGATGTGCCTGAAAGTGCATTTTAACCACGAGATTTGCACAC
AAGTCTTCCACAAAAGCATCTCTCGCCGTTGCACTAAATCTGTGACTTCGGTCGTCTC
AACCTTGTTTTACGACAAAAAAATGAGAACGACGAATCCGAAAGAGACTAAGATTG
TGATTGACACTACCGGCAGTACCAAACCTAAGCAGGACGATCTCATTCTCACTTGTT
TCAGAGGGTGGGTGAAGCAGTTGCAAATAGATTACAAAGGCAACGAAATAATGACG
GCAGCTGCCTCTCAAGGGCTGACCCGTAAAGGTGTGTATGCCGTTCGGTACAAGGTG
AATGAAAATCCTCTGTACGCACCCACCTCAGAACATGTGAACGTCCTACTGACCCGC
ACGGAGGACCGCATCGTGTGGAAAACACTAGCCGGCGACCCATGGATAAAAACACT
GACTGCCAAGTACCCTGGGAATTTCACTGCCACGATAGAGGAGTGGCAAGCAGAGC
ATGATGCCATCATGAGGCACATCTTGGAGAGACCGGACCCTACCGACGTCTTCCAG
AATAAGGCAAACGTGTGTTGGGCCAAGGCTTTAGTGCCGGTGCTGAAGACCGCTGG
CATAGACATGACCACTGAACAATGGAACACTGTGGATTATTTTGAAACGGACAAAG
CTCACTCAGCAGAGATAGTATTGAACCAACTATGCGTGAGGTTCTTTGGACTCGATC
TGGACTCCGGTCTATTTTCTGCACCCACTGTTCCGTTATCCATTAGGAATAATCACTG
GGATAACTCCCCGTCGCCTAACATGTACGGGCTGAATAAAGAAGTGGTCCGTCAGCT
CTCTCGCAGGTACCCACAACTGCCTCGGGCAGTTGCCACTGGAAGAGTCTATGACAT
GAACACTGGTACACTGCGCAATTATGATCCGCGCATAAACCTAGTACCTGTAAACAG
AAGACTGCCTCATGCTTTAGTCCTCCACCATAATGAACACCCACAGAGTGACTTTTC
TTCATTCGTCAGCAAATTGAAGGGCAGAACTGTCCTGGTGGTCGGGGAAAAGTTGTC
CGTCCCAGGCAAAATGGTTGACTGGTTGTCAGACCGGCCTGAGGCTACCTTCAGAGC
TCGGCTGGATTTAGGCATCCCAGGTGATGTGCCCAAATATGACATAATATTTGTTAA
TGTGAGGACCCCATATAAATACCATCACTATCAGCAGTGTGAAGACCATGCCATTAA
GCTTAGCATGTTGACCAAGAAAGCTTGTCTGCATCTGAATCCCGGCGGAACCTGTGT
CAGCATAGGTTATGGTTACGCTGACAGGGCCAGCGAAAGCATCATTGGTGCTATAG
CGCGGCAGTTCAAGTTTTCCCGGGTATGCAAACCGAAATCCTCACTTGAAGAGACGG
AAGTTCTGTTTGTATTCATTGGGTACGATCGCAAGGCCCGTACGCACAATcCTTACAA
GCTTTCATCAACCTTGACCAACATTTATACAGGTTCCAGACTCCACGAAGCCGGATG
TGCACCCTCATATCATGTGGTGCGAGGGGATATTGCCACGGCCACCGAAGGAGTGA
TTATAAATGCTGCTAACAGCAAAGGACAACCTGGCGGAGGGGTGTGCGGAGCGCTG
TATAAGAAATTCCCGGAAAGCTTCGATTTACAGCCGATCGAAGTAGGAAAAGCGCG
ACTGGTCAAAGGTGCAGCTAAACATATCATTCATGCCGTAGGACCAAACTTCAACA
AAGTTTCGGAGGTTGAAGGTGACAAACAGTTGGCAGAGGCTTATGAGTCCATCGCT
AAGATTGTCAACGATAACAATTACAAGTCAGTAGCGATTCCACTGTTGTCCACCGGC
ATCTTTTCCGGGAACAAAGATCGACTAACCCAATCATTGAACCATTTGCTGACAGCT
TTAGACACCACTGATGCAGATGTAGCCATATACTGCAGGGACAAGAAATGGGAAAT
GACTCTCAAGGAAGCAGTGGCTAGGAGAGAAGCAGTGGAGGAGATATGCATATCCG
ACGACTCTTCAGTGACAGAACCTGATGCAGAGCTGGTGAGGGTGCATCCGAAGAGT
TCTTTGGCTGGAAGGAAGGGCTACAGCACAAGCGATGGCAAAACTTTCTCATATTTG
GAAGGGACCAAGTTTCACCAGGCGGCCAAGGATATAGCAGAAATTAATGCCATGTG
GCCCGTTGCAACGGAGGCCAATGAGCAGGTATGCATGTATATCCTCGGAGAAAGCA
TGAGCAGTATTAGGTCGAAATGCCCCGTCGAAGAGTCGGAAGCCTCCACACCACCT
AGCACGCTGCCTTGCTTGTGCATCCATGCCATGACTCCAGAAAGAGTACAGCGCCTA
AAAGCCTCACGTCCAGAACAAATTACTGTGTGCTCATCCTTTCCATTGCCGAAGTAT
AGAATCACTGGTGTGCAGAAGATCCAATGCTCCCAGCCTATATTGTTCTCACCGAAA
GTGCCTGCGTATATTCATCCAAGGAAGTATCTCGTGGAAACACCACCGGTAGACGA
GACTCCGGAGCCATCGGCAGAGAACCAATCCACAGAGGGGACACCTGAACAACCAC
CACTTATAACCGAGGATGAGACCAGGACTAGAACGCCTGAGCCGATCATCATCGAA
GAGGAAGAAGAGGATAGCATAAGTTTGCTGTCAGATGGCCCGACCCACCAGGTGCT
GCAAGTCGAGGCAGACATTCACGGGCCGCCCTCTGTATCTAGCTCATCCTGGTCCAT
TCCTCATGCATCCGACTTTGATGTGGACAGTTTATCCATACTTGACACCCTGGAGGG
AGCTAGCGTGACCAGCGGGGCAACGTCAGCCGAGACTAACTCTTACTTCGCAAAGA
GTATGGAGTTTCTGGCGCGACCGGTGCCTGCGCCTCGAACAGTATTCAGGAACCCTC
CACATCCCGCTCCGCGCACAAGAACACCGTCACTTGCACCCAGCAGGGCCTGCTCG
AGAACCAGCCTAGTTTCCACCCCGCCAGGCGTGAATAGGGTGATCACTAGAGAGGA
GCTCGAGGCGCTTACCCCGTCACGCACTCCTAGCAGGTCGGTCTCGAGAACCAGCCT
GGTCTCCAACCCGCCAGGCGTAAATAGGGTGATTACAAGAGAGGAGTTTGAGGCGT
TCGTAGCACAACAACAATGACGGTTTGATGCGGGTGCATACATCTTTTCCTCCGACA
CCGGTCAAGGGCATTTACAACAAAAATCAGTAAGGCAAACGGTGCTATCCGAAGTG
GTGTTGGAGAGGACCGAATTGGAGATTTCGTATGCCCCGCGCCTCGACCAAGAAAA
AGAAGAATTACTACGCAAGAAATTACAGTTAAATCCCACACCTGCTAACAGAAGCA
GATACCAGTCCAGGAAGGTGGAGAACATGAAAGCCATAACAGCTAGACGTATTCTG
CAAGGCCTAGGGCATTATTTGAAGGCAGAAGGAAAAGTGGAGTGCTACCGAACCCT

-continued

GCATCCTGTTCCTTTGTATTCATCTAGTGTGAACCGTGCCTTTTCAAGCCCCAAGGTC
GCAGTGGAAGCCTGTAACGCCATGTTGAAAGAGAACTTTCCGACTGTGGCTTCTTAC
TGTATTATTCCAGAGTACGATGCCTATTTGGACATGGTTGACGGAGCTTCATGCTGC
TTAGACACTGCCAGTTTTTGCCCTGCAAAGCTGCGCAGCTTTCCAAAGAAACACTCC
TATTTGGAACCCACAATACGATCGGCAGTGCCTTCAGCGATCCAGAACACGCTCCAG
AACGTCCTGGCAGCTGCCACAAAAAGAAATTGCAATGTCACGCAAATGAGAGAATT
GCCCGTATTGGATTCGGCGGCCTTTAATGTGGAATGCTTCAAGAAATATGCGTGTAA
TAATGAATATTGGGAAACGTTTAAAGAAAACCCCATCAGGCTTACTGAAGAAAACG
TGGTAAATTACATTACCAAATTAAAAGGACCAAAAGCTGCTGCTCTTTTTGCGAAGA
CACATAATTTGAATATGTTGCAGGACATACCAATGGACAGGTTTGTAATGGACTTAA
AGAGAGACGTGAAAGTGACTCCAGGAACAAAACATACTGAAGAACGGCCCAAGGT
ACAGGTGATCCAGGCTGCCGATCCGCTAGCAACAGCGTATCTGTGCGGAATCCACC
GAGAGCTGGTTAGGAGATTAAATGCGGTCCTGCTTCCGAACATTCATACACTGTTTG
ATATGTCGGCTGAAGACTTTGACGCTATTATAGCCGAGCACTTCCAGCCTGGGGATT
GTGTTCTGGAAACTGACATCGCGTCGTTTGATAAAAGTGAGGACGACGCCATGGCTC
TGACCGCGTTAATGATTCTGGAAGACTTAGGTGTGGACGCAGAGCTGTTGACGCTGA
TTGAGGCGGCTTTCGGCGAAATTTCATCAATACATTTGCCCACTAAAACTAAATTTA
AATTCGGAGCCATGATGAAATCTGGAATGTTCCTCACACTGTTTGTGAACACAGTCA
TTAACATTGTAATCGCAAGCAGAGTGTTGAGAGAACGGCTAACCGGATCACCATGT
GCAGCATTCATTGGAGATGACAATATCGTGAAAGGAGTCAAATCGGACAAATTAAT
GGCAGACAGGTGCGCCACCTGGTTGAATATGGAAGTCAAGATTATAGATGCTGTGG
TGGGCGAGAAAGCGCCTTATTTCTGTGGAGGGTTTATTTTGTGTGACTCCGTGACCG
GCACAGCGTGCCGTGTGGCAGACCCCCTAAAAAGGCTGTTTAAGCTTGGCAAACCT
CTGGCAGCAGACGATGAACATGATGATGACAGGAGAAGGGCATTGCATGAAGAGTC
AACACGCTGGAACCGAGTGGGTATTCTTTCAGAGCTGTGCAAGGCAGTAGAATCAA
GGTATGAAACCGTAGGAACTTCCATCATAGTTATGGCCATGACTACTCTAGCTAGCA
GTGTTAAATCATTCAGCTACCTGAGAGGGGCCCCTATAACTCTCTACGGCTAACCTG
AATGGACTACGACATAGTCTAGTCCGCCAAGTTCGAAGGCGCGCCTCTAGAgccaccAT
GGTGAGCAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGCGATGCC
ACCTACGGCAAGCTGACCCTGAAGTTCATCTGCACCACCGGCAAGCTGCCCGTGCCC
TGGCCCACCCTCGTGACCACCCTGACCTACGGCGTGCAGTGCTTCAGCCGCTACCCC
GACCACATGAAGCAGCACGACTTCTTCAAGTCCGCCATGCCCGAAGGCTACGTCCA
GGAGCGCACCATCTTCTTCAAGGACGACGGCAACTACAAGACCCGCGCCGAGGTGA
AGTTCGAGGGCGACACCCTGGTGAACCGCATCGAGCTGAAGGGCATCGACTTCAAG
GAGGACGGCAACATCCTGGGGCACAAGCTGGAGTACAACTACAACAGCCACAACGT
CTATATCATGGCCGACAAGCAGAAGAACGGCATCAAGGTGAACTTCAAGATCCGCC
ACAACATCGAGGACGGCAGCGTGCAGCTCGCCGACCACTACCAGCAGAACACCCCC
ATCGGCGACGGCCCCGTGCTGCTGCCCGACAACCACTACCTGAGCACCCAGTCCGCC
CTGAGCAAAGACCCCAACGAGAAGCGCGATCACATGGTCCTGCTGGAGTTCGTGAC
CGCCGCCGGGATCACTCTCGGCATGGACGAGCTGTACAAGtagcATCGATGATATCGC
GGCCGCATACAGCAGCAATTGGCAAGCTGCTTACATAGAACTCGCGGCGATTGGCA
TGCCGCCTTAAAATTTTTATTTTATTTTTCTTTTCTTTTCCGAATCGGATTTTGTTTTTA
ATATTTCAAAAAAAAAAAAAAAA

SAM002

(SEQ ID NO: 36)

AAAAAAAAAACGCGTGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTGGCGCTTT
CTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATC
GTCTTGAGTCCAACCCGGTAAGACACGACTTATCGCCACTGGCAGCAGCCACTGGTA
ACAGGATTAGCAGAGCGAGGTATGTAGGCGGTGCTACAGAGTTCTTGAAGTGGTGG
CCTAACTACGGCTACACTAGAAGAACAGTATTTGGTATCTGCGCTCTGCTGAAGCCA
GTTACCTTCGGAAAAAGAGTTGGTAGCTCTTGATCCGGCAAACAAACCACCGCTGGT
AGCGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGTTA
CCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGC
CCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAG
TTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAG
AATAGTGTATGCGGCGACCGAGTTGCTCTTGCCCGGCGTCAATACGGGATAATACCG
CGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCAC
CCAACTGATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGC
GGATACATATTTGAATGTATTTAGAAAAATAAACAAATAGGGGTTCCGCGCACATTT
CCCCGAAAAGTGCCACCTGAGCTCTAATACGACTCACTATAGgATaGGCGGCGCATG
AGAGAAGCCCAGACCAATTACCTACCCAAAATGGAGAAAGTTCACGTTGACATCGA

-continued

GGAAGACAGCCCATTCCTCAGAGCTTTGCAGCGGAGCTTCCCGCAGTTTGAGGTAGA
AGCCAAGCAGGTCACTGATAATGACCATGCTAATGCCAGAGCGTTTTCGCATCTGGC
TTCAAAACTGATCGAAACGGAGGTGGACCCATCCGACACGATCCTTGACATTGGAA
GTGCGCCCGCCCGCAGAATGTATTCTAAGCACAAGTATCATTGTATCTGTCCGATGA
GATGTGCGGAAGATCCGGACAGATTGTATAAGTATGCAACTAAGCTGAAGAAAAAC
TGTAAGGAAATAACTGATAAGGAATTGGACAAGAAAATGAAGGAGCTGGCCGCCGT
CATGAGCGACCCTGACCTGGAAACTGAGACTATGTGCCTCCACGACGACGAGTCGT
GTCGCTACGAAGGGCAAGTCGCTGTTTACCAGGATGTATACGCGGTTGACGGACCG
ACAAGTCTCTATCACCAAGCCAATAAGGGAGTTAGAGTCGCCTACTGGATAGGCTTT
GACACCACCCCTTTTATGTTTAAGAACTTGGCTGGAGCATATCCATCATACTCTACC
AACTGGGCCGACGAAACCGTGTTAACGGCTCGTAACATAGGCCTATGCAGCTCTGA
CGTTATGGAGCGGTCACGTAGAGGGATGTCCATTCTTAGAAAGAAGTATTTGAAACC
ATCCAACAATGTTCTATTCTCTGTTGGCTCGACCATCTACCACGAGAAGAGGGACTT
ACTGAGGAGCTGGCACCTGCCGTCTGTATTTCACTTACGTGGCAAGCAAAATTACAC
ATGTCGGTGTGAGACTATAGTTAGTTGCGACGGGTACGTCGTTAAAAGAATAGCTAT
CAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCG
TGTGCACGTATGTGCCAGCTACATTGTGTGACCAAATGACTGGCATACTGGCAACAG
ATGTCAGTGCGGACGACGCGCAAAAACTGCTGGTTGGGCTCAACCAGCGTATAGTC
GTCAACGGTCGCACCCAGAGAAACACCAATACCATGAAAAATTACCTTTTGCCCGT
AGTGGCCCAGGCATTTGCTAGGTGGGCAAAGGAATATAAGGAAGATCAAGAAGATG
AAAGGCCACTAGGACTACGAGATAGACAGTTAGTCATGGGGTGTTGTTGGGCTTTTA
GAAGGCACAAGATAACATCTATTTATAAGCGCCCGGATACCCAAACCATCATCAAA
GTGAACAGCGATTTCCACTCATTCGTGCTGCCCAGGATAGGCAGTAACACATTGGAG
ATCGGGCTGAGAACAAGAATCAGGAAAATGTTAGAGGAGCACAAGGAGCCGTCAC
CTCTCATTACCGCCGAGGACGTACAAGAAGCTAAGTGCGCAGCCGATGAGGCTAAG
GAGGTGCGTGAAGCCGAGGAGTTGCGCGCAGCTCTACCACCTTTGGCAGCTGATGTT
GAGGAGCCCACTCTGGAAGCCGATGTCGACTTGATGTTACAAGAGGCTGGGGCCGG
CTCAGTGGAGACACCTCGTGGCTTGATAAAGGTTACCAGCTACGATGGCGAGGACA
AGATCGGCTCTTACGCTGTGCTTTCTCCGCAGGCTGTACTCAAGAGTGAAAAATTAT
CTTGCATCCACCCTCTCGCTGAACAAGTCATAGTGATAACACACTCTGGCCGAAAAG
GGCGTTATGCCGTGGAACCATACCATGGTAAAGTAGTGGTGCCAGAGGGACATGCA
ATACCCGTCCAGGACTTTCAAGCTCTGAGTGAAAGTGCCACCATTGTGTACAACGAA
CGTGAGTTCGTAAACAGGTACCTGCACCATATTGCCACACATGGAGGAGCGCTGAA
CACTGATGAAGAATATTACAAAACTGTCAAGCCCAGCGAGCACGACGGCGAATACC
TGTACGACATCGACAGGAAACAGTGCGTCAAGAAAGAACTAGTCACTGGGCTAGGG
CTCACAGGCGAGCTGGTGGATCCTCCCTTCCATGAATTCGCCTACGAGAGTCTGAGA
ACACGACCAGCCGCTCCTTACCAAGTACCAACCATAGGGGTGTATGGCGTGCCAGG
ATCAGGCAAGTCTGGCATCATTAAAAGCGCAGTCACCAAAAAAGATCTAGTGGTGA
GCGCCAAGAAAGAAAACTGTGCAGAAATTATAAGGGACGTCAAGAAAATGAAAGG
GCTGGACGTCAATGCCAGAACTGTGGACTCAGTGCTCTTGAATGGATGCAAACACCC
CGTAGAGACCCTGTATATTGACGAAGCTTTTGCTTGTCATGCAGGTACTCTCAGAGC
GCTCATAGCCATTATAAGACCTAAAAAGGCAGTGCTCTGCGGGGATCCCAAACAGT
GCGGTTTTTTTAACATGATGTGCCTGAAAGTGCATTTTAACCACGAGATTTGCACAC
AAGTCTTCCACAAAAGCATCTCTCGCCGTTGCACTAAATCTGTGACTTCGGTCGTCTC
AACCTTGTTTTACGACAAAAAAATGAGAACGACGAATCCGAAAGAGACTAAGATTG
TGATTGACACTACCGGCAGTACCAAACCTAAGCAGGACGATCTCATTCTCACTTGTT
TCAGAGGGTGGGTGAAGCAGTTGCAAATAGATTACAAAGGCAACGAAATAATGACG
GCAGCTGCCTCTCAAGGGCTGACCCGTAAAGGTGTGTATGCCGTTCGGTACAAGGTG
AATGAAAATCCTCTGTACGCACCCACCTCAGAACATGTGAACGTCCTACTGACCCGC
ACGGAGGACCGCATCGTGTGGAAAACACTAGCCGGCGACCCATGGATAAAAACACT
GACTGCCAAGTACCCTGGGAATTTCACTGCCACGATAGAGGAGTGGCAAGCAGAGC
ATGATGCCATCATGAGGCACATCTTGGAGAGACCGGACCCTACCGACGTCTTCCAG
AATAAGGCAAACGTGTGTTGGGCCAAGGCTTTAGTGCCGGTGCTGAAGACCGCTGG
CATAGACATGACCACTGAACAATGGAACACTGTGGATTATTTTGAAACGGACAAAG
CTCACTCAGCAGAGATAGTATTGAACCAACTATGCGTGAGGTTCTTTGGACTCGATC
TGGACTCCGGTCTATTTTCTGCACCCACTGTTCCGTTATCCATTAGGAATAATCACTG
GGATAACTCCCCGTCGCCTAACATGTACGGGCTGAATAAAGAAGTGGTCCGTCAGCT
CTCTCGCAGGTACCCACAACTGCCTCGGGCAGTTGCCACTGGAAGAGTCTATGACAT
GAACACTGGTACACTGCGCAATTATGATCCGCGCATAAACCTAGTACCTGTAAACAG
AAGACTGCCTCATGCTTTAGTCCTCCACCATAATGAACACCCACAGAGTGACTTTTC
TTCATTCGTCAGCAAATTGAAGGGCAGAACTGTCCTGGTGGTCGGGGAAAAGTTGTC
CGTCCCAGGCAAAATGGTTGACTGGTTGTCAGACCGGCCTGAGGCTACCTTCAGAGC
TCGGCTGGATTTAGGCATCCCAGGTGATGTGCCCAAATATGACATAATATTTGTTAA
TGTGAGGACCCCATATAAATACCATCACTATCAGCAGTGTGAAGACCATGCCATTAA
GCTTAGCATGTTGACCAAGAAAGCTTGTCTGCATCTGAATCCCGGCGGAACCTGTGT
CAGCATAGGTTATGGTTACGCTGACAGGGCCAGCGAAAGCATCATTGGTGCTATAG
CGCGGCAGTTCAAGTTTTCCCGGGTATGCAAACCGAAATCCTCACTTGAAGAGACGG
AAGTTCTGTTTGTATTCATTGGGTACGATCGCAAGGCCCGTACGCACAATtCTTACAA
GCTTTCATCAACCTTGACCAACATTTATACAGGTTCCAGACTCCACGAAGCCGGATG
TGCACCCTCATATCATGTGGTGCGAGGGGATATTGCCACGGCCACCGAAGGAGTGA
TTATAAATGCTGCTAACAGCAAAGGACAACCTGGCGGAGGGGTGTGCGGAGCGCTG
TATAAGAAATTCCCGGAAAGCTTCGATTTACAGCCGATCGAAGTAGGAAAAGCGCG
ACTGGTCAAAGGTGCAGCTAAACATATCATTCATGCCGTAGGACCAAACTTCAACA
AAGTTTCGGAGGTTGAAGGTGACAAACAGTTGGCAGAGGCTTATGAGTCCATCGCT
AAGATTGTCAACGATAACAATTACAAGTCAGTAGCGATTCCACTGTTGTCCACCGGC
ATCTTTTCCGGGAACAAAGATCGACTAACCCAATCATTGAACCATTTGCTGACAGCT
TTAGACACCACTGATGCAGATGTAGCCATATACTGCAGGGACAAGAAATGGGAAAT
GACTCTCAAGGAAGCAGTGGCTAGGAGAGAAGCAGTGGAGGAGATATGCATATCCG
ACGACTCTTCAGTGACAGAACCTGATGCAGAGCTGGTGAGGGTGCATCCGAAGAGT
TCTTTGGCTGGAAGGAAGGGCTACAGCACAAGCGATGGCAAAACTTTCTCATATTTG

-continued

GAAGGGACCAAGTTTCACCAGGCGGCCAAGGATATAGCAGAAATTAATGCCATGTG
GCCCGTTGCAACGGAGGCCAATGAGCAGGTATGCATGTATATCCTCGGAGAAAGCA
TGAGCAGTATTAGGTCGAAATGCCCCGTCGAAGAGTCGGAAGCCTCCACACCACCT
AGCACGCTGCCTTGCTTGTGCATCCATGCCATGACTCCAGAAAGAGTACAGCGCCTA
AAAGCCTCACGTCCAGAACAAATTACTGTGTGCTCATCCTTTCCATTGCCGAAGTAT
AGAATCACTGGTGTGCAGAAGATCCAATGCTCCCAGCCTATATTGTTCTCACCGAAA
GTGCCTGCGTATATTCATCCAAGGAAGTATCTCGTGGAAACACCACCGGTAGACGA
GACTCCGGAGCCATCGGCAGAGAACCAATCCACAGAGGGGACACCTGAACAACCAC
CACTTATAACCGAGGATGAGACCAGGACTAGAACGCCTGAGCCGATCATCATCGAA
GAGGAAGAAGAGGATAGCATAAGTTTGCTGTCAGATGGCCCGACCCACCAGGTGCT
GCAAGTCGAGGCAGACATTCACGGGCCGCCCTCTGTATCTAGCTCATCCTGGTCCAT
TCCTCATGCATCCGACTTTGATGTGGACAGTTTATCCATACTTGACACCCTGGAGGG
AGCTAGCGTGACCAGCGGGGCAACGTCAGCCGAGACTAACTCTTACTTCGCAAAGA
GTATGGAGTTTCTGGCGCGACCGGTGCCTGCGCCTCGAACAGTATTCAGGAACCCTC
CACATCCCGCTCCGCGCACAAGAACACCGTCACTTGCACCCAGCAGGGCCTGCTCG
AGAACCAGCCTAGTTTCCACCCCGCCAGGCGTGAATAGGGTGATCACTAGAGAGGA
GCTCGAGGCGCTTACCCCGTCACGCACTCCTAGCAGGTCGGTCTCGAGAACCAGCCT
GGTCTCCAACCCGCCAGGCGTAAATAGGGTGATTACAAGAGAGGAGTTTGAGGCGT
TCGTAGCACAACAACAATGACGGTTTGATGCGGGTGCATACATCTTTTCCTCCGACA
CCGGTCAAGGGCATTTACAACAAAAATCAGTAAGGCAAACGGTGCTATCCGAAGTG
GTGTTGGAGAGGACCGAATTGGAGATTTCGTATGCCCCGCGCCTCGACCAAGAAAA
AGAAGAATTACTACGCAAGAAATTACAGTTAAATCCCACACCTGCTAACAGAAGCA
GATACCAGTCCAGGAAGGTGGAGAACATGAAAGCCATAACAGCTAGACGTATTCTG
CAAGGCCTAGGGCATTATTTGAAGGCAGAAGGAAAAGTGGAGTGCTACCGAACCCT
GCATCCTGTTCCTTTGTATTCATCTAGTGTGAACCGTGCCTTTTCAAGCCCCAAGGTC
GCAGTGGAAGCCTGTAACGCCATGTTGAAAGAGAACTTTCCGACTGTGGCTTCTTAC
TGTATTATTCCAGAGTACGATGCCTATTTGGACATGGTTGACGGAGCTTCATGCTGC
TTAGACACTGCCAGTTTTTGCCCTGCAAAGCTGCGCAGCTTTCCAAAGAAACACTCC
TATTTGGAACCCACAATACGATCGGCAGTGCCTTCAGCGATCCAGAACACGCTCCAG
AACGTCCTGGCAGCTGCCACAAAAAGAAATTGCAATGTCACGCAAATGAGAGAATT
GCCCGTATTGGATTCGGCGGCCTTTAATGTGGAATGCTTCAAGAAATATGCGTGTAA
TAATGAATATTGGGAAACGTTTAAAGAAAACCCCATCAGGCTTACTGAAGAAAACG
TGGTAAATTACATTACCAAATTAAAAGGACCAAAAGCTGCTGCTCTTTTTGCGAAGA
CACATAATTTGAATATGTTGCAGGACATACCAATGGACAGGTTTGTAATGGACTTAA
AGAGAGACGTGAAAGTGACTCCAGGAACAAAACATACTGAAGAACGGCCCAAGGT
ACAGGTGATCCAGGCTGCCGATCCGCTAGCAACAGCGTATCTGTGCGGAATCCACC
GAGAGCTGGTTAGGAGATTAAATGCGGTCCTGCTTCCGAACATTCATACACTGTTTG
ATATGTCGGCTGAAGACTTTGACGCTATTATAGCCGAGCACTTCCAGCCTGGGGATT
GTGTTCTGGAAACTGACATCGCGTCGTTTGATAAAAGTGAGGACGACGCCATGGCTC
TGACCGCGTTAATGATTCTGGAAGACTTAGGTGTGGACGCAGAGCTGTTGACGCTGA
TTGAGGCGGCTTTCGGCGAAATTTCATCAATACATTTGCCCACTAAAACTAAATTTA
AATTCGGAGCCATGATGAAATCTGGAATGTTCCTCACACTGTTTGTGAACACAGTCA
TTAACATTGTAATCGCAAGCAGAGTGTTGAGAGAACGGCTAACCGGATCACCATGT
GCAGCATTCATTGGAGATGACAATATCGTGAAAGGAGTCAAATCGGACAAATTAAT
GGCAGACAGGTGCGCCACCTGGTTGAATATGGAAGTCAAGATTATAGATGCTGTGG
TGGGCGAGAAAGCGCCTTATTTCTGTGGAGGGTTTATTTTGTGTGACTCCGTGACCG
GCACAGCGTGCCGTGTGGCAGACCCCCTAAAAAGGCTGTTTAAGCTTGGCAAACCT
CTGGCAGCAGACGATGAACATGATGATGACAGGAGAAGGGCATTGCATGAAGAGTC
AACACGCTGGAACCGAGTGGGTATTCTTTCAGAGCTGTGCAAGGCAGTAGAATCAA
GGTATGAAACCGTAGGAACTTCCATCATAGTTATGGCCATGACTACTCTAGCTAGCA
GTGTTAAATCATTCAGCTACCTGAGAGGGGCCCCTATAACTCTCTACGGCTAACCTG
AATGGACTACGACATAGTCTAGTCCGCCAAGTTCGAAGGCGCGCCTCTAGAGCCAC
CATGGTGAGCAAGGGCGAGGAGCTGTTCACCGGGGTGGTGCCCATCCTGGTCG
AGCTGGACGGCGACGTAAACGGCCACAAGTTCAGCGTGTCCGGCGAGGGCGA
GGGCGATGCCACCTACGGCAAGCTGACCCTGAAGTTCATCTGCACCACCGGCA
AGCTGCCCGTGCCCTGGCCCACCCTCGTGACCACCCTGACCTACGGCGTGCAG
TGCTTCAGCCGCTACCCCGACCACATGAAGCAGCACGACTTCTTCAAGTCCGC
CATGCCCGAAGGCTACGTCCAGGAGCGCACCATCTTCTTCAAGGACGACGGCA
ACTACAAGACCCGCGCCGAGGTGAAGTTCGAGGGCGACACCCTGGTGAACCGC
ATCGAGCTGAAGGGCATCGACTTCAAGGAGGACGGCAACATCCTGGGGCACAA
GCTGGAGTACAACTACAACAGCCACAACGTCTATATCATGGCCGACAAGCAGA
AGAACGGCATCAAGGTGAACTTCAAGATCCGCCACAACATCGAGGACGGCAGC
GTGCAGCTCGCCGACCACTACCAGCAGAACACCCCCATCGGCGACGGCCCCGT
GCTGCTGCCCGACAACCACTACCTGAGCACCCAGTCCGCCCTGAGCAAAGACC
CCAACGAGAAGCGCGATCACATGGTCCTGCTGGAGTTCGTGACCGCCGCCGGG
ATCACTCTCGGCATGGACGAGCTGTACAAGTAGCATCGATGATATCGCGGCCGC
ATACAGCAGCAATTGGCAAGCTGCTTACATAGAACTCGCGGCGATTGGCATGCCGC
CTTAAAATTTTTATTTTATTTTTCTTTTCTTTTCCGAATCGGATTTTGTTTTTAATATTT
CAAAAAAAAAAAAAAAA

SAM003

(SEQ ID NO: 37)

AAAAAAAAAACGCGTGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTGGCGCTTT
CTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATC
GTCTTGAGTCCAACCCGGTAAGACACGACTTATCGCCACTGGCAGCAGCCACTGGTA
ACAGGATTAGCAGAGCGAGGTATGTAGGCGGTGCTACAGAGTTCTTGAAGTGGTGG

-continued

CCTAACTACGGCTACACTAGAAGAACAGTATTTGGTATCTGCGCTCTGCTGAAGCCA
GTTACCTTCGGAAAAAGAGTTGGTAGCTCTTGATCCGGCAAACAAACCACCGCTGGT
AGCGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGTTA
CCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGC
CCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAG
TTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAG
AATAGTGTATGCGGCGACCGAGTTGCTCTTGCCCGGCGTCAATACGGGATAATACCG
CGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCAC
CCAACTGATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGC
GGATACATATTTGAATGTATTTAGAAAAATAAACAAATAGGGGTTCCGCGCACATTT
CCCCGAAAAGTGCCACCTGAGCTCTAATACGACTCACTATAGgATaGGCGGCGCATG
AGAGAAGCCCAGACCAATTACCTACCCAAAATGGAGAAAGTTCACGTTGACATCGA
GGAAGACAGCCCATTCCTCAGAGCTTTGCAGCGGAGCTTCCCGCAGTTTGAGGTAGA
AGCCAAGCAGGTCACTGATAATGACCATGCTAATGCCAGAGCGTTTTCGCATCTGGC
TTCAAAACTGATCGAAACGGAGGTGGACCCATCCGACACGATCCTTGACATTGGAA
GTGCGCCCGCCCGCAGAATGTATTCTAAGCACAAGTATCATTGTATCTGTCCGATGA
GATGTGCGGAAGATCCGGACAGATTGTATAAGTATGCAACTAAGCTGAAGAAAAAC
TGTAAGGAAATAACTGATAAGGAATTGGACAAGAAAATGAAGGAGCTGGCCGCCGT
CATGAGCGACCCTGACCTGGAAACTGAGACTATGTGCCTCCACGACGACGAGTCGT
GTCGCTACGAAGGGCAAGTCGCTGTTTACCAGGATGTATACGCGGTTGACGGACCG
ACAAGTCTCTATCACCAAGCCAATAAGGGAGTTAGAGTCGCCTACTGGATAGGCTTT
GACACCACCCCTTTTATGTTTAAGAACTTGGCTGGAGCATATCCATCATACTCTACC
AACTGGGCCGACGAAACCGTGTTAACGGCTCGTAACATAGGCCTATGCAGCTCTGA
CGTTATGGAGCGGTCACGTAGAGGGATGTCCATTCTTAGAAAGAAGTATTTGAAACC
ATCCAACAATGTTCTATTCTCTGTTGGCTCGACCATCTACCACGAGAAGAGGGACTT
ACTGAGGAGCTGGCACCTGCCGTCTGTATTTCACTTACGTGGCAAGCAAAATTACAC
ATGTCGGTGTGAGACTATAGTTAGTTGCGACGGGTACGTCGTTAAAAGAATAGCTAT
CAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCG
TGTGCACGTATGTGCCAGCTACATTGTGTGACCAAATGACTGGCATACTGGCAACAG
ATGTCAGTGCGGACGACGCGCAAAAACTGCTGGTTGGGCTCAACCAGCGTATAGTC
GTCAACGGTCGCACCCAGAGAAACACCAATACCATGAAAAATTACCTTTTGCCCGT
AGTGGCCCAGGCATTTGCTAGGTGGGCAAAGGAATATAAGGAAGATCAAGAAGATG
AAAGGCCACTAGGACTACGAGATAGACAGTTAGTCATGGGGTGTTGTTGGGCTTTTA
GAAGGCACAAGATAACATCTATTTATAAGCGCCCGGATACCCAAACCATCATCAAA
GTGAACAGCGATTTCCACTCATTCGTGCTGCCCAGGATAGGCAGTAACACATTGGAG
ATCGGGCTGAGAACAAGAATCAGGAAAATGTTAGAGGAGCACAAGGAGCCGTCAC
CTCTCATTACCGCCGAGGACGTACAAGAAGCTAAGTGCGCAGCCGATGAGGCTAAG
GAGGTGCGTGAAGCCGAGGAGTTGCGCGCAGCTCTACCACCTTTGGCAGCTGATGTT
GAGGAGCCCACTCTGGAAGCCGATGTCGACTTGATGTTACAAGAGGCTGGGGCCGG
CTCAGTGGAGACACCTCGTGGCTTGATAAAGGTTACCAGCTACGATGGCGAGGACA
AGATCGGCTCTTACGCTGTGCTTTCTCCGCAGGCTGTACTCAAGAGTGAAAAATTAT
CTTGCATCCACCCTCTCGCTGAACAAGTCATAGTGATAACACACTCTGGCCGAAAAG
GGCGTTATGCCGTGGAACCATACCATGGTAAAGTAGTGGTGCCAGAGGGACATGCA
ATACCCGTCCAGGACTTTCAAGCTCTGAGTGAAAGTGCCACCATTGTGTACAACGAA
CGTGAGTTCGTAAACAGGTACCTGCACCATATTGCCACACATGGAGGAGCGCTGAA
CACTGATGAAGAATATTACAAAACTGTCAAGCCCAGCGAGCACGACGGCGAATACC
TGTACGACATCGACAGGAAACAGTGCGTCAAGAAAGAACTAGTCACTGGGCTAGGG
CTCACAGGCGAGCTGGTGGATCCTCCCTTCCATGAATTCGCCTACGAGAGTCTGAGA
ACACGACCAGCCGCTCCTTACCAAGTACCAACCATAGGGGTGTATGGCGTGCCAGG
ATCAGGCAAGTCTGGCATCATTAAAAGCGCAGTCACCAAAAAAGATCTAGTGGTGA
GCGCCAAGAAAGAAAACTGTGCAGAAATTATAAGGGACGTCAAGAAAATGAAAGG
GCTGGACGTCAATGCCAGAACTGTGGACTCAGTGCTCTTGAATGGATGCAAACACCC
CGTAGAGACCCTGTATATTGACGAAGCTTTTGCTTGTCATGCAGGTACTCTCAGAGC
GCTCATAGCCATTATAAGACCTAAAAAGGCAGTGCTCTGCGGGGATCCCAAACAGT
GCGGTTTTTTTAACATGATGTGCCTGAAAGTGCATTTTAACCACGAGATTTGCACAC
AAGTCTTCCACAAAAGCATCTCTCGCCGTTGCACTAAATCTGTGACTTCGGTCGTCTC
AACCTTGTTTTACGACAAAAAAATGAGAACGACGAATCCGAAAGAGACTAAGATTG
TGATTGACACTACCGGCAGTACCAAACCTAAGCAGGACGATCTCATTCTCACTTGTT
TCAGAGGGTGGGTGAAGCAGTTGCAAATAGATTACAAAGGCAACGAAATAATGACG
GCAGCTGCCTCTCAAGGGCTGACCCGTAAAGGTGTGTATGCCGTTCGGTACAAGGTG
AATGAAAATCCTCTGTACGCACCCACCTCAGAACATGTGAACGTCCTACTGACCCGC
ACGGAGGACCGCATCGTGTGGAAAACACTAGCCGGCGACCCATGGATAAAAACACT
GACTGCCAAGTACCCTGGGAATTTCACTGCCACGATAGAGGAGTGGCAAGCAGAGC
ATGATGCCATCATGAGGCACATCTTGGAGAGACCGGACCCTACCGACGTCTTCCAG
AATAAGGCAAACGTGTGTTGGGCCAAGGCTTTAGTGCCGGTGCTGAAGACCGCTGG
CATAGACATGACCACTGAACAATGGAACACTGTGGATTATTTTGAAACGGACAAAG
CTCACTCAGCAGAGATAGTATTGAACCAACTATGCGTGAGGTTCTTTGGACTCGATC

-continued

TGGACTCCGGTCTATTTTCTGCACCCACTGTTCCGTTATCCATTAGGAATAATCACTG
GGATAACTCCCCGTCGCCTAACATGTACGGGCTGAATAAAGAAGTGGTCCGTCAGCT
CTCTCGCAGGTACCCACAACTGCCTCGGGCAGTTGCCACTGGAAGAGTCTATGACAT
GAACACTGGTACACTGCGCAATTATGATCCGCGCATAAACCTAGTACCTGTAAACAG
AAGACTGCCTCATGCTTTAGTCCTCCACCATAATGAACACCCACAGAGTGACTTTTC
TTCATTCGTCAGCAAATTGAAGGGCAGAACTGTCCTGGTGGTCGGGGAAAAGTTGTC
CGTCCCAGGCAAAATGGTTGACTGGTTGTCAGACCGGCCTGAGGCTACCTTCAGAGC
TCGGCTGGATTTAGGCATCCCAGGTGATGTGCCCAAATATGACATAATATTTGTTAA
TGTGAGGACCCCATATAAATACCATCACTATCAGCAGTGTGAAGACCATGCCATTAA
GCTTAGCATGTTGACCAAGAAAGCTTGTCTGCATCTGAATCCCGGCGGAACCTGTGT
CAGCATAGGTTATGGTTACGCTGACAGGGCCAGCGAAAGCATCATTGGTGCTATAG
CGCGGCtGTTCAAGTTTTCCCGGGTATGCAAACCGAAATCCTCACTTGAAGAGACGG
AAGTTCTGTTTGTATTCATTGGGTACGATCGCAAGGCCCGTACGCACAATCCTTACA
AGCTTTCATCAACCTTGACCAACATTTATACAGGTTCCAGACTCCACGAAGCCGGAT
GTGCACCCTCATATCATGTGGTGCGAGGGGATATTGCCACGGCCACCGAAGGAGTG
ATTATAAATGCTGCTAACAGCAAAGGACAACCTGGCGGAGGGGTGTGCGGAGCGCT
GTATAAGAAATTCCCGGAAAGCTTCGATTTACAGCCGATCGAAGTAGGAAAAGCGC
GACTGGTCAAAGGTGCAGCTAAACATATCATTCATGCCGTAGGACCAAACTTCAAC
AAAGTTTCGGAGGTTGAAGGTGACAAACAGTTGGCAGAGGCTTATGAGTCCATCGC
TAAGATTGTCAACGATAACAATTACAAGTCAGTAGCGATTCCACTGTTGTCCACCGG
CATCTTTTCCGGGAACAAAGATCGACTAACCCAATCATTGAACCATTTGCTGACAGC
TTTAGACACCACTGATGCAGATGTAGCCATATACTGCAGGGACAAGAAATGGGAAA
TGACTCTCAAGGAAGCAGTGGCTAGGAGAGAAGCAGTGGAGGAGATATGCATATCC
GACGACTCTTCAGTGACAGAACCTGATGCAGAGCTGGTGAGGGTGCATCCGAAGAG
TTCTTTGGCTGGAAGGAAGGGCTACAGCACAAGCGATGGCAAAACTTTCTCATATTT
GGAAGGGACCAAGTTTCACCAGGCGGCCAAGGATATAGCAGAAATTAATGCCATGT
GGCCCGTTGCAACGGAGGCCAATGAGCAGGTATGCATGTATATCCTCGGAGAAAGC
ATGAGCAGTATTAGGTCGAAATGCCCCGTCGAAGAGTCGGAAGCCTCCACACCACC
TAGCACGCTGCCTTGCTTGTGCATCCATGCCATGACTCCAGAAAGAGTACAGCGCCT
AAAAGCCTCACGTCCAGAACAAATTACTGTGTGCTCATCCTTTCCATTGCCGAAGTA
TAGAATCACTGGTGTGCAGAAGATCCAATGCTCCCAGCCTATATTGTTCTCACCGAA
AGTGCCTGCGTATATTCATCCAAGGAAGTATCTCGTGGAAACACCACCGGTAGACG
AGACTCCGGAGCCATCGGCAGAGAACCAATCCACAGAGGGGACACCTGAACAACC
ACCACTTATAACCGAGGATGAGACCAGGACTAGAACGCCTGAGCCGATCATCATCG
AAGAGGAAGAAGAGGATAGCATAAGTTTGCTGTCAGATGGCCCGACCCACCAGGTG
CTGCAAGTCGAGGCAGACATTCACGGGCCGCCCTCTGTATCTAGCTCATCCTGGTCC
ATTCCTCATGCATCCGACTTTGATGTGGACAGTTTATCCATACTTGACACCCTGGAG
GGAGCTAGCGTGACCAGCGGGGCAACGTCAGCCGAGACTAACTCTTACTTCGCAAA
GAGTATGGAGTTTCTGGCGCGACCGGTGCCTGCGCCTCGAACAGTATTCAGGAACCC
TCCACATCCCGCTCCGCGCACAAGAACACCGTCACTTGCACCCAGCAGGGCCTGCTC
GAGAACCAGCCTAGTTTCCACCCCGCCAGGCGTGAATAGGGTGATCACTAGAGAGG
AGCTCGAGGCGCTTACCCCGTCACGCACTCCTAGCAGGTCGGTCTCGAGAACCAGCC
TGGTCTCCAACCCGCCAGGCGTAAATAGGGTGATTACAAGAGAGGAGTTTGAGGCG
TTCGTAGCACAACAACAATGACGGTTTGATGCGGGTGCATACATCTTTTCCTCCGAC
ACCGGTCAAGGGCATTTACAACAAAAATCAGTAAGGCAAACGGTGCTATCCGAAGT
GGTGTTGGAGAGGACCGAATTGGAGATTTCGTATGCCCCGCGCCTCGACCAAGAAA
AAGAAGAATTACTACGCAAGAAATTACAGTTAAATCCCACACCTGCTAACAGAAGC
AGATACCAGTCCAGGAAGGTGGAGAACATGAAAGCCATAACAGCTAGACGTATTCT
GCAAGGCCTAGGGCATTATTTGAAGGCAGAAGGAAAAGTGGAGTGCTACCGAACCC
TGCATCCTGTTCCTTTGTATTCATCTAGTGTGAACCGTGCCTTTTCAAGCCCCAAGGT
CGCAGTGGAAGCCTGTAACGCCATGTTGAAAGAGAACTTTCCGACTGTGGCTTCTTA
CTGTATTATTCCAGAGTACGATGCCTATTTGGACATGGTTGACGGAGCTTCATGCTG
CTTAGACACTGCCAGTTTTTGCCCTGCAAAGCTGCGCAGCTTTCCAAAGAAACACTC
CTATTTGGAACCCACAATACGATCGGCAGTGCCTTCAGCGATCCAGAACACGCTCCA
GAACGTCCTGGCAGCTGCCACAAAAAGAAATTGCAATGTCACGCAAATGAGAGAAT
TGCCCGTATTGGATTCGGCGGCCTTTAATGTGGAATGCTTCAAGAAATATGCGTGTA
ATAATGAATATTGGGAAACGTTTAAAGAAAACCCCATCAGGCTTACTGAAGAAAAC
GTGGTAAATTACATTACCAAATTAAAAGGACCAAAAGCTGCTGCTCTTTTTGCGAAG
ACACATAATTTGAATATGTTGCAGGACATACCAATGGACAGGTTTGTAATGGACTTA
AAGAGAGACGTGAAAGTGACTCCAGGAACAAAACATACTGAAGAACGGCCCAAGG
TACAGGTGATCCAGGCTGCCGATCCGCTAGCAACAGCGTATCTGTGCGGAATCCACC
GAGAGCTGGTTAGGAGATTAAATGCGGTCCTGCTTCCGAACATTCATACACTGTTTG
ATATGTCGGCTGAAGACTTTGACGCTATTATAGCCGAGCACTTCCAGCCTGGGGATT
GTGTTCTGGAAACTGACATCGCGTCGTTTGATAAAAGTGAGGACGACGCCATGGCTC
TGACCGCGTTAATGATTCTGGAAGACTTAGGTGTGGACGCAGAGCTGTTGACGCTGA
TTGAGGCGGCTTTCGGCGAAATTTCATCAATACATTTGCCCACTAAAACTAAATTTA
AATTCGGAGCCATGATGAAATCTGGAATGTTCCTCACACTGTTTGTGAACACAGTCA
TTAACATTGTAATCGCAAGCAGAGTGTTGAGAGAACGGCTAACCGGATCACCATGT
GCAGCATTCATTGGAGATGACAATATCGTGAAAGGAGTCAAATCGGACAAATTAAT
GGCAGACAGGTGCGCCACCTGGTTGAATATGGAAGTCAAGATTATAGATGCTGTGG
TGGGCGAGAAAGCGCCTTATTTCTGTGGAGGGTTTATTTTGTGTGACTCCGTGACCG
GCACAGCGTGCCGTGTGGCAGACCCCCTAAAAAGGCTGTTTAAGCTTGGCAAACCT
CTGGCAGCAGACGATGAACATGATGATGACAGGAGAAGGGCATTGCATGAAGAGTC
AACACGCTGGAACCGAGTGGGTATTCTTTCAGAGCTGTGCAAGGCAGTAGAATCAA
GGTATGAAACCGTAGGAACTTCCATCATAGTTATGGCCATGACTACTCTAGCTAGCA
GTGTTAAATCATTCAGCTACCTGAGAGGGGCCCCTATAACTCTCTACGGCTAACCTG
AATGGACTACGACATAGTCTAGTCCGCCAAGTTCGAAGGCGCGCCTCTAGAGCCAC
CATGGTGAGCAAGGGCGAGGAGCTGTTCACCGGGGTGGTGCCCATCCTGGTCG
AGCTGGACGGCGACGTAAACGGCCACAAGTTCAGCGTGTCCGGCGAGGGCGA
GGGCGATGCCACCTACGGCAAGCTGACCCTGAAGTTCATCTGCACCACCGGCA
AGCTGCCCGTGCCCTGGCCCACCCTCGTGACCACCCTGACCTACGGCGTGCAG

-continued

TGCTTCAGCCGCTACCCCGACCACATGAAGCAGCACGACTTCTTCAAGTCCGC
CATGCCCGAAGGCTACGTCCAGGAGCGCACCATCTTCTTCAAGGACGACGGCA
ACTACAAGACCCGCGCCGAGGTGAAGTTCGAGGGCGACACCCTGGTGAACCGC
ATCGAGCTGAAGGGCATCGACTTCAAGGAGGACGGCAACATCCTGGGGCACAA
GCTGGAGTACAACTACAACAGCCACAACGTCTATATCATGGCCGACAAGCAGA
AGAACGGCATCAAGGTGAACTTCAAGATCCGCCACAACATCGAGGACGGCAGC
GTGCAGCTCGCCGACCACTACCAGCAGAACACCCCCATCGGCGACGGCCCCGT
GCTGCTGCCCGACAACCACTACCTGAGCACCCAGTCCGCCCTGAGCAAAGACC
CCAACGAGAAGCGCGATCACATGGTCCTGCTGGAGTTCGTGACCGCCGCCGGG
ATCACTCTCGGCATGGACGAGCTGTACAAGTAGCATCGATGATATCGCGGCCGC
ATACAGCAGCAATTGGCAAGCTGCTTACATAGAACTCGCGGCGATTGGCATGCCGC
CTTAAAATTTTTATTTTATTTTTCTTTTCTTTTCCGAATCGGATTTTGTTTTTAATATTT
CAAAAAAAAAAAAAAAA

SAM004

(SEQ ID NO: 38)

AAAAAAAAAACGCGTGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTGGCGCTTT
CTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATC
GTCTTGAGTCCAACCCGGTAAGACACGACTTATCGCCACTGGCAGCAGCCACTGGTA
ACAGGATTAGCAGAGCGAGGTATGTAGGCGGTGCTACAGAGTTCTTGAAGTGGTGG
CCTAACTACGGCTACACTAGAAGAACAGTATTTGGTATCTGCGCTCTGCTGAAGCCA
GTTACCTTCGGAAAAAGAGTTGGTAGCTCTTGATCCGGCAAACAAACCACCGCTGGT
AGCGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGTTA
CCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGC
CCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAG
TTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAG
AATAGTGTATGCGGCGACCGAGTTGCTCTTGCCCGGCGTCAATACGGGATAATACCG
CGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCAC
CCAACTGATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGC
GGATACATATTTGAATGTATTTAGAAAAATAAACAAATAGGGGTTCCGCGCACATTT
CCCCGAAAAGTGCCACCTGAGCTCTAATACGACTCACTATAGgATaGGCGGCGCATG
AGAGAAGCCCAGACCAATTACCTACCCAAAATGGAGAAAGTTCACGTTGACATCGA
GGAAGACAGCCCATTCCTCAGAGCTTTGCAGCGGAGCTTCCCGCAGTTTGAGGTAGA
AGCCAAGCAGGTCACTGATAATGACCATGCTAATGCCAGAGCGTTTTCGCATCTGGC
TTCAAAACTGATCGAAACGGAGGTGGACCCATCCGACACGATCCTTGACATTGGAA
GTGCGCCCGCCCGCAGAATGTATTCTAAGCACAAGTATCATTGTATCTGTCCGATGA
GATGTGCGGAAGATCCGGACAGATTGTATAAGTATGCAACTAAGCTGAAGAAAAAC
TGTAAGGAAATAACTGATAAGGAATTGGACAAGAAAATGAAGGAGCTGGCCGCCGT
CATGAGCGACCCTGACCTGGAAACTGAGACTATGTGCCTCCACGACGACGAGTCGT
GTCGCTACGAAGGGCAAGTCGCTGTTTACCAGGATGTATACGCGGTTGACGGACCG
ACAAGTCTCTATCACCAAGCCAATAAGGGAGTTAGAGTCGCCTACTGGATAGGCTTT
GACACCACCCCTTTTATGTTTAAGAACTTGGCTGGAGCATATCCATCATACTCTACC
AACTGGGCCGACGAAACCGTGTTAACGGCTCGTAACATAGGCCTATGCAGCTCTGA
CGTTATGGAGCGGTCACGTAGAGGGATGTCCATTCTTAGAAAGAAGTATTTGAAACC
ATCCAACAATGTTCTATTCTCTGTTGGCTCGACCATCTACCACGAGAAGAGGGACTT
ACTGAGGAGCTGGCACCTGCCGTCTGTATTTCACTTACGTGGCAAGCAAAATTACAC
ATGTCGGTGTGAGACTATAGTTAGTTGCGACGGGTACGTCGTTAAAAGAATAGCTAT
CAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCG
TGTGCACGTATGTGCCAGCTACATTGTGTGACCAAATGACTGGCATACTGGCAACAG
ATGTCAGTGCGGACGACGCGCAAAAACTGCTGGTTGGGCTCAACCAGCGTATAGTC
GTCAACGGTCGCACCCAGAGAAACACCAATACCATGAAAAATTACCTTTTGCCCGT
AGTGGCCCAGGCATTTGCTAGGTGGGCAAAGGAATATAAGGAAGATCAAGAAGATG
AAAGGCCACTAGGACTACGAGATAGACAGTTAGTCATGGGGTGTTGTTGGGCTTTTA
GAAGGCACAAGATAACATCTATTTATAAGCGCCCGGATACCCAAACCATCATCAAA
GTGAACAGCGATTTCCACTCATTCGTGCTGCCCAGGATAGGCAGTAACACATTGGAG
ATCGGGCTGAGAACAAGAATCAGGAAAATGTTAGAGGAGCACAAGGAGCCGTCAC
CTCTCATTACCGCCGAGGACGTACAAGAAGCTAAGTGCGCAGCCGATGAGGCTAAG
GAGGTGCGTGAAGCCGAGGAGTTGCGCGCAGCTCTACCACCTTTGGCAGCTGATGTT
GAGGAGCCCACTCTGGAAGCCGATGTCGACTTGATGTTACAAGAGGCTGGGGCCGG
CTCAGTGGAGACACCTCGTGGCTTGATAAAGGTTACCAGCTACGATGGCGAGGACA
AGATCGGCTCTTACGCTGTGCTTTCTCCGCAGGCTGTACTCAAGAGTGAAAAATTAT
CTTGCATCCACCCTCTCGCTGAACAAGTCATAGTGATAACACACTCTGGCCGAAAAG

-continued

GGCGTTATGCCGTGGAACCATACCATGGTAAAGTAGTGGTGCCAGAGGGACATGCA
ATACCCGTCCAGGACTTTCAAGCTCTGAGTGAAAGTGCCACCATTGTGTACAACGAA
CGTGAGTTCGTAAACAGGTACCTGCACCATATTGCCACACATGGAGGAGCGCTGAA
CACTGATGAAGAATATTACAAAACTGTCAAGCCCAGCGAGCACGACGGCGAATACC
TGTACGACATCGACAGGAAACAGTGCGTCAAGAAAGAACTAGTCACTGGGCTAGGG
CTCACAGGCGAGCTGGTGGATCCTCCCTTCCATGAATTCGCCTACGAGAGTCTGAGA
ACACGACCAGCCGCTCCTTACCAAGTACCAACCATAGGGGTGTATGGCGTGCCAGG
ATCAGGCAAGTCTGGCATCATTAAAAGCGCAGTCACCAAAAAAGATCTAGTGGTGA
GCGCCAAGAAAGAAAACTGTGCAGAAATTATAAGGGACGTCAAGAAAATGAAAGG
GCTGGACGTCAATGCCAGAACTGTGGACTCAGTGCTCTTGAATGGATGCAAACACCC
CGTAGAGACCCTGTATATTGACGAAGCTTTTGCTTGTCATGCAGGTACTCTCAGAGC
GCTCATAGCCATTATAAGACCTAAAAAGGCAGTGCTCTGCGGGGATCCCAAACAGT
GCGGTTTTTTAACATGATGTGCCTGAAAGTGCATTTTAACCACGAGATTTGCACAC
AAGTCTTCCACAAAAGCATCTCTCGCCGTTGCACTAAATCTGTGACTTCGGTCGTCTC
AACCTTGTTTTACGACAAAAAAATGAGAACGACGAATCCGAAAGAGACTAAGATTG
TGATTGACACTACCGGCAGTACCAAACCTAAGCAGGACGATCTCATTCTCACTTGTT
TCAGAGGGTGGGTGAAGCAGTTGCAAATAGATTACAAAGGCAACGAAATAATGACG
GCAGCTGCCTCTCAAGGGCTGACCCGTAAAGGTGTGTATGCCGTTCGGTACAAGGTG
AATGAAAATCCTCTGTACGCACCCACCTCAGAACATGTGAACGTCCTACTGACCCGC
ACGGAGGACCGCATCGTGTGGAAAACACTAGCCGGCGACCCATGGATAAAAACACT
GACTGCCAAGTACCCTGGGAATTTCACTGCCACGATAGAGGAGTGGCAAGCAGAGC
ATGATGCCATCATGAGGCACATCTTGGAGAGACCGGACCCTACCGACGTCTTCCAG
AATAAGGCAAACGTGTGTTGGGCCAAGGCTTTAGTGCCGGTGCTGAAGACCGCTGG
CATAGACATGACCACTGAACAATGGAACACTGTGGATTATTTTGAAACGGACAAAG
CTCACTCAGCAGAGATAGTATTGAACCAACTATGCGTGAGGTTCTTTGGACTCGATC
TGGACTCCGGTCTATTTTCTGCACCCACTGTTCCGTTATCCATTAGGAATAATCACTG
GGATAACTCCCCGTCGCCTAACATGTACGGGCTGAATAAAGAAGTGGTCCGTCAGCT
CTCTCGCAGGTACCCACAACTGCCTCGGGCAGTTGCCACTGGAAGAGTCTATGACAT
GAACACTGGTACACTGCGCAATTATGATCCGCGCATAAACCTAGTACCTGTAAACAG
AAGACTGCCTCATGCTTTAGTCCTCCACCATAATGAACACCCACAGAGTGACTTTTC
TTCATTCGTCAGCAAATTGAAGGGCAGAACTGTCCTGGTGGTCGGGGAAAAGTTGTC
CGTCCCAGGCAAAATGGTTGACTGGTTGTCAGACCGGCCTGAGGCTACCTTCAGAGC
TCGGCTGGATTTAGGCATCCCAGGTGATGTGCCCAAATATGACATAATATTTGTTAA
TGTGAGGACCCCATATAAATACCATCACTATCAGCAGTGTGAAGACCATGCCATTAA
GCTTAGCATGTTGACCAAGAAAGCTTGTCTGCATCTGAATCCCGGCGGAACCTGTGT
CAGCATAGGTTATGGTTACGCTGACAGGGCCAGCGAAAGCATCATTGGTGCTATAG
CGCGGCAGTTCAAGTTTTCCCGGGTATGCAAACCGAAATCCTCACTTGAAGAGACGG
AAGTTCTGTTTGTATTCATTGGGTACGATCGCAAGGCCCGTACGCACAATtCTTACAA
GCTTTCATCAACCTTGACCAACATTTATACAGGTTCCAGACTCCACGAAGCCGGATG
TGCACCCTCATATCATGTGGTGCGAGGGGATATTGCCACGGCCACCGAAGGAGTGA
TTATAAATGCTGCTAACAGCAAAGGACAACCTGGCGGAGGGGTGTGCGGAGCGCTG
TATAAGAAATTCCCGGAAAGCTTCGATTTACAGCCGATCGAAGTAGGAAAAGCGCG
ACTGGTCAAAGGTGCAGCTAAACATATCATTCATGCCGTAGGACCAAACTTCAACA
AAGTTTCGGAGGTTGAAGGTGACAAACAGTTGGCAGAGGCTTATGAGTCCATCGCT
AAGATTGTCAACGATAACAATTACAAGTCAGTAGCGATTCCACTGTTGTCCACCGGC
ATCTTTTCCGGGAACAAAGATCGACTAACCCAATCATTGAACCATTTGCTGACAGCT
TTAGACACCACTGATGCAGATGTAGCCATATACTGCAGGGACAAGAAATGGGAAAT
GACTCTCAAGGAAGCAGTGGCTAGGAGAGAAGCAGTGGAGGAGATATGCATATCCG
ACGACTCTTCAGTGACAGAACCTGATGCAGAGCTGGTGAGGGTGCATCCGAAGAGT
TCTTTGGCTGGAAGGAAGGGCTACAGCACAAGCGATGGCAAAACTTTCTCATATTTG
GAAGGGACCAAGTTTCACCAGGCGGCCAAGGATATAGCAGAAATTAATGCCATGTG
GCCCGTTGCAACGGAGGCCAATGAGCAGGTATGCATGTATATCCTCGGAGAAAGCA
TGAGCAGTATTAGGTCGAAATGCCCCGTCGAAGAGTCGGAAGCCTCCACACCACCT
AGCACGCTGCCTTGCTTGTGCATCCATGCCATGACTCCAGAAAGAGTACAGCGCCTA
AAAGCCTCACGTCCAGAACAAATTACTGTGTGCTCATCCTTTCCATTGCCGAAGTAT
AGAATCACTGGTGTGCAGAAGATCCAATGCTCCCAGCCTATATTGTTCTCACCGAAA
GTGCCTGCGTATATTCATCCAAGGAAGTATCTCGTGGAAACACCACCGGTAGACGA
GACTCCGGAGCCATCGGCAGAGAACCAATCCACAGAGGGGACACCTGAACAACCAC
CACTTATAACCGAGGATGAGACCAGGACTAGAACGCCTGAGCCGATCATCATCGAA
GAGGAAGAAGAGGATAGCATAAGTTTGCTGTCAGATGGCCCGACCCACCAGGTGCT
GCAAGTCGAGGCAGACATTCACGGGCCGCCCTCTGTATCTAGCTCATCCTGGTCCAT
TCCTCATGCATCCGACTTTGATGTGGACAGTTTATCCATACTTGACACCCTGGAGGG
AGCTAGCGTGACCAGCGGGGCAACGTCAGCCGAGACTAACTCTTACTTCGCAAAGA
GTATGGAGTTTCTGGCGCGACCGGTGCCTGCGCCTCGAACAGTATTCAGGAACCCTC
CACATCCCGCTCCGCGCACAAGAACACCGTCACTTGCACCCAGCAGGGCCTGCTCG
AGAACCAGCCTAGTTTCCACCCCGCCAGGCGTGAATAGGGTGATCACTAGAGAGGA
GCTCGAGGCGCTTACCCCGTCACGCACTCCTAGCAGGTCGGTCTCGAGAACCAGCCT
GGTCTCCAACCCGCCAGGCGTAAATAGGGTGATTACAAGAGAGGAGTTTGAGGCGT
TCGTAGCACAACAACAATGACGGTTTGATGCGGGTGCATACATCTTTTCCTCCGACA
CCGGTCAAGGGCATTTACAACAAAAATCAGTAAGGCAAACGGTGCTATCCGAAGTG
GTGTTGGAGAGGACCGAATTGGAGATTTCGTATGCCCCGCGCCTCGACCAAGAAAA
AGAAGAATTACTACGCAAGAAATTACAGTTAAATCCCACACCTGCTAACAGAAGCA
GATACCAGTCCAGGAAGGTGGAGAACATGAAAGCCATAACAGCTAGACGTATTCTG
CAAGGCCTAGGGCATTATTTGAAGGCAGAAGGAAAAGTGGAGTGCTACCGAACCCT
GCATCCTGTTCCTTTGTATTCATCTAGTGTGAACCGTGCCTTTTCAAGCCCCAAGGTC
GCAGTGGAAGCCTGTAACGCCATGTTGAAAGAGAACTTTCCGACTGTGGCTTCTTAC
TGTATTATTCCAGAGTACGATGCCTATTTGGACATGGTTGACGGAGCTTCATGCTGC
TTAGACACTGCCAGTTTTTGCCCTGCAAAGCTGCGCAGCTTTCCAAAGAAACACTCC
TATTTGGAACCCACAATACGATCGGCAGTGCCTTCAGCGATCCAGAACACGCTCCAG
AACGTCCTGGCAGCTGCCACAAAAAGAAATTGCAATGTCACGCAAATGAGAGAATT
GCCCGTATTGGATTCGGCGGCCTTTAATGTGGAATGCTTCAAGAAATATGCGTGTAA

-continued

TAATGAATATTGGGAAACGTTTAAAGAAAACCCCATCAGGCTTACTGAAGAAAACG
TGGTAAATTACATTACCAAATTAAAAGGACCAAAAGCTGCTGCTCTTTTTGCGAAGA
CACATAATTTGAATATGTTGCAGGACATACCAATGGACAGGTTTGTAATGGACTTAA
AGAGAGACGTGAAAGTGACTCCAGGAACAAAACATACTGAAGAACGGCCCAAGGT
ACAGGTGATCCAGGCTGCCGATCCGCTAGCAACAGCGTATCTGTGCGGAATCCACC
GAGAGCTGGTTAGGAGATTAAATGCGGTCCTGCTTCCGAACATTCATACACTGTTTG
ATATGTCGGCTGAAGACTTTGACGCTATTATAGCCGAGCACTTCCAGCCTGGGGATT
GTGTTCTGGAAACTGACATCGCGTCGTTTGATAAAAGTGAGGACGACGCCATGGCTC
TGACCGCGTTAATGATTCTGGAAGACTTAGGTGTGGACGCAGAGCTGTTGACGCTGA
TTGAGGCGGCTTTCGGCGAAATTTCATCAATACATTTGCCCACTAAAACTAAATTTA
AATTCGGAGCCATGATGAAATCTGGAATGTTCCTCACACTGTTTGTGAACACAGTCA
TTAACATTGTAATCGCAAGCAGAGTGTTGAGAGAACGGCTAACCGGATCACCATGT
GCAGCATTCATTGGAGATGACAATATCGTGAAAGGAGTCAAATCGGACAAATTAAT
GGCAGACAGGTGCGCCACCTGGTTGAATATGGAAGTCAAGATTATAGATGCTGTGG
TGGGCGAGAAAGCGCCTTATTTCTGTGGAGGGTTTATTTTGTGTGACTCCGTGACCG
GCACAGCGTGCCGTGTGGCAGACCCCCTAAAAAGGCTGTTTAAGCTTGGCAAACCT
CTGGCAGCAGACGATGAACATGATGATGACAGGAGAAGGGCATTGCATGAAGAGTC
AACACGCTGGAACCGAGTGGGTATTCTTTCAGAGCTGTGCAAGGCAGTAGAATCAA
GGTATGAAACCGTAGGAACTTCCATCATAGTTATGGCCATGACTACTCTAGCTAGCA
GTGTTAAATCATTCAGCTACCTGAGAGGGGCCCCTATAACTCTCTACGGCTAACCTG
AATGGACTACGACATAGTCTAGTCCGCCAAGTTCGAAGGCGCGCCTCTAGAgccaccAT
GGTGAGCAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGCGATGCC
ACCTACGGCAAGCTGACCCTGAAGTTCATCTGCACCACCGGCAAGCTGCCCGTGCCC
TGGCCCACCCTCGTGACCACCCTGACCTACGGCGTGCAGTGCTTCAGCCGCTACCCC
GACCACATGAAGCAGCACGACTTCTTCAAGTCCGCCATGCCCGAAGGCTACGTCCA
GGAGCGCACCATCTTCTTCAAGGACGACGGCAACTACAAGACCCGCGCCGAGGTGA
AGTTCGAGGGCGACACCCTGGTGAACCGCATCGAGCTGAAGGGCATCGACTTCAAG
GAGGACGGCAACATCCTGGGGCACAAGCTGGAGTACAACTACAACAGCCACAACGT
CTATATCATGGCCGACAAGCAGAAGAACGGCATCAAGGTGAACTTCAAGATCCGCC
ACAACATCGAGGACGGCAGCGTGCAGCTCGCCGACCACTACCAGCAGAACACCCCC
ATCGGCGACGGCCCCGTGCTGCTGCCCGACAACCACTACCTGAGCACCCAGTCCGCC
CTGAGCAAAGACCCCAACGAGAAGCGCGATCACATGGTCCTGCTGGAGTTCGTGAC
CGCCGCCGGGATCACTCTCGGCATGGACGAGCTGTACAAGtagcATCGATGATATCGC
GGCCGCATACAGCAGCAATTGGCAAGCTGCTTACATAGAACTCGCGGCGATTGGCA
TGCCGCCTTAAAATTTTTATTTTATTTTTCTTTTCTTTTCCGAATCGGATTTTaTTTTTA
ATATTTCAAAAAAAAAAAAAAA

SAM005

(SEQ ID NO: 39)

AAAAAAAAAACGCGTGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTGGCGCTTT
CTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATC
GTCTTGAGTCCAACCCGGTAAGACACGACTTATCGCCACTGGCAGCAGCCACTGGTA
ACAGGATTAGCAGAGCGAGGTATGTAGGCGGTGCTACAGAGTTCTTGAAGTGGTGG
CCTAACTACGGCTACACTAGAAGAACAGTATTTGGTATCTGCGCTCTGCTGAAGCCA
GTTACCTTCGGAAAAAGAGTTGGTAGCTCTTGATCCGGCAAACAAACCACCGCTGGT
AGCGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGTTA
CCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGC
CCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAG
TTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAG
AATAGTGTATGCGGCGACCGAGTTGCTCTTGCCCGGCGTCAATACGGGATAATACCG
CGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCAC
CCAACTGATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGC
GGATACATATTTGAATGTATTTAGAAAAATAAACAAATAGGGGTTCCGCGCACATTT
CCCCGAAAAGTGCCACCTGAGCTCTAATACGACTCACTATAGgATaGGCGGCGCATG
AGAGAAGCCCAGACCAATTACCTACCCAAAATGGAGAAAGTTCACGTTGACATCGA
GGAAGACAGCCCATTCCTCAGAGCTTTGCAGCGGAGCTTCCCGCAGTTTGAGGTAGA
AGCCAAGCAGGTCACTGATAATGACCATGCTAATGCCAGAGCGTTTTCGCATCTGGC
TTCAAAACTGATCGAAACGGAGGTGGACCCATCCGACACGATCCTTGACATTGGAA
GTGCGCCCGCCCGCAGAATGTATTCTAAGCACAAGTATCATTGTATCTGTCCGATGA
GATGTGCGGAAGATCCGGACAGATTGTATAAGTATGCAACTAAGCTGAAGAAAAAC
TGTAAGGAAATAACTGATAAGGAATTGGACAAGAAAATGAAGGAGCTGGCCGCCGT
CATGAGCGACCCTGACCTGGAAACTGAGACTATGTGCCTCCACGACGACGAGTCGT

-continued

GTCGCTACGAAGGGCAAGTCGCTGTTTACCAGGATGTATACGCGGTTGACGGACCG
ACAAGTCTCTATCACCAAGCCAATAAGGGAGTTAGAGTCGCCTACTGGATAGGCTTT
GACACCACCCCTTTTATGTTTAAGAACTTGGCTGGAGCATATCCATCATACTCTACC
AACTGGGCCGACGAAACCGTGTTAACGGCTCGTAACATAGGCCTATGCAGCTCTGA
CGTTATGGAGCGGTCACGTAGAGGGATGTCCATTCTTAGAAAGAAGTATTTGAAACC
ATCCAACAATGTTCTATTCTCTGTTGGCTCGACCATCTACCACGAGAAGAGGGACTT
ACTGAGGAGCTGGCACCTGCCGTCTGTATTTCACTTACGTGGCAAGCAAAATTACAC
ATGTCGGTGTGAGACTATAGTTAGTTGCGACGGGTACGTCGTTAAAAGAATAGCTAT
CAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCG
TGTGCACGTATGTGCCAGCTACATTGTGTGACCAAATGACTGGCATACTGGCAACAG
ATGTCAGTGCGGACGACGCGCAAAAACTGCTGGTTGGGCTCAACCAGCGTATAGTC
GTCAACGGTCGCACCCAGAGAAACACCAATACCATGAAAAATTACCTTTTGCCCGT
AGTGGCCCAGGCATTTGCTAGGTGGGCAAAGGAATATAAGGAAGATCAAGAAGATG
AAAGGCCACTAGGACTACGAGATAGACAGTTAGTCATGGGGTGTTGTTGGGCTTTTA
GAAGGCACAAGATAACATCTATTTATAAGCGCCCGGATACCCAAACCATCATCAAA
GTGAACAGCGATTTCCACTCATTCGTGCTGCCCAGGATAGGCAGTAACACATTGGAG
ATCGGGCTGAGAACAAGAATCAGGAAAATGTTAGAGGAGCACAAGGAGCCGTCAC
CTCTCATTACCGCCGAGGACGTACAAGAAGCTAAGTGCGCAGCCGATGAGGCTAAG
GAGGTGCGTGAAGCCGAGGAGTTGCGCGCAGCTCTACCACCTTTGGCAGCTGATGTT
GAGGAGCCCACTCTGGAAGCCGATGTCGACTTGATGTTACAAGAGGCTGGGGCCGG
CTCAGTGGAGACACCTCGTGGCTTGATAAAGGTTACCAGCTACGATGGCGAGGACA
AGATCGGCTCTTACGCTGTGCTTTCTCCGCAGGCTGTACTCAAGAGTGAAAAATTAT
CTTGCATCCACCCTCTCGCTGAACAAGTCATAGTGATAACACACTCTGGCCGAAAAG
GGCGTTATGCCGTGGAACCATACCATGGTAAAGTAGTGGTGCCAGAGGGACATGCA
ATACCCGTCCAGGACTTTCAAGCTCTGAGTGAAAGTGCCACCATTGTGTACAACGAA
CGTGAGTTCGTAAACAGGTACCTGCACCATATTGCCACACATGGAGGAGCGCTGAA
CACTGATGAAGAATATTACAAAACTGTCAAGCCCAGCGAGCACGACGGCGAATACC
TGTACGACATCGACAGGAAACAGTGCGTCAAGAAAGAACTAGTCACTGGGCTAGGG
CTCACAGGCGAGCTGGTGGATCCTCCCTTCCATGAATTCGCCTACGAGAGTCTGAGA
ACACGACCAGCCGCTCCTTACCAAGTACCAACCATAGGGGTGTATGGCGTGCCAGG
ATCAGGCAAGTCTGGCATCATTAAAAGCGCAGTCACCAAAAAAGATCTAGTGGTGA
GCGCCAAGAAAGAAAACTGTGCAGAAATTATAAGGGACGTCAAGAAAATGAAAGG
GCTGGACGTCAATGCCAGAACTGTGGACTCAGTGCTCTTGAATGGATGCAAACACCC
CGTAGAGACCCTGTATATTGACGAAGCTTTTGCTTGTCATGCAGGTACTCTCAGAGC
GCTCATAGCCATTATAAGACCTAAAAAGGCAGTGCTCTGCGGGGATCCCAAACAGT
GCGGTTTTTTTAACATGATGTGCCTGAAAGTGCATTTTAACCACGAGATTTGCACAC
AAGTCTTCCACAAAAGCATCTCTCGCCGTTGCACTAAATCTGTGACTTCGGTCGTCTC
AACCTTGTTTTACGACAAAAAAATGAGAACGACGAATCCGAAAGAGACTAAGATTG
TGATTGACACTACCGGCAGTACCAAACCTAAGCAGGACGATCTCATTCTCACTTGTT
TCAGAGGGTGGGTGAAGCAGTTGCAAATAGATTACAAAGGCAACGAAATAATGACG
GCAGCTGCCTCTCAAGGGCTGACCCGTAAAGGTGTGTATGCCGTTCGGTACAAGGTG
AATGAAAATCCTCTGTACGCACCCACCTCAGAACATGTGAACGTCCTACTGACCCGC
ACGGAGGACCGCATCGTGTGGAAAACACTAGCCGGCGACCCATGGATAAAAACACT
GACTGCCAAGTACCCTGGGAATTTCACTGCCACGATAGAGGAGTGGCAAGCAGAGC
ATGATGCCATCATGAGGCACATCTTGGAGAGACCGGACCCTACCGACGTCTTCCAG
AATAAGGCAAACGTGTGTTGGGCCAAGGCTTTAGTGCCGGTGCTGAAGACCGCTGG
CATAGACATGACCACTGAACAATGGAACACTGTGGATTATTTTGAAACGGACAAAG
CTCACTCAGCAGAGATAGTATTGAACCAACTATGCGTGAGGTTCTTTGGACTCGATC
TGGACTCCGGTCTATTTTCTGCACCCACTGTTCCGTTATCCATTAGGAATAATCACTG
GGATAACTCCCCGTCGCCTAACATGTACGGGCTGAATAAAGAAGTGGTCCGTCAGCT
CTCTCGCAGGTACCCACAACTGCCTCGGGCAGTTGCCACTGGAAGAGTCTATGACAT
GAACACTGGTACACTGCGCAATTATGATCCGCGCATAAACCTAGTACCTGTAAACAG
AAGACTGCCTCATGCTTTAGTCCTCCACCATAATGAACACCCACAGAGTGACTTTTC
TTCATTCGTCAGCAAATTGAAGGGCAGAACTGTCCTGGTGGTCGGGGAAAAGTTGTC
CGTCCCAGGCAAAATGGTTGACTGGTTGTCAGACCGGCCTGAGGCTACCTTCAGAGC
TCGGCTGGATTTAGGCATCCCAGGTGATGTGCCCAAATATGACATAATATTTGTTAA
TGTGAGGACCCCATATAAATACCATCACTATCAGCAGTGTGAAGACCATGCCATTAA
GCTTAGCATGTTGACCAAGAAAGCTTGTCTGCATCTGAATCCCGGCGGAACCTGTGT
CAGCATAGGTTATGGTTACGCTGACAGGGCCAGCGAAAGCATCATTGGTGCTATAG
CGCGGCAGTTCAAGTTTTCCCGGGTATGCAAACCGAAATCCTCACTTGAAGAGACGG
AAGTTCTGTTTGTATTCATTGGGTACGATCGCAAGGCCCGTACGCACAATtCTTACAA
GCTTTCATCAACCTTGACCAACATTTATACAGGTTCCAGACTCCACGAAGCCGGATG
TGCACCCTCATATCATGTGGTGCGAGGGGATATTGCCACGGCCACCGAAGGAGTGA
TTATAAATGCTGCTAACAGCAAAGGACAACCTGGCGGAGGGGTGTGCGGAGCGCTG
TATAAGAAATTCCCGGAAAGCTTCGATTTACAGCCGATCGAAGTAGGAAAAGCGCG
ACTGGTCAAAGGTGCAGCTAAACATATCATTCATGCCGTAGGACCAAACTTCAACA
AAGTTTCGGAGGTTGAAGGTGACAAACAGTTGGCAGAGGCTTATGAGTCCATCGCT
AAGATTGTCAACGATAACAATTACAAGTCAGTAGCGATTCCACTGTTGTCCACCGGC
ATCTTTTCCGGGAACAAAGATCGACTAACCCAATCATTGAACCATTTGCTGACAGCT
TTAGACACCACTGATGCAGATGTAGCCATATACTGCAGGGACAAGAAATGGGAAAT
GACTCTCAAGGAAGCAGTGGCTAGGAGAGAAGCAGTGGAGGAGATATGCATATCCG
ACGACTCTTCAGTGACAGAACCTGATGCAGAGCTGGTGAGGGTGCATCCGAAGAGT
TCTTTGGCTGGAAGGAAGGGCTACAGCACAAGCGATGGCAAAACTTTCTCATATTTG
GAAGGGACCAAGTTTCACCAGGCGGCCAAGGATATAGCAGAAATTAATGCCATGTG
GCCCGTTGCAACGGAGGCCAATGAGCAGGTATGCATGTATATCCTCGGAGAAAGCA
TGAGCAGTATTAGGTCGAAATGCCCCGTCGAAGAGTCGGAAGCCTCCACACCACCT
AGCACGCTGCCTTGCTTGTGCATCCATGCCATGACTCCAGAAAGAGTACAGCGCCTA
AAAGCCTCACGTCCAGAACAAATTACTGTGTGCTCATCCTTTCCATTGCCGAAGTAT
AGAATCACTGGTGTGCAGAAGATCCAATGCTCCCAGCCTATATTGTTCTCACCGAAA
GTGCCTGCGTATATTCATCCAAGGAAGTATCTCGTGGAAACACCACCGGTAGACGA

-continued

GACTCCGGAGCCATCGGCAGAGAACCAATCCACAGAGGGGACACCTGAACAACCAC
CACTTATAACCGAGGATGAGACCAGGACTAGAACGCCTGAGCCGATCATCATCGAA
GAGGAAGAAGAGGATAGCATAAGTTTGCTGTCAGATGGCCCGACCCACCAGGTGCT
GCAAGTCGAGGCAGACATTCACGGGCCGCCCTCTGTATCTAGCTCATCCTGGTCCAT
TCCTCATGCATCCGACTTTGATGTGGACAGTTTATCCATACTTGACACCCTGGAGGG
AGCTAGCGTGACCAGCGGGGCAACGTCAGCCGAGACTAACTCTTACTTCGCAAAGA
GTATGGAGTTTCTGGCGCGACCGGTGCCTGCGCCTCGAACAGTATTCAGGAACCCTC
CACATCCCGCTCCGCGCACAAGAACACCGTCACTTGCACCCAGCAGGGCCTGCTCG
AGAACCAGCCTAGTTTCCACCCCGCCAGGCGTGAATAGGGTGATCACTAGAGAGGA
GCTCGAGGCGCTTACCCCGTCACGCACTCCTAGCAGGTCGGTCTCGAGAACCAGCCT
GGTCTCCAACCCGCCAGGCGTAAATAGGGTGATTACAAGAGAGGAGTTTGAGGCGT
TCGTAGCACAACAACAATGACGGTTTGATGCGGGTGCATACATCTTTTCCTCCGACA
CCGGTCAAGGGCATTTACAACAAAAATCAGTAAGGCAAACGGTGCTATCCGAAGTG
GTGTTGGAGAGGACCGAATTGGAGATTTCGTATGCCCCGCGCCTCGACCAAGAAAA
AGAAGAATTACTACGCAAGAAATTACAGTTAAATCCCACACCTGCTAACAGAAGCA
GATACCAGTCCAGGAAGGTGGAGAACATGAAAGCCATAACAGCTAGACGTATTCTG
CAAGGCCTAGGGCATTATTTGAAGGCAGAAGGAAAAGTGGAGTGCTACCGAACCCT
GCATCCTGTTCCTTTGTATTCATCTAGTGTGAACCGTGCCTTTTCAAGCCCCAAGGTC
GCAGTGGAAGCCTGTAACGCCATGTTGAAAGAGAACTTTCCGACTGTGGCTTCTTAC
TGTATTATTCCAGAGTACGATGCCTATTTGGACATGGTTGACGGAGCTTCATGCTGC
TTAGACACTGCCAGTTTTTGCCCTGCAAAGCTGCGCAGCTTTCCAAAGAAACACTCC
TATTTGGAACCCACAATACGATCGGCAGTGCCTTCAGCGATCCAGAACACGCTCCAG
AACGTCCTGGCAGCTGCCACAAAAAGAAATTGCAATGTCACGCAAATGAGAGAATT
GCCCGTATTGGATTCGGCGGCCTTTAATGTGGAATGCTTCAAGAAATATGCGTGTAA
TAATGAATATTGGGAAACGTTTAAAGAAAACCCCATCAGGCTTACTGAAGAAAACG
TGGTAAATTACATTACCAAATTAAAAGGACCAAAAGCTGCTGCTCTTTTTGCGAAGA
CACATAATTTGAATATGTTGCAGGACATACCAATGGACAGGTTTGTAATGGACTTAA
AGAGAGACGTGAAAGTGACTCCAGGAACAAAACATACTGAAGAACGGCCCAAGGT
ACAGGTGATCCAGGCTGCCGATCCGCTAGCAACAGCGTATCTGTGCGGAATCCACC
GAGAGCTGGTTAGGAGATTAAATGCGGTCCTGCTTCCGAACATTCATACACTGTTTG
ATATGTCGGCTGAAGACTTTGACGCTATTATAGCCGAGCACTTCCAGCCTGGGGATT
GTGTTCTGGAAACTGACATCGCGTCGTTTGATAAAAGTGAGGACGACGCCATGGCTC
TGACCGCGTTAATGATTCTGGAAGACTTAGGTGTGGACGCAGAGCTGTTGACGCTGA
TTGAGGCGGCTTTCGGCGAAATTTCATCAATACATTTGCCCACTAAAACTAAATTTA
AATTCGGAGCCATGATGAAATCTGGAATGTTCCTCACACTGTTTGTGAACACAGTCA
TTAACATTGTAATCGCAAGCAGAGTGTTGAGAGAACGGCTAACCGGATCACCATGT
GCAGCATTCATTGGAGATGACAATATCGTGAAAGGAGTCAAATCGGACAAATTAAT
GGCAGACAGGTGCGCCACCTGGTTGAATATGGAAGTCAAGATTATAGATGCTGTGG
TGGGCGAGAAAGCGCCTTATTTCTGTGGAGGGTTTATTTTGTGTGACTCCGTGACCG
GCACAGCGTGCCGTGTGGCAGACCCCCTAAAAAGGCTGTTTAAGCTTGGCAAACCT
CTGGCAGCAGACGATGAACATGATGATGACAGGAGAAGGGCATTGCATGAAGAGTC
AACACGCTGGAACCGAGTGGGTATTCTTTCAGAGCTGTGCAAGGCAGTAGAATCAA
GGTATGAAACCGTAGGAACTTCCATCATAGTTATGGCCATGACTACTCTAGCTAGCA
GTGTTAAATCATTCAGCTACCTGAGAGGGGCCCCTATAACTCTCTACGGCTAACCTG
AATGGACTACGACATAGTCTAGTCCGCCAAGTTCGAAGGCGCGCCTCTAGAgccaccAT
GGTGAGCAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGCGATGCC
ACCTACGGCAAGCTGACCCTGAAGTTCATCTGCACCACCGGCAAGCTGCCCGTGCCC
TGGCCCACCCTCGTGACCACCCTGACCTACGGCGTGCAGTGCTTCAGCCGCTACCCC
GACCACATGAAGCAGCACGACTTCTTCAAGTCCGCCATGCCCGAAGGCTACGTCCA
GGAGCGCACCATCTTCTTCAAGGACGACGGCAACTACAAGACCCGCGCCGAGGTGA
AGTTCGAGGGCGACACCCTGGTGAACCGCATCGAGCTGAAGGGCATCGACTTCAAG
GAGGACGGCAACATCCTGGGGCACAAGCTGGAGTACAACTACAACAGCCACAACGT
CTATATCATGGCCGACAAGCAGAAGAACGGCATCAAGGTGAACTTCAAGATCCGCC
ACAACATCGAGGACGGCAGCGTGCAGCTCGCCGACCACTACCAGCAGAACACCCCC
ATCGGCGACGGCCCCGTGCTGCTGCCCGACAACCACTACCTGAGCACCCAGTCCGCC
CTGAGCAAAGACCCCAACGAGAAGCGCGATCACATGGTCCTGCTGGAGTTCGTGAC
CGCCGCCGGGATCACTCTCGGCATGGACGAGCTGTACAAGtagcATCGATGATATCGC
GGCCGCATACAGCAGCAATTGGCAAGCTGCTTACATAGAACTCGCGGCGATTGGCA
TGCCGCCTTAAAATTTTTATTTTATTTTTCTTTTCTTTTCCGAATCaaATTTTGTTTTTA
ATATTTCAAAAAAAAAAAAAAAAA

SAM006

(SEQ ID NO: 40)

AAAAAAAAAACGCGTGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTGGCGCTTT
CTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATC
GTCTTGAGTCCAACCCGGTAAGACACGACTTATCGCCACTGGCAGCAGCCACTGGTA
ACAGGATTAGCAGAGCGAGGTATGTAGGCGGTGCTACAGAGTTCTTGAAGTGGTGG
CCTAACTACGGCTACACTAGAAGAACAGTATTTGGTATCTGCGCTCTGCTGAAGCCA
GTTACCTTCGGAAAAAGAGTTGGTAGCTCTTGATCCGGCAAACAAACCACCGCTGGT
AGCGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGTTA
CCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGC

-continued

CCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAG
TTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAG
AATAGTGTATGCGGCGACCGAGTTGCTCTTGCCCGGCGTCAATACGGGATAATACCG
CGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCAC
CCAACTGATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGC
GGATACATATTTGAATGTATTTAGAAAAATAAACAAATAGGGGTTCCGCGCACATTT
CCCCGAAAAGTGCCACCTGAGCTCTAATACGACTCACTATAGgATaGGCGGCGCATG
AGAGAAGCCCAGACCAATTACCTACCCAAAATGGAGAAAGTTCACGTTGACATCGA
GGAAGACAGCCCATTCCTCAGAGCTTTGCAGCGGAGCTTCCCGCAGTTTGAGGTAGA
AGCCAAGCAGGTCACTGATAATGACCATGCTAATGCCAGAGCGTTTTCGCATCTGGC
TTCAAAACTGATCGAAACGGAGGTGGACCCATCCGACACGATCCTTGACATTGGAA
GTGCGCCCGCCCGCAGAATGTATTCTAAGCACAAGTATCATTGTATCTGTCCGATGA
GATGTGCGGAAGATCCGGACAGATTGTATAAGTATGCAACTAAGCTGAAGAAAAAC
TGTAAGGAAATAACTGATAAGGAATTGGACAAGAAAATGAAGGAGCTGGCCGCCGT
CATGAGCGACCCTGACCTGGAAACTGAGACTATGTGCCTCCACGACGACGAGTCGT
GTCGCTACGAAGGGCAAGTCGCTGTTTACCAGGATGTATACGCGGTTGACGGACCG
ACAAGTCTCTATCACCAAGCCAATAAGGGAGTTAGAGTCGCCTACTGGATAGGCTTT
GACACCACCCCTTTTATGTTTAAGAACTTGGCTGGAGCATATCCATCATACTCTACC
AACTGGGCCGACGAAACCGTGTTAACGGCTCGTAACATAGGCCTATGCAGCTCTGA
CGTTATGGAGCGGTCACGTAGAGGGATGTCCATTCTTAGAAAGAAGTATTTGAAACC
ATCCAACAATGTTCTATTCTCTGTTGGCTCGACCATCTACCACGAGAAGAGGGACTT
ACTGAGGAGCTGGCACCTGCCGTCTGTATTTCACTTACGTGGCAAGCAAAATTACAC
ATGTCGGTGTGAGACTATAGTTAGTTGCGACGGGTACGTCGTTAAAAGAATAGCTAT
CAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCG
TGTGCACGTATGTGCCAGCTACATTGTGTGACCAAATGACTGGCATACTGGCAACAG
ATGTCAGTGCGGACGACGCGCAAAAACTGCTGGTTGGGCTCAACCAGCGTATAGTC
GTCAACGGTCGCACCCAGAGAAACACCAATACCATGAAAAATTACCTTTTGCCCGT
AGTGGCCCAGGCATTTGCTAGGTGGGCAAAGGAATATAAGGAAGATCAAGAAGATG
AAAGGCCACTAGGACTACGAGATAGACAGTTAGTCATGGGGTGTTGTTGGGCTTTTA
GAAGGCACAAGATAACATCTATTTATAAGCGCCCGGATACCCAAACCATCATCAAA
GTGAACAGCGATTTCCACTCATTCGTGCTGCCCAGGATAGGCAGTAACACATTGGAG
ATCGGGCTGAGAACAAGAATCAGGAAAATGTTAGAGGAGCACAAGGAGCCGTCAC
CTCTCATTACCGCCGAGGACGTACAAGAAGCTAAGTGCGCAGCCGATGAGGCTAAG
GAGGTGCGTGAAGCCGAGGAGTTGCGCGCAGCTCTACCACCTTTGGCAGCTGATGTT
GAGGAGCCCACTCTGGAAGCCGATGTCGACTTGATGTTACAAGAGGCTGGGGCCGG
CTCAGTGGAGACACCTCGTGGCTTGATAAAGGTTACCAGCTACGATGGCGAGGACA
AGATCGGCTCTTACGCTGTGCTTTCTCCGCAGGCTGTACTCAAGAGTGAAAAATTAT
CTTGCATCCACCCTCTCGCTGAACAAGTCATAGTGATAACACACTCTGGCCGAAAAG
GGCGTTATGCCGTGGAACCATACCATGGTAAAGTAGTGGTGCCAGAGGGACATGCA
ATACCCGTCCAGGACTTTCAAGCTCTGAGTGAAAGTGCCACCATTGTGTACAACGAA
CGTGAGTTCGTAAACAGGTACCTGCACCATATTGCCACACATGGAGGAGCGCTGAA
CACTGATGAAGAATATTACAAAACTGTCAAGCCCAGCGAGCACGACGGCGAATACC
TGTACGACATCGACAGGAAACAGTGCGTCAAGAAAGAACTAGTCACTGGGCTAGGG
CTCACAGGCGAGCTGGTGGATCCTCCCTTCCATGAATTCGCCTACGAGAGTCTGAGA
ACACGACCAGCCGCTCCTTACCAAGTACCAACCATAGGGGTGTATGGCGTGCCAGG
ATCAGGCAAGTCTGGCATCATTAAAAGCGCAGTCACCAAAAAAGATCTAGTGGTGA
GCGCCAAGAAAGAAAACTGTGCAGAAATTATAAGGGACGTCAAGAAAATGAAAGG
GCTGGACGTCAATGCCAGAACTGTGGACTCAGTGCTCTTGAATGGATGCAAACACCC
CGTAGAGACCCTGTATATTGACGAAGCTTTTGCTTGTCATGCAGGTACTCTCAGAGC
GCTCATAGCCATTATAAGACCTAAAAAGGCAGTGCTCTGCGGGGATCCCAAACAGT
GCGGTTTTTTAACATGATGTGCCTGAAAGTGCATTTTAACCACGAGATTTGCACAC
AAGTCTTCCACAAAAGCATCTCTCGCCGTTGCACTAAATCTGTGACTTCGGTCGTCTC
AACCTTGTTTTACGACAAAAAAATGAGAACGACGAATCCGAAAGAGACTAAGATTG
TGATTGACACTACCGGCAGTACCAAACCTAAGCAGGACGATCTCATTCTCACTTGTT
TCAGAGGGTGGGTGAAGCAGTTGCAAATAGATTACAAAGGCAACGAAATAATGACG
GCAGCTGCCTCTCAAGGGCTGACCCGTAAAGGTGTGTATGCCGTTCGGTACAAGGTG
AATGAAAATCCTCTGTACGCACCCACCTCAGAACATGTGAACGTCCTACTGACCCGC
ACGGAGGACCGCATCGTGTGGAAAACACTAGCCGGCGACCCATGGATAAAAACACT
GACTGCCAAGTACCCTGGGAATTTCACTGCCACGATAGAGGAGTGGCAAGCAGAGC
ATGATGCCATCATGAGGCACATCTTGGAGAGACCGGACCCTACCGACGTCTTCCAG
AATAAGGCAAACGTGTGTTGGGCCAAGGCTTTAGTGCCGGTGCTGAAGACCGCTGG
CATAGACATGACCACTGAACAATGGAACACTGTGGATTATTTTGAAACGGACAAAG
CTCACTCAGCAGAGATAGTATTGAACCAACTATGCGTGAGGTTCTTTGGACTCGATC
TGGACTCCGGTCTATTTTCTGCACCCACTGTTCCGTTATCCATTAGGAATAATCACTG
GGATAACTCCCCGTCGCCTAACATGTACGGGCTGAATAAAGAAGTGGTCCGTCAGCT
CTCTCGCAGGTACCCACAACTGCCTCGGGCAGTTGCCACTGGAAGAGTCTATGACAT
GAACACTGGTACACTGCGCAATTATGATCCGCGCATAAACCTAGTACCTGTAAACAG
AAGACTGCCTCATGCTTTAGTCCTCCACCATAATGAACACCCACAGAGTGACTTTTC
TTCATTCGTCAGCAAATTGAAGGGCAGAACTGTCCTGGTGGTCGGGGAAAAGTTGTC
CGTCCCAGGCAAAATGGTTGACTGGTTGTCAGACCGGCCTGAGGCTACCTTCAGAGC
TCGGCTGGATTTAGGCATCCCAGGTGATGTGCCCAAATATGACATAATATTTGTTAA

-continued

TGTGAGGACCCCATATAAATACCATCACTATCAGCAGTGTGAAGACCATGCCATTAA
GCTTAGCATGTTGACCAAGAAAGCTTGTCTGCATCTGAATCCCGGCGGAACCTGTGT
CAGCATAGGTTATGGTTACGCTGACAGGGCCAGCGAAAGCATCATTGGTGCTATAG
CGCGGCAGTTCAAGTTTTCCCGGGTATGCAAACCGAAATCCTCACTTGAAGAGACGG
AAGTTCTGTTTGTATTCATTGGGTACGATCGCAAGGCCCGTACGCACAATtCTTACAA
GCTTTCATCAACCTTGACCAACATTTATACAGGTTCCAGACTCCACGAAGCCGGATG
TGCACCCTCATATCATGTGGTGCGAGGGGATATTGCCACGGCCACCGAAGGAGTGA
TTATAAATGCTGCTAACAGCAAAGGACAACCTGGCGGAGGGGTGTGCGGAGCGCTG
TATAAGAAATTCCCGGAAAGCTTCGATTTACAGCCGATCGAAGTAGGAAAAGCGCG
ACTGGTCAAAGGTGCAGCTAAACATATCATTCATGCCGTAGGACCAAACTTCAACA
AAGTTTCGGAGGTTGAAGGTGACAAACAGTTGGCAGAGGCTTATGAGTCCATCGCT
AAGATTGTCAACGATAACAATTACAAGTCAGTAGCGATTCCACTGTTGTCCACCGGC
ATCTTTTCCGGGAACAAAGATCGACTAACCCAATCATTGAACCATTTGCTGACAGCT
TTAGACACCACTGATGCAGATGTAGCCATATACTGCAGGGACAAGAAATGGGAAAT
GACTCTCAAGGAAGCAGTGGCTAGGAGAGAAGCAGTGGAGGAGATATGCATATCCG
ACGACTCTTCAGTGACAGAACCTGATGCAGAGCTGGTGAGGGTGCATCCGAAGAGT
TCTTTGGCTGGAAGGAAGGGCTACAGCACAAGCGATGGCAAAACTTTCTCATATTTG
GAAGGGACCAAGTTTCACCAGGCGGCCAAGGATATAGCAGAAATTAATGCCATGTG
GCCCGTTGCAACGGAGGCCAATGAGCAGGTATGCATGTATATCCTCGGAGAAAGCA
TGAGCAGTATTAGGTCGAAATGCCCCGTCGAAGAGTCGGAAGCCTCCACACCACCT
AGCACGCTGCCTTGCTTGTGCATCCATGCCATGACTCCAGAAAGAGTACAGCGCCTA
AAAGCCTCACGTCCAGAACAAATTACTGTGTGCTCATCCTTTCCATTGCCGAAGTAT
AGAATCACTGGTGTGCAGAAGATCCAATGCTCCCAGCCTATATTGTTCTCACCGAAA
GTGCCTGCGTATATTCATCCAAGGAAGTATCTCGTGGAAACACCACCGGTAGACGA
GACTCCGGAGCCATCGGCAGAGAACCAATCCACAGAGGGGACACCTGAACAACCAC
CACTTATAACCGAGGATGAGACCAGGACTAGAACGCCTGAGCCGATCATCATCGAA
GAGGAAGAAGAGGATAGCATAAGTTTGCTGTCAGATGGCCCGACCCACCAGGTGCT
GCAAGTCGAGGCAGACATTCACGGGCCGCCCTCTGTATCTAGCTCATCCTGGTCCAT
TCCTCATGCATCCGACTTTGATGTGGACAGTTTATCCATACTTGACACCCTGGAGGG
AGCTAGCGTGACCAGCGGGGCAACGTCAGCCGAGACTAACTCTTACTTCGCAAAGA
GTATGGAGTTTCTGGCGCGACCGGTGCCTGCGCCTCGAACAGTATTCAGGAACCCTC
CACATCCCGCTCCGCGCACAAGAACACCGTCACTTGCACCCAGCAGGGCCTGCTCG
AGAACCAGCCTAGTTTCCACCCCGCCAGGCGTGAATAGGGTGATCACTAGAGAGGA
GCTCGAGGCGCTTACCCCGTCACGCACTCCTAGCAGGTCGGTCTCGAGAACCAGCCT
GGTCTCCAACCCGCCAGGCGTAAATAGGGTGATTACAAGAGAGGAGTTTGAGGCGT
TCGTAGCACAACAACAATGACGGTTTGATGCGGGTGCATACATCTTTTCCTCCGACA
CCGGTCAAGGGCATTTACAACAAAAATCAGTAAGGCAAACGGTGCTATCCGAAGTG
GTGTTGGAGAGGACCGAATTGGAGATTTCGTATGCCCCGCGCCTCGACCAAGAAAA
AGAAGAATTACTACGCAAGAAATTACAGTTAAATCCCACACCTGCTAACAGAAGCA
GATACCAGTCCAGGAAGGTGGAGAACATGAAAGCCATAACAGCTAGACGTATTCTG
CAAGGCCTAGGGCATTATTTGAAGGCAGAAGGAAAAGTGGAGTGCTACCGAACCCT
GCATCCTGTTCCTTTGTATTCATCTAGTGTGAACCGTGCCTTTTCAAGCCCCAAGGTC
GCAGTGGAAGCCTGTAACGCCATGTTGAAAGAGAACTTTCCGACTGTGGCTTCTTAC
TGTATTATTCCAGAGTACGATGCCTATTTGGACATGGTTGACGGAGCTTCATGCTGC
TTAGACACTGCCAGTTTTTGCCCTGCAAAGCTGCGCAGCTTTCCAAAGAAACACTCC
TATTTGGAACCCACAATACGATCGGCAGTGCCTTCAGCGATCCAGAACACGCTCCAG
AACGTCCTGGCAGCTGCCACAAAAAGAAATTGCAATGTCACGCAAATGAGAGAATT
GCCCGTATTGGATTCGGCGGCCTTTAATGTGGAATGCTTCAAGAAATATGCGTGTAA
TAATGAATATTGGGAAACGTTTAAAGAAAACCCCATCAGGCTTACTGAAGAAAACG
TGGTAAATTACATTACCAAATTAAAAGGACCAAAAGCTGCTGCTCTTTTTGCGAAGA
CACATAATTTGAATATGTTGCAGGACATACCAATGGACAGGTTTGTAATGGACTTAA
AGAGAGACGTGAAAGTGACTCCAGGAACAAAACATACTGAAGAACGGCCCAAGGT
ACAGGTGATCCAGGCTGCCGATCCGCTAGCAACAGCGTATCTGTGCGGAATCCACC
GAGAGCTGGTTAGGAGATTAAATGCGGTCCTGCTTCCGAACATTCATACACTGTTTG
ATATGTCGGCTGAAGACTTTGACGCTATTATAGCCGAGCACTTCCAGCCTGGGGATT
GTGTTCTGGAAACTGACATCGCGTCGTTTGATAAAAGTGAGGACGACGCCATGGCTC
TGACCGCGTTAATGATTCTGGAAGACTTAGGTGTGGACGCAGAGCTGTTGACGCTGA
TTGAGGCGGCTTTCGGCGAAATTTCATCAATACATTTGCCCACTAAAACTAAATTTA
AATTCGGAGCCATGATGAAATCTGGAATGTTCCTCACACTGTTTGTGAACACAGTCA
TTAACATTGTAATCGCAAGCAGAGTGTTGAGAGAACGGCTAACCGGATCACCATGT
GCAGCATTCATTGGAGATGACAATATCGTGAAAGGAGTCAAATCGGACAAATTAAT
GGCAGACAGGTGCGCCACCTGGTTGAATATGGAAGTCAAGATTATAGATGCTGTGG
TGGGCGAGAAAGCGCCTTATTTCTGTGGAGGGTTTATTTTGTGTGACTCCGTGACCG
GCACAGCGTGCCGTGTGGCAGACCCCCTAAAAAGGCTGTTTAAGCTTGGCAAACCT
CTGGCAGCAGACGATGAACATGATGATGACAGGAGAAGGGCATTGCATGAAGAGTC
AACACGCTGGAACCGAGTGGGTATTCTTTCAGAGCTGTGCAAGGCAGTAGAATCAA
GGTATGAAACCGTAGGAACTTCCATCATAGTTATGGCCATGACTACTCTAGCTAGCA
GTGTTAAATCATTCAGCTACCTGAGAGGGGCCCCTATAACTCTCTACGGCTAACCTG
AATGGACTACGACATAGTCTAGTCCGCCAAGTTCGAAGGCGCGCCTCTAGAgccaccAT
GGTGAGCAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGCGATGCC
ACCTACGGCAAGCTGACCCTGAAGTTCATCTGCACCACCGGCAAGCTGCCCGTGCCC
TGGCCCACCCTCGTGACCACCCTGACCTACGGCGTGCAGTGCTTCAGCCGCTACCCC
GACCACATGAAGCAGCACGACTTCTTCAAGTCCGCCATGCCCGAAGGCTACGTCCA
GGAGCGCACCATCTTCTTCAAGGACGACGGCAACTACAAGACCCGCGCCGAGGTGA
AGTTCGAGGGCGACACCCTGGTGAACCGCATCGAGCTGAAGGGCATCGACTTCAAG
GAGGACGGCAACATCCTGGGGCACAAGCTGGAGTACAACTACAACAGCCACAACGT
CTATATCATGGCCGACAAGCAGAAGAACGGCATCAAGGTGAACTTCAAGATCCGCC
ACAACATCGAGGACGGCAGCGTGCAGCTCGCCGACCACTACCAGCAGAACACCCCC
ATCGGCGACGGCCCCGTGCTGCTGCCCGACAACCACTACCTGAGCACCCAGTCCGCC
CTGAGCAAAGACCCCAACGAGAAGCGCGATCACATGGTCCTGCTGGAGTTCGTGAC -continued CGCCGCCGGGATCACTCTCGGCATGGACGAGCTGTACAAGtagcATCGATGATATCGC
GGCCGCATACAGCAGCAATTGGCAAGCTGCTTACATAGAACTCGCGGCGATTGGCA
TGCCGCCTTAAAATTTTTATTTTATTTTTCTTTTCTTTTCCGAATCaaATTTTaTTTTTAA
TATTTCAAAAAAAAAAAAAAAA

MOD001

(SEQ ID NO: 41)

AAAAAAAAAACGCGTGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTGGCGCTTT
CTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATC
GTCTTGAGTCCAACCCGGTAAGACACGACTTATCGCCACTGGCAGCAGCCACTGGTA
ACAGGATTAGCAGAGCGAGGTATGTAGGCGGTGCTACAGAGTTCTTGAAGTGGTGG
CCTAACTACGGCTACACTAGAAGAACAGTATTTGGTATCTGCGCTCTGCTGAAGCCA
GTTACCTTCGGAAAAAGAGTTGGTAGCTCTTGATCCGGCAAACAAACCACCGCTGGT
AGCGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGTTA
CCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGC
CCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAG
TTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAG
AATAGTGTATGCGGCGACCGAGTTGCTCTTGCCCGGCGTCAATACGGGATAATACCG
CGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCAC
CCAACTGATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGC
GGATACATATTTGAATGTATTTAGAAAAATAAACAAATAGGGGTTCCGCGCACATTT
CCCCGAAAAGTGCCACCTGAGCTCTAATACGACTCACTATAGgatagGCGGCGCATGA
GAGAAGCCCAGACCAATTACCTACCCAAAACTTCCATCATAGTTATGGCCATGACTA
CTCTAGCTAGCAGTGTTAAATCATTCAGCTACCTGAGAGGGGCCCCTATAACTCTCT
ACGGCTAACCTGAATGGACTACGACATAGTCTAGTCCGCCAAGTTCGAAGGCGCGC
CTCTAGAGCCACCATGGTGAGCAAGGGCGAGGAGCTGTTCACCGGGGTGGTGC
CCATCCTGGTCGAGCTGGACGGCGACGTAAACGGCCACAAGTTCAGCGTGTCC
GGCGAGGGCGAGGGCGATGCCACCTACGGCAAGCTGACCCTGAAGTTCATCTG
CACCACCGGCAAGCTGCCCGTGCCCTGGCCCACCCTCGTGACCACCCTGACCT
ACGGCGTGCAGTGCTTCAGCCGCTACCCCGACCACATGAAGCAGCACGACTTC
TTCAAGTCCGCCATGCCCGAAGGCTACGTCCAGGAGCGCACCATCTTCTTCAA
GGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACAT
CCTGGGGCACAAGCTGGAGTACAACTACAACAGCCACAACGTCTATATCATGG
CCGACAAGCAGAAGAACGGCATCAAGGTGAACTTCAAGATCCGCCACAACATC
GAGGACGGCAGCGTGCAGCTCGCCGACCACTACCAGCAGAACACCCCCATCGG
CGACGGCCCCGTGCTGCTGCCCGACAACCACTACCTGAGCACCCAGTCCGCCC
TGAGCAAAGACCCCAACGAGAAGCGCGATCACATGGTCCTGCTGGAGTTCGTG
ACCGCCGCCGGGATCACTCTCGGCATGGACGAGCTGTACAAGTAGCATCGATG
ATATCGCGGCCGCATACAGCAGCAATTGGCAAGCTGCTTACATAGAACTCGCGGCG
ATTGGCATGCCGCCTTAAAATTTTTATTTTATTTTTCTTTTCTTTTCCGAATCGGATTT
TGTTTTTAATATTTCAAAAAAAAAAAAAAAA

T7-VEE-GFP (SEQ ID NO: 42)

AAAAAAAAAACGCGTCGAGGGGAATTAATTCTTGAAGACGAAAGGGCCAGGTGGC
ACTTTTCGGGGAAATGTGCGCGGAACCCCTATTTGTTTATTTTTCTAAATACATTCAA
ATATGTATCCGCTCATGAGACAATAACCCTGATAAATGCTTCAATAATATTGAAAAA
GGAAGAGTATGAGTATTCAACATTTCCGTGTCGCCCTTATTCCCTTTTTTGCGGCATT
TTGCCTTCCTGTTTTTGCTCACCCAGAAACGCTGGTGAAAGTAAAAGATGCTGAAGA
TCAGTTGGGTGCACGAGTGGGTTACATCGAACTGGATCTCAACAGCGGTAAGATCCT
TGAGAGTTTTCGCCCCGAAGAACGTTTTCCAATGATGAGCACTTTTAAAGTTCTGCT
ATGTGGCGCGGTATTATCCCGTGTTGACGCCGGGCAAGAGCAACTCGGTCGCCGCAT
ACACTATTCTCAGAATGACTTGGTTGAGTACTCACCAGTCACAGAAAAGCATCTTAC
GGATGGCATGACAGTAAGAGAATTATGCAGTGCTGCCATAACCATGAGTGATAACA
CTGCGGCCAACTTACTTCTGACAACGATCGGAGGACCGAAGGAGCTAACCGCTTTTT
TGCACAACATGGGGGATCATGTAACTCGCCTTGATCGTTGGGAACCGGAGCTGAAT
GAAGCCATACCAAACGACGAGCGTGACACCACGATGCCTGTAGCAATGGCAACAAC
GTTGCGCAAACTATTAACTGGCGAACTACTTACTCTAGCTTCCCGGCAACAATTAAT
AGACTGGATGGAGGCGGATAAAGTTGCAGGACCACTTCTGCGCTCGGCCCTTCCGG
CTGGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGACGG
GGAGTCAGGCAACTATGGATGAACGAAATAGACAGATCGCTGAGATAGGTGCCTCA

-continued

CTGATTAAGCATTGGTAACTGTCAGACCAAGTTTACTCATATATACTTTAGATTGATT
TAAAACTTCATTTTTAATTTAAAAGGATCTAGGTGAAGATCCTTTTTGATAATCTCAT
GACCAAAATCCCTTAACGTGAGTTTTCGTTCCACTGAGCGTCAGACCCCGTAGAAAA
GATCAAAGGATCTTCTTGAGATCCTTTTTTTCTGCGCGTAATCTGCTGCTTGCAAACA
AAAAAACCACCGCTACCAGCGGTGGTTTGTTTGCCGGATCAAGAGCTACCAACTCTT
TTTCCGAAGGTAACTGGCTTCAGCAGAGCGCAGATACCAAATACTGTCCTTCTAGTG
TAGCCGTAGTTAGGCCACCACTTCAAGAACTCTGTAGCACCGCCTACATACCTCGCT
CTGCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGGGG
TTCGTGCACACAGCCCAGCTTGGAGCGAACGACCTACACCGAACTGAGATACCTAC
AGCGTGAGCTATGAGAAAGCGCCACGCTTCCCGAAGGGAGAAAGGCGGACAGGTAT
CCGGTAAGCGGCAGGGTCGGAACAGGAGAGCGCACGAGGGAGCTTCCAGGGGGAA
ACGCCTGGTATCTTTATAGTCCTGTCGGGTTTCGCCACCTCTGACTTGAGCGTCGATT
TTTGTGATGCTCGTCAGGGGGGCGGAGCCTATGGAAAAACGCCAGCAACGCGAGCT
CTAATACGACTCACTATAGATGGGCGGCGCATGAGAGAAGCCCAGACCAATTACCT
ACCCAAAATGGAGAAAGTTCACGTTGACATCGAGGAAGACAGCCCATTCCTCAGAG
CTTTGCAGCGGAGCTTCCCGCAGTTTGAGGTAGAAGCCAAGCAGGTCACTGATAATG
ACCATGCTAATGCCAGAGCGTTTTCGCATCTGGCTTCAAAACTGATCGAAACGGAGG
TGGACCCATCCGACACGATCCTTGACATTGGAAGTGCGCCCGCCCGCAGAATGTATT
CTAAGCACAAGTATCATTGTATCTGTCCGATGAGATGTGCGGAAGATCCGGACAGAT
TGTATAAGTATGCAACTAAGCTGAAGAAAAACTGTAAGGAAATAACTGATAAGGAA
TTGGACAAGAAAATGAAGGAGCTGGCCGCCGTCATGAGCGACCCTGACCTGGAAAC
TGAGACTATGTGCCTCCACGACGACGAGTCGTGTCGCTACGAAGGGCAAGTCGCTGT
TTACCAGGATGTATACGCGGTTGACGGACCGACAAGTCTCTATCACCAAGCCAATAA
GGGAGTTAGAGTCGCCTACTGGATAGGCTTTGACACCACCCCTTTTATGTTTAAGAA
CTTGGCTGGAGCATATCCATCATACTCTACCAACTGGGCCGACGAAACCGTGTTAAC
GGCTCGTAACATAGGCCTATGCAGCTCTGACGTTATGGAGCGGTCACGTAGAGGGA
TGTCCATTCTTAGAAAGAAGTATTTGAAACCATCCAACAATGTTCTATTCTCTGTTGG
CTCGACCATCTACCACGAGAAGAGGGACTTACTGAGGAGCTGGCACCTGCCGTCTG
TATTTCACTTACGTGGCAAGCAAAATTACACATGTCGGTGTGAGACTATAGTTAGTT
GCGACGGGTACGTCGTTAAAAGAATAGCTATCAGTCCAGGCCTGTATGGGAAGCCT
TCAGGCTATGCTGCTACGATGCACCGCGAGGGATTCTTGTGCTGCAAAGTGACAGAC
ACATTGAACGGGGAGAGGGTCTCTTTTCCCGTGTGCACGTATGTGCCAGCTACATTG
TGTGACCAAATGACTGGCATACTGGCAACAGATGTCAGTGCGGACGACGCGCAAAA
ACTGCTGGTTGGGCTCAACCAGCGTATAGTCGTCAACGGTCGCACCCAGAGAAACA
CCAATACCATGAAAAATTACCTTTTGCCCGTAGTGGCCCAGGCATTTGCTAGGTGGG
CAAAGGAATATAAGGAAGATCAAGAAGATGAAAGGCCACTAGGACTACGAGATAG
ACAGTTAGTCATGGGGTGTTGTTGGGCTTTTAGAAGGCACAAGATAACATCTATTTA
TAAGCGCCCGGATACCCAAACCATCATCAAAGTGAACAGCGATTTCCACTCATTCGT
GCTGCCCAGGATAGGCAGTAACACATTGGAGATCGGGCTGAGAACAAGAATCAGGA
AAATGTTAGAGGAGCACAAGGAGCCGTCACCTCTCATTACCGCCGAGGACGTACAA
GAAGCTAAGTGCGCAGCCGATGAGGCTAAGGAGGTGCGTGAAGCCGAGGAGTTGCG
CGCAGCTCTACCACCTTTGGCAGCTGATGTTGAGGAGCCCACTCTGGAGGCAGACGT
CGACTTGATGTTACAAGAGGCTGGGGCCGGCTCAGTGGAGACACCTCGTGGCTTGAT
AAAGGTTACCAGCTACGATGGCGAGGACAAGATCGGCTCTTACGCTGTGCTTTCTCC
GCAGGCTGTACTCAAGAGTGAAAAATTATCTTGCATCCACCCTCTCGCTGAACAAGT
CATAGTGATAACACACTCTGGCCGAAAAGGGCGTTATGCCGTGGAACCATACCATG
GTAAAGTAGTGGTGCCAGAGGGACATGCAATACCCGTCCAGGACTTTCAAGCTCTG
AGTGAAAGTGCCACCATTGTGTACAACGAACGTGAGTTCGTAAACAGGTACCTGCA
CCATATTGCCACACATGGAGGAGCGCTGAACACTGATGAAGAATATTACAAAACTG
TCAAGCCCAGCGAGCACGACGGCGAATACCTGTACGACATCGACAGGAAACAGTGC
GTCAAGAAAGAACTAGTCACTGGGCTAGGGCTCACAGGCGAGCTGGTGGATCCTCC
CTTCCATGAATTCGCCTACGAGAGTCTGAGAACACGACCAGCCGCTCCTTACCAAGT
ACCAACCATAGGGGTGTATGGCGTGCCAGGATCAGGCAAGTCTGGCATCATTAAAA
GCGCAGTCACCAAAAAAGATCTAGTGGTGAGCGCCAAGAAAGAAAACTGTGCAGA
AATTATAAGGGACGTCAAGAAAATGAAAGGGCTGGACGTCAATGCCAGAACTGTGG
ACTCAGTGCTCTTGAATGGATGCAAACACCCCGTAGAGACCCTGTATATTGACGAAG
CTTTTGCTTGTCATGCAGGTACTCTCAGAGCGCTCATAGCCATTATAAGACCTAAAA
AGGCAGTGCTCTGCGGGGATCCCAAACAGTGCGGTTTTTTTAACATGATGTGCCTGA
AAGTGCATTTTAACCACGAGATTTGCACACAAGTCTTCCACAAAAGCATCTCTCGCC
GTTGCACTAAATCTGTGACTTCGGTCGTCTCAACCTTGTTTTACGACAAAAAAATGA
GAACGACGAATCCGAAAGAGACTAAGATTGTGATTGACACTACCGGCAGTACCAAA
CCTAAGCAGGACGATCTCATTCTCACTTGTTTCAGAGGGTGGGTGAAGCAGTTGCAA
ATAGATTACAAAGGCAACGAAATAATGACGGCAGCTGCCTCTCAAGGGCTGACCCG
TAAAGGTGTGTATGCCGTTCGGTACAAGGTGAATGAAAATCCTCTGTACGCACCCAC
CTCAGAACATGTGAACGTCCTACTGACCCGCACGGAGGACCGCATCGTGTGGAAAA
CACTAGCCGGCGACCCATGGATAAAAACACTGACTGCCAAGTACCCTGGGAATTTC
ACTGCCACGATAGAGGAGTGGCAAGCAGAGCATGATGCCATCATGAGGCACATCTT
GGAGAGACCGGACCCTACCGACGTCTTCCAGAATAAGGCAAACGTGTGTTGGGCCA
AGGCTTTAGTGCCGGTGCTGAAGACCGCTGGCATAGACATGACCACTGAACAATGG
AACACTGTGGATTATTTTGAAACGGACAAAGCTCACTCAGCAGAGATAGTATTGAA
CCAACTATGCGTGAGGTTCTTTGGACTCGATCTGGACTCCGGTCTATTTTCTGCACCC
ACTGTTCCGTTATCCATTAGGAATAATCACTGGGATAACTCCCCGTCGCCTAACATG
TACGGGCTGAATAAAGAAGTGGTCCGTCAGCTCTCTCGCAGGTACCCACAACTGCCT
CGGGCAGTTGCCACTGGAAGAGTCTATGACATGAACACTGGTACACTGCGCAATTAT
GATCCGCGCATAAACCTAGTACCTGTAAACAGAAGACTGCCTCATGCTTTAGTCCTC
CACCATAATGAACACCCACAGAGTGACTTTTCTTCATTCGTCAGCAAATTGAAGGGC
AGAACTGTCCTGGTGGTCGGGGAAAAGTTGTCCGTCCCAGGCAAAATGGTTGACTG
GTTGTCAGACCGGCCTGAGGCTACCTTCAGAGCTCGGCTGGATTTAGGCATCCCAGG
TGATGTGCCCAAATATGACATAATATTTGTTAATGTGAGGACCCCATATAAATACCA
TCACTATCAGCAGTGTGAAGACCATGCCATTAAGCTTAGCATGTTGACCAAGAAAGC

-continued

TTGTCTGCATCTGAATCCCGGCGGAACCTGTGTCAGCATAGGTTATGGTTACGCTGA
CAGGGCCAGCGAAAGCATCATTGGTGCTATAGCGCGGCAGTTCAAGTTTTCCCGGGT
ATGCAAACCGAAATCCTCACTTGAAGAGACGGAAGTTCTGTTTGTATTCATTGGGTA
CGATCGCAAGGCCCGTACGCACAATTCTTACAAGCTTTCATCAACCTTGACCAACAT
TTATACAGGTTCCAGACTCCACGAAGCCGGATGTGCACCCTCATATCATGTGGTGCG
AGGGGATATTGCCACGGCCACCGAAGGAGTGATTATAAATGCTGCTAACAGCAAAG
GACAACCTGGCGGAGGGGTGTGCGGAGCGCTGTATAAGAAATTCCCGGAAAGCTTC
GATTTACAGCCGATCGAAGTAGGAAAAGCGCGACTGGTCAAAGGTGCAGCTAAACA
TATCATTCATGCCGTAGGACCAAACTTCAACAAAGTTTCGGAGGTTGAAGGTGACAA
ACAGTTGGCAGAGGCTTATGAGTCCATCGCTAAGATTGTCAACGATAACAATTACAA
GTCAGTAGCGATTCCACTGTTGTCCACCGGCATCTTTTCCGGGAACAAAGATCGACT
AACCCAATCATTGAACCATTTGCTGACAGCTTTAGACACCACTGATGCAGATGTAGC
CATATACTGCAGGGACAAGAAATGGGAAATGACTCTCAAGGAAGCAGTGGCTAGGA
GAGAAGCAGTGGAGGAGATATGCATATCCGACGACTCTTCAGTGACAGAACCTGAT
GCAGAGCTGGTGAGGGTGCATCCGAAGAGTTCTTTGGCTGGAAGGAAGGGCTACAG
CACAAGCGATGGCAAAACTTTCTCATATTTGGAAGGGACCAAGTTTCACCAGGCGG
CCAAGGATATAGCAGAAATTAATGCCATGTGGCCCGTTGCAACGGAGGCCAATGAG
CAGGTATGCATGTATATCCTCGGAGAAAGCATGAGCAGTATTAGGTCGAAATGCCC
CGTCGAAGAGTCGGAAGCCTCCACACCACCTAGCACGCTGCCTTGCTTGTGCATCCA
TGCCATGACTCCAGAAAGAGTACAGCGCCTAAAAGCCTCACGTCCAGAACAAATTA
CTGTGTGCTCATCCTTTCCATTGCCGAAGTATAGAATCACTGGTGTGCAGAAGATCC
AATGCTCCCAGCCTATATTGTTCTCACCGAAAGTGCCTGCGTATATTCATCCAAGGA
AGTATCTCGTGGAAACACCACCGGTAGACGAGACTCCGGAGCCATCGGCAGAGAAC
CAATCCACAGAGGGGACACCTGAACAACCACCACTTATAACCGAGGATGAGACCAG
GACTAGAACGCCTGAGCCGATCATCATCGAAGAGGAAGAAGAGGATAGCATAAGTT
TGCTGTCAGATGGCCCGACCCACCAGGTGCTGCAAGTCGAGGCAGACATTCACGGG
CCGCCCTCTGTATCTAGCTCATCCTGGTCCATTCCTCATGCATCCGACTTTGATGTGG
ACAGTTTATCCATACTTGACACCCTGGAGGGAGCTAGCGTGACCAGCGGGGCAACG
TCAGCCGAGACTAACTCTTACTTCGCAAAGAGTATGGAGTTTCTGGCGCGACCGGTG
CCTGCGCCTCGAACAGTATTCAGGAACCCTCCACATCCCGCTCCGCGCACAAGAACA
CCGTCACTTGCACCCAGCAGGGCCTGCTCGAGAACCAGCCTAGTTTCCACCCCGCCA
GGCGTGAATAGGGTGATCACTAGAGAGGAGCTCGAGGCGCTTACCCCGTCACGCAC
TCCTAGCAGGTCGGTCTCGAGAACCAGCCTGGTCTCCAACCCGCCAGGCGTAAATA
GGGTGATTACAAGAGAGGAGTTTGAGGCGTTCGTAGCACAACAACAATGACGGTTT
GATGCGGGTGCATACATCTTTTCCTCCGACACCGGTCAAGGGCATTTACAACAAAAA
TCAGTAAGGCAAACGGTGCTATCCGAAGTGGTGTTGGAGAGGACCGAATTGGAGAT
TTCGTATGCCCCGCGCCTCGACCAAGAAAAAGAAGAATTACTACGCAAGAAATTAC
AGTTAAATCCCACACCTGCTAACAGAAGCAGATACCAGTCCAGGAAGGTGGAGAAC
ATGAAAGCCATAACAGCTAGACGTATTCTGCAAGGCCTAGGGCATTATTTGAAGGC
AGAAGGAAAAGTGGAGTGCTACCGAACCCTGCATCCTGTTCCTTTGTATTCATCTAG
TGTGAACCGTGCCTTTTCAAGCCCCAAGGTCGCAGTGGAAGCCTGTAACGCCATGTT
GAAAGAGAACTTTCCGACTGTGGCTTCTTACTGTATTATTCCAGAGTACGATGCCTA
TTTGGACATGGTTGACGGAGCTTCATGCTGCTTAGACACTGCCAGTTTTTGCCCTGCA
AAGCTGCGCAGCTTTCCAAAGAAACACTCCTATTTGGAACCCACAATACGATCGGC
AGTGCCTTCAGCGATCCAGAACACGCTCCAGAACGTCCTGGCAGCTGCCACAAAAA
GAAATTGCAATGTCACGCAAATGAGAGAATTGCCCGTATTGGATTCGGCGGCCTTTA
ATGTGGAATGCTTCAAGAAATATGCGTGTAATAATGAATATTGGGAAACGTTTAAA
GAAAACCCCATCAGGCTTACTGAAGAAAACGTGGTAAATTACATTACCAAATTAAA
AGGACCAAAAGCTGCTGCTCTTTTTGCGAAGACACATAATTTGAATATGTTGCAGGA
CATACCAATGGACAGGTTTGTAATGGACTTAAAGAGAGACGTGAAAGTGACTCCAG
GAACAAAACATACTGAAGAACGGCCCAAGGTACAGGTGATCCAGGCTGCCGATCCG
CTAGCAACAGCGTATCTGTGCGGAATCCACCGAGAGCTGGTTAGGAGATTAAATGC
GGTCCTGCTTCCGAACATTCATACACTGTTTGATATGTCGGCTGAAGACTTTGACGCT
ATTATAGCCGAGCACTTCCAGCCTGGGGATTGTGTTCTGGAAACTGACATCGCGTCG
TTTGATAAAAGTGAGGACGACGCCATGGCTCTGACCGCGTTAATGATTCTGGAAGAC
TTAGGTGTGGACGCAGAGCTGTTGACGCTGATTGAGGCGGCTTTCGGCGAAATTTCA
TCAATACATTTGCCCACTAAAACTAAATTTAAATTCGGAGCCATGATGAAATCTGGA
ATGTTCCTCACACTGTTTGTGAACACAGTCATTAACATTGTAATCGCAAGCAGAGTG
TTGAGAGAACGGCTAACCGGATCACCATGTGCAGCATTCATTGGAGATGACAATAT
CGTGAAAGGAGTCAAATCGGACAAATTAATGGCAGACAGGTGCGCCACCTGGTTGA
ATATGGAAGTCAAGATTATAGATGCTGTGGTGGGCGAGAAAGCGCCTTATTTCTGTG
GAGGGTTTATTTTGTGTGACTCCGTGACCGGCACAGCGTGCCGTGTGGCAGACCCCC
TAAAAAGGCTGTTTAAGCTTGGCAAACCTCTGGCAGCAGACGATGAACATGATGAT
GACAGGAGAAGGGCATTGCATGAAGAGTCAACACGCTGGAACCGAGTGGGTATTCT
TTCAGAGCTGTGCAAGGCAGTAGAATCAAGGTATGAAACCGTAGGAACTTCCATCA
TAGTTATGGCCATGACTACTCTAGCTAGCAGTGTTAAATCATTCAGCTACCTGAGAG
GGGCCCCTATAACTCTCTACGGCTAACCTGAATGGACTACGACATAGTCTAGTCCGC
CAAGTCTAGCATATGGGCGCGCCCTCAGCATCGATTCAATTCGCCACCATGGTGAGC
AAGGGCGAGGAGCTGTTCACCGGGGTGGTGCCCATCCTGGTCGAGCTGGACGGCGA
CGTAAACGGCCACAAGTTCAGCGTGTCCGGCGAGGGCGAGGGCGATGCCACCTACG
GCAAGCTGACCCTGAAGTTCATCTGCACCACCGGCAAGCTGCCCGTGCCCTGGCCCA
CCCTCGTGACCACCCTGACCTACGGCGTGCAGTGCTTCAGCCGCTACCCCGACCACA
TGAAGCAGCACGACTTCTTCAAGTCCGCCATGCCCGAAGGCTACGTCCAGGAGCGC
ACCATCTTCTTCAAGGACGACGGCAACTACAAGACCCGCGCCGAGGTGAAGTTCGA
GGGCGACACCCTGGTGAACCGCATCGAGCTGAAGGGCATCGACTTCAAGGAGGACG
GCAACATCCTGGGGCACAAGCTGGAGTACAACTACAACAGCCACAACGTCTATATC
ATGGCCGACAAGCAGAAGAACGGCATCAAGGTGAACTTCAAGATCCGCCACAACAT
CGAGGACGGCAGCGTGCAGCTCGCCGACCACTACCAGCAGAACACCCCCATCGGCG
ACGGCCCCGTGCTGCTGCCCGACAACCACTACCTGAGCACCCAGTCCGCCCTGAGCA
AAGACCCCAACGAGAAGCGCGATCACATGGTCCTGCTGGAGTTCGTGACCGCCGCC
GGGATCACTCTCGGCATGGACGAGCTGTACAAGTAGTCTAGAGTCGACCCGGGCGG

-continued

CCGCAACTAACTTAAGCTAGCAACGGTTTCCCTCTAGCGGGATCAATTCCGCCCCCC
CCCCCTAACGTTACTGGCCGAAGCCGCTTGGAATAAGGCCGGTGTGCGTTTGTCTAT
ATGTTATTTTCCACCATATTGCCGTCTTTTGGCAATGTGAGGGCCCGGAAACCTGGC
CCTGTCTTCTTGACGAGCATTCCTAGGGGTCTTTCCCCTCTCGCCAAAGGAATGCAA
GGTCTGTTGAATGTCGTGAAGGAAGCAGTTCCTCTGGAAGCTTCTTGAAGACAAACA
ACGTCTGTAGCGACCCTTTGCAGGCAGCGGAACCCCCCACCTGGCGACAGGTGCCTC
TGCGGCCAAAAGCCACGTGTATAAGATACACCTGCAAAGGCGGCACAACCCCAGTG
CCACGTTGTGAGTTGGATAGTTGTGGAAAGAGTCAAATGGCTCTCCTCAAGCGTATT
CAACAAGGGGCTGAAGGATGCCCAGAAGGTACCCCATTGTATGGGATCTGATCTGG
GGCCTCGGTGCACATGCTTTACATGTGTTTAGTCGAGGTTAAAAAAACGTCTAGGCC
CCCCGAACCACGGGGACGTGGTTTTCCTTTGAAAAACACGATAATACCATGACCGA
GTACAAGCCCACGGTGCGCCTCGCCACCCGCGACGACGTCCCCAGGGCCGTACGCA
CCCTCGCCGCCGCGTTCGCCGACTACCCCGCCACGCGCCACACCGTCGATCCGGACC
GCCACATCGAGCGGGTCACCGAGCTGCAAGAACTCTTCCTCACGCGCGTCGGGCTC
GACATCGGCAAGGTGTGGGTCGCGGACGACGGCGCCGCGGTGGCGGTCTGGACCAC
GCCGGAGAGCGTCGAAGCGGGGGCGGTGTTCGCCGAGATCGGCCCGCGCATGGCCG
AGTTGAGCGGTTCCCGGCTGGCCGCGCAGCAACAGATGGAAGGCCTCCTGGCGCCG
CACCGGCCCAAGGAGCCCGCGTGGTTCCTGGCCACCGTCGGCGTCTCGCCCGACCAC
CAGGGCAAGGGTCTGGGCAGCGCCGTCGTGCTCCCCGGAGTGGAGGCGGCCGAGCG
CGCCGGGGTGCCCGCCTTCCTGGAGACCTCCGCGCCCCGCAACCTCCCCTTCTACGA
GCGGCTCGGCTTCACCGTCACCGCCGACGTCGAGGTGCCCGAAGGACCGCGCACCT
GGTGCATGACCCGCAAGCCCGGTGCCTGAGAATTGGCAAGCTGCTTACATAGAACT
CGCGGCGATTGGCATGCCGCCTTAAAATTTTTATTTTATTTTTTCTTTTCTTTTCCGAA
TCGGATTTTGTTTTTAATATTTCAAAAAAAAAAAAAAA

Contig 1

(SEQ ID NO: 27)

ATGGAGAAAGTTCACGTTGACATCGAGGAAGACAGCCCATTCCTCAGAGCTTTGCA
GCGGAGCTTCCCGCAGTTTGAGGTAGAAGCCAAGCAGGTCACTGATAATGACCATG
CTAATGCCAGAGCGTTTTCGCATCTGGCTTCAAAACTGATCGAAACGGAGGTGGACC
CATCCGACACGATCCTTGACATTGGAAGTGCGCCCGCCCGCAGAATGTATTCTAAGC
ACAAGTATCATTGTATCTGTCCGATGAGATGTGCGGAAGATCCGGACAGATTGTATA
AGTATGCAACTAAGCTGAAGAAAAACTGTAAGGAAATAACTGATAAGGAATTGGAC
AAGAAAATGAAGGAGCTGGCCGCCGTCATGAGCGACCCTGACCTGGAAACTGAGAC
TATGTGCCTCCACGACGACGAGTCGTGTCGCTACGAAGGGCAAGTCGCTGTTTACCA
GGATGTATACGCGGTTGACGGACCGACAAGTCTCTATCACCAAGCCAATAAGGGAG
TTAGAGTCGCCTACTGGATAGGCTTTGACACCACCCCTTTTATGTTTAAGAACTTGGC
TGGAGCATATCCATCATACTCTACCAACTGGGCCGACGAAACCGTGTTAACGGCTCG
TAACATAGGCCTATGCAGCTCTGACGTTATGGAGCGGTCACGTAGAGGGATGTCCAT
TCTTAGAAAGAAGTATTTGAAACCATCCAACAATGTTCTATTCTCTGTTGGCTCGAC
CATCTACCACGAGAAGAGGGACTTACTGAGGAGCTGGCACCTGCCGTCTGTATTTCA
CTTACGTGGCAAGCAAAATTACACATGTCGGTGTGAGACTATAGTTAGTTGCGACGG
GTACGTCGTTAAAAGAATAGCTATCAGTCCAGGCCTGTATGGGAAGCCTTCAGGCTA
TGCTGCTACGATGCACCGCGAGGGATTCTTGTGCTGCAAAGTGACAGACACATTGAA
CGGGGAGAGGGTCTCTTTTCCCGTGTGCACGTATGTGCCAGCTACATTGTGTGACCA
AATGACTGGCATACTGGCAACAGATGTCAGTGCGGACGACGCGCAAAAACTGCTGG
TTGGGCTCAACCAGCGTATAGTCGT

Contig 2

(SEQ ID NO: 28)

TGGCAACAGATGTCAGTGCGGACGACGCGCAAAAACTGCTGGTTGGGCTCAACCAG
CGTATAGTCGTCAACGGTCGCACCCAGAGAAACACCAATACCATGAAAAATTACCT
TTTGCCCGTAGTGGCCCAGGCATTTGCTAGGTGGGCAAAGGAATATAAGGAAGATC
AAGAAGATGAAAGGCCACTAGGACTACGAGATAGACAGTTAGTCATGGGGTGTTGT
TGGGCTTTTAGAAGGCACAAGATAACATCTATTTATAAGCGCCCGGATACCCAAACC
ATCATCAAAGTGAACAGCGATTTCCACTCATTCGTGCTGCCCAGGATAGGCAGTAAC
ACATTGGAGATCGGGCTGAGAACAAGAATCAGGAAAATGTTAGAGGAGCACAAGG
AGCCGTCACCTCTCATTACCGCCGAGGACGTACAAGAAGCTAAGTGCGCAGCCGAT
GAGGCTAAGGAGGTGCGTGAAGCCGAGGAGTTGCGCGCAGCTCTACCACCTTTGGC
AGCTGATGTTGAGGAGCCCACTCTGGAAGCCGATGTCGACTTGATGTTACAAGAGG
CTGGGGCCGGCTCAGTGGAGACACCTCGTGGCTTGATAAAGGTTACCAGCTACGAT
GGCGAGGACAAGATCGGCTCTTACGCTGTGCTTTCTCCGCAGGCTGTACTCAAGAGT
GAAAAATTATCTTGCATCCACCCTCTCGCTGAACAAGTCATAGTGATAACACACTCT
GGCCGAAAAGGGCGTTATGCCGTGGAACCATACCATGGTAAAGTAGTGGTGCCAGA
GGGACATGCAATACCCGTCCAGGACTTTCAAGCTCTGAGTGAAAGTGCCACCATTGT
GTACAACGAACGTGAGTTCGTAAACAGGTACCTGCACCATATTGCCACACATGGAG
GAGCGCTGAACACTGATGAAGAATATTACAAAACTGTCAAGCCCAGCGAGCACGAC
GGCGAATACCTGTACGACATCGACAGGAAACAGTGCGTCAAGAAAGAACTAGTCAC
TGGGCTAGGGCTCACAGGCGAGCTGGTGGATCCTCCCTTCCATGAATTCGCCTACGA
GAGTCTGAGAACACGACCAGCCGCTCCTTACCAAGTACCAACCATAGGGGTGTATG
GCGTGCCAGGATCAGGCAAGTCTGGCATCATTA

Contig 3

(SEQ ID NO: 29)

TACCAAGTACCAACCATAGGGGTGTATGGCGTGCCAGGATCAGGCAAGTCTGGCAT
CATTAAAAGCGCAGTCACCAAAAAAGATCTAGTGGTGAGCGCCAAGAAAGAAAACT
GTGCAGAAATTATAAGGGACGTCAAGAAAATGAAAGGGCTGGACGTCAATGCCAGA
ACTGTGGACTCAGTGCTCTTGAATGGATGCAAACACCCCGTAGAGACCCTGTATATT
GACGAAGCTTTTGCTTGTCATGCAGGTACTCTCAGAGCGCTCATAGCCATTATAAGA
CCTAAAAAGGCAGTGCTCTGCGGGGATCCCAAACAGTGCGGTTTTTTAACATGATG
TGCCTGAAAGTGCATTTTAACCACGAGATTTGCACACAAGTCTTCCACAAAAGCATC

-continued

TCTCGCCGTTGCACTAAATCTGTGACTTCGGTCGTCTCAACCTTGTTTTACGACAAAA
AAATGAGAACGACGAATCCGAAAGAGACTAAGATTGTGATTGACACTACCGGCAGT
ACCAAACCTAAGCAGGACGATCTCATTCTCACTTGTTTCAGAGGGTGGGTGAAGCAG
TTGCAAATAGATTACAAAGGCAACGAAATAATGACGGCAGCTGCCTCTCAAGGGCT
GACCCGTAAAGGTGTGTATGCCGTTCGGTACAAGGTGAATGAAAATCCTCTGTACGC
ACCCACCTCAGAACATGTGAACGTCCTACTGACCCGCACGGAGGACCGCATCGTGT
GGAAAACACTAGCCGGCGACCCATGGATAAAAACACTGACTGCCAAGTACCCTGGG
AATTTCACTGCCACGATAGAGGAGTGGCAAGCAGAGCATGATGCCATCATGAGGCA
CATCTTGGAGAGACCGGACCCTACCGACGTCTTCCAGAATAAGGCAAACGTGTGTTG
GGCCAAGGCTTTAGTGCCGGTGCTGAAGACCGCTGGCATAGACATGACCACTGAAC
AATGGAACACTGTGGATTATTTTGAAACGGACAAAGCTCACTCAGCAGAGATAGTA
TTGAACCAACTATGCGTGAGGTTCTTTGGACTCGATCTGGACTCCGGTCTATTTTCTG
CACCCACTGTTCCGTTATCCATTAGGAATAATCACTGGGATAACTCCCCGTCGCCTA
ACATGTACGGGCTGAA

Contig 4

(SEQ ID NO: 30)

GAATAATCACTGGGATAACTCCCCGTCGCCTAACATGTACGGGCTGAATAAAGAAG
TGGTCCGTCAGCTCTCTCGCAGGTACCCACAACTGCCTCGGGCAGTTGCCACTGGAA
GAGTCTATGACATGAACACTGGTACACTGCGCAATTATGATCCGCGCATAAACCTAG
TACCTGTAAACAGAAGACTGCCTCATGCTTTAGTCCTCCACCATAATGAACACCCAC
AGAGTGACTTTTCTTCATTCGTCAGCAAATTGAAGGGCAGAACTGTCCTGGTGGTCG
GGGAAAAGTTGTCCGTCCCAGGCAAAATGGTTGACTGGTTGTCAGACCGGCCTGAG
GCTACCTTCAGAGCTCGGCTGGATTTAGGCATCCCAGGTGATGTGCCCAAATATGAC
ATAATATTTGTTAATGTGAGGACCCCATATAAATACCATCACTATCAGCAGTGTGAA
GACCATGCCATTAAGCTTAGCATGTTGACCAAGAAAGCTTGTCTGCATCTGAATCCC
GGCGGAACCTGTGTCAGCATAGGTTATGGTTACGCTGACAGGGCCAGCGAAAGCAT
CATTGGTGCTATAGCGCGGCAGTTCAAGTTTTCCCGGGTATGCAAACCGAAATCCTC
ACTTGAAGAGACGGAAGTTCTGTTTGTATTCATTGGGTACGATCGCAAGGCCCGTAC
GCACAATtCTTACAAGCTTTCATCAACCTTGACCAACATTTATACAGGTTCCAGACTC
CACGAAGCCGGATGTGCACCCTCATATCATGTGGTGCGAGGGGATATTGCCACGGC
CACCGAAGGAGTGATTATAAATGCTGCTAACAGCAAAGGACAACCTGGCGGAGGGG
TGTGCGGAGCGCTGTATAAGAAATTCCCGGAAAGCTTCGATTTACAGCCGATCGAA
GTAGGAAAAGCGCGACTGGTCAAAGGTGCAGCTAAACATATCATTCATGCCGTAGG
ACCAAACTTCAACAAAGTTTCGGAGGTTGAAGGTGACAAACAGTTGGCAGAGGCTT
ATGAGTCCATCGCTAAGATTGTCAACGATAACAATTACAAGTCAGTAGCGATTCCAC
TGTTGTCCACCGGCATCTTTTCCGGGAACAAAGATCGACTAACCCAATCATTGAACC
ATTTGCTGACAGCTTTAGACACCACTGATGCAGATG

Contig 5

(SEQ ID NO: 31)

ATTGAACCATTTGCTGACAGCTTTAGACACCACTGATGCAGATGTAGCCATATACTG
CAGGGACAAGAAATGGGAAATGACTCTCAAGGAAGCAGTGGCTAGGAGAGAAGCA
GTGGAGGAGATATGCATATCCGACGACTCTTCAGTGACAGAACCTGATGCAGAGCT
GGTGAGGGTGCATCCGAAGAGTTCTTTGGCTGGAAGGAAGGGCTACAGCACAAGCG
ATGGCAAAACTTTCTCATATTTGGAAGGGACCAAGTTTCACCAGGCGGCCAAGGAT
ATAGCAGAAATTAATGCCATGTGGCCCGTTGCAACGGAGGCCAATGAGCAGGTATG
CATGTATATCCTCGGAGAAAGCATGAGCAGTATTAGGTCGAAATGCCCCGTCGAAG
AGTCGGAAGCCTCCACACCACCTAGCACGCTGCCTTGCTTGTGCATCCATGCCATGA
CTCCAGAAAGAGTACAGCGCCTAAAAGCCTCACGTCCAGAACAAATTACTGTGTGC
TCATCCTTTCCATTGCCGAAGTATAGAATCACTGGTGTGCAGAAGATCCAATGCTCC
CAGCCTATATTGTTCTCACCGAAAGTGCCTGCGTATATTCATCCAAGGAAGTATCTC
GTGGAAACACCACCGGTAGACGAGACTCCGGAGCCATCGGCAGAGAACCAATCCAC
AGAGGGGACACCTGAACAACCACCACTTATAACCGAGGATGAGACCAGGACTAGA
ACGCCTGAGCCGATCATCATCGAAGAGGAAGAAGAGGATAGCATAAGTTTGCTGTC
AGATGGCCCGACCCACCAGGTGCTGCAAGTCGAGGCAGACATTCACGGGCCGCCCT
CTGTATCTAGCTCATCCTGGTCCATTCCTCATGCATCCGACTTTGATGTGGACAGTTT
ATCCATACTTGACACCCTGGAGGGAGCTAGCGTGACCAGCGGGGCAACGTCAGCCG
AGACTAACTCTTACTTCGCAAAGAGTATGGAGTTTCTGGCGCGACCGGTGCCTGCGC
CTCGAACAGTATTCAGGAACCCTCCACATCCCGCTCCGCGCACAAGAACACCGTCAC
TTGCACCCAGCAGGGCCTGCTCGAGAACCAGCCTAGTTTCCACCCCGCCAGGCGTGA
ATAGGGTGATCACTAGAGAGGA

Contig 6

(SEQ ID NO: 32)

AGAACCAGCCTAGTTTCCACCCCGCCAGGCGTGAATAGGGTGATCACTAGAGAGGA
GCTCGAGGCGCTTACCCCGTCACGCACTCCTAGCAGGTCGGTCTCGAGAACCAGCCT
GGTCTCCAACCCGCCAGGCGTAAATAGGGTGATTACAAGAGAGGAGTTTGAGGCGT
TCGTAGCACAACAACAATGACGGTTTGATGCGGGTGCATACATCTTTTCCTCCGACA
CCGGTCAAGGGCATTTACAACAAAAATCAGTAAGGCAAACGGTGCTATCCGAAGTG
GTGTTGGAGAGGACCGAATTGGAGATTTCGTATGCCCCGCGCCTCGACCAAGAAAA
AGAAGAATTACTACGCAAGAAATTACAGTTAAATCCCACACCTGCTAACAGAAGCA
GATACCAGTCCAGGAAGGTGGAGAACATGAAAGCCATAACAGCTAGACGTATTCTG
CAAGGCCTAGGGCATTATTTGAAGGCAGAAGGAAAAGTGGAGTGCTACCGAACCCT
GCATCCTGTTCCTTTGTATTCATCTAGTGTGAACCGTGCCTTTTCAAGCCCCAAGGTC
GCAGTGGAAGCCTGTAACGCCATGTTGAAAGAGAACTTTCCGACTGTGGCTTCTTAC
TGTATTATTCCAGAGTACGATGCCTATTTGGACATGGTTGACGGAGCTTCATGCTGC
TTAGACACTGCCAGTTTTTGCCCTGCAAAGCTGCGCAGCTTTCCAAAGAAACACTCC
TATTTGGAACCCACAATACGATCGGCAGTGCCTTCAGCGATCCAGAACACGCTCCAG
AACGTCCTGGCAGCTGCCACAAAAAGAAATTGCAATGTCACGCAAATGAGAGAATT
GCCCGTATTGGATTCGGCGGCCTTTAATGTGGAATGCTTCAAGAAATATGCGTGTAA

-continued

```
TAATGAATATTGGGAAACGTTTAAAGAAAACCCCATCAGGCTTACTGAAGAAAACG
TGGTAAATTACATTACCAAATTAAAAGGACCAAAAGCTGCTGCTCTTTTTGCGAAGA
CACATAATTTGAATATGTTGCAGGACATACCAATGGACAGGTTTGTAATGGACTTAA
AGAGAGACGTGAAAGTGACTCCAGGAACAAAACATACTGAAGAACGGCCCAAGGT
ACAGGTGATCCAGGCTGCCGATCCGCTAGCAACAGCGTATCTGTGCGGAATCCACC
GAGAGCTGGTTA
```

Contig 7

(SEQ ID NO: 33)

```
GCTAGCAACAGCGTATCTGTGCGGAATCCACCGAGAGCTGGTTAGGAGATTAAATG
CGGTCCTGCTTCCGAACATTCATACACTGTTTGATATGTCGGCTGAAGACTTTGACG
CTATTATAGCCGAGCACTTCCAGCCTGGGGATTGTGTTCTGGAAACTGACATCGCGT
CGTTTGATAAAAGTGAGGACGACGCCATGGCTCTGACCGCGTTAATGATTCTGGAAG
ACTTAGGTGTGGACGCAGAGCTGTTGACGCTGATTGAGGCGGCTTTCGGCGAAATTT
CATCAATACATTTGCCCACTAAAACTAAATTTAAATTCGGAGCCATGATGAAATCTG
GAATGTTCCTCACACTGTTTGTGAACACAGTCATTAACATTGTAATCGCAAGCAGAG
TGTTGAGAGAACGGCTAACCGGATCACCATGTGCAGCATTCATTGGAGATGACAAT
ATCGTGAAAGGAGTCAAATCGGACAAATTAATGGCAGACAGGTGCGCCACCTGGTT
GAATATGGAAGTCAAGATTATAGATGCTGTGGTGGGCGAGAAAGCGCCTTATTTCTG
TGGAGGGTTTATTTTGTGTGACTCCGTGACCGGCACAGCGTGCCGTGTGGCAGACCC
CCTAAAAAGGCTGTTTAAGCTTGGCAAACCTCTGGCAGCAGACGATGAACATGATG
ATGACAGGAGAAGGGCATTGCATGAAGAGTCAACACGCTGGAACCGAGTGGGTATT
CTTTCAGAGCTGTGCAAGGCAGTAGAATCAAGGTATGAAACCGTAGGAACTTCCAT
CATAGTTATGGCCATGACTACTCTAGCTAGCAGTGTTAAATCATTCAGCTACCTGAG
AGGGGCCCCTATAACTCTCTACGGCTAACCTGAATGGACTACGACATAGTCTAGTCC
GCCAAGTTCGAAGGCGCGCCTCTAGAGCCACCATGACCGAGTACAAGCCCACGGTG
CGCCTCGCCACCCGCGACGACGTCCCCAGGGCCGTACGCACCCTCGCCGCCGCGTTC
GCCGACTACCCCGCCACGCGCCACACCGTCGATCCGGACCGCCACATCGAGCGGGT
CACCGAGCTGCAAGAACTCTTCCT
```

Contig 8

(SEQ ID NO: 34)

```
CACGCGCGTCGGGCTCGACATCGGCAAGGTGTGGGTCGCGGACGACGGCGCCGCGG
TGGCGGTCTGGACCACGCCGGAGAGCGTCGAAGCGGGGGCGGTGTTCGCCGAGATC
GGCCCGCGCATGGCCGAGTTGAGCGGTTCCCGGCTGGCCGCGCAGCAACAGATGGA
AGGCCTCCTGGCGCCGCACCGGCCCAAGGAGCCCGCGTGGTTCCTGGCCACCGTCG
GCGTCTCGCCCGACCACCAGGGCAAGGGTCTGGGCAGCGCCGTCGTGCTCCCCGGA
GTGGAGGCGGCCGAGCGCGCCGGGGTGCCCGCCTTCCTGGAGACCTCCGCGCCCCG
CAACCTCCCCTTCTACGAGCGGCTCGGCTTCACCGTCACCGCCGACGTCGAGGTGCC
CGAAGGACCGCGCACCTGGTGCATGACCCGCAAGCCCGGTGCCTGACATCGATGAT
ATCGCGGCCGCATACAGCAGCAATTGGCAAGCTGCTTACATAGAACTCGCGGCGAT
TGGCATGCCGCCTTAAAATTTTTATTTTATTTTTCTTTTCTTTTCCGAATCGGATTTTG
TTTTTAATATTTCAAAAAAAAAAAAAAAA
```

In addition, it is to be understood that any particular aspect of the present disclosure that falls within the prior art may be explicitly excluded from any one or more of the claims. Since such aspects are deemed to be part of the whole of the present disclosure, any part of the whole disclosure may be excluded even if the exclusion is not set forth explicitly herein.

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

The invention claimed is:

1. An in vitro method of increasing the copy number of a nucleic acid comprising:
   a) contacting cells with a nucleic acid encoding two expression units, the nucleic acid comprising:
      i) an origin of replication sequence (Ori);
      ii) a first expression unit encoding a first nucleotide sequence that is operably linked to a first promoter; and
      iii) a second expression unit encoding a second nucleotide sequence that is operably linked to a second promoter, wherein the second promoter comprises an engineered T7 promoter comprising the nucleotide sequence of SEQ ID NO: 47 (TAATACGACTCACTATAGG) operably linked to a 5' UTR and wherein the 5' UTR is 3' to SEQ ID NO: 47;
   wherein the first expression unit encodes a selectable marker and the second expression unit encodes a self-amplifying mRNA (sa-mRNA);
   b) selecting cells that express the selectable marker;
   c) subculturing the selected cells to obtain a population of cells that express the selectable marker; and
   d) propagating the population of cells to increase the copy number of the nucleic acid.

2. An in vitro method of increasing the copy number of a nucleic acid comprising:
   a) contacting cells with a nucleic acid encoding two expression units, the nucleic acid comprising:
      i) an origin of replication sequence (Ori);
      ii) a first expression unit encoding a first nucleotide sequence that is operably linked to a first promoter; and
      iii) a second expression unit encoding a second nucleotide sequence that is operably linked to a second promoter,
   wherein the first expression unit encodes a selectable marker and the second expression unit encodes a self-amplifying mRNA (sa-mRNA);
   b) selecting cells that express the selectable marker;
   c) subculturing the selected cells to obtain a population of cells that express the selectable marker; and
   d) propagating the population of cells to increase the copy number of the nucleic acid wherein the nucleic acid has at least 90% sequence identity to SAM001 (SEQ ID NO: 35), SAM002 (SEQ ID NO: 36), SAM003 (SEQ ID NO: 37), SAM004 (SEQ ID NO: 38), SAM005 (SEQ ID NO: 39), SAM006 (SEQ ID NO: 40), MOD001 (SEQ ID NO: 41), or T7-VEE-GFP (SEQ ID NO: 42).

3. The in vitro method of claim 1, wherein the first expression unit comprises the following operably linked nucleic acid sequence in a 5' to 3' direction or in a 3' to 5' direction:

Pr1-SM wherein

Pr1 is the first promoter sequence, and

SM is the selectable marker.

4. The in vitro method of claim 1, wherein the first promoter is an ampicillin resistance (AmpR) promoter, a kanamycin resistance (KanR) promoter, a chloramphenicol resistance (CamR) promoter, an erythromycin resistance (ErmR) promoter, and a tetracycline resistance (TetR) promoter, and/or wherein the selectable marker is AmpR, KanR, CamR, ErmR, or TetR.

5. The in vitro method of claim 1, wherein the second expression unit comprises the following operably linked nucleic acid sequence from 5' to 3':

Pr2-5'UTR-nsP-SGP-GOI-3'UTR-PolyA wherein

Pr2 is the second promoter sequence for in vitro transcription,

5'UTR is a 5' untranslated region, nsP is a plurality of non-structural replicase domain sequences, SGP is a subgenomic promoter, GOI is one or more genes of interest, 3'UTR is a 3' untranslated region, and Poly-A is a 3' poly-adenylated tail (poly-A tail).

6. The in vitro method of claim 5, wherein at least one gene of interest (GOI), encodes a therapeutic polypeptide, a prophylactic polypeptide, a diagnostic polypeptide, an antigen, or a non-coding gene that encodes regulatory structures.

7. The in vitro method of claim 5, wherein at least one GOI encodes a non-coding gene that encodes at least one regulatory structure, wherein the at least one regulatory structure is a small interfering RNA (siRNA), a micro-RNA (miRNA), a guide RNA (gRNA), a self-activating RNA (saRNA), a transfer RNA (tRNA), or a long intergenic non-coding (lincRNA).

8. The in vitro method of claim 1, wherein at least one GOI encodes an infectious disease antigen, an allergic antigen, or a tumor antigen.

9. The in vitro method of claim 5, wherein the plurality of non-structural replicase domain sequences are obtained from a Group IV positive single strand RNA virus selected from the group comprising Picornaviridae, Togaviridae, Coronaviridae, Hepeviridae, Caliciviridae, Flaviviridae, and Astroviridae.

10. The in vitro method of claim 5, wherein the plurality of non-structural replicase domain sequences are obtained from an alphavirus selected from the group comprising Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus.

11. The in vitro method of claim 5, wherein the plurality of non-structural replicase domain sequences are alphavirus nonstructural proteins 1-4 (nsP1-4).

12. The in vitro method of claim 5, wherein the plurality of non-structural replicase domain sequences are obtained from the TC-83 strain of Venezuelan Equine Encephalitis virus (VEE).

13. The in vitro method of claim 1, wherein the nucleic acid sequence comprises from 5' to 3':

a) Ori-SM-Pr1-L2-Pr2-5'UTR-nsP-L3-GOI-L4-3'UTR-PolyA;

b) L1-Ori-SM-Pr1-Pr2-5'UTR-nsP-L3-GOI-L4-3'UTR-PolyA c) L1-Ori-SM-Pr1-L2-Pr2-5'UTR-nsP-GOI-L4-3'UTR-PolyA;

d) L1-Ori-SM-Pr1-L2-Pr2-5'UTR-nsP-L3-GOI-3'UTR-PolyA; or e) L1-Ori-SM-Pr1-L2-Pr2-5'UTR-nsP-SGP-L3-GOI-L4-3'UTR-PolyA, wherein L1 is a first linker, Ori is an origin of replication sequence, SM is a selectable marker, Pr1 is a first promoter sequence, L2 is a second linker, Pr2 is a second promoter sequence, 5'UTR is a 5' untranslated region, nsP is a plurality of non-structural replicase domain sequences, L3 is a third linker, SGP is a subgenomic promoter, GOI is one or more genes of interest, L4 is a fourth linker, 3'UTR is a 3' untranslated region, and Poly-A is a 3' poly-adenylated tail (poly-A tail).

14. The in vitro method of claim 13, wherein each of L1, L2, L3, and L4 is independently selected from a nucleic acid a sequence comprising CGCGTGATAACGCAGGAAAGAACATGTGAGCAAAAGGCCAGCAAAAGGCCGGAACCGTAAAAAGGCCGCGTTGCTGGCGTT (SEQ ID NO: 43),

CACATTTCCCCGAAAAGTGCCACCTGAGCTC (SEQ ID NO: 44),

TTCGAAGGCGCGCCTCTAGAGCCACC (SEQ ID NO: 45),
or

CATCGATGATATCGCGGCCGCATACAGCAGC (SEQ ID NO: 46),
or wherein L1 comprises SEQ ID NO: 43
(CGCGTGATAACGCAGGAAAGAACATGTGAGCAAAAGGCCAGCAAAAGGCCAGGAACCGTAAAAAGGCCGCGTTGCTGGCGTT);

L2 comprises SEQ ID NO: 44
(CACATTTCCCCGAAAAGTGCCACCTGAGCTC);

L3 comprises SEQ ID NO: 45
(TTCGAAGGCGCGCCTCTAGAGCCACC);
and

L4 comprises SEQ ID NO: 46
(CATCGATGATATCGCGGCCGCATACAGCAGC).

15. The in vitro method of claim 2, wherein the second promoter comprises an engineered T7 promoter comprising the nucleotide sequence of SEQ ID NO: 47 (TAATACGACTCACTATAGG) operably linked to a 5' UTR.

16. The in vitro method of claim 15, wherein the 5' UTR is 3' to SEQ ID NO: 47 and wherein the 5' UTR comprises nucleotide sequence ATAGG.

17. An in vitro method of increasing the copy number of a nucleic acid comprising:

a) contacting cells with a nucleic acid encoding two expression units, the nucleic acid comprising:

i) an origin of replication sequence (Ori);

ii) a first expression unit encoding a first nucleotide sequence that is operably linked to a first promoter; and iii) a second expression unit encoding a second nucleotide sequence that is operably linked to a second promoter, wherein the first expression unit encodes a selectable marker and the second expression unit encodes a self-amplifying mRNA (sa-mRNA); wherein the nucleic acid further comprises one or more linkers, wherein at least one of the one or more linkers comprises TTCGAAGGCGCGCCTCTAGAGCCACC (SEQ ID NO: 45);

b) selecting cells that express the selectable marker;

c) subculturing the selected cells to obtain a population of cells that express the selectable marker; and d) propagating the population of cells to increase the copy number of the nucleic acid.

18. The in vitro method of claim 17, wherein the first expression unit comprises the following operably linked nucleic acid sequence in a 5' to 3' direction or in a 3' to 5' direction:

Pr1-SM wherein

Pr1 is the first promoter sequence, and

SM is the selectable marker.

19. The in vitro method of claim 17, wherein the first promoter is an ampicillin resistance (AmpR) promoter, a kanamycin resistance (KanR) promoter, a chloramphenicol resistance (CamR) promoter, an erythromycin resistance (ErmR) promoter, and a tetracycline resistance (TetR) promoter, and/or wherein the selectable marker is AmpR, KanR, CamR, ErmR, or TetR.

20. The in vitro method of claim 17, wherein the second expression unit comprises the following operably linked nucleic acid sequence from 5' to 3':

Pr2-5'UTR-nsP-SGP-GOI-3'UTR-PolyA wherein

Pr2 is the second promoter sequence for in vitro transcription,

5'UTR is a 5' untranslated region, nsP is a plurality of non-structural replicase domain sequences, SGP is a subgenomic promoter, GOI is one or more genes of interest, 3'UTR is a 3' untranslated region, and Poly-A is a 3' poly-adenylated tail (poly-A tail).

21. The in vitro method of claim 20, wherein at least one gene of interest (GOI), encodes a therapeutic polypeptide, a prophylactic polypeptide, a diagnostic polypeptide, an antigen, or a non-coding gene that encodes regulatory structures.

22. The in vitro method of claim 20, wherein at least one GOI encodes a non-coding gene that encodes at least one regulatory structure, wherein the at least one regulatory structure is a small interfering RNA (siRNA), a micro-RNA (miRNA), a guide RNA (gRNA), a self-activating RNA (saRNA), a transfer RNA (tRNA), or a long intergenic non-coding (lincRNA).

23. The in vitro method of claim 17, wherein at least one GOI encodes an infectious disease antigen, an allergic antigen, or a tumor antigen.

24. The in vitro method of claim 20, wherein the plurality of non-structural replicase domain sequences are obtained from the TC-83 strain of Venezuelan Equine Encephalitis virus (VEE).

25. The in vitro method of claim 17, wherein the nucleic acid sequence comprises from 5' to 3':

a) Ori-SM-Pr1-L2-Pr2-5'UTR-nsP-L3-GOI-L4-3'UTR-PolyA;

b) L1-Ori-SM-Pr1-Pr2-5'UTR-nsP-L3-GOI-L4-3'UTR-PolyA c) L1-Ori-SM-Pr1-L2-Pr2-5'UTR-nsP-GOI-L4-3'UTR-PolyA;

d) L1-Ori-SM-Pr1-L2-Pr2-5'UTR-nsP-L3-GOI-3'UTR-PolyA; or e) L1-Ori-SM-Pr1-L2-Pr2-5'UTR-nsP-SGP-L3-GOI-L4-3'UTR-PolyA, wherein L1 is a first linker, Ori is an origin of replication sequence, SM is a selectable marker, Pr1 is a first promoter sequence, L2 is a second linker, Pr2 is a second promoter sequence, 5'UTR is a 5' untranslated region, nsP is a plurality of non-structural replicase domain sequences, L3 is a third linker, SGP is a subgenomic promoter, GOI is one or more genes of interest, L4 is a fourth linker, 3'UTR is a 3' untranslated region, and Poly-A is a 3' poly-adenylated tail (poly-A tail).

26. The in vitro method of claim 25, wherein each of L1, L2, L3, and L4 is independently selected from a nucleic acid a sequence comprising

```
                                        (SEQ ID NO: 43)
CGCGTGATAACGCAGGAAAGAACATGTGAGCAAAAGGCCAGCAAAAGGC
CAGGAACCGTAAAAAGGCCGCGTTGCTGGCGTT,

                                        (SEQ ID NO: 44)
CACATTTCCCCGAAAAGTGCCACCTGAGCTC,

                                        (SEQ ID NO: 45)
TTCGAAGGCGCGCCTCTAGAGCCACC, or

                                        (SEQ ID NO: 46)
CATCGATGATATCGCGGCCGCATACAGCAGC, or

wherein L1 comprises SEQ ID NO: 43
(CGCGTGATAACGCAGGAAAGAACATGTGAGCAAAAGGCCAGCAAAAGG
CCAGGAACCGTAAAAAGGCCGCGTTGCTGGCGTT);

L2 comprises SEQ ID NO: 44
(CACATTTCCCCGAAAAGTGCCACCTGAGCTC);

L3 comprises SEQ ID NO: 45
(TTCGAAGGCGCGCCTCTAGAGCCACC); and

L4 comprises SEQ ID NO: 46
(CATCGATGATATCGCGGCCGCATACAGCAGC).
```

27. The in vitro method of claim 17, wherein the second promoter comprises an engineered T7 promoter comprising the nucleotide sequence of SEQ ID NO: 47 (TAATACGACTCACTATAGG) operably linked to a 5' UTR.

28. The in vitro method of claim 27, wherein the 5' UTR is 3' to SEQ ID NO: 47 and wherein the 5' UTR comprises nucleotide sequence ATAGG.

29. The in vitro method of claim 1, wherein the 5' UTR comprises nucleotide sequence ATAGG.

* * * * *

SEQUENCE LISTING

```
Sequence total quantity: 54
SEQ ID NO: 1            moltype = RNA  length = 3813
FEATURE                 Location/Qualifiers
source                  1..3813
                        mol_type = other RNA
                        organism = synthetic construct
SEQUENCE: 1
atgtttgtgt tcttggtgtt gcttccactg gtcagttccc aatgcgttaa tctcaccacc  60
cgaactcaac tcccacccgc atatacaaat tccttcacca gaggagtgta ctatcctgac  120
aaagtgtttc ggtcaagtgt cctccactct actcaggacc tctttctgcc tttcttttct  180
aacgttacat ggtttcatgt gatctctggg acaaacggca ccaaacgctt cgacaaccct  240
gtattgccat tcaatgatgg ggtgtacttt gcctccatcg agaaatccaa catcattcga  300
ggatggattt tcgggactac tctggactca aagacacaga gcctgctgat cgttaacaac  360
gccacaaacg ttgtcatcaa agtgtgcgaa ttccagtttt gcaatgatcc cttcctggac  420
cacaagaata acaagtcctg gatggagagc gaatttcggg tctacagcag cgcaaacaac  480
tgcaccttcg agtacgtgag tcaacccttt ctgatggacc tggaagggaa acagggaaac  540
ttcaagaacc tgagagagtt tgtctttaag aacatcgacg gctattttaa gatctatagt  600
aagcatacgc ctatcattgt aagggagccc gaggatcttc cccagggctt ttcagccctg  660
gaacctttgg ttgacttgcc tattggtatc aatatcacca gatttcagac ccttctggca  720
ttgcatcggt cttatcttac tccaggtgat tcctcctccg ggtggactgc cggcgccgct  780
gcctactatg tcggctatct gcaaccaaga acgttcctgc tcaagtacaa cgaaaacggc  840
actattacgg atgctgttga ttgtgccctg gaccctctgt ctgagactaa atgcaccctc  900
```

-continued

```
aagagcttta ccgttgagaa ggggatttac caaaccagta atttccgggt ccaacccacc  960
gaaagcattg tgcggttccc aaatatcacc aatctgtgtc cctttgatga agtgttcaat  1020
gctacaaggt ttgcttctgt gtacgcatgg aataggaaac gcatctccaa ttgtgtcgct  1080
gattactccg tgctgtacaa tctggcccca ttcttcacct tcaagtgtta tggcgtttca  1140
cctaccaaac ttaacgacct gtgcttcact aatgtgtatg ccgactcttt tgtgatacga  1200
ggcgatgaag tgagacagat tgcaccaggg cagaccggca acattgccga ctacaactac  1260
aagcttccag atgactttac cggatgtgtt attgcatgga actcaaacaa gctggattcc  1320
aaggtgagcg gcaactataa ctacctgtat agactgttca ggaaatccaa cctgaaacca  1380
ttcgagcgag atataagcac agaaatctac caggctggaa acaaaccctg caacggcgtg  1440
gctgggttca actgctactt cccattgcgc agttacagct tcagacctac atacggggtg  1500
ggtcaccaac cctatcgtgt cgtagtcctg agttttgagc tcctccatgc cccagccaca  1560
gtctgtggcc ccaagaaaag caccaatctg gtgaagaaca aatgcgtgaa ctttaacttt  1620
aacggactca agggaaccgg cgtattgacg gagagtaaca agaagttcct gccattccag  1680
cagttcggtc gcgatattgc cgacactacc gacgctgtcc gagatcccca gacattggag  1740
attcttgata tcacaccctg tagtttcggc ggagtgagcg tgattacgcc cggaaccaat  1800
accagcaatc aggttgccgt cctgtatcag ggcgtgaatt gcaccgaggt acctgtcgcc  1860
atccacgctg accaacttac acccacatgg cgagtatatt ccaccggctc caacgtcttt  1920
cagacacgtg ctggatgtct gatcggtgca gaatatgtta ataatagcta cgagtgtgat  1980
atccccatcg gtgctggaat atgcgcctct tatcaaactc aaaccaaatc tcacaggcgg  2040
gcacgtagtg tagcatccca aagtatcatt gcctacacaa tgagcctcgg tgctgagaat  2100
tctgtcgcct acagcaacaa ctccattgct atccctacta acttcacaat cagtgtgaca  2160
actgaaattc tgcccgtatc tatgaccaaa acaagcgttg actgcaccat gtacatctgt  2220
ggcgattcta ccgaatgtag caatctcctc ctgcaatacg gatcattctg cactcagctg  2280
aagcgtgccc tcacaggtat tgcagttgag caggacaaga atacgcagga agtgtttgcc  2340
caggtgaagc aaatctacaa aactccaccc ataaaatact ttggcggatt caatttctca  2400
cagatcctgc ccgatccctc aaaaccctcc aagcgtagct ttatcgagga tctgctcttc  2460
aacaaggtaa ccctcgcaga tgccggtttc atcaagcagt atggcgattg tctgggagac  2520
atcgccgctc gggacctgat ctgtgcacag aagttcaaag gactgaccgt gctgcctccc  2580
ttgctgaccg acgagatgat agcccaatac actagcgccc tgctggccgg caccatcact  2640
tctgggtgga cattcggagc tggcgctgcc cttcagattc cttttgctat gcagatggcc  2700
taccgcttta acggcatcgg tgtgacacaa aacgttctgt atgaaaacca gaaactcatc  2760
gccaaccagt tcaacagtgc tatcggtaag atacaggata gcctgtcatc cactgccagc  2820
gcattgggaa agttgcagga tgtagtgaac cacaatgccc aggcacttaa caccctggtg  2880
aaacagctct cttcaaagtt tggtgccatt tctagcgtgc tgaatgacat atttagccgg  2940
ttggacaagg tggaggctga agtgcagatt gataggctga taactgggcg ccttcagtct  3000
cttcagacct atgtgaccca gcagctcatc cgcgctgctg aaattcgcgc atccgctaac  3060
ctggcagcaa ccaaaatgtc cgagtgtgtg ctgggtcagt ctaagagagt ggacttttgc  3120
gggaaggggt atcacctgat gtcttttcct cagtctgcac cccatggtgt ggtctttctg  3180
cacgtgactt atgtcccagc tcaggaaaag aacttcacta cagccccagc catctgccac  3240
gatgggaaag cccactttcc cagggaaggc gtattcgtgt ccaatggtac tcattggttc  3300
gtcactcaga gaaatttcta cgagccccag attataacca ctgacaatac atttgtatcc  3360
ggcaattgtg atgtggttat cggtattgtg aataatactg tttacgatcc tttgcagcca  3420
gagctggact ccttcaagga ggagcttgac aaatatttta agaatcacac atcacctgac  3480
gtcgacctcg gagatatttc aggaatcaat gcttccgtgg tcaatattca gaaggagata  3540
gacaggctga atgaggttgc caagaacctc aacgagtctc tgatcgatct gcaggagttg  3600
ggcaagtacg aacagtatat caaatggcct tggtacattt ggcttgggtt cattgctggg  3660
ctgatagcta tcgtcatggt gacaattatg ttgtgttgca tgacatcctg ctgtagttgt  3720
ctgaagggct gctgctcatg cggcagctgt tgcaagttcg acgaggacga ttctgagccc  3780
gtgctgaagg gcgtgaaact gcactacaca tga                               3813

SEQ ID NO: 2            moltype = RNA  length = 3813
FEATURE                 Location/Qualifiers
source                  1..3813
                        mol_type = other RNA
                        organism = synthetic construct
SEQUENCE: 2
atgtttgtgt tcttggtgtt gcttccactg gtcagttccc aatgcgttaa tctcaccacc  60
cgaactcaac tcccacccgc atatacaaat tccttcacca gaggagtgta ctatcctgac  120
aaagtgtttc ggtcaagtgt cctccactct actcaggacc tctttctgcc tttctttttct  180
aacgttacat ggtttcatgt gatctctggg acaaacggca ccaaacgctt cgacaaccct  240
gtattgccat tcaatgatgg ggtgtacttt gcctccatcg agaaatccaa catcattcga  300
ggatggattt tcgggactac tctggactca aagacacaga gcctgctgat cgttaacaac  360
gccacaaacg ttgtcatcaa agtgtgcgaa ttccagtttt gcaatgatcc cttcctggac  420
cacaagaata acaagtcctg gatggagagc gaatttcggg tctacagcag cgcaaacaac  480
tgcaccttcg agtacgtgag tcaacccttt ctgatggacc tggaagggaa acagggaaac  540
ttcaagaacc tgagagagtt tgtctttaag aacatcgacg gctattttaa gatctatagt  600
aagcatacgc ctatcattgt aagggagccc gaggatcttc cccagggctt ttcagccctg  660
gaacctttgg ttgacttgcc tattggtatc aatatcacca gatttcagac ccttctggca  720
ttgcatcggt cttatcttac tccaggtgat tcctcctccg ggtggactgc cggcgccgct  780
gcctactatg tcggctatct gcaaccaaga acgttcctgc tcaagtacaa cgaaaacggc  840
actattacgg atgctgttga ttgtgccctg gaccctctgt ctgagactaa atgcaccctc  900
aagagcttta ccgttgagaa ggggatttac caaaccagta atttccgggt ccaacccacc  960
gaaagcattg tgcggttccc aaatatcacc aatctgtgtc cctttgatga agtgttcaat  1020
gctacaaggt ttgcttctgt gtacgcatgg aataggaaac gcatctccaa ttgtgtcgct  1080
gattactccg tgctgtacaa tctggcccca ttcttcacct tcaagtgtta tggcgtttca  1140
cctaccaaac ttaacgacct gtgcttcact aatgtgtatg ccgactcttt tgtgatacga  1200
ggcgatgaag tgagacagat tgcaccaggg cagaccggca acattgccga ctacaactac  1260
aagcttccag atgactttac cggatgtgtt attgcatgga actcaaacaa gctggattcc  1320
aaggtgagcg gcaactataa ctacctgtat agactgttca ggaaatccaa cctgaaacca  1380
```

-continued

```
ttcgagcgag atataagcac agaaatctac caggctggaa acaaaccctg caacggcgtg  1440
gctgggttca actgctactt cccattgcgc agttacagct tcagacctac atacggggtg  1500
ggtcaccaac cctatcgtgt cgtagtcctg agttttgagc tcctccatgc cccagccaca  1560
gtctgtggcc ccaagaaaag caccaatctg gtgaagaaca aatgcgtgaa ctttaacttt  1620
aacggactca agggaaccgg cgtattgacg gagagtaaca agaagttcct gccattccag  1680
cagttcggtc gcgatattgc cgacactacc gacgctgtcc gagatcccca gacattggag  1740
attcttgata tcacaccctg tagtttcggc ggagtgagcg tgattacgcc cggaaccaat  1800
accagcaatc aggttgccgt cctgtatcag ggcgtgaatt gcaccgaggt acctgtcgcc  1860
atccacgctg accaacttac acccacatgg cgagtatatt ccaccggctc caacgtcttt  1920
cagacacgtg ctggatgtct gatcggtgca gaatatgtta ataatagcta cgagtgtgat  1980
atccccatcg gtgctggaat atgcgcctct tatcaaactc aaaccaaatc tcacaggcgg  2040
gcacgtagtg tagcatccca aagtatcatt gcctacacaa tgagcctcgg tgctgagaat  2100
tctgtcgcct acagcaacaa ctccattgct atccctacta acttcacaat cagtgtgaca  2160
actgaaattc tgcccgtatc tatgaccaaa acaagcgttg actgcaccat gtacatctgt  2220
ggcgattcta ccgaatgtag caatctcctc ctgcaatacg gatcattctg cactcagctg  2280
aagcgtgccc tcacaggtat tgcagttgag caggacaaga atacgcagga agtgtttgcc  2340
caggtgaagc aaatctacaa aactccaccc ataaaatact ttggcggatt caatttctca  2400
cagatcctgc ccgatccctc aaaaccctcc aagcgtagct ttatcgagga tctgctcttc  2460
aacaaggtaa ccctcgcaga tgccggtttc atcaagcagt atggcgattg tctgggagac  2520
atcgccgctc gggacctgat ctgtgcacag aagttcaaag gactgaccgt gctgcctccc  2580
ttgctgaccg acgagatgat agcccaatac actagcgccc tgctggccgg caccatcact  2640
tctgggtgga cattcggagc tggcgctgcc cttcagattc cttttgctat gcagatggcc  2700
taccgcttta acggcatcgg tgtgacacaa aacgttctgt atgaaaacca gaaactcatc  2760
gccaaccagt tcaacagtgc tatcggtaag atacaggata gcctgtcatc cactgccagc  2820
gcattgggaa agttgcagga tgtagtgaac cacaatgccc aggcacttaa caccctggtg  2880
aaacagctct cttcaaagtt tggtgccatt tctagcgtgc tgaatgacat atttagccgg  2940
ttggaccctc cggaggctga agtgcagatt gataggctga taactgggcg ccttcagtct  3000
cttcagacct atgtgaccca gcagctcatc cgcgctgctg aaattcgcgc atccgctaac  3060
ctggcagcaa ccaaaatgtc cgagtgtgtg ctgggtcagt ctaagagagt ggacttttgc  3120
gggaaggggt atcacctgat gtcttttcct cagtctgcac cccatggtgt ggtctttctg  3180
cacgtgactt atgtcccagc tcaggaaaag aacttcacta cagccccagc catctgccac  3240
gatgggaaag cccactttcc cagggaaggc gtattcgtgt ccaatggtac tcattggttc  3300
gtcactcaga gaaatttcta cgagccccag attataacca ctgacaatac atttgtatcc  3360
ggcaattgtg atgtggttat cgggattgtg aataatactg tttacgatcc tttgcagcca  3420
gagctggact ccttcaagga ggagcttgac aaatatttta agaatcacac atcacctgac  3480
gtcgacctcg gagatatttc aggaatcaat gcttccgtgg tcaatattca gaaggagata  3540
gacaggctga atgaggttgc caagaacctc aacgagtctc tgatcgatct gcaggagttg  3600
ggcaagtacg aacagtatat caaatggcct tggtacattt ggcttgggtt cattgctggg  3660
ctgatagcta tcgtcatggt gacaattatg ttgtgttgca tgacatcctg ctgtagttgt  3720
ctgaagggct gctgctcatg cggcagctgt tgcaagttcg acgaggacga ttctgagccc  3780
gtgctgaagg gcgtgaaact gcactacaca tga                               3813

SEQ ID NO: 3            moltype = RNA  length = 3813
FEATURE                 Location/Qualifiers
source                  1..3813
                        mol_type = other RNA
                        organism = synthetic construct
SEQUENCE: 3
atgtttgtgt tcttggtgtt gcttccactg gtcagttccc aatgcgttaa tctcatcacc  60
cgaactcaat cctatacaaa ttccttcacc agaggagtgt actatcctga caaagtgttt  120
cggtcaagtg tcctccactc tactcaggac ctctttctgc ctttcttttc taacgttaca  180
tggtttcatg caatccatgt gtctgggaca aacggcacca aacgcttcga caaccctgta  240
ttgccattca atgatggggt gtactttgcc tccacagaga aatccaacat cattcgagga  300
tggatttttcg ggactactct ggactcaaag acacagagcc tgctgatcgt taacaacgcc  360
acaaacgttg tcatcaaagt gtgcgaattc cagttttgca atgatccctt cctggacgtg  420
tactatcaca agaataacaa gtcctggatg gagagcgaat ttcgggtcta cagcagcgca  480
aacaactgca ccttcgagta cgtgagtcaa ccctttctga tggacctgga agggaaacag  540
ggaaacttca agaacctgag agagtttgtc tttaagaaca tcgacggcta ttttaagatc  600
tatagtaagc atacgcctat caacctggga agggatcttc cccagggctt ttcagccctg  660
gaacctttgg ttgacttgcc tattggtatc aatatcacca gatttcagac ccttctggca  720
ttgcatcggt cttatcttac tccaggtgat tcctcctccg ggtggactgc cggcgccgct  780
gcctactatg tcggctatct gcaaccaaga acgttcctgc tcaagtacaa cgaaaacggc  840
actattacgg atgctgttga ttgtgccctg gaccctctgt ctgagactaa atgcaccctc  900
aagagcttta ccgttgagaa ggggatttac caaaccagta atttccgggt ccaacccacc  960
gaaagcattg tgcggttccc aaatatcacc aatctgtgtc cctttgatga agtgttcaat  1020
gctacaaggt ttgcttctgt gtacgcatgg aataggaaac gcatctccaa ttgtgtcgct  1080
gattactccg tgctgtacaa ttttgcccca ttcttcgctt tcaagtgtta tggcgtttca  1140
cctaccaaac ttaacgacct gtgcttcact aatgtgtatg ccgactcttt tgtgatacga  1200
ggcaatgaag tgagccagat tgcaccaggg cagaccggca acattgccga ctacaactac  1260
aagcttccag atgactttac cggatgtgtt attgcatgga actcaaacaa gctggattcc  1320
aaggtgggtg gcaactataa ctacctgtat agactgttca ggaaatccaa cctgaaacca  1380
ttcgagcgag atataagcac agaaatctac caggctggaa acaaaccctg caacggcgtg  1440
gctgggttca actgctactt cccattgcgc agttacggat tcagacctac atacggggtg  1500
ggtcaccaac cctatcgtgt cgtagtcctg agttttgagc tcctccatgc cccagccaca  1560
gtctgtggcc ccaagaaaag caccaatctg gtgaagaaca aatgcgtgaa ctttaacttt  1620
aacggactca caggaaccgg cgtattgacg gagagtaaca agaagttcct gccattccag  1680
cagttcggtc gcgatattgc cgacactacc gacgctgtcc gagatcccca gacattggag  1740
attcttgata tcacaccctg tagtttcggc ggagtgagcg tgattacgcc cggaaccaat  1800
accagcaatc aggttgccgt cctgtatcag ggcgtgaatt gcaccgaggt acctgtcgcc  1860
```

-continued

```
atccacgctg accaacttac acccacatgg cgagtatatt ccaccggctc caacgtcttt  1920
cagacacgtg ctggatgtct gatcggtgca gaatatgtta ataatagcta cgagtgtgat  1980
atccccatcg gtgctggaat atgcgcctct tatcaaactc aaaccaaatc tcacaggcgg  2040
gcacgtagtg tagcatccca aagtatcatt gcctacacaa tgagcctcgg tgctgagaat  2100
tctgtcgcct acagcaacaa ctccattgct atccctacta acttcacaat cagtgtgaca  2160
actgaaattc tgcccgtatc tatgaccaaa acaagcgttg actgcaccat gtacatctgt  2220
ggcgattcta ccgaatgtag caatctcctc ctgcaatacg gatcattctg cactcagctg  2280
aagcgtgccc tcacaggtat tgcagttgag caggacaaga atacgcagga agtgtttgcc  2340
caggtgaagc aaatctacaa aactccaccc ataaaatact ttggcggatt caatttctca  2400
cagatcctgc ccgatccctc aaaaccctcc aagcgtagct ttatcgagga tctgctcttc  2460
aacaaggtaa ccctcgcaga tgccggtttc atcaagcagt atggcgattg tctgggagac  2520
atcgccgctc gggacctgat ctgtgcacag aagttcaatg gactgaccgt gctgcctccc  2580
ttgctgaccg acgagatgat agcccaatac actagcgccc tgctggccgg caccatcact  2640
tctgggtgga cattcggagc tggcgctgcc cttcagattc cttttgctat gcagatggcc  2700
taccgcttta acggcatcgg tgtgacacaa aacgttctgt atgaaaacca gaaactcatc  2760
gccaaccagt tcaacagtgc tatcggtaag atacaggata gcctgtcatc cactgccagc  2820
gcattgggaa agttgcagga tgtagtgaac cacaatgccc aggcacttaa caccctggtg  2880
aaacagctct cttcaaagtt tggtgccatt tctagcgtgc tgaatgacat actgagccgg  2940
ttggacaagg tggaggctga agtgcagatt gataggctga taactgggcg ccttcagtct  3000
cttcagacct atgtgaccca gcagctcatc cgcgctgctg aaattcgcgc atccgctaac  3060
ctggcagcaa ccaaaatgtc cgagtgtgtg ctgggtcagt ctaagagagt ggacttttgc  3120
gggaaggggt atcacctgat gtcttttcct cagtctgcac cccatggtgt ggtctttctg  3180
cacgtgactt atgtcccagc tcaggaaaag aacttcacta cagccccagc catctgccac  3240
gatgggaaag cccactttcc cagggaaggc gtattcgtgt ccaatggtac tcattggttc  3300
gtcactcaga gaaatttcta cgagccccag attataacca ctgacaatac atttgtatcc  3360
ggcaattgtg atgtggttat cgggattgtg aataatactg tttacgatcc tttgcagcca  3420
gagctggact ccttcaagga ggagcttgac aaatatttta agaatcacac atcacctgac  3480
gtcgacctcg gagatatttc aggaatcaat gcttccgtgg tcaatattca gaaggagata  3540
gacaggctga atgaggttgc caagaacctc aacgagtctc tgatcgatct gcaggagttg  3600
ggcaagtacg aacagtatat caaatggcct tggtacattt ggcttgggtt cattgctggg  3660
ctgatagcta tcgtcatggt gacaattatg ttgtgttgca tgacatcctg ctgtagttgt  3720
ctgaagggct gctgctcatg cggcagctgt tgcaagttcg acgaggacga ttctgagccc  3780
gtgctgaagg gcgtgaaact gcactacaca tga                               3813

SEQ ID NO: 4           moltype = RNA  length = 3813
FEATURE                Location/Qualifiers
source                 1..3813
                       mol_type = other RNA
                       organism = synthetic construct
SEQUENCE: 4
atgtttgtgt tcttggtgtt gcttccactg gtcagttccc aatgcgttaa tctcatcacc  60
cgaactcaat cctatacaaa ttccttcacc agaggagtgt actatcctga caaagtgttt  120
cggtcaagtg tcctccactc tactcaggac ctctttctgc ctttcttttc taacgttaca  180
tggtttcatg caatccatgt gtctgggaca aacggcacca aacgcttcga caaccctgta  240
ttgccattca atgatggggt gtactttgcc tccacagaga aatccaacat cattcgagga  300
tggattttcg ggactactct ggactcaaag acacagagcc tgctgatcgt taacaacgcc  360
acaaacgttg tcatcaaagt gtgcgaattc cagttttgca atgatccctt cctggacgtg  420
tactatcaca agaataacaa gtcctggatg gagagcgaat ttcgggtcta cagcagcgca  480
aacaactgca ccttcgagta cgtgagtcaa cccttttctga tggacctgga agggaaacag  540
ggaaacttca agaacctgag agagtttgtc tttaagaaca tcgacggcta ttttaagatc  600
tatagtaagc atacgcctat caacctggga agggatcttc cccagggctt ttcagccctg  660
gaacctttgg ttgacttgcc tattggtatc aatatcacca gatttcagac ccttctggca  720
ttgcatcggt cttatcttac tccaggtgat tcctcctccg ggtggactgc cggcgccgct  780
gcctactatg tcggctatct gcaaccaaga acgttcctgc tcaagtacaa cgaaaacggc  840
actattacgg atgctgttga ttgtgccctg gaccctctgt ctgagactaa atgcaccctc  900
aagagcttta ccgttgagaa ggggatttac caaaccagta atttccgggt ccaacccacc  960
gaaagcattg tgcggttccc aaatatcacc aatctgtgtc cctttgatga agtgttcaat  1020
gctacaaggt ttgcttctgt gtacgcatgg aataggaaac gcatctccaa ttgtgtcgct  1080
gattactccg tgctgtacaa ttttgcccca ttcttcgctt tcaagtgtta tggcgtttca  1140
cctaccaaac ttaacgacct gtgcttcact aatgtgtatg ccgactcttt tgtgatacga  1200
ggcaatgaag tgagccagat tgcaccaggg cagaccggca acattgccga ctacaactac  1260
aagcttccag atgactttac cggatgtgtt attgcatgga actcaaacaa gctggattcc  1320
aaggtgggtg gcaactataa ctacctgtat agactgttca ggaaatccaa cctgaaacca  1380
ttcgagcgag atataagcac agaaatctac caggctggaa acaaaccctg caacggcgtg  1440
gctgggttca actgctactt cccattgcgc agttacggat tcagacctac atacggggtg  1500
ggtcaccaac cctatcgtgt cgtagtcctg agttttgagc tcctccatgc cccagccaca  1560
gtctgtggcc ccaagaaaag caccaatctg gtgaagaaca aatgcgtgaa ctttaacttt  1620
aacggactca caggaaccgg cgtattgacg gagagtaaca agaagttcct gccattccag  1680
cagttcggtc gcgatattgc cgacactacc gacgctgtcc gagatcccca gacattggag  1740
attcttgata tcacaccctg tagtttcggc ggagtgagcg tgattacgcc cggaaccaat  1800
accagcaatc aggttgccgt cctgtatcag ggcgtgaatt gcaccgaggt acctgtcgcc  1860
atccacgctg accaacttac acccacatgg cgagtatatt ccaccggctc caacgtcttt  1920
cagacacgtg ctggatgtct gatcggtgca gaatatgtta ataatagcta cgagtgtgat  1980
atccccatcg gtgctggaat atgcgcctct tatcaaactc aaaccaaatc tcacaggcgg  2040
gcacgtagtg tagcatccca aagtatcatt gcctacacaa tgagcctcgg tgctgagaat  2100
tctgtcgcct acagcaacaa ctccattgct atccctacta acttcacaat cagtgtgaca  2160
actgaaattc tgcccgtatc tatgaccaaa acaagcgttg actgcaccat gtacatctgt  2220
ggcgattcta ccgaatgtag caatctcctc ctgcaatacg gatcattctg cactcagctg  2280
aagcgtgccc tcacaggtat tgcagttgag caggacaaga atacgcagga agtgtttgcc  2340
```

-continued

```
caggtgaagc aaatctacaa aactccaccc ataaaatact ttggcggatt caatttctca  2400
cagatcctgc ccgatccctc aaaaccctcc aagcgtagct ttatcgagga tctgctcttc  2460
aacaaggtaa ccctcgcaga tgccggtttc atcaagcagt atggcgattg tctgggagac  2520
atcgccgctc gggacctgat ctgtgcacag aagttcaatg gactgaccgt gctgcctccc  2580
ttgctgaccg acgagatgat agcccaatac actagcgccc tgctggccgg caccatcact  2640
tctgggtgga cattcggagc tggcgctgcc cttcagattc cttttgctat gcagatggcc  2700
taccgcttta acggcatcgg tgtgacacaa aacgttctgt atgaaaacca gaaactcatc  2760
gccaaccagt tcaacagtgc tatcggtaag atacaggata gcctgtcatc cactgccagc  2820
gcattgggaa agttgcagga tgtagtgaac cacaatgccc aggcacttaa caccctggtg  2880
aaacagctct cttcaaagtt tggtgccatt tctagcgtgc tgaatgacat actgagccgg  2940
ttggaccctc cggaggctga agtgcagatt gataggctga taactgggcg ccttcagtct  3000
cttcagacct atgtgaccca gcagctcatc cgcgctgctg aaattcgcgc atccgctaac  3060
ctggcagcaa ccaaaatgtc cgagtgtgtg ctgggtcagt ctaagagagt ggacttttgc  3120
gggaaggggt atcacctgat gtcttttcct cagtctgcac cccatggtgt ggtctttctg  3180
cacgtgactt atgtcccagc tcaggaaaag aacttcacta cagccccagc catctgccac  3240
gatgggaaag cccactttcc cagggaaggc gtattcgtgt ccaatggtac tcattggttc  3300
gtcactcaga gaaatttcta cgagccccag attataacca ctgacaatac atttgtatcc  3360
ggcaattgtg atgtggttat cgggattgtg aataatactg tttacgatcc tttgcagcca  3420
gagctggact ccttcaagga ggagcttgac aaatatttta agaatcacac atcacctgac  3480
gtcgacctcg gagatatttc aggaatcaat gcttccgtgg tcaatattca gaaggagata  3540
gacaggctga atgaggttgc caagaacctc aacgagtctc tgatcgatct gcaggagttg  3600
ggcaagtacg aacagtatat caaatggcct tggtacattt ggcttgggtt cattgctggg  3660
ctgatagcta tcgtcatggt gacaattatg ttgtgttgca tgacatcctg ctgtagttgt  3720
ctgaagggct gctgctcatg cggcagctgt tgcaagttcg acgaggacga ttctgagccc  3780
gtgctgaagg gcgtgaaact gcactacaca tga                               3813
```

```
SEQ ID NO: 5            moltype = RNA  length = 3618
FEATURE                 Location/Qualifiers
source                  1..3618
                        mol_type = other RNA
                        organism = synthetic construct
SEQUENCE: 5
atgtttgtgt tcttggtgtt gcttccactg gtcagttccc aatgcgttaa tctcaccacc  60
cgaactcaac tcccacccgc atatacaaat tccttcacca gaggagtgta ctatcctgac  120
aaagtgtttc ggtcaagtgt cctccactct actcaggacc tctttctgcc tttcttttct  180
aacgttacat ggtttcatgt gatctctggg acaaacggca ccaaacgctt cgacaaccct  240
gtattgccat tcaatgatgg ggtgtacttt gcctccatcg agaaatccaa catcattcga  300
ggatggattt tcgggactac tctggactca aagacacaga gcctgctgat cgttaacaac  360
gccacaaacg ttgtcatcaa agtgtgcgaa ttccagtttt gcaatgatcc cttcctggac  420
cacaagaata acaagtcctg gatggagagc gaatttcggg tctacagcag cgcaaacaac  480
tgcaccttcg agtacgtgag tcaacccttt ctgatggacc tggaagggaa acagggaaac  540
ttcaagaacc tgagagagtt tgtctttaag aacatcgacg gctattttaa gatctatagt  600
aagcatacgc ctatcattgt aagggagccc gaggatcttc cccagggctt ttcagccctg  660
gaacctttgg ttgacttgcc tattggtatc aatatcacca gatttcagac ccttctggca  720
ttgcatcggt cttatcttac tccaggtgat tcctcctccg ggtggactgc cggcgccgct  780
gcctactatg tcggctatct gcaaccaaga acgttcctgc tcaagtacaa cgaaaacggc  840
actattacgg atgctgttga ttgtgccctg gaccctctgt ctgagactaa atgcaccctc  900
aagagcttta ccgttgagaa ggggatttac caaaccagta atttccgggt ccaacccacc  960
gaaagcattg tgcggttccc aaatatcacc aatctgtgtc cctttgatga agtgttcaat  1020
gctacaaggt ttgcttctgt gtacgcatgg aataggaaac gcatctccaa ttgtgtcgct  1080
gattactccg tgctgtacaa tctggcccca ttcttcacct tcaagtgtta tggcgtttca  1140
cctaccaaac ttaacgacct gtgcttcact aatgtgtatg ccgactcttt tgtgatacga  1200
ggcgatgaag tgagacagat tgcaccaggg cagaccggca acattgccga ctacaactac  1260
aagcttccag atgactttac cggatgtgtt attgcatgga actcaaacaa gctggattcc  1320
aaggtgagcg gcaactataa ctacctgtat agactgttca ggaaatccaa cctgaaacca  1380
ttcgagcgag atataagcac agaaatctac caggctggaa acaaaccctg caacggcgtg  1440
gctgggttca actgctactt cccattgcgc agttacagct tcagacctac atacggggtg  1500
ggtcaccaac cctatcgtgt cgtagtcctg agttttgagc tcctccatgc cccagccaca  1560
gtctgtggcc ccaagaaaag caccaatctg gtgaagaaca aatgcgtgaa ctttaacttt  1620
aacggactca agggaaccgg cgtattgacg gagagtaaca agaagttcct gccattccag  1680
cagttcggtc gcgatattgc cgacactacc gacgctgtcc gagatcccca gacattggag  1740
attcttgata tcacaccctg tagtttcggc ggagtgagcg tgattacgcc cggaaccaat  1800
accagcaatc aggttgccgt cctgtatcag ggcgtgaatt gcaccgaggt acctgtcgcc  1860
atccacgctg accaacttac acccacatgg cgagtatatt ccaccggctc caacgtcttt  1920
cagacacgtg ctggatgtct gatcggtgca gaatatgtta ataatagcta cgagtgtgat  1980
atccccatcg gtgctggaat atgcgcctct tatcaaactc aaaccaaatc tcacaggcgg  2040
gcacgtagtg tagcatccca aagtatcatt gcctacacaa tgagcctcgg tgctgagaat  2100
tctgtcgcct acagcaacaa ctccattgct atccctacta acttcacaat cagtgtgaca  2160
actgaaattc tgcccgtatc tatgaccaaa acaagcgttg actgcaccat gtacatctgt  2220
ggcgattcta ccgaatgtag caatctcctc ctgcaatacg gatcattctg cactcagctg  2280
aagcgtgccc tcacaggtat tgcagttgag caggacaaga atacgcagga agtgtttgcc  2340
caggtgaagc aaatctacaa aactccaccc ataaaatact ttggcggatt caatttctca  2400
cagatcctgc ccgatccctc aaaaccctcc aagcgtagct ttatcgagga tctgctcttc  2460
aacaaggtaa ccctcgcaga tgccggtttc atcaagcagt atggcgattg tctgggagac  2520
atcgccgctc gggacctgat ctgtgcacag aagttcaaag gactgaccgt gctgcctccc  2580
ttgctgaccg acgagatgat agcccaatac actagcgccc tgctggccgg caccatcact  2640
tctgggtgga cattcggagc tggcgctgcc cttcagattc cttttgctat gcagatggcc  2700
taccgcttta acggcatcgg tgtgacacaa aacgttctgt atgaaaacca gaaactcatc  2760
gccaaccagt tcaacagtgc tatcggtaag atacaggata gcctgtcatc cactgccagc  2820
```

```
gcattgggaa agttgcagga tgtagtgaac cacaatgccc aggcacttaa caccctggtg  2880
aaacagctct cttcaaagtt tggtgccatt tctagcgtgc tgaatgacat atttagccgg  2940
ttggacaagg tggaggctga agtgcagatt gataggctga taactgggcg ccttcagtct  3000
cttcagacct atgtgaccca gcagctcatc cgcgctgctg aaattcgcgc atccgctaac  3060
ctggcagcaa ccaaaatgtc cgagtgtgtg ctgggtcagt ctaagagagt ggacttttgc  3120
gggaaggggt atcacctgat gtcttttcct cagtctgcac cccatggtgt ggtctttctg  3180
cacgtgactt atgtcccagc tcaggaaaag aacttcacta cagcccccagc catctgccac  3240
gatgggaaag cccactttcc cagggaaggc gtattcgtgt ccaatggtac tcattggttc  3300
gtcactcaga gaaatttcta cgagccccag attataacca ctgacaatac atttgtatcc  3360
ggcaattgtg atgtggttat cggggattgtg aataatactg tttacgatcc tttgcagcca  3420
gagctggact ccttcaagga ggagcttgac aaatatttta agaatcacac atcacctgac  3480
gtcgacctcg gagatatttc aggaatcaat gcttccgtgg tcaatattca gaaggagata  3540
gacaggctga atgaggttgc caagaacctc aacgagtctc tgatcgatct gcaggagttg  3600
ggcaagtacg aacagtaa                                                3618

SEQ ID NO: 6           moltype = RNA  length = 3618
FEATURE                Location/Qualifiers
source                 1..3618
                       mol_type = other RNA
                       organism = synthetic construct
SEQUENCE: 6
atgtttgtgt tcttggtgtt gcttccactg gtcagttccc aatgcgttaa tctcaccacc  60
cgaactcaac tcccacccgc atatacaaat tccttcacca gaggagtgta ctatcctgac  120
aaagtgtttc ggtcaagtgt cctccactct actcaggacc tctttctgcc tttcttttct  180
aacgttacat ggtttcatgt gatctctggg acaaacggca ccaaacgctt cgacaaccct  240
gtattgccat tcaatgatgg ggtgtacttt gcctccatcg agaaatccaa catcattcga  300
ggatggattt tcgggactac tctggactca aagacacaga gcctgctgat cgttaacaac  360
gccacaaacg ttgtcatcaa agtgtgcgaa ttccagtttt gcaatgatcc cttcctggac  420
cacaagaata acaagtcctg gatggagagc gaatttcggg tctacagcag cgcaaacaac  480
tgcaccttcg agtacgtgag tcaacccttt ctgatggacc tggaagggaa acagggaaac  540
ttcaagaacc tgagagagtt tgtctttaag aacatcgacg gctattttaa gatctatagt  600
aagcatacgc ctatcattgt aagggagccc gaggatcttc cccagggctt ttcagccctg  660
gaacctttgg ttgacttgcc tattggtatc aatatcacca gatttcagac ccttctggca  720
ttgcatcggt cttatcttac tccaggtgat tcctcctccg ggtggactgc cggcgccgct  780
gcctactatg tcggctatct gcaaccaaga acgttcctgc tcaagtacaa cgaaaacggc  840
actattacgg atgctgttga ttgtgccctg gaccctctgt ctgagactaa atgcaccctc  900
aagagcttta ccgttgagaa ggggatttac caaaccagta atttccgggt ccaacccacc  960
gaaagcattg tgcggttccc aaatatcacc aatctgtgtc cctttgatga agtgttcaat  1020
gctacaaggt ttgcttctgt gtacgcatgg aataggaaac gcatctccaa ttgtgtcgct  1080
gattactccg tgctgtacaa tctggcccca ttcttcacct tcaagtgtta tggcgtttca  1140
cctaccaaac ttaacgacct gtgcttcact aatgtgtatg ccgactcttt tgtgatacga  1200
ggcgatgaag tgagacagat tgcaccaggg cagaccggca acattgccga ctacaactac  1260
aagcttccag atgactttac cggatgtgtt attgcatgga actcaaacaa gctggattcc  1320
aaggtgagcg gcaactataa ctacctgtat agactgttca ggaaatccaa cctgaaacca  1380
ttcgagcgag atataagcac agaaatctac caggctggaa acaaaccctg caacggcgtg  1440
gctgggttca actgctactt cccattgcgc agttacagct tcagacctac atacggggtg  1500
ggtcaccaac cctatcgtgt cgtagtcctg agttttgagc tcctccatgc cccagccaca  1560
gtctgtggcc ccaagaaaag caccaatctg gtgaagaaca aatgcgtgaa ctttaacttt  1620
aacggactca agggaaccgg cgtattgacg gagagtaaca agaagttcct gccattccag  1680
cagttcggtc gcgatattgc cgacactacc gacgctgtcc gagatcccca gacattggag  1740
attcttgata tcacaccctg tagtttcggc ggagtgagcg tgattacgcc cggaaccaat  1800
accagcaatc aggttgccgt cctgtatcag ggcgtgaatt gcaccgaggt acctgtcgcc  1860
atccacgctg accaacttac acccacatgg cgagtatatt ccaccggctc caacgtcttt  1920
cagacacgtg ctggatgtct gatcggtgca gaatatgtta ataatagcta cgagtgtgat  1980
atccccatcg gtgctggaat atgcgcctct tatcaaactc aaaccaaatc tcacaggcgg  2040
gcacgtagtg tagcatccca aagtatcatt gcctacacaa tgagcctcgg tgctgagaat  2100
tctgtcgcct acagcaacaa ctccattgct atccctacta acttcacaat cagtgtgaca  2160
actgaaattc tgcccgtatc tatgaccaaa acaagcgttg actgcaccat gtacatctgt  2220
ggcgattcta ccgaatgtag caatctcctc ctgcaatacg gatcattctg cactcagctg  2280
aagcgtgccc tcacaggtat tgcagttgag caggacaaga atacgcagga agtgtttgcc  2340
caggtgaagc aaatctacaa aactccaccc ataaaatact ttggcggatt caatttctca  2400
cagatcctgc ccgatccctc aaaaccctcc aagcgtagct ttatcgagga tctgctcttc  2460
aacaaggtaa ccctcgcaga tgccggtttc atcaagcagt atggcgattg tctgggagac  2520
atcgccgctc gggacctgat ctgtgcacag aagttcaaag gactgaccgt gctgcctccc  2580
ttgctgaccg acgagatgat agcccaatac actagcgccc tgctggccgg caccatcact  2640
tctgggtgga cattcggagc tggcgctgcc cttcagattc cttttgctat gcagatggcc  2700
taccgcttta acggcatcgg tgtgacacaa aacgttctgt atgaaaacca gaaactcatc  2760
gccaaccagt tcaacagtgc tatcggtaag atacaggata gcctgtcatc cactgccagc  2820
gcattgggaa agttgcagga tgtagtgaac cacaatgccc aggcacttaa caccctggtg  2880
aaacagctct cttcaaagtt tggtgccatt tctagcgtgc tgaatgacat atttagccgg  2940
ttggaccctc cggaggctga agtgcagatt gataggctga taactgggcg ccttcagtct  3000
cttcagacct atgtgaccca gcagctcatc cgcgctgctg aaattcgcgc atccgctaac  3060
ctggcagcaa ccaaaatgtc cgagtgtgtg ctgggtcagt ctaagagagt ggacttttgc  3120
gggaaggggt atcacctgat gtcttttcct cagtctgcac cccatggtgt ggtctttctg  3180
cacgtgactt atgtcccagc tcaggaaaag aacttcacta cagcccccagc catctgccac  3240
gatgggaaag cccactttcc cagggaaggc gtattcgtgt ccaatggtac tcattggttc  3300
gtcactcaga gaaatttcta cgagccccag attataacca ctgacaatac atttgtatcc  3360
ggcaattgtg atgtggttat cggggattgtg aataatactg tttacgatcc tttgcagcca  3420
gagctggact ccttcaagga ggagcttgac aaatatttta agaatcacac atcacctgac  3480
```

```
gtcgacctcg gagatatttc aggaatcaat gcttccgtgg tcaatattca gaaggagata  3540
gacaggctga atgaggttgc caagaacctc aacgagtctc tgatcgatct gcaggagttg  3600
ggcaagtacg aacagtaa                                                3618

SEQ ID NO: 7           moltype = RNA  length = 3618
FEATURE                Location/Qualifiers
source                 1..3618
                       mol_type = other RNA
                       organism = synthetic construct
SEQUENCE: 7
atgtttgtgt tcttggtgtt gcttccactg gtcagttccc aatgcgttaa tctcatcacc  60
cgaactcaat cctatacaaa ttccttcacc agaggagtgt actatcctga caaagtgttt  120
cggtcaagtg tcctccactc tactcaggac ctctttctgc ctttcttttc taacgttaca  180
tggtttcatg caatccatgt gtctgggaca aacggcacca aacgcttcga caaccctgta  240
ttgccattca atgatggggt gtactttgcc tccacagaga aatccaacat cattcgagga  300
tggattttcg ggactactct ggactcaaag acacagagcc tgctgatcgt taacaacgcc  360
acaaacgttg tcatcaaagt gtgcgaattc cagttttgca atgatccctt cctggacgtg  420
tactatcaca agaataacaa gtcctggatg gagagcgaat ttcgggtcta cagcagcgca  480
aacaactgca ccttcgagta cgtgagtcaa ccctttctga tggacctgga agggaaacag  540
ggaaacttca agaacctgag agagtttgtc tttaagaaca tcgacggcta ttttaagatc  600
tatagtaagc atacgcctat caacctggga agggatcttc cccagggctt ttcagccctg  660
gaacctttgg ttgacttgcc tattggtatc aatatcacca gatttcagac ccttctggca  720
ttgcatcggt cttatcttac tccaggtgat tcctcctccg ggtggactgc cggcgccgct  780
gcctactatg tcggctatct gcaaccaaga acgttcctgc tcaagtacaa cgaaaacggc  840
actattacgg atgctgttga ttgtgccctg gaccctctgt ctgagactaa atgcaccctc  900
aagagcttta ccgttgagaa ggggatttac caaaccagta atttccgggt ccaacccacc  960
gaaagcattg tgcggttccc aaatatcacc aatctgtgtc cctttgatga agtgttcaat  1020
gctacaaggt ttgcttctgt gtacgcatgg aataggaaac gcatctccaa ttgtgtcgct  1080
gattactccg tgctgtacaa ttttgcccca ttcttcgctt tcaagtgtta tggcgtttca  1140
cctaccaaac ttaacgacct gtgcttcact aatgtgtatg ccgactcttt tgtgatacga  1200
ggcaatgaag tgagccagat tgcaccaggg cagaccggca acattgccga ctacaactac  1260
aagcttccag atgactttac cggatgtgtt attgcatgga actcaaacaa gctggattcc  1320
aaggtgggtg gcaactataa ctacctgtat agactgttca ggaaatccaa cctgaaacca  1380
ttcgagcgag atataagcac agaaatctac caggctggaa acaaaccctg caacggcgtg  1440
gctgggttca actgctactt cccattgcgc agttacggat tcagacctac atacggggtg  1500
ggtcaccaac cctatcgtgt cgtagtcctg agttttgagc tcctccatgc cccagccaca  1560
gtctgtggcc ccaagaaaag caccaatctg gtgaagaaca aatgcgtgaa ctttaacttt  1620
aacggactca caggaaccgg cgtattgacg gagagtaaca agaagttcct gccattccag  1680
cagttcggtc gcgatattgc cgacactacc gacgctgtcc gagatcccca gacattggag  1740
attcttgata tcacaccctg tagtttcggc ggagtgagcg tgattacgcc cggaaccaat  1800
accagcaatc aggttgccgt cctgtatcag ggcgtgaatt gcaccgaggt acctgtcgcc  1860
atccacgctg accaacttac acccacatgg cgagtatatt ccaccggctc caacgtcttt  1920
cagacacgtg ctggatgtct gatcggtgca gaatatgtta ataatagcta cgagtgtgat  1980
atccccatcg gtgctggaat atgcgcctct tatcaaactc aaaccaaatc tcacaggcgg  2040
gcacgtagtg tagcatccca aagtatcatt gcctacacaa tgagcctcgg tgctgagaat  2100
tctgtcgcct acagcaacaa ctccattgct atccctacta acttcacaat cagtgtgaca  2160
actgaaattc tgcccgtatc tatgaccaaa acaagcgttg actgcaccat gtacatctgt  2220
ggcgattcta ccgaatgtag caatctcctc ctgcaatacg gatcattctg cactcagctg  2280
aagcgtgccc tcacaggtat tgcagttgag caggacaaga atacgcagga agtgtttgcc  2340
caggtgaagc aaatctacaa aactccaccc ataaaatact ttggcggatt caatttctca  2400
cagatcctgc ccgatccctc aaaaccctcc aagcgtagct ttatcgagga tctgctcttc  2460
aacaaggtaa ccctcgcaga tgccggtttc atcaagcagt atggcgattg tctgggagac  2520
atcgccgctc gggacctgat ctgtgcacag aagttcaatg gactgaccgt gctgcctccc  2580
ttgctgaccg acgagatgat agcccaatac actagcgccc tgctggccgg caccatcact  2640
tctgggtgga cattcggagc tggcgctgcc cttcagattc cttttgctat gcagatggcc  2700
taccgcttta acggcatcgg tgtgacacaa aacgttctgt atgaaaacca gaaactcatc  2760
gccaaccagt tcaacagtgc tatcggtaag atacaggata gcctgtcatc cactgccagc  2820
gcattgggaa agttgcagga tgtagtgaac cacaatgccc aggcacttaa caccctggtg  2880
aaacagctct cttcaaagtt tggtgccatt tctagcgtgc tgaatgacat actgagccgg  2940
ttggacaagg tggaggctga agtgcagatt gataggctga taactgggcg ccttcagtct  3000
cttcagacct atgtgaccca gcagctcatc cgcgctgctg aaattcgcgc atccgctaac  3060
ctggcagcaa ccaaaatgtc cgagtgtgtg ctgggtcagt ctaagagagt ggacttttgc  3120
gggaaggggt atcacctgat gtcttttcct cagtctgcac cccatggtgt ggtctttctg  3180
cacgtgactt atgtcccagc tcaggaaaag aacttcacta cagccccagc catctgccac  3240
gatgggaaag cccactttcc cagggaaggc gtattcgtgt ccaatggtac tcattggttc  3300
gtcactcaga gaaatttcta cgagccccag attataacca ctgacaatac atttgtatcc  3360
ggcaattgtg atgtggttat cgggattgtg aataatactg tttacgatcc tttgcagcca  3420
gagctggact ccttcaagga ggagcttgac aaatatttta agaatcacac atcacctgac  3480
gtcgacctcg gagatatttc aggaatcaat gcttccgtgg tcaatattca gaaggagata  3540
gacaggctga atgaggttgc caagaacctc aacgagtctc tgatcgatct gcaggagttg  3600
ggcaagtacg aacagtaa                                                3618
```

```
SEQ ID NO: 8            moltype = RNA  length = 3618
FEATURE                 Location/Qualifiers
source                  1..3618
                        mol_type = other RNA
                        organism = synthetic construct
SEQUENCE: 8
atgtttgtgt tcttggtgtt gcttccactg gtcagttccc aatgcgttaa tctcatcacc  60
cgaactcaat cctatacaaa ttccttcacc agaggagtgt actatcctga caaagtgttt  120
cggtcaagtg tcctccactc tactcaggac ctctttctgc ctttctttc taacgttaca  180
tggtttcatg caatccatgt gtctgggaca aacggcacca aacgcttcga caaccctgta  240
ttgccattca atgatggggt gtactttgcc tccacagaga aatccaacat cattcgagga  300
tggattttcg ggactactct ggactcaaag acacagagcc tgctgatcgt taacaacgcc  360
acaaacgttg tcatcaaagt gtgcgaattc cagttttgca atgatccctt cctggacgtg  420
tactatcaca agaataacaa gtcctggatg gagagcgaat ttcgggtcta cagcagcgca  480
aacaactgca ccttcgagta cgtgagtcaa ccctttctga tggacctgga agggaaacag  540
ggaaacttca agaacctgag agagtttgtc tttaagaaca tcgacggcta ttttaagatc  600
tatagtaagc atacgcctat caacctggga agggatcttc cccagggctt ttcagccctg  660
gaacctttgg ttgacttgcc tattggtatc aatatcacca gatttcagac ccttctggca  720
ttgcatcggt cttatcttac tccaggtgat tcctcctccg ggtggactgc cggcgccgct  780
gcctactatg tcggctatct gcaaccaaga acgttcctgc tcaagtacaa cgaaaacggc  840
actattacgg atgctgttga ttgtgccctg gaccctctgt ctgagactaa atgcaccctc  900
aagagcttta ccgttgagaa ggggatttac caaaccagta atttccgggt ccaacccacc  960
gaaagcattg tgcggttccc aaatatcacc aatctgtgtc cctttgatga agtgttcaat  1020
gctacaaggt ttgcttctgt gtacgcatgg aataggaaac gcatctccaa ttgtgtcgct  1080
gattactccg tgctgtacaa ttttgcccca ttcttcgctt tcaagtgtta tggcgtttca  1140
cctaccaaac ttaacgacct gtgcttcact aatgtgtatg ccgactcttt tgtgatacga  1200
ggcaatgaag tgagccagat tgcaccaggg cagaccggca acattgccga ctacaactac  1260
aagcttccag atgactttac cggatgtgtt attgcatgga actcaaacaa gctggattcc  1320
aaggtgggtg gcaactataa ctacctgtat agactgttca ggaaatccaa cctgaaacca  1380
ttcgagcgag atataagcac agaaatctac caggctggaa acaaaccctg caacggcgtg  1440
gctgggttca actgctactt cccattgcgc agttacggat tcagacctac atacggggtg  1500
ggtcaccaac cctatcgtgt cgtagtcctg agttttgagc tcctccatgc cccagccaca  1560
gtctgtggcc ccaagaaaag caccaatctg gtgaagaaca aatgcgtgaa ctttaacttt  1620
aacggactca caggaaccgg cgtattgacg gagagtaaca agaagttcct gccattccag  1680
cagttcggtc gcgatattgc cgacactacc gacgctgtcc gagatcccca gacattggag  1740
attcttgata tcacaccctg tagtttcggc ggagtgagcg tgattacgcc cggaaccaat  1800
accagcaatc aggttgccgt cctgtatcag ggcgtgaatt gcaccgaggt acctgtcgcc  1860
atccacgctg accaacttac acccacatgg cgagtatatt ccaccggctc caacgtcttt  1920
cagacacgtg ctggatgtct gatcggtgca gaatatgtta ataatagcta cgagtgtgat  1980
atccccatcg gtgctggaat atgcgcctct tatcaaactc aaaccaaatc tcacaggcgg  2040
gcacgtagtg tagcatccca aagtatcatt gcctacacaa tgagcctcgg tgctgagaat  2100
tctgtcgcct acagcaacaa ctccattgct atccctacta acttcacaat cagtgtgaca  2160
actgaaattc tgcccgtatc tatgaccaaa acaagcgttg actgcaccat gtacatctgt  2220
ggcgattcta ccgaatgtag caatctcctc ctgcaatacg gatcattctg cactcagctg  2280
aagcgtgccc tcacaggtat tgcagttgag caggacaaga atacgcagga agtgtttgcc  2340
caggtgaagc aaatctacaa aactccaccc ataaaatact ttggcggatt caatttctca  2400
cagatcctgc ccgatccctc aaaaccctcc aagcgtagct ttatcgagga tctgctcttc  2460
aacaaggtaa ccctcgcaga tgccggtttc atcaagcagt atggcgattg tctgggagac  2520
atcgccgctc gggacctgat ctgtgcacag aagttcaatg gactgaccgt gctgcctccc  2580
ttgctgaccg acgagatgat agcccaatac actagcgccc tgctggccgg caccatcact  2640
tctgggtgga cattcggagc tggcgctgcc cttcagattc cttttgctat gcagatggcc  2700
taccgcttta acggcatcgg tgtgacacaa aacgttctgt atgaaaacca gaaactcatc  2760
gccaaccagt tcaacagtgc tatcggtaag atacaggata gcctgtcatc cactgccagc  2820
gcattgggaa agttgcagga tgtagtgaac cacaatgccc aggcacttaa caccctggtg  2880
aaacagctct cttcaaagtt tggtgccatt tctagcgtgc tgaatgacat actgagccgg  2940
ttggaccctc cggaggctga agtgcagatt gataggctga taactgggcg ccttcagtct  3000
cttcagacct atgtgaccca gcagctcatc cgcgctgctg aaattcgcgc atccgctaac  3060
ctggcagcaa ccaaaatgtc cgagtgtgtg ctgggtcagt ctaagagagt ggacttttgc  3120
gggaaggggt atcacctgat gtcttttcct cagtctgcac cccatggtgt ggtctttctg  3180
cacgtgactt atgtcccagc tcaggaaaag aacttcacta cagccccagc catctgccac  3240
gatgggaaag cccactttcc cagggaaggc gtattcgtgt ccaatggtac tcattggttc  3300
gtcactcaga gaaatttcta cgagccccag attataacca ctgacaatac atttgtatcc  3360
ggcaattgtg atgtggttat cgggattgtg aataatactg tttacgatcc tttgcagcca  3420
gagctggact ccttcaagga ggagcttgac aaatatttta agaatcacac atcacctgac  3480
gtcgacctcg gagatatttc aggaatcaat gcttccgtgg tcaatattca gaaggagata  3540
gacaggctga atgaggttgc caagaacctc aacgagtctc tgatcgatct gcaggagttg  3600
ggcaagtacg aacagtaa                                                3618

SEQ ID NO: 9            moltype = RNA  length = 38
FEATURE                 Location/Qualifiers
source                  1..38
                        mol_type = genomic RNA
                        organism = unidentified
SEQUENCE: 9
taacctgaat ggactacgac atagtctagt ccgccaag                          38
```

```
SEQ ID NO: 10          moltype = RNA  length = 18
FEATURE                Location/Qualifiers
source                 1..18
                       mol_type = genomic RNA
                       organism = unidentified
SEQUENCE: 10
ttcgaaggcg cgcctcta                                              18

SEQ ID NO: 11          moltype = RNA  length = 92
FEATURE                Location/Qualifiers
source                 1..92
                       mol_type = genomic RNA
                       organism = unidentified
SEQUENCE: 11
gaacttccat catagttatg gccatgacta ctctagctag cagtgttaaa tcattcagct  60
acctgagagg ggcccctata actctctacg gc                              92

SEQ ID NO: 12          moltype = RNA  length = 30
FEATURE                Location/Qualifiers
source                 1..30
                       mol_type = genomic RNA
                       organism = unidentified
SEQUENCE: 12
atcgatgata tcgcggccgc atacagcagc                                 30

SEQ ID NO: 13          moltype = RNA  length = 2040
FEATURE                Location/Qualifiers
source                 1..2040
                       mol_type = other RNA
                       organism = unidentified
SEQUENCE: 13
atgacctccc ggcttgtgag ggtactggct gctgctatgc tggtggctgc tgctgtgagt  60
gtggcaatgt gggagcttga aaaagacgtc tatgtagtag aagtggactg gacacctgat  120
gctcctggcg agacagttaa cctcacatgc gatacccctg aggaagatga tatcacctgg  180
acttctgacc agagacacgg ggtgattggg agcggcaaaa ccctgacgat cactgtgaag  240
gagtttctgg acgccggcca gtatacctgt cacaaggggg gggagaccct gagtcatagc  300
cacctgttgc tgcacaagaa ggagaatggc atctggtcta cagagatcct gaagaacttt  360
aagaacaaga ccttcctgaa gtgtgaagca ccaaactaca gtggtcgctt tacctgcagc  420
tggctggtcc aaagaaacat ggacctgaaa tttaatataa agagtagctc ttcgagtcct  480
gattccaggg ccgtgacgtg cggcatggca agcctttcag ccgaaaaagt cacgctggat  540
cagcgagact atgagaagta cagcgttagc tgtcaggagg acgtaacttg cccgactgcc  600
gaggagactc tgcccataga gctcgctctg gaggccaggc agcagaacaa atatgagaat  660
tacagcacta gtttctttat tagagacatc atcaaacccg acccacccaa gaatctgcag  720
atgaagccgc tgaagaatag tcaggtcgag gtttcctggg aatatccaga ttcatggtcc  780
actccgcatt cttatttttc cttaaaattc tttgttagga ttcagcggaa aaaagaaaag  840
atgaaagaga cggaggaagg gtgcaaccag aagggggcct tcctggtgga aaagacaagc  900
actgaggtcc aatgtaaggg tgggaacgtt tgcgtgcagg ctcaggatcg ctactacaac  960
agcagttgct ctaagtgggc ctgcgtacct tgtcgcgtca ggagtggagg ggggtcaggg  1020
ggtggctcag gcggcggcag tgggggcagc agggtgatcc cagtgtctgg gccggcccgt  1080
tgcttgtctc aatccagaaa cctcctcaag accactgacg atatggtaaa gactgcccga  1140
gagaagctaa aacactactc ttgtacagct gaagatatag accatgagga tataacacgg  1200
gaccagacct ctactctgaa aacctgtctg cctcttgagc tgcacaagaa cgagtcctgt  1260
ctggctaccc gcgaaacctc aagcacaacc agaggtagtt gcctgccccc acaaaagaca  1320
tcgcttatga tgaccttgtg tctgggatct atttatgagg acctgaagat gtaccaaact  1380
gagttccagg caataaatgc tgctctccag aatcacaatc atcaacaaat catccttgat  1440
aaggggatgc tggtcgcaat cgacgagctc atgcaatcgc tgaaccacaa tggggaaacc  1500
ctcaggcaga aaccaccggt gggagaggcc gacccctacc gtgttaaaat gaagttgtgt  1560
attcttttgc atgcattctc tacaagagtc gttaccatca atcgcgtcat ggggtacctg  1620
tcatcagccg gcggtagtgg tggtgggagc cacaagtcct ccccccaggg tccggatcgg  1680
ctcttgatca gactgagaca tctgattgat attgtcgagc agttgaagat ctatgagaat  1740
gacctcgatc ctgagttact gagtgcccca caggacgtta aagggcactg tgaacacgcc  1800
gcatttgctt gttttcagaa ggccaagctg aaaccttcta atcccgggaa taacaaaact  1860
ttcattatcg atctcgtcgc gcagctgagg cggcgacttc ctgcacggcg gggggggaaa  1920
aagcaaaagc acatcgcaaa gtgtccctca tgcgactctt acgagaaacg taccccctaag  1980
gagttccttg aaagactcaa atggctgctg caaaagatga tccaccagca tctcagctag  2040

SEQ ID NO: 14          moltype = RNA  length = 65
FEATURE                Location/Qualifiers
source                 1..65
                       mol_type = other RNA
                       organism = unidentified
SEQUENCE: 14
atgacctccc ggcttgtgag ggtactggct gctgctatgc tggtggctgc tgctgtgagt  60
gtggc                                                            65
```

```
SEQ ID NO: 15          moltype = RNA  length = 939
FEATURE                Location/Qualifiers
source                 1..939
                       mol_type = other RNA
                       organism = unidentified
SEQUENCE: 15
atgtgggagc ttgaaaaaga cgtctatgta gtagaagtgg actggacacc tgatgctcct  60
ggcgagacag ttaacctcac atgcgatacc cctgaggaag atgatatcac ctggacttct  120
gaccagagac acggggtgat tgggagcggc aaaaccctga cgatcactgt gaaggagttt  180
ctggacgccg gccagtatac ctgtcacaag gggggggaga ccctgagtca tagccacctg  240
ttgctgcaca agaaggagaa tggcatctgg tctacagaga tcctgaagaa ctttaagaac  300
aagaccttcc tgaagtgtga agcaccaaac tacagtggtc gctttacctg cagctggctg  360
gtccaaagaa acatggacct gaaatttaat ataaagagta gctcttcgag tcctgattcc  420
agggccgtga cgtgcggcat ggcaagcctt tcagccgaaa aagtcacgct ggatcagcga  480
gactatgaga agtacagcgt tagctgtcag gaggacgtaa cttgcccgac tgccgaggag  540
actctgccca tagagctcgc tctggaggcc aggcagcaga acaaatatga gaattacagc  600
actagtttct ttattagaga catcatcaaa cccgacccac ccaagaatct gcagatgaag  660
ccgctgaaga atagtcaggt cgaggtttcc tgggaatatc cagattcatg gtccactccg  720
cattcttatt tttccttaaa attctttgtt aggattcagc ggaaaaaaga aaagatgaaa  780
gagacggagg aagggtgcaa ccagaagggg gccttcctgg tggaaaagac aagcactgag  840
gtccaatgta agggtgggaa cgtttgcgtg caggctcagg atcgctacta caacagcagt  900
tgctctaagt gggcctgcgt accttgtcgc gtcaggagt                        939

SEQ ID NO: 16          moltype = RNA  length = 45
FEATURE                Location/Qualifiers
source                 1..45
                       mol_type = other RNA
                       organism = synthetic construct
SEQUENCE: 16
ggagggggt cagggggtgg ctcaggcggc ggcagtgggg gcagc                  45

SEQ ID NO: 17          moltype = RNA  length = 579
FEATURE                Location/Qualifiers
source                 1..579
                       mol_type = other RNA
                       organism = unidentified
SEQUENCE: 17
agggtgatcc cagtgtctgg gccggcccgt tgcttgtctc aatccagaaa cctcctcaag  60
accactgacg atatggtaaa gactgcccga gagaagctaa aacactactc ttgtacagct  120
gaagatatag accatgagga tataacacgg gaccagacct ctactctgaa aacctgtctg  180
cctcttgagc tgcacaagaa cgagtcctgt ctggctaccc gcgaaacctc aagcacaacc  240
agaggtagtt gcctgccccc acaaaagaca tcgcttatga tgaccttgtg tctgggatct  300
atttatgagg acctgaagat gtaccaaact gagttccagg caataaatgc tgctctccag  360
aatcacaatc atcaacaaat catccttgat aaggggatgc tggtcgcaat cgacgagctc  420
atgcaatcgc tgaaccacaa tggggaaacc ctcaggcaga aaccaccggt gggagaggcc  480
gacccctacc gtgttaaaat gaagttgtgt attcttttgc atgcattctc tacaagagtc  540
gttaccatca atcgcgtcat ggggtacctg tcatcagcc                        579

SEQ ID NO: 18          moltype = RNA  length = 21
FEATURE                Location/Qualifiers
source                 1..21
                       mol_type = other RNA
                       organism = synthetic construct
SEQUENCE: 18
ggcggtagtg gtggtgggag c                                           21

SEQ ID NO: 19          moltype = RNA  length = 426
FEATURE                Location/Qualifiers
source                 1..426
                       mol_type = other RNA
                       organism = unidentified
SEQUENCE: 19
gggtacctgt catcagccgg cggtagtggt ggtgggagcc acaagtcctc cccccagggt  60
ccggatcggc tcttgatcag actgagacat ctgattgata ttgtcgagca gttgaagatc  120
tatgagaatg acctcgatcc tgagttactg agtgccccac aggacgttaa agggcactgt  180
gaacacgccg catttgcttg ttttcagaag gccaagctga aaccttctaa tcccgggaat  240
aacaaaactt tcattatcga tctcgtcgcg cagctgaggc ggcgacttcc tgcacggcgg  300
ggggggaaaa agcaaaagca catcgcaaag tgtccctcat gcgactctta cgagaaacgt  360
acccctaagg agttccttga aagactcaaa tggctgctgc aaaagatgat ccaccagcat  420
ctcagc                                                            426
```

```
SEQ ID NO: 20           moltype = RNA  length = 2037
FEATURE                 Location/Qualifiers
source                  1..2037
                        mol_type = other RNA
                        organism = unidentified
SEQUENCE: 20
atgacgtctc gactggtccg tgttcttgcg gcagctatgc tggtggcagc tgccgttagc  60
gtagccatat gggaactgaa gaaggatgtc tatgtagttg agctggactg gtaccccgac  120
gcgccaggcg aaatggtggt gctcacatgc gacacaccag aggaggacgg aatcacttgg  180
accctggacc agtcttcaga ggtgcttggg tccggtaaaa ccttgaccat acaggtaaag  240
gagttcggtg acgcaggcca gtacacatgt cacaagggcg gggaagtgct ctcacattca  300
ctcctttgc tccacaagaa ggaggatggg atatggtcga ctgacatttt gaaagaccag  360
aaggagccta agaataaaac cttcctgcgg tgcgaggcaa aaaattattc agggcgattt  420
acatgttggt ggcttaccac catttcgacc gatttaacat tttccgtgaa gtcttcaaga  480
ggcagctcag atccacaggg tgtcacatgc ggggccgcaa ccctgtccgc agaaagggtg  540
cggggggata ataaggaata cgaatactcc gtggaatgcc aagaggattc tgcatgccct  600
gccgccgagg aaagtctgcc cattgaagta atggtggacg ctgtgcataa gcttaagtac  660
gagaattaca cctcctcatt cttcataagg gatatcatta aacctgatcc accaaagaac  720
ctgcagctca agcctctgaa gaatagcagg caggtcgagg taagctggga gtatcctgat  780
acctggtcca ccccccacag ttatttcagc ctcaccttct gcgtccaagt ccagggaaag  840
agcaagagag agaagaagga tagggtgttc acagataaga cttcagctac tgtgatctgc  900
agaaagaatg cgtctatctc tgtgcgagca caagacaggt actacagttc tagctggagc  960
gagtgggcat cagtcccctg cagtggtggc ggaagcggag ggggcagcgg aggtgggagc  1020
ggagggagca ggaacctccc agttgctaca cctgacccgg gaatgtttcc atgcctccac  1080
cattcccaga atctcctccg agccgtgtcc aatatgctgc aaaaggctcg gcagaccttg  1140
gagttttacc cttgcacctc agaagaaatc gatcatgagg atatcacaaa ggataagacg  1200
agcactgttg aggcatgcct gcccctggag ctaactaaga atgagtcttg cctgaacagc  1260
agggagactt ccttcattac caacggtagc tgtcttgcca gcaggaagac atcttttatg  1320
atggccctgt gtctatctag catatatgaa gacctgaaga tgtaccaggt ggaattcaaa  1380
accatgaatg ctaagcttct catggatccc aagaggcaaa tcttcctgga ccagaatatg  1440
cttgctgtca tagatgaact gatgcaggcg ttgaatttta acagcgagac ggtgcctcaa  1500
aaaagctcac tggaagaacc tgatttttat aaaacgaaga tcaagctgtg tattttacta  1560
cacgccttta gaatccgcgc tgttaccatc gacagagtaa tgtcctacct aaatgcttca  1620
ggagggtcag gaggaggatc ccaggacagg catatgatcc ggatgcggca gctgatcgat  1680
attgtagacc agttgaagaa ttatgtgaac gacttagtgc cggaattcct ccccgccccc  1740
gaggacgtgg agactaattg tgagtggtct gcattctcat gcttccaaaa agcacagctg  1800
aagagtgcca ataccggcaa taacgaaagg atcatcaatg taagtataaa gaagttaaaa  1860
cgcaaaccgc ccagtaccaa cgctggacgc aggcaaaaac acaggctgac atgcccctcg  1920
tgtgattcgt acgaaaaaaa acctccaaag gaattcctgg aaaggttcaa gtccttatta  1980
cagaaaatga ttcaccagca cctgagtagt aggacccacg gatccgaaga ctcctag     2037

SEQ ID NO: 21           moltype = RNA  length = 57
FEATURE                 Location/Qualifiers
source                  1..57
                        mol_type = other RNA
                        organism = Homo sapiens
SEQUENCE: 21
atggactgga cctggcgaat actgttcttg gttgccgccg ctacagggac tcacgca     57

SEQ ID NO: 22           moltype = RNA  length = 918
FEATURE                 Location/Qualifiers
source                  1..918
                        mol_type = other RNA
                        organism = Homo sapiens
SEQUENCE: 22
atatgggagc tgaagaagga cgtgtatgtc gtggagctgg actggtaccc agatgctcct  60
ggcgaaatgg tggttttaac atgtgatacc cccgaggagg acggcatcac atggactctg  120
gaccagagtt ctgaggtgct ggggtccggc aagactctga caatccaggt taaggagttc  180
ggcgacgcag gacagtacac ttgtcacaag ggaggtgagg tgctttctca cagcctgttg  240
ctgctccata agaaggaaga cggtatttgg tcaaccgaca tcctcaagga ccagaaggag  300
cccaaaaaca agacctttct gagatgtgag gccaagaatt acagcggtag attcacttgt  360
tggtggctca ccaccatatc cacagacttg accttcagtg tcaaaagttc acgagggagc  420
tcagatcctc aaggcgttac ctgtggcgca gcgacgctgt ccgcagaaag agtcagggga  480
gacaacaagg aatacgagta ctctgtcgag tgccaggagg attccgcctg tccggccgca  540
gaggagtctt tacctattga ggtgatggtc gatgccgtgc acaagcttaa gtacgagaat  600
tacacatcaa gtttttcat ccgcgacatc attaaacctg atccaccaaa gaacctgcag  660
ctcaagcctc tgaagaatag caggcaggtc gaggtaagct gggagtatcc tgatacctgg  720
tccacccccc acagttattt cagcctcacc ttctgcgtcc aagtccaggg aaagagcaag  780
agagagaaga aggatagggt gttcacagat aagacttcag ctactgtgat ctgcagaaag  840
aatgcgtcta tctctgtgcg agcacaagac aggtactaca gttctagctg gagcgagtgg  900
gcatcagtcc cctgcagt                                               918
```

```
SEQ ID NO: 23          moltype = RNA  length = 45
FEATURE                Location/Qualifiers
source                 1..45
                       mol_type = other RNA
                       organism = synthetic construct
SEQUENCE: 23
ggtggcggaa gcggaggggg cagcggaggt gggagcggag ggagc                 45

SEQ ID NO: 24          moltype = RNA  length = 591
FEATURE                Location/Qualifiers
source                 1..591
                       mol_type = other RNA
                       organism = Homo sapiens
SEQUENCE: 24
aggaacctcc cagttgctac acctgacccg ggaatgtttc catgcctcca ccattcccag  60
aatctcctcc gagccgtgtc caatatgctg caaaaggctc ggcagacctt ggagttttac  120
ccttgcacct cagaagaaat cgatcatgag gatatcacaa aggataagac gagcactgtt  180
gaggcatgcc tgcccctgga gctaactaag aatgagtctt gcctgaacag cagggagact  240
tccttcatta ccaacggtag ctgtcttgcc agcaggaaga catcttttat gatggccctg  300
tgtctatcta gcatatatga agacctgaag atgtaccagg tggaattcaa aaccatgaat  360
gctaagcttc tcatggatcc caagaggcaa atcttcctgg accagaatat gcttgctgtc  420
atagatgaac tgatgcaggc gttgaatttt aacagcgaga cggtgcctca aaaaagctca  480
ctggaagaac ctgattttta taaaacgaag atcaagctgt gtattttact acacgccttt  540
agaatccgcg ctgttaccat cgacagagta atgtcctacc taaatgcttc a          591

SEQ ID NO: 25          moltype = RNA  length = 21
FEATURE                Location/Qualifiers
source                 1..21
                       mol_type = other RNA
                       organism = synthetic construct
SEQUENCE: 25
ggagggtcag gaggaggatc c                                           21

SEQ ID NO: 26          moltype = RNA  length = 393
FEATURE                Location/Qualifiers
source                 1..393
                       mol_type = other RNA
                       organism = Homo sapiens
SEQUENCE: 26
caggacaggc atatgatccg gatgcggcag ctgatcgata ttgtagacca gttgaagaat  60
tatgtgaacg acttagtgcc ggaattcctc cccgcccccg aggacgtgga gactaattgt  120
gagtggtctg cattctcatg cttccaaaaa gcacagctga agagtgccaa taccggcaat  180
aacgaaagga tcatcaatgt aagtataaag aagttaaaac gcaaaccgcc cagtaccaac  240
gctggacgca ggcaaaaaca caggctgaca tgcccctcgt gtgattcgta cgaaaaaaaa  300
cctccaaagg aattcctgga aaggttcaag tccttattac agaaaatgat tcaccagcac  360
ctgagtagta ggacccacgg atccgaagac tcc                              393

SEQ ID NO: 27          moltype = RNA  length = 1103
FEATURE                Location/Qualifiers
source                 1..1103
                       mol_type = other RNA
                       organism = synthetic construct
SEQUENCE: 27
atggagaaag ttcacgttga catcgaggaa gacagcccat tcctcagagc tttgcagcgg  60
agcttcccgc agtttgaggt agaagccaag caggtcactg ataatgacca tgctaatgcc  120
agagcgtttt cgcatctggc ttcaaaactg atcgaaacgg aggtggaccc atccgacacg  180
atccttgaca ttggaagtgc gcccgcccgc agaatgtatt ctaagcacaa gtatcattgt  240
atctgtccga tgagatgtgc ggaagatccg gacagattgt ataagtatgc aactaagctg  300
aagaaaaact gtaaggaaat aactgataag gaattggaca agaaaatgaa ggagctggcc  360
gccgtcatga gcgaccctga cctggaaact gagactatgt gcctccacga cgacgagtcg  420
tgtcgctacg aagggcaagt cgctgtttac caggatgtat acgcggttga cggaccgaca  480
agtctctatc accaagccaa taagggagtt agagtcgcct actggatagg ctttgacacc  540
accccttta tgtttaagaa cttggctgga gcatatccat catactctac caactgggcc  600
gacgaaaccg tgttaacggc tcgtaacata ggcctatgca gctctgacgt tatggagcgg  660
tcacgtagag ggatgtccat tcttagaaag aagtatttga aaccatccaa caatgttcta  720
ttctctgttg gctcgaccat ctaccacgag aagagggact tactgaggag ctggcacctg  780
ccgtctgtat ttcacttacg tggcaagcaa aattacacat gtcggtgtga gactatagtt  840
agttgcgacg ggtacgtcgt taaaagaata gctatcagtc caggcctgta tgggaagcct  900
tcaggctatg ctgctacgat gcaccgcgag ggattcttgt gctgcaaagt gacagacaca  960
ttgaacgggg agagggtctc ttttcccgtg tgcacgtatg tgccagctac attgtgtgac  1020
caaatgactg gcatactggc aacagatgtc agtgcggacg acgcgcaaaa actgctggtt  1080
gggctcaacc agcgtatagt cgt                                         1103
```

-continued

```
SEQ ID NO: 28          moltype = RNA  length = 1158
FEATURE                Location/Qualifiers
source                 1..1158
                       mol_type = other RNA
                       organism = synthetic construct
SEQUENCE: 28
tggcaacaga tgtcagtgcg gacgacgcgc aaaaactgct ggttgggctc aaccagcgta  60
tagtcgtcaa cggtcgcacc cagagaaaca ccaataccat gaaaaattac cttttgcccg  120
tagtggccca ggcatttgct aggtgggcaa aggaatataa ggaagatcaa gaagatgaaa  180
ggccactagg actacgagat agacagttag tcatggggtg ttgttgggct tttagaaggc  240
acaagataac atctatttat aagcgcccgg atacccaaac catcatcaaa gtgaacagcg  300
atttccactc attcgtgctg cccaggatag gcagtaacac attggagatc gggctgagaa  360
caagaatcag gaaaatgtta gaggagcaca aggagccgtc acctctcatt accgccgagg  420
acgtacaaga agctaagtgc gcagccgatg aggctaagga ggtgcgtgaa gccgaggagt  480
tgcgcgcagc tctaccacct ttggcagctg atgttgagga gcccactctg gaagccgatg  540
tcgacttgat gttacaagag gctggggccg gctcagtgga gacacctcgt ggcttgataa  600
aggttaccag ctacgatggc gaggacaaga tcggctctta cgctgtgctt tctccgcagg  660
ctgtactcaa gagtgaaaaa ttatcttgca tccaccctct cgctgaacaa gtcatagtga  720
taacacactc tggccgaaaa gggcgttatg ccgtggaacc ataccatggt aaagtagtgg  780
tgccagaggg acatgcaata cccgtccagg actttcaagc tctgagtgaa agtgccacca  840
ttgtgtacaa cgaacgtgag ttcgtaaaca ggtacctgca ccatattgcc acacatggag  900
gagcgctgaa cactgatgaa gaatattaca aaactgtcaa gcccagcgag cacgacggcg  960
aatacctgta cgacatcgac aggaaacagt gcgtcaagaa agaactagtc actgggctag  1020
ggctcacagg cgagctggtg gatcctccct tccatgaatt cgcctacgag agtctgagaa  1080
cacgaccagc cgctccttac caagtaccaa ccatagggt gtatggcgtg ccaggatcag  1140
gcaagtctgg catcatta                                            1158

SEQ ID NO: 29          moltype = RNA  length = 1148
FEATURE                Location/Qualifiers
source                 1..1148
                       mol_type = other RNA
                       organism = synthetic construct
SEQUENCE: 29
taccaagtac caaccatagg ggtgtatggc gtgccaggat caggcaagtc tggcatcatt  60
aaaagcgcag tcaccaaaaa agatctagtg gtgagcgcca agaaagaaaa ctgtgcagaa  120
attataaggg acgtcaagaa aatgaaaggg ctggacgtca atgccagaac tgtggactca  180
gtgctcttga atggatgcaa acaccccgta gagaccctgt atattgacga agcttttgct  240
tgtcatgcag gtactctcag agcgctcata gccattataa gacctaaaaa ggcagtgctc  300
tgcggggatc ccaaacagtg cggttttttt aacatgatgt gcctgaaagt gcattttaac  360
cacgagattt gcacacaagt cttccacaaa agcatctctc gccgttgcac taaatctgtg  420
acttcggtcg tctcaacctt gttttacgac aaaaaaatga gaacgacgaa tccgaaagag  480
actaagattg tgattgacac taccggcagt accaaaccta agcaggacga tctcattctc  540
acttgtttca gagggtgggt gaagcagttg caaatagatt acaaaggcaa cgaaataatg  600
acggcagctg cctctcaagg gctgacccgt aaaggtgtgt atgccgttcg gtacaaggtg  660
aatgaaaatc ctctgtacgc acccacctca gaacatgtga acgtcctact gacccgcacg  720
gaggaccgca tcgtgtggaa aacactagcc ggcgacccat ggataaaaac actgactgcc  780
aagtaccctg ggaatttcac tgccacgata gaggagtggc aagcagagca tgatgccatc  840
atgaggcaca tcttggagag accggaccct accgacgtct tccagaataa ggcaaacgtg  900
tgttgggcca aggctttagt gccggtgctg aagaccgctg gcatagacat gaccactgaa  960
caatggaaca ctgtggatta ttttgaaacg gacaaagctc actcagcaga gatagtattg  1020
aaccaactat gcgtgaggtt ctttggactc gatctggact ccggtctatt ttctgcaccc  1080
actgttccgt tatccattag gaataatcac tgggataact ccccgtcgcc taacatgtac  1140
gggctgaa                                                       1148

SEQ ID NO: 30          moltype = RNA  length = 1169
FEATURE                Location/Qualifiers
source                 1..1169
                       mol_type = other RNA
                       organism = synthetic construct
SEQUENCE: 30
gaataatcac tgggataact ccccgtcgcc taacatgtac gggctgaata aagaagtggt  60
ccgtcagctc tctcgcaggt acccacaact gcctcgggca gttgccactg gaagagtcta  120
tgacatgaac actggtacac tgcgcaatta tgatccgcgc ataaacctag tacctgtaaa  180
cagaagactg cctcatgctt tagtcctcca ccataatgaa cacccacaga gtgacttttc  240
ttcattcgtc agcaaattga aggcagaac tgtcctggtg gtcggggaaa agttgtccgt  300
cccaggcaaa atggttgact ggttgtcaga ccggcctgag gctaccttca gagctcggct  360
ggatttaggc atcccaggtg atgtgcccaa atatgacata atatttgtta atgtgaggac  420
cccatataaa taccatcact atcagcagtg tgaagaccat gccattaagc ttagcatgtt  480
gaccaagaaa gcttgtctgc atctgaatcc cggcggaacc tgtgtcagca taggttatgg  540
ttacgctgac agggccagcg aaagcatcat tggtgctata gcgcggcagt tcaagttttc  600
ccgggtatgc aaaccgaaat cctcacttga agagacggaa gttctgtttg tattcattgg  660
gtacgatcgc aaggcccgta cgcacaattc ttacaagctt tcatcaacct tgaccaacat  720
ttatacaggt tccagactcc acgaagccgg atgtgcaccc tcatatcatg tggtgcgagg  780
ggatattgcc acggccaccg aaggagtgat tataaatgct gctaacagca aaggacaacc  840
tggcggaggg gtgtgcggag cgctgtataa gaaattcccg gaaagcttcg atttacagcc  900
gatcgaagta ggaaaagcgc gactggtcaa aggtgcagct aaacatatca ttcatgccgt  960
aggaccaaac ttcaacaaag tttcggaggt tgaaggtgac aaacagttgg cagaggctta  1020
tgagtccatc gctaagattg tcaacgataa caattacaag tcagtagcga ttccactgtt  1080
```

```
gtccaccggc atcttttccg ggaacaaaga tcgactaacc caatcattga accatttgct  1140
gacagcttta gacaccactg atgcagatg                                    1169

SEQ ID NO: 31          moltype = RNA  length = 1149
FEATURE                Location/Qualifiers
source                 1..1149
                       mol_type = other RNA
                       organism = synthetic construct
SEQUENCE: 31
attgaaccat ttgctgacag ctttagacac cactgatgca gatgtagcca tatactgcag  60
ggacaagaaa tgggaaatga ctctcaagga agcagtggct aggagagaag cagtggagga  120
gatatgcata tccgacgact cttcagtgac agaacctgat gcagagctgg tgagggtgca  180
tccgaagagt tctttggctg gaaggaaggg ctacagcaca agcgatggca aaactttctc  240
atatttggaa gggaccaagt ttcaccaggc ggccaaggat atagcagaaa ttaatgccat  300
gtggcccgtt gcaacggagg ccaatgagca ggtatgcatg tatatcctcg gagaaagcat  360
gagcagtatt aggtcgaaat gccccgtcga agagtcggaa gcctccacac cacctagcac  420
gctgccttgc ttgtgcatcc atgccatgac tccagaaaga gtacagcgcc taaaagcctc  480
acgtccagaa caaattactg tgtgctcatc ctttccattg ccgaagtata gaatcactgg  540
tgtgcagaag atccaatgct cccagcctat attgttctca ccgaaagtgc ctgcgtatat  600
tcatccaagg aagtatctcg tggaaacacc accggtagac gagactccgg agccatcggc  660
agagaaccaa tccacagagg ggacacctga acaaccacca cttataaccg aggatgagac  720
caggactaga acgcctgagc cgatcatcat cgaagaggaa gaagaggata gcataagttt  780
gctgtcagat ggcccgaccc accaggtgct gcaagtcgag gcagacattc acggccgcc  840
ctctgtatct agctcatcct ggtccattcc tcatgcatcc gactttgatg tggacagttt  900
atccatactt gacaccctgg agggagctag cgtgaccagc ggggcaacgt cagccgagac  960
taactcttac ttcgcaaaga gtatggagtt tctggcgcga ccggtgcctg cgcctcgaac  1020
agtattcagg aaccctccac atcccgctcc gcgcacaaga acaccgtcac ttgcacccag  1080
cagggcctgc tcgagaacca gcctagtttc caccccgcca ggcgtgaata gggtgatcac  1140
tagagagga                                                          1149

SEQ ID NO: 32          moltype = RNA  length = 1198
FEATURE                Location/Qualifiers
source                 1..1198
                       mol_type = other RNA
                       organism = synthetic construct
SEQUENCE: 32
agaaccagcc tagtttccac cccgccaggc gtgaataggg tgatcactag agaggagctc  60
gaggcgctta ccccgtcacg cactcctagc aggtcggtct cgagaaccag cctggtctcc  120
aacccgccag gcgtaaatag ggtgattaca agagaggagt ttgaggcgtt cgtagcacaa  180
caacaatgac ggtttgatgc gggtgcatac atcttttcct ccgacaccgg tcaagggcat  240
ttacaacaaa aatcagtaag gcaaacggtg ctatccgaag tggtgttgga gaggaccgaa  300
ttggagattt cgtatgcccc gcgcctcgac caagaaaaag aagaattact acgcaagaaa  360
ttacagttaa atcccacacc tgctaacaga agcagatacc agtccaggaa ggtggagaac  420
atgaaagcca taacagctag acgtattctg caaggcctag ggcattattt gaaggcagaa  480
ggaaaagtgg agtgctaccg aaccctgcat cctgttcctt tgtattcatc tagtgtgaac  540
cgtgcctttt caagccccaa ggtcgcagtg gaagcctgta acgccatgtt gaaagagaac  600
tttccgactg tggcttctta ctgtattatt ccagagtacg atgcctattt ggacatggtt  660
gacggagctt catgctgctt agacactgcc agtttttgcc ctgcaaagct gcgcagcttt  720
ccaaagaaac actcctattt ggaacccaca atacgatcgg cagtgccttc agcgatccag  780
aacacgctcc agaacgtcct ggcagctgcc acaaaaagaa attgcaatgt cacgcaaatg  840
agagaattgc ccgtattgga ttcggcggcc tttaatgtgg aatgcttcaa gaaatatgcg  900
tgtaataatg aatattggga aacgtttaaa gaaaacccca tcaggcttac tgaagaaaac  960
gtggtaaatt acattaccaa attaaaagga ccaaaagctg ctgctctttt tgcgaagaca  1020
cataatttga atatgttgca ggacatacca atggacaggt ttgtaatgga cttaaagaga  1080
gacgtgaaag tgactccagg aacaaaacat actgaagaac ggcccaaggt acaggtgatc  1140
caggctgccg atccgctagc aacagcgtat ctgtgcggaa tccaccgaga gctggtta    1198

SEQ ID NO: 33          moltype = RNA  length = 1099
FEATURE                Location/Qualifiers
source                 1..1099
                       mol_type = other RNA
                       organism = synthetic construct
SEQUENCE: 33
gctagcaaca gcgtatctgt gcggaatcca ccgagagctg gttaggagat taaatgcggt  60
cctgcttccg aacattcata cactgtttga tatgtcggct gaagactttg acgctattat  120
agccgagcac ttccagcctg ggattgtgt  tctggaaact gacatcgcgt cgtttgataa  180
aagtgaggac gacgccatgg ctctgaccgc gttaatgatt ctggaagact taggtgtgga  240
cgcagagctg ttgacgctga ttgaggcggc tttcggcgaa atttcatcaa tacatttgcc  300
cactaaaact aaatttaaat tcggagccat gatgaaatct ggaatgttcc tcacactgtt  360
tgtgaacaca gtcattaaca ttgtaatcgc aagcagagtg ttgagagaac ggctaaccgg  420
atcaccatgt gcagcattca ttggagatga caatatcgtg aaaggagtca aatcggacaa  480
attaatggca gacaggtgcg ccacctggtt gaatatggaa gtcaagatta tagatgctgt  540
ggtgggcgag aaagcgcctt atttctgtgg agggtttatt ttgtgtgact ccgtgaccgg  600
cacagcgtgc cgtgtggcag acccccctaaa aaggctgttt aagcttggca aacctctggc  660
agcagacgat gaacatgatg atgacaggag aagggcattg catgaagagt caacacgctg  720
gaaccgagtg ggtattcttt cagagctgtg caaggcagta gaatcaaggt atgaaaccgt  780
aggaacttcc atcatagtta tggccatgac tactctagct agcagtgtta aatcattcag  840
ctacctgaga ggggccccta taactctcta cggctaacct gaatggacta cgacatagtc  900
tagtccgcca agttcgaagg cgcgcctcta gagccaccat gaccgagtac aagcccacgg  960
```

```
tgcgcctcgc cacccgcgac gacgtcccca gggccgtacg caccctcgcc gccgcgttcg  1020
ccgactaccc cgccacgcgc cacaccgtcg atccggaccg ccacatcgag cgggtcaccg  1080
agctgcaaga actcttcct                                               1099

SEQ ID NO: 34          moltype = RNA  length = 593
FEATURE                Location/Qualifiers
source                 1..593
                       mol_type = other RNA
                       organism = synthetic construct
SEQUENCE: 34
cacgcgcgtc gggctcgaca tcggcaaggt gtgggtcgcg gacgacggcg ccgcggtggc  60
ggtctggacc acgccggaga gcgtcgaagc gggggcggtg ttcgccgaga tcggcccgcg  120
catggccgag ttgagcggtt cccggctggc cgcgcagcaa cagatggaag gcctcctggc  180
gccgcaccgg cccaaggagc ccgcgtggtt cctggccacc gtcggcgtct cgcccgacca  240
ccagggcaag ggtctgggca gcgccgtcgt gctccccgga gtggaggcgg ccgagcgcgc  300
cggggtgccc gccttcctgg agacctccgc gccccgcaac ctccccttct acgagcggct  360
cggcttcacc gtcaccgccg acgtcgaggt gcccgaagga ccgcgcacct ggtgcatgac  420
ccgcaagccc ggtgcctgac atcgatgata tcgcggccgc atacagcagc aattggcaag  480
ctgcttacat agaactcgcg gcgattggca tgccgcctta aaatttttat tttatttttc  540
ttttcttttc cgaatcggat tttgttttta atatttcaaa aaaaaaaaaa aaa         593

SEQ ID NO: 35          moltype = RNA  length = 10325
FEATURE                Location/Qualifiers
source                 1..10325
                       mol_type = other RNA
                       organism = synthetic construct
SEQUENCE: 35
aaaaaaaaaa cgcgtgataa cgcaggaaag aacatgtgag caaaaggcca gcaaaaggcc  60
aggaaccgta aaaaggccgc gttgctggcg tttttccata ggctccgccc ccctgacgag  120
catcacaaaa atcgacgctc aagtcagagg tggcgaaacc cgacaggact ataaagatac  180
caggcgtttc cccctggaag ctccctcgtg cgctctcctg ttccgaccct gccgcttacc  240
ggatacctgt ccgcctttct cccttcggga agcgtggcgc tttctcatag ctcacgctgt  300
aggtatctca gttcggtgta ggtcgttcgc tccaagctgg gctgtgtgca cgaacccccc  360
gttcagcccg accgctgcgc cttatccggt aactatcgtc ttgagtccaa cccggtaaga  420
cacgacttat cgccactggc agcagccact ggtaacagga ttagcagagc gaggtatgta  480
ggcggtgcta cagagttctt gaagtggtgg cctaactacg gctacactag aagaacagta  540
tttggtatct gcgctctgct gaagccagtt accttcggaa aaagagttgg tagctcttga  600
tccggcaaac aaaccaccgc tggtagcggt ttttttgttt gcaagcagca gattacgcgc  660
agaaaaaaag gatctcaaga agatcctttg atcttttcta cggggtctga cgctcagtgg  720
aacgaaaact cacgttaagg gattttggtc atgagattat caaaaaggat cttcacctag  780
atccttttaa attaaaaatg aagttttaaa tcaatctaaa gtatatatga gtaaacttgg  840
tctgacagtt accaatgctt aatcagtgag gcacctatct cagcgatctg tctatttcgt  900
tcatccatag ttgcctgact ccccgtcgtg tagataacta cgatacggga gggcttacca  960
tctggcccca gtgctgcaat gataccgcga gacccacgct caccggctcc agatttatca  1020
gcaataaacc agccagccgg aagggccgag cgcagaagtg gtcctgcaac tttatccgcc  1080
tccatccagt ctattaattg ttgccgggaa gctagagtaa gtagttcgcc agttaatagt  1140
ttgcgcaacg ttgttgccat tgctacaggc atcgtggtgt cacgctcgtc gtttggtatg  1200
gcttcattca gctccggttc ccaacgatca aggcgagtta catgatcccc catgttgtgc  1260
aaaaaagcgg ttagctcctt cggtcctccg atcgttgtca gaagtaagtt ggccgcagtg  1320
ttatcactca tggttatggc agcactgcat aattctctta ctgtcatgcc atccgtaaga  1380
tgcttttctg tgactggtga gtactcaacc aagtcattct gagaatagtg tatgcggcga  1440
ccgagttgct cttgcccggc gtcaatacgg gataataccg cgccacatag cagaacttta  1500
aaagtgctca tcattggaaa acgttcttcg gggcgaaaac tctcaaggat cttaccgctg  1560
ttgagatcca gttcgatgta acccactcgt gcacccaact gatcttcagc atcttttact  1620
ttcaccagcg tttctgggtg agcaaaaaca ggaaggcaaa atgccgcaaa aaagggaata  1680
agggcgacac ggaaatgttg aatactcata ctcttccttt ttcaatatta ttgaagcatt  1740
tatcagggtt attgtctcat gagcggatac atatttgaat gtatttagaa aaataaacaa  1800
ataggggttc cgcgcacatt tccccgaaaa gtgccacctg agctctaata cgactcacta  1860
taggataggc ggcgcatgag agaagcccag accaattacc tacccaaaat ggagaaagtt  1920
cacgttgaca tcgaggaaga cagcccattc ctcagagctt tgcagcggag cttcccgcag  1980
tttgaggtag aagccaagca ggtcactgat aatgaccatg ctaatgccag agcgttttcg  2040
catctggctt caaaactgat cgaaacggag gtggacccat ccgacacgat ccttgacatt  2100
ggaagtgcgc ccgcccgcag aatgtattct aagcacaagt atcattgtat ctgtccgatg  2160
agatgtgcgg aagatccgga cagattgtat aagtatgcaa ctaagctgaa gaaaaactgt  2220
aaggaaataa ctgataagga attggacaag aaaatgaagg agctggccgc cgtcatgagc  2280
gaccctgacc tggaaactga gactatgtgc ctccacgacg acgagtcgtg tcgctacgaa  2340
gggcaagtcg ctgtttacca ggatgtatac gcggttgacg gaccgacaag tctctatcac  2400
caagccaata agggagttag agtcgcctac tggataggct ttgacaccac cccttttatg  2460
tttaagaact tggctggagc atatccatca tactctacca actgggccga cgaaaccgtg  2520
ttaacggctc gtaacatagg cctatgcagc tctgacgtta tggagcggtc acgtagaggg  2580
atgtccattc ttagaaagaa gtatttgaaa ccatccaaca atgttctatt ctctgttggc  2640
tcgaccatct accacgagaa gagggactta ctgaggagct ggcacctgcc gtctgtattt  2700
cacttacgtg gcaagcaaaa ttacacatgt cggtgtgaga ctatagttag ttgcgacggg  2760
tacgtcgtta aaagaatagc tatcagtcca ggcctgtatg ggaagccttc aggctatgct  2820
gctacgatgc accgcgaggg attcttgtgc tgcaaagtga cagacacatt gaacggggag  2880
agggtctctt ttcccgtgtg cacgtatgtg ccagctacat tgtgtgacca aatgactggc  2940
atactggcaa cagatgtcag tgcggacgac gcgcaaaaac tgctggttgg gctcaaccag  3000
cgtatagtcg tcaacggtcg cacccagaga aacaccaata ccatgaaaaa ttaccttttg  3060
cccgtagtgg cccaggcatt tgctaggtgg gcaaaggaat ataaggaaga tcaagaagat  3120
```

-continued

```
gaaaggccac taggactacg agatagacag ttagtcatgg ggtgttgttg ggcttttaga  3180
aggcacaaga taacatctat ttataagcgc ccggataccc aaaccatcat caaagtgaac  3240
agcgatttcc actcattcgt gctgcccagg ataggcagta acacattgga gatcgggctg  3300
agaacaagaa tcaggaaaat gttagaggag cacaaggagc cgtcacctct cattaccgcc  3360
gaggacgtac aagaagctaa gtgcgcagcc gatgaggcta aggaggtgcg tgaagccgag  3420
gagttgcgcg cagctctacc acctttggca gctgatgttg aggagcccac tctggaagcc  3480
gatgtcgact tgatgttaca agaggctggg gccggctcag tggagacacc tcgtggcttg  3540
ataaaggtta ccagctacga tggcgaggac aagatcggct cttacgctgt gctttctccg  3600
caggctgtac tcaagagtga aaaattatct tgcatccacc ctctcgctga acaagtcata  3660
gtgataacac actctggccg aaaagggcgt tatgccgtgg aaccatacca tggtaaagta  3720
gtggtgccag agggacatgc aatacccgtc caggactttc aagctctgag tgaaagtgcc  3780
accattgtgt acaacgaacg tgagttcgta aacaggtacc tgcaccatat tgccacacat  3840
ggaggagcgc tgaacactga tgaagaatat tacaaaactg tcaagcccag cgagcacgac  3900
ggcgaatacc tgtacgacat cgacaggaaa cagtgcgtca agaaagaact agtcactggg  3960
ctagggctca caggcgagct ggtggatcct cccttccatg aattcgccta cgagagtctg  4020
agaacacgac cagccgctcc ttaccaagta ccaaccatag ggtgtatggg cgtgccagga  4080
tcaggcaagt ctggcatcat taaaagcgca gtcaccaaaa aagatctagt ggtgagcgcc  4140
aagaaagaaa actgtgcaga aattataagg gacgtcaaga aaatgaaagg gctggacgtc  4200
aatgccagaa ctgtggactc agtgctcttg aatggatgca aacaccccgt agagaccctg  4260
tatattgacg aagcttttgc ttgtcatgca ggtactctca gagcgctcat agccattata  4320
agacctaaaa aggcagtgct ctgcggggat cccaaacagt gcggtttttt taacatgatg  4380
tgcctgaaag tgcattttaa ccacgagatt tgcacacaag tcttccacaa aagcatctct  4440
cgccgttgca ctaaatctgt gacttcggtc gtctcaacct tgttttacga caaaaaaatg  4500
agaacgacga atccgaaaga gactaagatt gtgattgaca ctaccggcag taccaaacct  4560
aagcaggacg atctcattct cacttgtttc agagggtggg tgaagcagtt gcaaatagat  4620
tacaaaggca acgaaataat gacggcagct gcctctcaag ggctgacccg taaaggtgtg  4680
tatgccgttc ggtacaaggt gaatgaaaat cctctgtacg cacccacctc agaacatgtg  4740
aacgtcctac tgacccgcac ggaggaccgc atcgtgtgga aaacactagc cggcgaccca  4800
tggataaaaa cactgactgc caagtaccct gggaatttca ctgccacgat agaggagtgg  4860
caagcagagc atgatgccat catgaggcac atcttggaga gaccggaccc taccgacgtc  4920
ttccagaata aggcaaacgt gtgttgggcc aaggctttag tgccggtgct gaagaccgct  4980
ggcatagaca tgaccactga acaatggaac actgtggatt attttgaaac ggacaaagct  5040
cactcagcag agatagtatt gaaccaacta tgcgtgaggt tctttggact cgatctggac  5100
tccggtctat tttctgcacc cactgttccg ttatccatta ggaataatca ctgggataac  5160
tccccgtcgc ctaacatgta cggcctgaat aaagaagtgg tccgtcagct ctctcgcagg  5220
tacccacaac tgcctcgggc agttgccact ggaagagtct atgacatgaa cactggtaca  5280
ctgcgcaatt atgatccgcg cataaaccta gtacctgtaa acagaagact gcctcatgct  5340
ttagtcctcc accataatga acacccacag agtgactttt cttcattcgt cagcaaattg  5400
aagggcagaa ctgtcctggt ggtcggggaa aagttgtccg tcccaggcaa aatggttgac  5460
tggttgtcag accggcctga ggctaccttc agagctcggc tggatttagg catcccaggt  5520
gatgtgccca aatatgacat aatatttgtt aatgtgagga ccccatataa ataccatcac  5580
tatcagcagt gtgaagacca tgccattaag cttagcatgt tgaccaagaa agcttgtctg  5640
catctgaatc ccggcggaac ctgtgtcagc ataggttatg gttacgctga cagggccagc  5700
gaaagcatca ttggtgctat agcgcggcag ttcaagtttt cccgggtatg caaaccgaaa  5760
tcctcacttg aagagacgga agttctgttt gtattcattg ggtacgatcg caaggcccgt  5820
acgcacaatc cttacaagct ttcatcaacc ttgaccaaca tttatacagg ttccagactc  5880
cacgaagccg gatgtgcacc ctcatatcat gtggtgcgag gggatattgc cacggccacc  5940
gaaggagtga ttataaatgc tgctaacagc aaaggacaac ctggcggagg ggtgtgcgga  6000
gcgctgtata agaaattccc ggaaagcttc gatttacagc cgatcgaagt aggaaaagcg  6060
cgactggtca aaggtgcagc taaacatatc attcatgccg taggaccaaa cttcaacaaa  6120
gtttcggagg ttgaaggtga caaacagttg gcagaggctt atgagtccat cgctaagatt  6180
gtcaacgata acaattacaa gtcagtagcg attccactgt tgtccaccgg catcttttcc  6240
gggaacaaag atcgactaac ccaatcattg aaccatttgc tgacagcttt agacaccact  6300
gatgcagatg tagccatata ctgcagggac aagaaatggg aaatgactct caaggaagca  6360
gtggctagga gagaagcagt ggaggagata tgcatatccg acgactcttc agtgacagaa  6420
cctgatgcag agctggtgag ggtgcatccg aagagttctt tggctggaag gaagggctac  6480
agcacaagcg atggcaaaac tttctcatat ttggaaggga ccaagtttca ccaggcggcc  6540
aaggatatag cagaaattaa tgccatgtgg cccgttgcaa cggaggccaa tgagcaggta  6600
tgcatgtata tcctcggaga aagcatgagc agtattaggt cgaaatgccc cgtcgaagag  6660
tcggaagcct ccacaccacc tagcacgctg ccttgcttgt gcatccatgc catgactcca  6720
gaaagagtac agcgcctaaa agcctcacgt ccagaacaaa ttactgtgtg ctcatccttt  6780
ccattgccga agtatagaat cactggtgtg cagaagatcc aatgctccca gcctatattg  6840
ttctcaccga aagtgcctgc gtatattcat ccaaggaagt atctcgtgga aacaccaccg  6900
gtagacgaga ctccggagcc atcggcagag aaccaatcca cagaggggac acctgaacaa  6960
ccaccactta taaccgagga tgagaccagg actagaacgc ctgagccgat catcatcgaa  7020
gaggaagaag aggatagcat aagtttgctg tcagatggcc cgacccacca ggtgctgcaa  7080
gtcgaggcag acattcacgg gccgccctct gtatctagct catcctggtc cattcctcat  7140
gcatccgact ttgatgtgga cagtttatcc atacttgaca ccctggaggg agctagcgtg  7200
accagcgggg caacgtcagc cgagactaac tcttacttcg caaagagtat ggagtttctg  7260
gcgcgaccgg tgcctgcgcc tcgaacagta ttcaggaacc ctccacatcc cgctccgcgc  7320
acaagaacac cgtcacttgc acccagcagg gcctgctcga gaaccagcct agtttccacc  7380
ccgccaggcg tgaatagggt gatcactaga gaggagctcg aggcgcttac cccgtcacgc  7440
actcctagca ggtcggtctc gagaaccagc ctggtctcca acccgccagg cgtaaatagg  7500
gtgattacaa gagaggagtt tgaggcgttc gtagcacaac aacaatgacg gtttgatgcg  7560
ggtgcataca tcttttcctc cgacaccggt caagggcatt tacaacaaaa atcagtaagg  7620
caaacggtgc tatccgaagt ggtgttggag aggaccgaat tggagatttc gtatgccccg  7680
cgcctcgacc aagaaaaaga agaattacta cgcaagaaat tacagttaaa tcccacacct  7740
gctaacagaa gcagatacca gtccaggaag gtggagaaca tgaaagccat aacagctaga  7800
cgtattctgc aaggcctagg gcattatttg aaggcagaag gaaaagtgga gtgctaccga  7860
```

```
accctgcatc ctgttccttt gtattcatct agtgtgaacc gtgccttttc aagccccaag  7920
gtcgcagtgg aagcctgtaa cgccatgttg aaagagaact ttccgactgt ggcttcttac  7980
tgtattattc cagagtacga tgcctatttg gacatggttg acggagcttc atgctgctta  8040
gacactgcca gtttttgccc tgcaaagctg cgcagctttc caaagaaaca ctcctatttg  8100
gaacccacaa tacgatcggc agtgccttca gcgatccaga acacgctcca gaacgtcctg  8160
gcagctgcca caaaaagaaa ttgcaatgtc acgcaaatga gagaattgcc cgtattggat  8220
tcggcggcct ttaatgtgga atgcttcaag aaatatgcgt gtaataatga atattgggaa  8280
acgtttaaag aaaaccccat caggcttact gaagaaaacg tggtaaatta cattaccaaa  8340
ttaaaaggac caaaagctgc tgctcttttt gcgaagacac ataatttgaa tatgttgcag  8400
gacataccaa tggacaggtt tgtaatggac ttaaagagag acgtgaaagt gactccagga  8460
acaaaacata ctgaagaacg gcccaaggta caggtgatcc aggctgccga tccgctagca  8520
acagcgtatc tgtgcggaat ccaccgagag ctggttagga gattaaatgc ggtcctgctt  8580
ccgaacattc atacactgtt tgatatgtcg gctgaagact ttgacgctat tatagccgag  8640
cacttccagc ctggggattg tgttctggaa actgacatcg cgtcgtttga taaaagtgag  8700
gacgacgcca tggctctgac cgcgttaatg attctggaag acttaggtgt ggacgcagag  8760
ctgttgacgc tgattgaggc ggctttcggc gaaatttcat caatacattt gcccactaaa  8820
actaaattta aattcggagc catgatgaaa tctggaatgt tcctcacact gtttgtgaac  8880
acagtcatta acattgtaat cgcaagcaga gtgttgagag aacggctaac cggatcacca  8940
tgtgcagcat tcattggaga tgacaatatc gtgaaaggag tcaaatcgga caaattaatg  9000
gcagacaggt gcgccacctg gttgaatatg gaagtcaaga ttatagatgc tgtggtgggc  9060
gagaaagcgc cttatttctg tggagggttt attttgtgtg actccgtgac cggcacagcg  9120
tgccgtgtgg cagacccccct aaaaaggctg tttaagcttg gcaaacctct ggcagcagac  9180
gatgaacatg atgatgacag gagaagggca ttgcatgaag agtcaacacg ctggaaccga  9240
gtgggtattc tttcagagct gtgcaaggca gtagaatcaa ggtatgaaac cgtaggaact  9300
tccatcatag ttatggccat gactactcta gctagcagtg ttaaatcatt cagctacctg  9360
agaggggccc ctataactct ctacggctaa cctgaatgga ctacgacata gtctagtccg  9420
ccaagttcga aggcgcgcct ctagagccac catggtgagc aagggcgagg agctgttcac  9480
cggggtggtg cccatcctgg tcgagctgga cggcgacgta aacggccaca agttcagcgt  9540
gtccggcgag ggcgagggcg atgccaccta cggcaagctg accctgaagt tcatctgcac  9600
caccggcaag ctgcccgtgc cctggcccac cctcgtgacc accctgacct acggcgtgca  9660
gtgcttcagc cgctaccccg accacatgaa gcagcacgac ttcttcaagt ccgccatgcc  9720
cgaaggctac gtccaggagc gcaccatctt cttcaaggac gacggcaact acaagacccg  9780
cgccgaggtg aagttcgagg gcgacaccct ggtgaaccgc atcgagctga agggcatcga  9840
cttcaaggag gacggcaaca tcctggggca caagctggag tacaactaca acagccacaa  9900
cgtctatatc atggccgaca agcagaagaa cggcatcaag gtgaacttca agatccgcca  9960
caacatcgag gacggcagcg tgcagctcgc cgaccactac cagcagaaca cccccatcgg  10020
cgacggcccc gtgctgctgc ccgacaacca ctacctgagc acccagtccg ccctgagcaa  10080
agaccccaac gagaagcgcg atcacatggt cctgctggag ttcgtgaccg ccgccgggat  10140
cactctcggc atggacgagc tgtacaagta gcatcgatga tatcgcggcc gcatacagca  10200
gcaattggca agctgcttac atagaactcg cggcgattgg catgccgcct taaaattttt  10260
attttatttt tcttttcttt tccgaatcgg attttgtttt taatatttca aaaaaaaaaa  10320
aaaaa                                                              10325

SEQ ID NO: 36           moltype = RNA  length = 10325
FEATURE                 Location/Qualifiers
source                  1..10325
                        mol_type = other RNA
                        organism = synthetic construct
SEQUENCE: 36
aaaaaaaaaa cgcgtgataa cgcaggaaag aacatgtgag caaaaggcca gcaaaaggcc  60
aggaaccgta aaaaggccgc gttgctggcg tttttccata ggctccgccc ccctgacgag  120
catcacaaaa atcgacgctc aagtcagagg tggcgaaacc cgacaggact ataaagatac  180
caggcgtttc cccctggaag ctccctcgtg cgctctcctg ttccgaccct gccgcttacc  240
ggatacctgt ccgcctttct cccttcggga agcgtggcgc tttctcatag ctcacgctgt  300
aggtatctca gttcggtgta ggtcgttcgc tccaagctgg gctgtgtgca cgaacccccc  360
gttcagcccg accgctgcgc cttatccggt aactatcgtc ttgagtccaa cccggtaaga  420
cacgacttat cgccactggc agcagccact ggtaacagga ttagcagagc gaggtatgta  480
ggcggtgcta cagagttctt gaagtggtgg cctaactacg gctacactag aagaacagta  540
tttggtatct gcgctctgct gaagccagtt accttcggaa aaagagttgg tagctcttga  600
tccggcaaac aaaccaccgc tggtagcggt ttttttgttt gcaagcagca gattacgcgc  660
agaaaaaaag gatctcaaga agatcctttg atcttttcta cggggtctga cgctcagtgg  720
aacgaaaact cacgttaagg gattttggtc atgagattat caaaaaggat cttcacctag  780
atccttttaa attaaaaatg aagttttaaa tcaatctaaa gtatatatga gtaaacttgg  840
tctgacagtt accaatgctt aatcagtgag gcacctatct cagcgatctg tctatttcgt  900
tcatccatag ttgcctgact ccccgtcgtg tagataacta cgatacggga gggcttacca  960
tctggcccca gtgctgcaat gataccgcga gacccacgct caccggctcc agatttatca  1020
gcaataaacc agccagccgg aagggccgag cgcagaagtg gtcctgcaac tttatccgcc  1080
tccatccagt ctattaattg ttgccgggaa gctagagtaa gtagttcgcc agttaatagt  1140
ttgcgcaacg ttgttgccat tgctacaggc atcgtggtgt cacgctcgtc gtttggtatg  1200
gcttcattca gctccggttc ccaacgatca aggcgagtta catgatcccc catgttgtgc  1260
aaaaaagcgg ttagctcctt cggtcctccg atcgttgtca gaagtaagtt ggccgcagtg  1320
ttatcactca tggttatggc agcactgcat aattctctta ctgtcatgcc atccgtaaga  1380
tgcttttctg tgactggtga gtactcaacc aagtcattct gagaatagtg tatgcggcga  1440
ccgagttgct cttgcccggc gtcaatacgg gataataccg cgccacatag cagaacttta  1500
aaagtgctca tcattggaaa acgttcttcg gggcgaaaac tctcaaggat cttaccgctg  1560
ttgagatcca gttcgatgta acccactcgt gcacccaact gatcttcagc atcttttact  1620
ttcaccagcg tttctgggtg agcaaaaaca ggaaggcaaa atgccgcaaa aaagggaata  1680
agggcgacac ggaaatgttg aatactcata ctcttccttt ttcaatatta ttgaagcatt  1740
tatcagggtt attgtctcat gagcggatac atatttgaat gtatttagaa aaataaacaa  1800
```

```
atagggggttc cgcgcacatt tccccgaaaa gtgccacctg agctctaata cgactcacta  1860
taggataggc ggcgcatgag agaagcccag accaattacc tacccaaaat ggagaaagtt  1920
cacgttgaca tcgaggaaga cagcccattc ctcagagctt tgcagcggag cttcccgcag  1980
tttgaggtag aagccaagca ggtcactgat aatgaccatg ctaatgccag agcgttttcg  2040
catctggctt caaaactgat cgaaacggag gtggacccat ccgacacgat ccttgacatt  2100
ggaagtgcgc ccgcccgcag aatgtattct aagcacaagt atcattgtat ctgtccgatg  2160
agatgtgcgg aagatccgga cagattgtat aagtatgcaa ctaagctgaa gaaaaactgt  2220
aaggaaataa ctgataagga attggacaag aaaatgaagg agctggccgc cgtcatgagc  2280
gaccctgacc tggaaactga gactatgtgc ctccacgacg acgagtcgtg tcgctacgaa  2340
gggcaagtcg ctgtttacca ggatgtatac gcggttgacg gaccgacaag tctctatcac  2400
caagccaata agggagttag agtcgcctac tggataggct ttgacaccac cccttttatg  2460
tttaagaact tggctggagc atatccatca tactctacca actgggccga cgaaaccgtg  2520
ttaacggctc gtaacatagg cctatgcagc tctgacgtta tggagcggtc acgtagaggg  2580
atgtccattc ttagaaagaa gtatttgaaa ccatccaaca atgttctatt ctctgttggc  2640
tcgaccatct accacgagaa gagggactta ctgaggagct ggcacctgcc gtctgtattt  2700
cacttacgtg gcaagcaaaa ttacacatgt cggtgtgaga ctatagttag ttgcgacggg  2760
tacgtcgtta aaagaatagc tatcagtcca ggcctgtatg ggaagccttc aggctatgct  2820
gctacgatgc accgcgaggg attcttgtgc tgcaaagtga cagacacatt gaacggggag  2880
agggtctctt ttcccgtgtg cacgtatgtg ccagctacat tgtgtgacca aatgactggc  2940
atactggcaa cagatgtcag tgcggacgac gcgcaaaaac tgctggttgg gctcaaccag  3000
cgtatagtcg tcaacggtcg cacccagaga aacaccaata ccatgaaaaa ttacctttttg  3060
cccgtagtgg cccaggcatt tgctaggtgg gcaaaggaat ataaggaaga tcaagaagat  3120
gaaaggccac taggactacg agatagacag ttagtcatgg ggtgttgttg ggcttttaga  3180
aggcacaaga taacatctat ttataagcgc ccggataccc aaaccatcat caaagtgaac  3240
agcgatttcc actcattcgt gctgcccagg ataggcagta acacattgga gatcgggctg  3300
agaacaagaa tcaggaaaat gttagaggag cacaaggagc cgtcacctct cattaccgcc  3360
gaggacgtac aagaagctaa gtgcgcagcc gatgaggcta aggaggtgcg tgaagccgag  3420
gagttgcgcg cagctctacc acctttggca gctgatgttg aggagcccac tctggaagcc  3480
gatgtcgact tgatgttaca agaggctggg gccggctcag tggagacacc tcgtggcttg  3540
ataaaggtta ccagctacga tggcgaggac aagatcggct cttacgctgt gctttctccg  3600
caggctgtac tcaagagtga aaaattatct tgcatccacc ctctcgctga acaagtcata  3660
gtgataacac actctggccg aaaagggcgt tatgccgtgg aaccatacca tggtaaagta  3720
gtggtgccag agggacatgc aatacccgtc caggactttc aagctctgag tgaaagtgcc  3780
accattgtgt acaacgaacg tgagttcgta aacaggtacc tgcaccatat tgccacacat  3840
ggaggagcgc tgaacactga tgaagaatat tacaaaactg tcaagcccag cgagcacgac  3900
ggcgaatacc tgtacgacat cgacaggaaa cagtgcgtca agaaagaact agtcactggg  3960
ctagggctca caggcgagct ggtggatcct cccttccatg aattcgccta cgagagtctg  4020
agaacacgac cagccgctcc ttaccaagta ccaaccatag ggtgtatggg cgtgccagga  4080
tcaggcaagt ctggcatcat taaaagcgca gtcaccaaaa aagatctagt ggtgagcgcc  4140
aagaaagaaa actgtgcaga aattataagg gacgtcaaga aaatgaaagg gctggacgtc  4200
aatgccagaa ctgtggactc agtgctcttg aatggatgca aacaccccgt agagaccctg  4260
tatattgacg aagcttttgc ttgtcatgca ggtactctca gagcgctcat agccattata  4320
agacctaaaa aggcagtgct ctgcggggat cccaaacagt gcggtttttt taacatgatg  4380
tgcctgaaag tgcattttaa ccacgagatt tgcacacaag tcttccacaa aagcatctct  4440
cgccgttgca ctaaatctgt gacttcggtc gtctcaacct tgttttacga caaaaaaatg  4500
agaacgacga atccgaaaga gactaagatt gtgattgaca ctaccggcag taccaaacct  4560
aagcaggacg atctcattct cacttgtttc agagggtggg tgaagcagtt gcaaatagat  4620
tacaaaggca acgaaataat gacggcagct gcctctcaag ggctgacccg taaaggtgtg  4680
tatgccgttc ggtacaaggt gaatgaaaat cctctgtacg cacccacctc agaacatgtg  4740
aacgtcctac tgacccgcac ggaggaccgc atcgtgtgga aaacactagc cggcgaccca  4800
tggataaaaa cactgactgc caagtaccct gggaatttca ctgccacgat agaggagtgg  4860
caagcagagc atgatgccat catgaggcac atcttggaga gaccggaccc taccgacgtc  4920
ttccagaata aggcaaacgt gtgttgggcc aaggctttag tgccggtgct gaagaccgct  4980
ggcatagaca tgaccactga acaatggaac actgtggatt attttgaaac ggacaaagct  5040
cactcagcag agatagtatt gaaccaacta tgcgtgaggt tctttggact cgatctggac  5100
tccggtctat tttctgcacc cactgttccg ttatccatta ggaataatca ctgggataac  5160
tccccgtcgc ctaacatgta cgggctgaat aaagaagtgg tccgtcagct ctctcgcagg  5220
tacccacaac tgcctcgggc agttgccact ggaagagtct atgacatgaa cactggtaca  5280
ctgcgcaatt atgatccgcg cataaaccta gtacctgtaa acagaagact gcctcatgct  5340
ttagtcctcc accataatga acacccacag agtgactttt cttcattcgt cagcaaattg  5400
aagggcagaa ctgtcctggt ggtcggggaa aagttgtccg tcccaggcaa aatggttgac  5460
tggttgtcag accggcctga ggctaccttc agagctcggc tggatttagg catcccaggt  5520
gatgtgccca aatatgacat aatatttgtt aatgtgagga ccccatataa ataccatcac  5580
tatcagcagt gtgaagacca tgccattaag cttagcatgt tgaccaagaa agcttgtctg  5640
catctgaatc ccggcggaac ctgtgtcagc ataggttatg gttacgctga cagggccagc  5700
gaaagcatca ttggtgctat agcgcggcag ttcaagtttt cccgggtatg caaaccgaaa  5760
tcctcacttg aagagacgga agttctgttt gtattcattg ggtacgatcg caaggcccgt  5820
acgcacaatt cttacaagct ttcatcaacc ttgaccaaca tttatacagg ttccagactc  5880
cacgaagccg gatgtgcacc ctcatatcat gtggtgcgag gggatattgc cacggccacc  5940
gaaggagtga ttataaatgc tgctaacagc aaaggacaac ctggcggagg ggtgtgcgga  6000
gcgctgtata agaaattccc ggaaagcttc gatttacagc cgatcgaagt aggaaaagcg  6060
cgactggtca aggtgcagc taaacatatc attcatgccg taggaccaaa cttcaacaaa  6120
gtttcggagg ttgaaggtga caaacagttg gcagaggctt atgagtccat cgctaagatt  6180
gtcaacgata acaattacaa gtcagtagcg attccactgt tgtccaccgg catcttttcc  6240
gggaacaaag atcgactaac ccaatcattg aaccatttgc tgacagcttt agacaccact  6300
gatgcagatg tagccatata ctgcagggac aagaaatggg aaatgactct caaggaagca  6360
gtggctagga gagaagcagt ggaggagata tgcatatccg acgactcttc agtgacagaa  6420
cctgatgcag agctggtgag ggtgcatccg aagagttctt tggctggaag gaagggctac  6480
agcacaagcg atggcaaaac tttctcatat ttggaaggga ccaagtttca ccaggcggcc  6540
```

-continued

```
aaggatatag cagaaattaa tgccatgtgg cccgttgcaa cggaggccaa tgagcaggta  6600
tgcatgtata tcctcggaga aagcatgagc agtattaggt cgaaatgccc cgtcgaagag  6660
tcggaagcct ccacaccacc tagcacgctg ccttgcttgt gcatccatgc catgactcca  6720
gaaagagtac agcgcctaaa agcctcacgt ccagaacaaa ttactgtgtg ctcatccttt  6780
ccattgccga agtatagaat cactggtgtg cagaagatcc aatgctccca gcctatattg  6840
ttctcaccga aagtgcctgc gtatattcat ccaaggaagt atctcgtgga aacaccaccg  6900
gtagacgaga ctccggagcc atcggcagag aaccaatcca cagaggggac acctgaacaa  6960
ccaccactta taaccgagga tgagaccagg actagaacgc ctgagccgat catcatcgaa  7020
gaggaagaag aggatagcat aagtttgctg tcagatggcc cgacccacca ggtgctgcaa  7080
gtcgaggcag acattcacgg gccgccctct gtatctagct catcctggtc cattcctcat  7140
gcatccgact ttgatgtgga cagtttatcc atacttgaca ccctggaggg agctagcgtg  7200
accagcgggg caacgtcagc cgagactaac tcttacttcg caaagagtat ggagtttctg  7260
gcgcgaccgg tgcctgcgcc tcgaacagta ttcaggaacc ctccacatcc cgctccgcgc  7320
acaagaacac cgtcacttgc acccagcagg gcctgctcga gaaccagcct agtttccacc  7380
ccgccaggcg tgaatagggt gatcactaga gaggagctcg aggcgcttac cccgtcacgc  7440
actcctagca ggtcggtctc gagaaccagc ctggtctcca acccgccagg cgtaaatagg  7500
gtgattacaa gagaggagtt tgaggcgttc gtagcacaac aacaatgacg gtttgatgcg  7560
ggtgcataca tcttttcctc cgacaccggt caagggcatt tacaacaaaa atcagtaagg  7620
caaacggtgc tatccgaagt ggtgttggag aggaccgaat tggagatttc gtatgccccg  7680
cgcctcgacc aagaaaaaga agaattacta cgcaagaaat tacagttaaa tcccacacct  7740
gctaacagaa gcagatacca gtccaggaag gtggagaaca tgaaagccat aacagctaga  7800
cgtattctgc aaggcctagg gcattatttg aaggcagaag gaaaagtgga gtgctaccga  7860
accctgcatc ctgttccttt gtattcatct agtgtgaacc gtgccttttc aagccccaag  7920
gtcgcagtgg aagcctgtaa cgccatgttg aaagagaact ttccgactgt ggcttcttac  7980
tgtattattc cagagtacga tgcctatttg gacatggttg acggagcttc atgctgctta  8040
gacactgcca gtttttgccc tgcaaagctg cgcagctttc caaagaaaca ctcctatttg  8100
gaacccacaa tacgatcggc agtgccttca gcgatccaga acacgctcca gaacgtcctg  8160
gcagctgcca caaaaagaaa ttgcaatgtc acgcaaatga gagaattgcc cgtattggat  8220
tcggcggcct ttaatgtgga atgcttcaag aaatatgcgt gtaataatga atattgggaa  8280
acgtttaaag aaaaccccat caggcttact gaagaaaacg tggtaaatta cattaccaaa  8340
ttaaaaggac caaaagctgc tgctcttttt gcgaagacac ataatttgaa tatgttgcag  8400
gacataccaa tggacaggtt tgtaatggac ttaaagagag acgtgaaagt gactccagga  8460
acaaaacata ctgaagaacg gcccaaggta caggtgatcc aggctgccga tccgctagca  8520
acagcgtatc tgtgcggaat ccaccgagag ctggttagga gattaaatgc ggtcctgctt  8580
ccgaacattc atacactgtt tgatatgtcg gctgaagact ttgacgctat tatagccgag  8640
cacttccagc ctggggattg tgttctggaa actgacatcg cgtcgtttga taaaagtgag  8700
gacgacgcca tggctctgac cgcgttaatg attctggaag acttaggtgt ggacgcagag  8760
ctgttgacgc tgattgaggc ggctttcggc gaaatttcat caatacattt gcccactaaa  8820
actaaattta aattcggagc catgatgaaa tctggaatgt tcctcacact gtttgtgaac  8880
acagtcatta acattgtaat cgcaagcaga gtgttgagag aacggctaac cggatcacca  8940
tgtgcagcat tcattggaga tgacaatatc gtgaaaggag tcaaatcgga caaattaatg  9000
gcagacaggt gcgccacctg gttgaatatg gaagtcaaga ttatagatgc tgtggtgggc  9060
gagaaagcgc cttatttctg tggagggttt attttgtgtg actccgtgac cggcacagcg  9120
tgccgtgtgg cagacccccct aaaaaggctg tttaagcttg gcaaacctct ggcagcagac  9180
gatgaacatg atgatgacag gagaagggca ttgcatgaag agtcaacacg ctggaaccga  9240
gtgggtattc tttcagagct gtgcaaggca gtagaatcaa ggtatgaaac cgtaggaact  9300
tccatcatag ttatggccat gactactcta gctagcagtg ttaaatcatt cagctacctg  9360
agaggggccc ctataactct ctacggctaa cctgaatgga ctacgacata gtctagtccg  9420
ccaagttcga aggcgcgcct ctagagccac catggtgagc aagggcgagg agctgttcac  9480
cggggtggtg cccatcctgg tcgagctgga cggcgacgta aacggccaca agttcagcgt  9540
gtccggcgag ggcgagggcg atgccaccta cggcaagctg accctgaagt tcatctgcac  9600
caccggcaag ctgcccgtgc cctggcccac cctcgtgacc accctgacct acggcgtgca  9660
gtgcttcagc cgctaccccg accacatgaa gcagcacgac ttcttcaagt ccgccatgcc  9720
cgaaggctac gtccaggagc gcaccatctt cttcaaggac gacggcaact acaagacccg  9780
cgccgaggtg aagttcgagg gcgacaccct ggtgaaccgc atcgagctga agggcatcga  9840
cttcaaggag gacggcaaca tcctggggca caagctggag tacaactaca acagccacaa  9900
cgtctatatc atggccgaca agcagaagaa cggcatcaag gtgaacttca agatccgcca  9960
caacatcgag gacggcagcg tgcagctcgc cgaccactac cagcagaaca cccccatcgg  10020
cgacggcccc gtgctgctgc ccgacaacca ctacctgagc acccagtccg ccctgagcaa  10080
agaccccaac gagaagcgcg atcacatggt cctgctggag ttcgtgaccg ccgccgggat  10140
cactctcggc atggacgagc tgtacaagta gcatcgatga tatcgcggcc gcatacagca  10200
gcaattggca agctgcttac atagaactcg cggcgattgg catgccgcct taaaattttt  10260
attttatttt tcttttcttt tccgaatcgg attttgtttt taatatttca aaaaaaaaaa  10320
aaaaa                                                               10325

SEQ ID NO: 37          moltype = RNA  length = 10325
FEATURE                Location/Qualifiers
source                 1..10325
                       mol_type = other RNA
                       organism = synthetic construct
SEQUENCE: 37
aaaaaaaaaa cgcgtgataa cgcaggaaag aacatgtgag caaaaggcca gcaaaaggcc  60
aggaaccgta aaaaggccgc gttgctggcg tttttccata ggctccgccc ccctgacgag  120
catcacaaaa atcgacgctc aagtcagagg tggcgaaacc cgacaggact ataaagatac  180
caggcgtttc cccctggaag ctccctcgtg cgctctcctg ttccgaccct gccgcttacc  240
ggatacctgt ccgcctttct cccttcggga agcgtggcgc tttctcatag ctcacgctgt  300
aggtatctca gttcggtgta ggtcgttcgc tccaagctgg gctgtgtgca cgaacccccc  360
gttcagcccg accgctgcgc cttatccggt aactatcgtc ttgagtccaa cccggtaaga  420
cacgacttat cgccactggc agcagccact ggtaacagga ttagcagagc gaggtatgta  480
```

-continued

```
ggcggtgcta cagagttctt gaagtggtgg cctaactacg gctacactag aagaacagta  540
tttggtatct gcgctctgct gaagccagtt accttcggaa aaagagttgg tagctcttga  600
tccggcaaac aaaccaccgc tggtagcggt ttttttgttt gcaagcagca gattacgcgc  660
agaaaaaaag gatctcaaga agatcctttg atcttttcta cggggtctga cgctcagtgg  720
aacgaaaact cacgttaagg gattttggtc atgagattat caaaaaggat cttcacctag  780
atccttttaa attaaaaatg aagttttaaa tcaatctaaa gtatatatga gtaaacttgg  840
tctgacagtt accaatgctt aatcagtgag gcacctatct cagcgatctg tctatttcgt  900
tcatccatag ttgcctgact ccccgtcgtg tagataacta cgatacggga gggcttacca  960
tctggcccca gtgctgcaat gataccgcga gacccacgct caccggctcc agatttatca  1020
gcaataaacc agccagccgg aagggccgag cgcagaagtg gtcctgcaac tttatccgcc  1080
tccatccagt ctattaattg ttgccgggaa gctagagtaa gtagttcgcc agttaatagt  1140
ttgcgcaacg ttgttgccat tgctacaggc atcgtggtgt cacgctcgtc gtttggtatg  1200
gcttcattca gctccggttc ccaacgatca aggcgagtta catgatcccc catgttgtgc  1260
aaaaaagcgg ttagctcctt cggtcctccg atcgttgtca gaagtaagtt ggccgcagtg  1320
ttatcactca tggttatggc agcactgcat aattctctta ctgtcatgcc atccgtaaga  1380
tgcttttctg tgactggtga gtactcaacc aagtcattct gagaatagtg tatgcggcga  1440
ccgagttgct cttgcccggc gtcaatacgg gataataccg cgccacatag cagaacttta  1500
aaagtgctca tcattggaaa acgttcttcg gggcgaaaac tctcaaggat cttaccgctg  1560
ttgagatcca gttcgatgta acccactcgt gcacccaact gatcttcagc atcttttact  1620
ttcaccagcg tttctgggtg agcaaaaaca ggaaggcaaa atgccgcaaa aaagggaata  1680
agggcgacac ggaaatgttg aatactcata ctcttccttt ttcaatatta ttgaagcatt  1740
tatcagggtt attgtctcat gagcggatac atatttgaat gtatttagaa aaataaacaa  1800
ataggggttc cgcgcacatt tccccgaaaa gtgccacctg agctctaata cgactcacta  1860
taggatagc ggcgcatgag agaagcccag accaattacc tacccaaaat ggagaaagtt  1920
cacgttgaca tcgaggaaga cagcccattc ctcagagctt tgcagcggag cttcccgcag  1980
tttgaggtag aagccaagca ggtcactgat aatgaccatg ctaatgccag agcgttttcg  2040
catctggctt caaaactgat cgaaacggag gtggacccat ccgacacgat ccttgacatt  2100
ggaagtgcgc ccgcccgcag aatgtattct aagcacaagt atcattgtat ctgtccgatg  2160
agatgtgcgg aagatccgga cagattgtat aagtatgcaa ctaagctgaa gaaaaactgt  2220
aaggaaataa ctgataagga attggacaag aaaatgaagg agctggccgc cgtcatgagc  2280
gaccctgacc tggaaactga gactatgtgc ctccacgacg acgagtcgtg tcgctacgaa  2340
gggcaagtcg ctgtttacca ggatgtatac gcggttgacg gaccgacaag tctctatcac  2400
caagccaata agggagttag agtcgcctac tggataggct ttgacaccac cccttttatg  2460
tttaagaact tggctggagc atatccatca tactctacca actgggccga cgaaaccgtg  2520
ttaacggctc gtaacatagg cctatgcagc tctgacgtta tggagcggtc acgtagaggg  2580
atgtccattc ttagaaagaa gtatttgaaa ccatccaaca atgttctatt ctctgttggc  2640
tcgaccatct accacgagaa gagggactta ctgaggagct ggcacctgcc gtctgtattt  2700
cacttacgtg gcaagcaaaa ttacacatgt cggtgtgaga ctatagttag ttgcgacggg  2760
tacgtcgtta aaagaatagc tatcagtcca ggcctgtatg ggaagccttc aggctatgct  2820
gctacgatgc accgcgaggg attcttgtgc tgcaaagtga cagacacatt gaacggggag  2880
agggtctctt ttcccgtgtg cacgtatgtg ccagctacat tgtgtgacca aatgactggc  2940
atactggcaa cagatgtcag tgcggacgac gcgcaaaaac tgctggttgg gctcaaccag  3000
cgtatagtcg tcaacggtcg cacccagaga aacaccaata ccatgaaaaa ttaccttttg  3060
cccgtagtgg cccaggcatt tgctaggtgg gcaaaggaat ataaggaaga tcaagaagat  3120
gaaaggccac taggactacg agatagacag ttagtcatgg ggtgttgttg ggcttttaga  3180
aggcacaaga taacatctat ttataagcgc ccggataccc aaaccatcat caaagtgaac  3240
agcgatttcc actcattcgt gctgcccagg ataggcagta acacattgga gatcgggctg  3300
agaacaagaa tcaggaaaat gttagaggag cacaaggagc cgtcacctct cattaccgcc  3360
gaggacgtac aagaagctaa gtgcgcagcc gatgaggcta aggaggtgcg tgaagccgag  3420
gagttgcgcg cagctctacc acctttggca gctgatgttg aggagcccac tctggaagcc  3480
gatgtcgact tgatgttaca agaggctggg gccggctcag tggagacacc tcgtggcttg  3540
ataaaggtta ccagctacga tggcgaggac aagatcggct cttacgctgt gctttctccg  3600
caggctgtac tcaagagtga aaaattatct tgcatccacc ctctcgctga acaagtcata  3660
gtgataacac actctggccg aaaagggcgt tatgccgtgg aaccatacca tggtaaagta  3720
gtggtgccag agggacatgc aatacccgtc caggactttc aagctctgag tgaaagtgcc  3780
accattgtgt acaacgaacg tgagttcgta aacaggtacc tgcaccatat tgccacacat  3840
ggaggagcgc tgaacactga tgaagaatat tacaaaactg tcaagcccag cgagcacgac  3900
ggcgaatacc tgtacgacat cgacaggaaa cagtgcgtca agaaagaact agtcactggg  3960
ctagggctca caggcgagct ggtggatcct cccttccatg aattcgccta cgagagtctg  4020
agaacacgac cagccgctcc ttaccaagta ccaaccatag ggggtgtatgg cgtgccagga  4080
tcaggcaagt ctggcatcat taaaagcgca gtcaccaaaa aagatctagt ggtgagcgcc  4140
aagaaagaaa actgtgcaga aattataagg gacgtcaaga aaatgaaagg gctggacgtc  4200
aatgccagaa ctgtggactc agtgctcttg aatggatgca aacacccccgt agagaccctg  4260
tatattgacg aagcttttgc ttgtcatgca ggtactctca gagcgctcat agccattata  4320
agacctaaaa aggcagtgct ctgcggggat cccaaacagt gcggtttttt taacatgatg  4380
tgcctgaaag tgcattttaa ccacgagatt tgcacacaag tcttccacaa aagcatctct  4440
cgccgttgca ctaaatctgt gacttcggtc gtctcaacct tgttttacga caaaaaaatg  4500
agaacgacga atccgaaaga gactaagatt gtgattgaca ctaccggcag taccaaacct  4560
aagcaggacg atctcattct cacttgtttc agagggtggg tgaagcagtt gcaaatagat  4620
tacaaaggca acgaaataat gacggcagct gcctctcaag ggctgacccg taaaggtgtg  4680
tatgccgttc ggtacaaggt gaatgaaaat cctctgtacg cacccacctc agaacatgtg  4740
aacgtcctac tgacccgcac ggaggaccgc atcgtgtgga aaacactagc cggcgaccca  4800
tggataaaaa cactgactgc caagtaccct gggaatttca ctgccacgat agaggagtgg  4860
caagcagagc atgatgccat catgaggcac atcttggaga gaccggaccc taccgacgtc  4920
ttccagaata aggcaaacgt gtgttgggcc aaggctttag tgccggtgct gaagaccgct  4980
ggcatagaca tgaccactga acaatggaac actgtggatt attttgaaac ggacaaagct  5040
cactcagcag agatagtatt gaaccaacta tgcgtgaggt tctttggact cgatctggac  5100
tccggtctat tttctgcacc cactgttccg ttatccatta ggaataatca ctgggataac  5160
tccccgtcgc ctaacatgta cgggctgaat aaagaagtgg tccgtcagct ctctcgcagg  5220
```

-continued

```
tacccacaac tgcctcgggc agttgccact ggaagagtct atgacatgaa cactggtaca  5280
ctgcgcaatt atgatccgcg cataaaccta gtacctgtaa acagaagact gcctcatgct  5340
ttagtcctcc accataatga acacccacag agtgactttt cttcattcgt cagcaaattg  5400
aagggcagaa ctgtcctggt ggtcggggaa aagttgtccg tcccaggcaa aatggttgac  5460
tggttgtcag accggcctga ggctaccttc agagctcggc tggatttagg catcccaggt  5520
gatgtgccca aatatgacat aatatttgtt aatgtgagga ccccatataa ataccatcac  5580
tatcagcagt gtgaagacca tgccattaag cttagcatgt tgaccaagaa agcttgtctg  5640
catctgaatc ccggcggaac ctgtgtcagc ataggttatg gttacgctga cagggccagc  5700
gaaagcatca ttggtgctat agcgcggctg ttcaagtttt cccgggtatg caaaccgaaa  5760
tcctcacttg aagagacgga agttctgttt gtattcattg ggtacgatcg caaggcccgt  5820
acgcacaatc cttacaagct ttcatcaacc ttgaccaaca tttatacagg ttccagactc  5880
cacgaagccg gatgtgcacc ctcatatcat gtggtgcgag gggatattgc cacggccacc  5940
gaaggagtga ttataaatgc tgctaacagc aaaggacaac ctggcggagg ggtgtgcgga  6000
gcgctgtata agaaattccc ggaaagcttc gatttacagc cgatcgaagt aggaaaagcg  6060
cgactggtca aaggtgcagc taaacatatc attcatgccg taggaccaaa cttcaacaaa  6120
gtttcggagg ttgaaggtga caaacagttg gcagaggctt atgagtccat cgctaagatt  6180
gtcaacgata acaattacaa gtcagtagcg attccactgt tgtccaccgg catcttttcc  6240
gggaacaaag atcgactaac ccaatcattg aaccatttgc tgacagcttt agacaccact  6300
gatgcagatg tagccatata ctgcagggac aagaaatggg aaatgactct caaggaagca  6360
gtggctagga gagaagcagt ggaggagata tgcatatccg acgactcttc agtgacagaa  6420
cctgatgcag agctggtgag ggtgcatccg aagagttctt tggctggaag gaagggctac  6480
agcacaagcg atggcaaaac tttctcatat ttggaaggga ccaagtttca ccaggcggcc  6540
aaggatatag cagaaattaa tgccatgtgg cccgttgcaa cggaggccaa tgagcaggta  6600
tgcatgtata tcctcggaga aagcatgagc agtattaggt cgaaatgccc cgtcgaagag  6660
tcggaagcct ccacaccacc tagcacgctg ccttgcttgt gcatccatgc catgactcca  6720
gaaagagtac agcgcctaaa agcctcacgt ccagaacaaa ttactgtgtg ctcatccttt  6780
ccattgccga agtatagaat cactggtgtg cagaagatcc aatgctccca gcctatattg  6840
ttctcaccga aagtgcctgc gtatattcat ccaaggaagt atctcgtgga aacaccaccg  6900
gtagacgaga ctccggagcc atcggcagag aaccaatcca cagaggggac acctgaacaa  6960
ccaccactta taaccgagga tgagaccagg actagaacgc ctgagccgat catcatcgaa  7020
gaggaagaag aggatagcat aagtttgctg tcagatggcc cgacccacca ggtgctgcaa  7080
gtcgaggcag acattcacgg gccgccctct gtatctagct catcctggtc cattcctcat  7140
gcatccgact ttgatgtgga cagtttatcc atacttgaca ccctggaggg agctagcgtg  7200
accagcgggg caacgtcagc cgagactaac tcttacttcg caaagagtat ggagtttctg  7260
gcgcgaccgg tgcctgcgcc tcgaacagta ttcaggaacc ctccacatcc cgctccgcgc  7320
acaagaacac cgtcacttgc acccagcagg gcctgctcga gaaccagcct agtttccacc  7380
ccgccaggcg tgaatagggt gatcactaga gaggagctcg aggcgcttac cccgtcacgc  7440
actcctagca ggtcggtctc gagaaccagc ctggtctcca acccgccagg cgtaaatagg  7500
gtgattacaa gagaggagtt tgaggcgttc gtagcacaac aacaatgacg gtttgatgcg  7560
ggtgcataca tcttttcctc cgacaccggt caagggcatt tacaacaaaa atcagtaagg  7620
caaacggtgc tatccgaagt ggtgttggag aggaccgaat tggagatttc gtatgccccg  7680
cgcctcgacc aagaaaaaga agaattacta cgcaagaaat tacagttaaa tcccacacct  7740
gctaacagaa gcagatacca gtccaggaag gtggagaaca tgaaagccat aacagctaga  7800
cgtattctgc aaggcctagg gcattatttg aaggcagaag gaaaagtgga gtgctaccga  7860
accctgcatc ctgttccttt gtattcatct agtgtgaacc gtgccttttc aagccccaag  7920
gtcgcagtgg aagcctgtaa cgccatgttg aaagagaact ttccgactgt ggcttcttac  7980
tgtattattc cagagtacga tgcctatttg gacatggttg acggagcttc atgctgctta  8040
gacactgcca gtttttgccc tgcaaagctg cgcagctttc caaagaaaca ctcctatttg  8100
gaacccacaa tacgatcggc agtgccttca gcgatccaga acacgctcca gaacgtcctg  8160
gcagctgcca caaaaagaaa ttgcaatgtc acgcaaatga gagaattgcc cgtattggat  8220
tcggcggcct ttaatgtgga atgcttcaag aaatatgcgt gtaataatga atattgggaa  8280
acgtttaaag aaaaccccat caggcttact gaagaaaacg tggtaaatta cattaccaaa  8340
ttaaaaggac caaaagctgc tgctcttttt gcgaagacac ataatttgaa tatgttgcag  8400
gacataccaa tggacaggtt tgtaatggac ttaaagagag acgtgaaagt gactccagga  8460
acaaaacata ctgaagaacg gcccaaggta caggtgatcc aggctgccga tccgctagca  8520
acagcgtatc tgtgcggaat ccaccgagag ctggttagga gattaaatgc ggtcctgctt  8580
ccgaacattc atacactgtt tgatatgtcg gctgaagact ttgacgctat tatagccgag  8640
cacttccagc ctggggattg tgttctggaa actgacatcg cgtcgtttga taaaagtgag  8700
gacgacgcca tggctctgac cgcgttaatg attctggaag acttaggtgt ggacgcagag  8760
ctgttgacgc tgattgaggc ggctttcggc gaaatttcat caatacattt gcccactaaa  8820
actaaattta aattcggagc catgatgaaa tctggaatgt tcctcacact gtttgtgaac  8880
acagtcatta acattgtaat cgcaagcaga gtgttgagag aacggctaac cggatcacca  8940
tgtgcagcat tcattggaga tgacaatatc gtgaaaggag tcaaatcgga caaattaatg  9000
gcagacaggt gcgccacctg gttgaatatg gaagtcaaga ttatagatgc tgtggtgggc  9060
gagaaagcgc cttatttctg tggagggttt attttgtgtg actccgtgac cggcacagcg  9120
tgccgtgtgg cagacccccct aaaaaggctg tttaagcttg gcaaacctct ggcagcagac  9180
gatgaacatg atgatgacag gagaagggca ttgcatgaag agtcaacacg ctggaaccga  9240
gtgggtattc tttcagagct gtgcaaggca gtagaatcaa ggtatgaaac cgtaggaact  9300
tccatcatag ttatggccat gactactcta gctagcagtg ttaaatcatt cagctacctg  9360
agaggggccc ctataactct ctacggctaa cctgaatgga ctacgacata gtctagtccg  9420
ccaagttcga aggcgcgcct ctagagccac catggtgagc aagggcgagg agctgttcac  9480
cggggtggtg cccatcctgg tcgagctgga cggcgacgta aacggccaca agttcagcgt  9540
gtccggcgag ggcgagggcg atgccaccta cggcaagctg accctgaagt tcatctgcac  9600
caccggcaag ctgcccgtgc cctggcccac cctcgtgacc accctgacct acggcgtgca  9660
gtgcttcagc cgctaccccg accacatgaa gcagcacgac ttcttcaagt ccgccatgcc  9720
cgaaggctac gtccaggagc gcaccatctt cttcaaggac gacggcaact acaagacccg  9780
cgccgaggtg aagttcgagg gcgacaccct ggtgaaccgc atcgagctga agggcatcga  9840
cttcaaggag gacggcaaca tcctggggca caagctggag tacaactaca acagccacaa  9900
cgtctatatc atggccgaca agcagaagaa cggcatcaag gtgaacttca agatccgcca  9960
```

-continued

```
caacatcgag gacggcagcg tgcagctcgc cgaccactac cagcagaaca cccccatcgg  10020
cgacggcccc gtgctgctgc ccgacaacca ctacctgagc acccagtccg ccctgagcaa  10080
agaccccaac gagaagcgcg atcacatggt cctgctggag ttcgtgaccg ccgccgggat  10140
cactctcggc atggacgagc tgtacaagta gcatcgatga tatcgcggcc gcatacagca  10200
gcaattggca agctgcttac atagaactcg cggcgattgg catgccgcct taaaattttt  10260
attttatttt tcttttcttt tccgaatcgg attttgtttt taatatttca aaaaaaaaaa  10320
aaaaa                                                              10325

SEQ ID NO: 38          moltype = RNA  length = 10325
FEATURE                Location/Qualifiers
source                 1..10325
                       mol_type = other RNA
                       organism = synthetic construct
SEQUENCE: 38
aaaaaaaaaa cgcgtgataa cgcaggaaag aacatgtgag caaaaggcca gcaaaaggcc  60
aggaaccgta aaaaggccgc gttgctggcg tttttccata ggctccgccc ccctgacgag  120
catcacaaaa atcgacgctc aagtcagagg tggcgaaacc cgacaggact ataaagatac  180
caggcgtttc cccctggaag ctccctcgtg cgctctcctg ttccgaccct gccgcttacc  240
ggatacctgt ccgcctttct cccttcggga agcgtggcgc tttctcatag ctcacgctgt  300
aggtatctca gttcggtgta ggtcgttcgc tccaagctgg gctgtgtgca cgaacccccc  360
gttcagcccg accgctgcgc cttatccggt aactatcgtc ttgagtccaa cccggtaaga  420
cacgacttat cgccactggc agcagccact ggtaacagga ttagcagagc gaggtatgta  480
ggcggtgcta cagagttctt gaagtggtgg cctaactacg gctacactag aagaacagta  540
tttggtatct gcgctctgct gaagccagtt accttcggaa aaagagttgg tagctcttga  600
tccggcaaac aaaccaccgc tggtagcggt ttttttgttt gcaagcagca gattacgcgc  660
agaaaaaaag gatctcaaga agatcctttg atcttttcta cggggtctga cgctcagtgg  720
aacgaaaact cacgttaagg gattttggtc atgagattat caaaaaggat cttcacctag  780
atccttttaa attaaaaatg aagttttaaa tcaatctaaa gtatatatga gtaaacttgg  840
tctgacagtt accaatgctt aatcagtgag gcacctatct cagcgatctg tctatttcgt  900
tcatccatag ttgcctgact ccccgtcgtg tagataacta cgatacggga gggcttacca  960
tctggcccca gtgctgcaat gataccgcga gacccacgct caccggctcc agatttatca  1020
gcaataaacc agccagccgg aagggccgag cgcagaagtg gtcctgcaac tttatccgcc  1080
tccatccagt ctattaattg ttgccgggaa gctagagtaa gtagttcgcc agttaatagt  1140
ttgcgcaacg ttgttgccat tgctacaggc atcgtggtgt cacgctcgtc gtttggtatg  1200
gcttcattca gctccggttc ccaacgatca aggcgagtta catgatcccc catgttgtgc  1260
aaaaaagcgg ttagctcctt cggtcctccg atcgttgtca gaagtaagtt ggccgcagtg  1320
ttatcactca tggttatggc agcactgcat aattctctta ctgtcatgcc atccgtaaga  1380
tgcttttctg tgactggtga gtactcaacc aagtcattct gagaatagtg tatgcggcga  1440
ccgagttgct cttgcccggc gtcaatacgg gataataccg cgccacatag cagaacttta  1500
aaagtgctca tcattggaaa acgttcttcg gggcgaaaac tctcaaggat cttaccgctg  1560
ttgagatcca gttcgatgta acccactcgt gcacccaact gatcttcagc atcttttact  1620
ttcaccagcg tttctgggtg agcaaaaaca ggaaggcaaa atgccgcaaa aaagggaata  1680
agggcgacac ggaaatgttg aatactcata ctcttccttt ttcaatatta ttgaagcatt  1740
tatcagggtt attgtctcat gagcggatac atatttgaat gtatttagaa aaataaacaa  1800
ataggggttc cgcgcacatt tccccgaaaa gtgccacctg agctctaata cgactcacta  1860
taggataggc ggcgcatgag agaagcccag accaattacc tacccaaaat ggagaaagtt  1920
cacgttgaca tcgaggaaga cagcccattc ctcagagctt tgcagcggag cttcccgcag  1980
tttgaggtag aagccaagca ggtcactgat aatgaccatg ctaatgccag agcgttttcg  2040
catctggctt caaaactgat cgaaacggag gtggacccat ccgacacgat ccttgacatt  2100
ggaagtgcgc ccgcccgcag aatgtattct aagcacaagt atcattgtat ctgtccgatg  2160
agatgtgcgg aagatccgga cagattgtat aagtatgcaa ctaagctgaa gaaaaactgt  2220
aaggaaataa ctgataagga attggacaag aaaatgaagg agctggccgc cgtcatgagc  2280
gaccctgacc tggaaactga gactatgtgc ctccacgacg acgagtcgtg tcgctacgaa  2340
gggcaagtcg ctgtttacca ggatgtatac gcggttgacg gaccgacaag tctctatcac  2400
caagccaata agggagttag agtcgcctac tggataggct ttgacaccac cccttttatg  2460
tttaagaact tggctggagc atatccatca tactctacca actgggccga cgaaaccgtg  2520
ttaacggctc gtaacatagg cctatgcagc tctgacgtta tggagcggtc acgtagaggg  2580
atgtccattc ttagaaagaa gtatttgaaa ccatccaaca atgttctatt ctctgttggc  2640
tcgaccatct accacgagaa gagggactta ctgaggagct ggcacctgcc gtctgtattt  2700
cacttacgtg gcaagcaaaa ttacacatgt cggtgtgaga ctatagttag ttgcgacggg  2760
tacgtcgtta aaagaatagc tatcagtcca ggcctgtatg ggaagccttc aggctatgct  2820
gctacgatgc accgcgaggg attcttgtgc tgcaaagtga cagacacatt gaacggggag  2880
agggtctctt ttcccgtgtg cacgtatgtg ccagctacat tgtgtgacca aatgactggc  2940
atactggcaa cagatgtcag tgcggacgac gcgcaaaaac tgctggttgg gctcaaccag  3000
cgtatagtcg tcaacggtcg cacccagaga aacaccaata ccatgaaaaa ttacctttttg  3060
cccgtagtgg cccaggcatt tgctaggtgg gcaaaggaat ataaggaaga tcaagaagat  3120
gaaaggccac taggactacg agatagacag ttagtcatgg ggtgttgttg ggcttttaga  3180
aggcacaaga taacatctat ttataagcgc ccggataccc aaaccatcat caaagtgaac  3240
agcgatttcc actcattcgt gctgcccagg ataggcagta acacattgga gatcgggctg  3300
agaacaagaa tcaggaaaat gttagaggag cacaaggagc cgtcacctct cattaccgcc  3360
gaggacgtac aagaagctaa gtgcgcagcc gatgaggcta aggaggtgcg tgaagccgag  3420
gagttgcgcg cagctctacc acctttggca gctgatgttg aggagcccac tctggaagcc  3480
gatgtcgact tgatgttaca agaggctggg gccggctcag tggagacacc tcgtggcttg  3540
ataaaggtta ccagctacga tggcgaggac aagatcggct cttacgctgt gctttctccg  3600
caggctgtac tcaagagtga aaaattatct tgcatccacc ctctcgctga acaagtcata  3660
gtgataacac actctggccg aaaagggcgt tatgccgtgg aaccatacca tggtaaagta  3720
gtggtgccag agggacatgc aatacccgtc caggactttc aagctctgag tgaaagtgcc  3780
accattgtgt acaacgaacg tgagttcgta aacaggtacc tgcaccatat tgccacacat  3840
ggaggagcgc tgaacactga tgaagaatat tacaaaactg tcaagcccag cgagcacgac  3900
```

-continued

```
ggcgaatacc tgtacgacat cgacaggaaa cagtgcgtca agaaagaact agtcactggg  3960
ctagggctca caggcgagct ggtggatcct cccttccatg aattcgccta cgagagtctg  4020
agaacacgac cagccgctcc ttaccaagta ccaaccatag gggtgtatgg cgtgccagga  4080
tcaggcaagt ctggcatcat taaaagcgca gtcaccaaaa aagatctagt ggtgagcgcc  4140
aagaaagaaa actgtgcaga aattataagg gacgtcaaga aaatgaaagg gctggacgtc  4200
aatgccagaa ctgtggactc agtgctcttg aatggatgca aacaccccgt agagaccctg  4260
tatattgacg aagcttttgc ttgtcatgca ggtactctca gagcgctcat agccattata  4320
agacctaaaa aggcagtgct ctgcggggat cccaaacagt gcggtttttt taacatgatg  4380
tgcctgaaag tgcattttaa ccacgagatt tgcacacaag tcttccacaa aagcatctct  4440
cgccgttgca ctaaatctgt gacttcggtc gtctcaacct tgttttacga caaaaaaatg  4500
agaacgacga atccgaaaga gactaagatt gtgattgaca ctaccggcag taccaaacct  4560
aagcaggacg atctcattct cacttgtttc agagggtggg tgaagcagtt gcaaatagat  4620
tacaaaggca acgaaataat gacggcagct gcctctcaag ggctgacccg taaaggtgtg  4680
tatgccgttc ggtacaaggt gaatgaaaat cctctgtacg cacccacctc agaacatgtg  4740
aacgtcctac tgacccgcac ggaggaccgc atcgtgtgga aaacactagc cggcgaccca  4800
tggataaaaa cactgactgc caagtaccct gggaatttca ctgccacgat agaggagtgg  4860
caagcagagc atgatgccat catgaggcac atcttggaga gaccggaccc taccgacgtc  4920
ttccagaata aggcaaacgt gtgttgggcc aaggctttag tgccggtgct gaagaccgct  4980
ggcatagaca tgaccactga acaatggaac actgtggatt attttgaaac ggacaaagct  5040
cactcagcag agatagtatt gaaccaacta tgcgtgaggt tctttggact cgatctggac  5100
tccggtctat tttctgcacc cactgttccg ttatccatta ggaataatca ctgggataac  5160
tccccgtcgc ctaacatgta cgggctgaat aaagaagtgg tccgtcagct ctctcgcagg  5220
tacccacaac tgcctcgggc agttgccact ggaagagtct atgacatgaa cactggtaca  5280
ctgcgcaatt atgatccgcg cataaaccta gtacctgtaa acagaagact gcctcatgct  5340
ttagtcctcc accataatga acacccacag agtgactttt cttcattcgt cagcaaattg  5400
aagggcagaa ctgtcctggt ggtcggggaa aagttgtccg tcccaggcaa aatggttgac  5460
tggttgtcag accggcctga ggctaccttc agagctcggc tggatttagg catcccaggt  5520
gatgtgccca aatatgacat aatatttgtt aatgtgagga ccccatataa ataccatcac  5580
tatcagcagt gtgaagacca tgccattaag cttagcatgt tgaccaagaa agcttgtctg  5640
catctgaatc ccggcggaac ctgtgtcagc ataggttatg gttacgctga cagggccagc  5700
gaaagcatca ttggtgctat agcgcggcag ttcaagtttt cccgggtatg caaaccgaaa  5760
tcctcacttg aagagacgga agttctgttt gtattcattg ggtacgatcg caaggcccgt  5820
acgcacaatt cttacaagct ttcatcaacc ttgaccaaca tttatacagg ttccagactc  5880
cacgaagccg gatgtgcacc ctcatatcat gtggtgcgag gggatattgc cacggccacc  5940
gaaggagtga ttataaatgc tgctaacagc aaaggacaac ctggcggagg ggtgtgcgga  6000
gcgctgtata agaaattccc ggaaagcttc gatttacagc cgatcgaagt aggaaaagcg  6060
cgactggtca aggtgcagc taaacatatc attcatgccg taggaccaaa cttcaacaaa  6120
gtttcggagg ttgaaggtga caaacagttg gcagaggctt atgagtccat cgctaagatt  6180
gtcaacgata acaattacaa gtcagtagcg attccactgt tgtccaccgg catcttttcc  6240
gggaacaaag atcgactaac ccaatcattg aaccatttgc tgacagcttt agacaccact  6300
gatgcagatg tagccatata ctgcagggac aagaaatggg aaatgactct caaggaagca  6360
gtggctagga gagaagcagt ggaggagata tgcatatccg acgactcttc agtgacagaa  6420
cctgatgcag agctggtgag ggtgcatccg aagagttctt tggctggaag gaagggctac  6480
agcacaagcg atggcaaaac tttctcatat ttggaaggga ccaagtttca ccaggcggcc  6540
aaggatatag cagaaattaa tgccatgtgg cccgttgcaa cggaggccaa tgagcaggta  6600
tgcatgtata tcctcggaga aagcatgagc agtattaggt cgaaatgccc cgtcgaagag  6660
tcggaagcct ccacaccacc tagcacgctg ccttgcttgt gcatccatgc catgactcca  6720
gaaagagtac agcgcctaaa agcctcacgt ccagaacaaa ttactgtgtg ctcatccttt  6780
ccattgccga agtatagaat cactggtgtg cagaagatcc aatgctccca gcctatattg  6840
ttctcaccga aagtgcctgc gtatattcat ccaaggaagt atctcgtgga aacaccaccg  6900
gtagacgaga ctccggagcc atcggcagag aaccaatcca cagaggggac acctgaacaa  6960
ccaccactta taaccgagga tgagaccagg actagaacgc ctgagccgat catcatcgaa  7020
gaggaagaag aggatagcat aagtttgctg tcagatggcc cgacccacca ggtgctgcaa  7080
gtcgaggcag acattcacgg gccgccctct gtatctagct catcctggtc cattcctcat  7140
gcatccgact ttgatgtgga cagtttatcc atacttgaca ccctggaggg agctagcgtg  7200
accagcgggg caacgtcagc cgagactaac tcttacttcg caaagagtat ggagtttctg  7260
gcgcgaccgg tgcctgcgcc tcgaacagta ttcaggaacc ctccacatcc cgctccgcgc  7320
acaagaacac cgtcacttgc acccagcagg gcctgctcga gaaccagcct agtttccacc  7380
ccgccaggcg tgaatagggt gatcactaga gaggagctcg aggcgcttac cccgtcacgc  7440
actcctagca ggtcggtctc gagaaccagc ctggtctcca acccgccagg cgtaaatagg  7500
gtgattacaa gagaggagtt tgaggcgttc gtagcacaac aacaatgacg gtttgatgcg  7560
ggtgcataca tcttttcctc cgacaccggt caagggcatt tacaacaaaa atcagtaagg  7620
caaacggtgc tatccgaagt ggtgttggag aggaccgaat tggagatttc gtatgccccg  7680
cgcctcgacc aagaaaaaga agaattacta cgcaagaaat tacagttaaa tcccacacct  7740
gctaacagaa gcagatacca gtccaggaag gtggagaaca tgaaagccat aacagctaga  7800
cgtattctgc aaggcctagg gcattatttg aaggcagaag gaaaagtgga gtgctaccga  7860
accctgcatc ctgttccttt gtattcatct agtgtgaacc gtgccttttc aagccccaag  7920
gtcgcagtgg aagcctgtaa cgccatgttg aaagagaact ttccgactgt ggcttcttac  7980
tgtattattc cagagtacga tgcctatttg gacatggttg acggagcttc atgctgctta  8040
gacactgcca gtttttgccc tgcaaagctg cgcagctttc caaagaaaca ctcctatttg  8100
gaacccacaa tacgatcggc agtgccttca gcgatccaga acacgctcca gaacgtcctg  8160
gcagctgcca caaaaagaaa ttgcaatgtc acgcaaatga gagaattgcc cgtattggat  8220
tcggcggcct ttaatgtgga atgcttcaag aaatatgcgt gtaataatga atattgggaa  8280
acgtttaaag aaaaccccat caggcttact gaagaaaacg tggtaaatta cattaccaaa  8340
ttaaaaggac caaaagctgc tgctcttttt gcgaagacac ataatttgaa tatgttgcag  8400
gacataccaa tggacaggtt tgtaatggac ttaaagagag acgtgaaagt gactccagga  8460
acaaaacata ctgaagaacg gcccaaggta caggtgatcc aggctgccga tccgctagca  8520
acagcgtatc tgtgcggaat ccaccgagag ctggttagga gattaaatgc ggtcctgctt  8580
ccgaacattc atacactgtt tgatatgtcg gctgaagact ttgacgctat tatagccgag  8640
```

-continued

```
cacttccagc ctggggattg tgttctggaa actgacatcg cgtcgtttga taaaagtgag  8700
gacgacgcca tggctctgac cgcgttaatg attctggaag acttaggtgt ggacgcagag  8760
ctgttgacgc tgattgaggc ggctttcggc gaaatttcat caatacattt gcccactaaa  8820
actaaattta aattcggagc catgatgaaa tctggaatgt tcctcacact gtttgtgaac  8880
acagtcatta acattgtaat cgcaagcaga gtgttgagag aacggctaac cggatcacca  8940
tgtgcagcat tcattggaga tgacaatatc gtgaaaggag tcaaatcgga caaattaatg  9000
gcagacaggt gcgccacctg gttgaatatg gaagtcaaga ttatagatgc tgtggtgggc  9060
gagaaagcgc cttatttctg tggagggttt attttgtgtg actccgtgac cggcacagcg  9120
tgccgtgtgg cagaccccct aaaaaggctg tttaagcttg gcaaacctct ggcagcagac  9180
gatgaacatg atgatgacag gagaagggca ttgcatgaag agtcaacacg ctggaaccga  9240
gtgggtattc tttcagagct gtgcaaggca gtagaatcaa ggtatgaaac cgtaggaact  9300
tccatcatag ttatggccat gactactcta gctagcagtg ttaaatcatt cagctacctg  9360
agaggggccc ctataactct ctacggctaa cctgaatgga ctacgacata gtctagtccg  9420
ccaagttcga aggcgcgcct ctagagccac catggtgagc aagggcgagg agctgttcac  9480
cggggtggtg cccatcctgg tcgagctgga cggcgacgta aacggccaca agttcagcgt  9540
gtccggcgag ggcgagggcg atgccaccta cggcaagctg accctgaagt tcatctgcac  9600
caccggcaag ctgcccgtgc cctggcccac cctcgtgacc accctgacct acggcgtgca  9660
gtgcttcagc cgctaccccg accacatgaa gcagcacgac ttcttcaagt ccgccatgcc  9720
cgaaggctac gtccaggagc gcaccatctt cttcaaggac gacggcaact acaagacccg  9780
cgccgaggtg aagttcgagg gcgacaccct ggtgaaccgc atcgagctga agggcatcga  9840
cttcaaggag gacggcaaca tcctggggca caagctggag tacaactaca acagccacaa  9900
cgtctatatc atggccgaca agcagaagaa cggcatcaag gtgaacttca agatccgcca  9960
caacatcgag gacggcagcg tgcagctcgc cgaccactac cagcagaaca cccccatcgg  10020
cgacggcccc gtgctgctgc ccgacaacca ctacctgagc acccagtccg ccctgagcaa  10080
agaccccaac gagaagcgcg atcacatggt cctgctggag ttcgtgaccg ccgccgggat  10140
cactctcggc atggacgagc tgtacaagta gcatcgatga tatcgcggcc gcatacagca  10200
gcaattggca agctgcttac atagaactcg cggcgattgg catgccgcct taaaattttt  10260
attttatttt tcttttcttt tccgaatcgg attttatttt taatatttca aaaaaaaaaa  10320
aaaaa                                                              10325

SEQ ID NO: 39          moltype = RNA  length = 10325
FEATURE                Location/Qualifiers
source                 1..10325
                       mol_type = other RNA
                       organism = synthetic construct
SEQUENCE: 39
aaaaaaaaaa cgcgtgataa cgcaggaaag aacatgtgag caaaaggcca gcaaaaggcc  60
aggaaccgta aaaaggccgc gttgctggcg tttttccata ggctccgccc ccctgacgag  120
catcacaaaa atcgacgctc aagtcagagg tggcgaaacc cgacaggact ataaagatac  180
caggcgtttc cccctggaag ctccctcgtg cgctctcctg ttccgaccct gccgcttacc  240
ggatacctgt ccgcctttct cccttcggga agcgtggcgc tttctcatag ctcacgctgt  300
aggtatctca gttcggtgta ggtcgttcgc tccaagctgg gctgtgtgca cgaacccccc  360
gttcagcccg accgctgcgc cttatccggt aactatcgtc ttgagtccaa cccggtaaga  420
cacgacttat cgccactggc agcagccact ggtaacagga ttagcagagc gaggtatgta  480
ggcggtgcta cagagttctt gaagtggtgg cctaactacg gctacactag aagaacagta  540
tttggtatct gcgctctgct gaagccagtt accttcggaa aaagagttgg tagctcttga  600
tccggcaaac aaaccaccgc tggtagcggt ttttttgttt gcaagcagca gattacgcgc  660
agaaaaaaag gatctcaaga agatcctttg atcttttcta cggggtctga cgctcagtgg  720
aacgaaaact cacgttaagg gattttggtc atgagattat caaaaaggat cttcacctag  780
atccttttaa attaaaaatg aagttttaaa tcaatctaaa gtatatatga gtaaacttgg  840
tctgacagtt accaatgctt aatcagtgag gcacctatct cagcgatctg tctatttcgt  900
tcatccatag ttgcctgact ccccgtcgtg tagataacta cgatacggga gggcttacca  960
tctggcccca gtgctgcaat gataccgcga gacccacgct caccggctcc agatttatca  1020
gcaataaacc agccagccgg aagggccgag cgcagaagtg gtcctgcaac tttatccgcc  1080
tccatccagt ctattaattg ttgccgggaa gctagagtaa gtagttcgcc agttaatagt  1140
ttgcgcaacg ttgttgccat tgctacaggc atcgtggtgt cacgctcgtc gtttggtatg  1200
gcttcattca gctccggttc ccaacgatca aggcgagtta catgatcccc catgttgtgc  1260
aaaaaagcgg ttagctcctt cggtcctccg atcgttgtca gaagtaagtt ggccgcagtg  1320
ttatcactca tggttatggc agcactgcat aattctctta ctgtcatgcc atccgtaaga  1380
tgcttttctg tgactggtga gtactcaacc aagtcattct gagaatagtg tatgcggcga  1440
ccgagttgct cttgcccggc gtcaatacgg gataataccg cgccacatag cagaacttta  1500
aaagtgctca tcattggaaa acgttcttcg gggcgaaaac tctcaaggat cttaccgctg  1560
ttgagatcca gttcgatgta acccactcgt gcacccaact gatcttcagc atcttttact  1620
ttcaccagcg tttctgggtg agcaaaaaca ggaaggcaaa atgccgcaaa aaagggaata  1680
agggcgacac ggaaatgttg aatactcata ctcttccttt ttcaatatta ttgaagcatt  1740
tatcagggtt attgtctcat gagcggatac atatttgaat gtatttagaa aaataaacaa  1800
ataggggttc cgcgcacatt tccccgaaaa gtgccacctg agctctaata cgactcacta  1860
taggataggc ggcgcatgag agaagcccag accaattacc tacccaaaat ggagaaagtt  1920
cacgttgaca tcgaggaaga cagcccattc ctcagagctt tgcagcggag cttcccgcag  1980
tttgaggtag aagccaagca ggtcactgat aatgaccatg ctaatgccag agcgttttcg  2040
catctggctt caaaactgat cgaaacggag gtggacccat ccgacacgat ccttgacatt  2100
ggaagtgcgc ccgcccgcag aatgtattct aagcacaagt atcattgtat ctgtccgatg  2160
agatgtgcgg aagatccgga cagattgtat aagtatgcaa ctaagctgaa gaaaaactgt  2220
aaggaaataa ctgataagga attggacaag aaaatgaagg agctggccgc cgtcatgagc  2280
gaccctgacc tggaaactga gactatgtgc ctccacgacg acgagtcgtg tcgctacgaa  2340
gggcaagtcg ctgtttacca ggatgtatac gcggttgacg gaccgacaag tctctatcac  2400
caagccaata agggagttag agtcgcctac tggataggct ttgacaccac ccccttttatg  2460
tttaagaact tggctggagc atatccatca tactctacca actgggccga cgaaaccgtg  2520
ttaacggctc gtaacatagg cctatgcagc tctgacgtta tggagcggtc acgtagaggg  2580
```

-continued

```
atgtccattc ttagaaagaa gtatttgaaa ccatccaaca atgttctatt ctctgttggc  2640
tcgaccatct accacgagaa gagggactta ctgaggagct ggcacctgcc gtctgtattt  2700
cacttacgtg gcaagcaaaa ttacacatgt cggtgtgaga ctatagttag ttgcgacggg  2760
tacgtcgtta aaagaatagc tatcagtcca ggcctgtatg ggaagccttc aggctatgct  2820
gctacgatgc accgcgaggg attcttgtgc tgcaaagtga cagacacatt gaacggggag  2880
agggtctctt ttcccgtgtg cacgtatgtg ccagctacat tgtgtgacca aatgactggc  2940
atactggcaa cagatgtcag tgcggacgac gcgcaaaaac tgctggttgg gctcaaccag  3000
cgtatagtcg tcaacggtcg cacccagaga aacaccaata ccatgaaaaa ttaccttttg  3060
cccgtagtgg cccaggcatt tgctaggtgg gcaaaggaat ataaggaaga tcaagaagat  3120
gaaaggccac taggactacg agatagacag ttagtcatgg ggtgttgttg ggcttttaga  3180
aggcacaaga taacatctat ttataagcgc ccggataccc aaaccatcat caaagtgaac  3240
agcgatttcc actcattcgt gctgcccagg ataggcagta acacattgga gatcgggctg  3300
agaacaagaa tcaggaaaat gttagaggag cacaaggagc cgtcacctct cattaccgcc  3360
gaggacgtac aagaagctaa gtgcgcagcc gatgaggcta aggaggtgcg tgaagccgag  3420
gagttgcgcg cagctctacc acctttggca gctgatgttg aggagcccac tctggaagcc  3480
gatgtcgact tgatgttaca agaggctggg gccggctcag tggagacacc tcgtggcttg  3540
ataaaggtta ccagctacga tggcgaggac aagatcggct cttacgctgt gctttctccg  3600
caggctgtac tcaagagtga aaaattatct tgcatccacc ctctcgctga acaagtcata  3660
gtgataacac actctggccg aaaagggcgt tatgccgtgg aaccatacca tggtaaagta  3720
gtggtgccag agggacatgc aatacccgtc caggactttc aagctctgag tgaaagtgcc  3780
accattgtgt acaacgaacg tgagttcgta aacaggtacc tgcaccatat tgccacacat  3840
ggaggagcgc tgaacactga tgaagaatat tacaaaactg tcaagcccag cgagcacgac  3900
ggcgaatacc tgtacgacat cgacaggaaa cagtgcgtca agaaagaact agtcactggg  3960
ctagggctca caggcgagct ggtggatcct cccttccatg aattcgccta cgagagtctg  4020
agaacacgac cagccgctcc ttaccaagta ccaaccatag gggtgtatgg cgtgccagga  4080
tcaggcaagt ctggcatcat taaaagcgca gtcaccaaaa aagatctagt ggtgagcgcc  4140
aagaaagaaa actgtgcaga aattataagg gacgtcaaga aaatgaaagg gctggacgtc  4200
aatgccagaa ctgtggactc agtgctcttg aatggatgca aacaccccgt agagaccctg  4260
tatattgacg aagcttttgc ttgtcatgca ggtactctca gagcgctcat agccattata  4320
agacctaaaa aggcagtgct ctgcggggat cccaaacagt gcggtttttt taacatgatg  4380
tgcctgaaag tgcattttaa ccacgagatt tgcacacaag tcttccacaa aagcatctct  4440
cgccgttgca ctaaatctgt gacttcggtc gtctcaacct tgttttacga caaaaaaatg  4500
agaacgacga atccgaaaga gactaagatt gtgattgaca ctaccggcag taccaaacct  4560
aagcaggacg atctcattct cacttgtttc agagggtggg tgaagcagtt gcaaatagat  4620
tacaaaggca acgaaataat gacggcagct gcctctcaag ggctgacccg taaaggtgtg  4680
tatgccgttc ggtacaaggt gaatgaaaat cctctgtacg cacccacctc agaacatgtg  4740
aacgtcctac tgacccgcac ggaggaccgc atcgtgtgga aaacactagc cggcgaccca  4800
tggataaaaa cactgactgc caagtaccct gggaatttca ctgccacgat agaggagtgg  4860
caagcagagc atgatgccat catgaggcac atcttggaga gaccggaccc taccgacgtc  4920
ttccagaata aggcaaacgt gtgttgggcc aaggctttag tgccggtgct gaagaccgct  4980
ggcatagaca tgaccactga acaatggaac actgtggatt attttgaaac ggacaaagct  5040
cactcagcag agatagtatt gaaccaacta tgcgtgaggt tctttggact cgatctggac  5100
tccggtctat tttctgcacc cactgttccg ttatccatta ggaataatca ctgggataac  5160
tccccgtcgc ctaacatgta cgggctgaat aaagaagtgg tccgtcagct ctctcgcagg  5220
tacccacaac tgcctcgggc agttgccact ggaagagtct atgacatgaa cactggtaca  5280
ctgcgcaatt atgatccgcg cataaaccta gtacctgtaa acagaagact gcctcatgct  5340
ttagtcctcc accataatga acacccacag agtgactttt cttcattcgt cagcaaattg  5400
aagggcagaa ctgtcctggt ggtcggggaa aagttgtccg tcccaggcaa aatggttgac  5460
tggttgtcag accggcctga ggctaccttc agagctcggc tggatttagg catcccaggt  5520
gatgtgccca aatatgacat aatatttgtt aatgtgagga ccccatataa ataccatcac  5580
tatcagcagt gtgaagacca tgccattaag cttagcatgt tgaccaagaa agcttgtctg  5640
catctgaatc ccggcggaac ctgtgtcagc ataggttatg gttacgctga cagggccagc  5700
gaaagcatca ttggtgctat agcgcggcag ttcaagtttt cccgggtatg caaaccgaaa  5760
tcctcacttg aagagacgga agttctgttt gtattcattg ggtacgatcg caaggcccgt  5820
acgcacaatt cttacaagct ttcatcaacc ttgaccaaca tttatacagg ttccagactc  5880
cacgaagccg gatgtgcacc ctcatatcat gtggtgcgag ggggatattgc cacggccacc  5940
gaaggagtga ttataaatgc tgctaacagc aaaggacaac ctggcggagg ggtgtgcgga  6000
gcgctgtata agaaattccc ggaaagcttc gatttacagc cgatcgaagt aggaaaagcg  6060
cgactggtca aaggtgcagc taaacatatc attcatgccg taggaccaaa cttcaacaaa  6120
gtttcggagg ttgaaggtga caaacagttg gcagaggctt atgagtccat cgctaagatt  6180
gtcaacgata acaattacaa gtcagtagcg attccactgt tgtccaccgg catcttttcc  6240
gggaacaaag atcgactaac ccaatcattg aaccatttgc tgacagcttt agacaccact  6300
gatgcagatg tagccatata ctgcagggac aagaaatggg aaatgactct caaggaagca  6360
gtggctagga gagaagcagt ggaggagata tgcatatccg acgactcttc agtgacagaa  6420
cctgatgcag agctggtgag ggtgcatccg aagagttctt tggctggaag gaagggctac  6480
agcacaagcg atggcaaaac tttctcatat ttggaaggga ccaagtttca ccaggcggcc  6540
aaggatatag cagaaattaa tgccatgtgg cccgttgcaa cggaggccaa tgagcaggta  6600
tgcatgtata tcctcggaga aagcatgagc agtattaggt cgaaatgccc cgtcgaagag  6660
tcggaagcct ccacaccacc tagcacgctg ccttgcttgt gcatccatgc catgactcca  6720
gaaagagtac agcgcctaaa agcctcacgt ccagaacaaa ttactgtgtg ctcatccttt  6780
ccattgccga agtatagaat cactggtgtg cagaagatcc aatgctccca gcctatattg  6840
ttctcaccga aagtgcctgc gtatattcat ccaaggaagt atctcgtgga aacaccaccg  6900
gtagacgaga ctccggagcc atcggcagag aaccaatcca cagaggggac acctgaacaa  6960
ccaccactta taaccgagga tgagaccagg actagaacgc ctgagccgat catcatcgaa  7020
gaggaagaag aggatagcat aagtttgctg tcagatggcc cgacccacca ggtgctgcaa  7080
gtcgaggcag acattcacgg gccgccctct gtatctagct catcctggtc cattcctcat  7140
gcatccgact ttgatgtgga cagtttatcc atacttgaca ccctggaggg agctagcgtg  7200
accagcgggg caacgtcagc cgagactaac tcttacttcg caaagagtat ggagtttctg  7260
gcgcgaccgg tgcctgcgcc tcgaacagta ttcaggaacc ctccacatcc cgctccgcgc  7320
```

```
acaagaacac cgtcacttgc acccagcagg gcctgctcga gaaccagcct agtttccacc  7380
ccgccaggcg tgaatagggt gatcactaga gaggagctcg aggcgcttac cccgtcacgc  7440
actcctagca ggtcggtctc gagaaccagc ctggtctcca acccgccagg cgtaaatagg  7500
gtgattacaa gagaggagtt tgaggcgttc gtagcacaac aacaatgacg gtttgatgcg  7560
ggtgcataca tcttttcctc cgacaccggt caagggcatt tacaacaaaa atcagtaagg  7620
caaacggtgc tatccgaagt ggtgttggag aggaccgaat tggagatttc gtatgccccg  7680
cgcctcgacc aagaaaaaga agaattacta cgcaagaaat tacagttaaa tcccacacct  7740
gctaacagaa gcagatacca gtccaggaag gtggagaaca tgaaagccat aacagctaga  7800
cgtattctgc aaggcctagg gcattatttg aaggcagaag gaaaagtgga gtgctaccga  7860
accctgcatc ctgttccttt gtattcatct agtgtgaacc gtgccttttc aagccccaag  7920
gtcgcagtgg aagcctgtaa cgccatgttg aaagagaact ttccgactgt ggcttcttac  7980
tgtattattc cagagtacga tgcctatttg gacatggttg acggagcttc atgctgctta  8040
gacactgcca gtttttgccc tgcaaagctg cgcagctttc caaagaaaca ctcctatttg  8100
gaacccacaa tacgatcggc agtgccttca gcgatccaga acacgctcca gaacgtcctg  8160
gcagctgcca caaaaagaaa ttgcaatgtc acgcaaatga gagaattgcc cgtattggat  8220
tcggcggcct ttaatgtgga atgcttcaag aaatatgcgt gtaataatga atattgggaa  8280
acgtttaaag aaaaccccat caggcttact gaagaaaacg tggtaaatta cattaccaaa  8340
ttaaaaggac caaaagctgc tgctcttttt gcgaagacac ataatttgaa tatgttgcag  8400
gacataccaa tggacaggtt tgtaatggac ttaaagagag acgtgaaagt gactccagga  8460
acaaaacata ctgaagaacg gcccaaggta caggtgatcc aggctgccga tccgctagca  8520
acagcgtatc tgtgcggaat ccaccgagag ctggttagga gattaaatgc ggtcctgctt  8580
ccgaacattc atacactgtt tgatatgtcg gctgaagact ttgacgctat tatagccgag  8640
cacttccagc ctggggattg tgttctggaa actgacatcg cgtcgtttga taaaagtgag  8700
gacgacgcca tggctctgac cgcgttaatg attctggaag acttaggtgt ggacgcagag  8760
ctgttgacgc tgattgaggc ggctttcggc gaaatttcat caatacattt gcccactaaa  8820
actaaattta aattcggagc catgatgaaa tctggaatgt tcctcacact gtttgtgaac  8880
acagtcatta acattgtaat cgcaagcaga gtgttgagag aacggctaac cggatcacca  8940
tgtgcagcat tcattggaga tgacaatatc gtgaaaggag tcaaatcgga caaattaatg  9000
gcagacaggt gcgccacctg gttgaatatg gaagtcaaga ttatagatgc tgtggtgggc  9060
gagaaagcgc cttatttctg tggagggttt attttgtgtg actccgtgac cggcacagcg  9120
tgccgtgtgg cagacccccct aaaaaggctg tttaagcttg gcaaacctct ggcagcagac  9180
gatgaacatg atgatgacag gagaagggca ttgcatgaag agtcaacacg ctggaaccga  9240
gtgggtattc tttcagagct gtgcaaggca gtagaatcaa ggtatgaaac cgtaggaact  9300
tccatcatag ttatggccat gactactcta gctagcagtg ttaaatcatt cagctacctg  9360
agaggggccc ctataactct ctacggctaa cctgaatgga ctacgacata gtctagtccg  9420
ccaagttcga aggcgcgcct ctagagccac catggtgagc aagggcgagg agctgttcac  9480
cggggtggtg cccatcctgg tcgagctgga cggcgacgta aacggccaca agttcagcgt  9540
gtccggcgag ggcgagggcg atgccaccta cggcaagctg accctgaagt tcatctgcac  9600
caccggcaag ctgcccgtgc cctggcccac cctcgtgacc accctgacct acggcgtgca  9660
gtgcttcagc cgctaccccg accacatgaa gcagcacgac ttcttcaagt ccgccatgcc  9720
cgaaggctac gtccaggagc gcaccatctt cttcaaggac gacggcaact acaagacccg  9780
cgccgaggtg aagttcgagg gcgacaccct ggtgaaccgc atcgagctga agggcatcga  9840
cttcaaggag gacggcaaca tcctggggca caagctggag tacaactaca acagccacaa  9900
cgtctatatc atggccgaca agcagaagaa cggcatcaag gtgaacttca agatccgcca  9960
caacatcgag gacggcagcg tgcagctcgc cgaccactac cagcagaaca cccccatcgg  10020
cgacggcccc gtgctgctgc ccgacaacca ctacctgagc acccagtccg ccctgagcaa  10080
agaccccaac gagaagcgcg atcacatggt cctgctggag ttcgtgaccg ccgccgggat  10140
cactctcggc atggacgagc tgtacaagta gcatcgatga tatcgcggcc gcatacagca  10200
gcaattggca agctgcttac atagaactcg cggcgattgg catgccgcct taaaattttt  10260
attttatttt tcttttcttt tccgaatcaa attttgtttt taatatttca aaaaaaaaaa  10320
aaaaa                                                              10325

SEQ ID NO: 40          moltype = RNA  length = 10325
FEATURE                Location/Qualifiers
source                 1..10325
                       mol_type = other RNA
                       organism = synthetic construct
SEQUENCE: 40
aaaaaaaaaa cgcgtgataa cgcaggaaag aacatgtgag caaaaggcca gcaaaaggcc  60
aggaaccgta aaaaggccgc gttgctggcg tttttccata ggctccgccc ccctgacgag  120
catcacaaaa atcgacgctc aagtcagagg tggcgaaacc cgacaggact ataaagatac  180
caggcgtttc cccctggaag ctccctcgtg cgctctcctg ttccgaccct gccgcttacc  240
ggatacctgt ccgcctttct cccttcggga agcgtggcgc tttctcatag ctcacgctgt  300
aggtatctca gttcggtgta ggtcgttcgc tccaagctgg gctgtgtgca cgaacccccc  360
gttcagcccg accgctgcgc cttatccggt aactatcgtc ttgagtccaa cccggtaaga  420
cacgacttat cgccactggc agcagccact ggtaacagga ttagcagagc gaggtatgta  480
ggcggtgcta cagagttctt gaagtggtgg cctaactacg gctacactag aagaacagta  540
tttggtatct gcgctctgct gaagccagtt accttcggaa aaagagttgg tagctcttga  600
tccggcaaac aaaccaccgc tggtagcggt ttttttgttt gcaagcagca gattacgcgc  660
agaaaaaaag gatctcaaga agatcctttg atcttttcta cggggtctga cgctcagtgg  720
aacgaaaact cacgttaagg gattttggtc atgagattat caaaaaggat cttcacctag  780
atccttttaa attaaaaatg aagttttaaa tcaatctaaa gtatatatga gtaaacttgg  840
tctgacagtt accaatgctt aatcagtgag gcacctatct cagcgatctg tctatttcgt  900
tcatccatag ttgcctgact ccccgtcgtg tagataacta cgatacggga gggcttacca  960
tctggcccca gtgctgcaat gataccgcga gacccacgct caccggctcc agatttatca  1020
gcaataaacc agccagccgg aagggccgag cgcagaagtg gtcctgcaac tttatccgcc  1080
tccatccagt ctattaattg ttgccgggaa gctagagtaa gtagttcgcc agttaatagt  1140
ttgcgcaacg ttgttgccat tgctacaggc atcgtggtgt cacgctcgtc gtttggtatg  1200
gcttcattca gctccggttc ccaacgatca aggcgagtta catgatcccc catgttgtgc  1260
```

-continued

```
aaaaaagcgg ttagctcctt cggtcctccg atcgttgtca gaagtaagtt ggccgcagtg  1320
ttatcactca tggttatggc agcactgcat aattctctta ctgtcatgcc atccgtaaga  1380
tgcttttctg tgactggtga gtactcaacc aagtcattct gagaatagtg tatgcggcga  1440
ccgagttgct cttgcccggc gtcaatacgg gataataccg cgccacatag cagaacttta  1500
aaagtgctca tcattggaaa acgttcttcg gggcgaaaac tctcaaggat cttaccgctg  1560
ttgagatcca gttcgatgta acccactcgt gcacccaact gatcttcagc atcttttact  1620
ttcaccagcg tttctgggtg agcaaaaaca ggaaggcaaa atgccgcaaa aaagggaata  1680
agggcgacac ggaaatgttg aatactcata ctcttccttt ttcaatatta ttgaagcatt  1740
tatcagggtt attgtctcat gagcggatac atatttgaat gtatttagaa aaataaacaa  1800
ataggggttc cgcgcacatt tccccgaaaa gtgccacctg agctctaata cgactcacta  1860
taggataggc ggcgcatgag agaagcccag accaattacc tacccaaaat ggagaaagtt  1920
cacgttgaca tcgaggaaga cagcccattc ctcagagctt tgcagcggag cttcccgcag  1980
tttgaggtag aagccaagca ggtcactgat aatgaccatg ctaatgccag agcgttttcg  2040
catctggctt caaaactgat cgaaacggag gtggacccat ccgacacgat ccttgacatt  2100
ggaagtgcgc ccgcccgcag aatgtattct aagcacaagt atcattgtat ctgtccgatg  2160
agatgtgcgg aagatccgga cagattgtat aagtatgcaa ctaagctgaa gaaaaactgt  2220
aaggaaataa ctgataagga attggacaag aaaatgaagg agctggccgc cgtcatgagc  2280
gaccctgacc tggaaactga gactatgtgc ctccacgacg acgagtcgtg tcgctacgaa  2340
gggcaagtcg ctgtttacca ggatgtatac gcggttgacg gaccgacaag tctctatcac  2400
caagccaata agggagttag agtcgcctac tggataggct ttgacaccac cccttttatg  2460
tttaagaact tggctggagc atatccatca tactctacca actgggccga cgaaaccgtg  2520
ttaacggctc gtaacatagg cctatgcagc tctgacgtta tggagcggtc acgtagaggg  2580
atgtccattc ttagaaagaa gtatttgaaa ccatccaaca atgttctatt ctctgttggc  2640
tcgaccatct accacgagaa gagggactta ctgaggagct ggcacctgcc gtctgtattt  2700
cacttacgtg gcaagcaaaa ttacacatgt cggtgtgaga ctatagttag ttgcgacggg  2760
tacgtcgtta aaagaatagc tatcagtcca ggcctgtatg ggaagccttc aggctatgct  2820
gctacgatgc accgcgaggg attcttgtgc tgcaaagtga cagacacatt gaacggggag  2880
agggtctctt ttcccgtgtg cacgtatgtg ccagctacat tgtgtgacca aatgactggc  2940
atactggcaa cagatgtcag tgcggacgac gcgcaaaaac tgctggttgg gctcaaccag  3000
cgtatagtcg tcaacggtcg cacccagaga aacaccaata ccatgaaaaa ttaccttttg  3060
cccgtagtgg cccaggcatt tgctaggtgg gcaaaggaat ataaggaaga tcaagaagat  3120
gaaaggccac taggactacg agatagacag ttagtcatgg ggtgttgttg ggcttttaga  3180
aggcacaaga taacatctat ttataagcgc ccggataccc aaaccatcat caaagtgaac  3240
agcgatttcc actcattcgt gctgcccagg ataggcagta acacattgga gatcgggctg  3300
agaacaagaa tcaggaaaat gttagaggag cacaaggagc cgtcacctct cattaccgcc  3360
gaggacgtac aagaagctaa gtgcgcagcc gatgaggcta aggaggtgcg tgaagccgag  3420
gagttgcgcg cagctctacc acctttggca gctgatgttg aggagcccac tctggaagcc  3480
gatgtcgact tgatgttaca agaggctggg gccggctcag tggagacacc tcgtggcttg  3540
ataaaggtta ccagctacga tggcgaggac aagatcggct cttacgctgt gctttctccg  3600
caggctgtac tcaagagtga aaaattatct tgcatccacc ctctcgctga acaagtcata  3660
gtgataacac actctggccg aaaagggcgt tatgccgtgg aaccatacca tggtaaagta  3720
gtggtgccag agggacatgc aatacccgtc caggactttc aagctctgag tgaaagtgcc  3780
accattgtgt acaacgaacg tgagttcgta aacaggtacc tgcaccatat tgccacacat  3840
ggaggagcgc tgaacactga tgaagaatat tacaaaactg tcaagcccag cgagcacgac  3900
ggcgaatacc tgtacgacat cgacaggaaa cagtgcgtca agaaagaact agtcactggg  3960
ctagggctca caggcgagct ggtggatcct cccttccatg aattcgccta cgagagtctg  4020
agaacacgac cagccgctcc ttaccaagta ccaaccatag ggtgtatggg cgtgccagga  4080
tcaggcaagt ctggcatcat taaaagcgca gtcaccaaaa aagatctagt ggtgagcgcc  4140
aagaaagaaa actgtgcaga aattataagg gacgtcaaga aaatgaaagg gctggacgtc  4200
aatgccagaa ctgtggactc agtgctcttg aatggatgca aacaccccgt agagaccctg  4260
tatattgacg aagcttttgc ttgtcatgca ggtactctca gagcgctcat agccattata  4320
agacctaaaa aggcagtgct ctgcggggat cccaaacagt gcggtttttt taacatgatg  4380
tgcctgaaag tgcattttaa ccacgagatt tgcacacaag tcttccacaa aagcatctct  4440
cgccgttgca ctaaatctgt gacttcggtc gtctcaacct tgttttacga caaaaaaatg  4500
agaacgacga atccgaaaga gactaagatt gtgattgaca ctaccggcag taccaaacct  4560
aagcaggacg atctcattct cacttgtttc agagggtggg tgaagcagtt gcaaatagat  4620
tacaaaggca acgaaataat gacggcagct gcctctcaag ggctgacccg taaaggtgtg  4680
tatgccgttc ggtacaaggt gaatgaaaat cctctgtacg cacccacctc agaacatgtg  4740
aacgtcctac tgacccgcac ggaggaccgc atcgtgtgga aaacactagc cggcgaccca  4800
tggataaaaa cactgactgc caagtaccct gggaatttca ctgccacgat agaggagtgg  4860
caagcagagc atgatgccat catgaggcac atcttggaga gaccggaccc taccgacgtc  4920
ttccagaata aggcaaacgt gtgttgggcc aaggctttag tgccggtgct gaagaccgct  4980
ggcatagaca tgaccactga acaatggaac actgtggatt attttgaaac ggacaaagct  5040
cactcagcag agatagtatt gaaccaacta tgcgtgaggt tctttggact cgatctggac  5100
tccggtctat tttctgcacc cactgttccg ttatccatta ggaataatca ctgggataac  5160
tccccgtcgc ctaacatgta cggctgaat aaagaagtgg tccgtcagct ctctcgcagg  5220
tacccacaac tgcctcgggc agttgccact ggaagagtct atgacatgaa cactggtaca  5280
ctgcgcaatt atgatccgcg cataaaccta gtacctgtaa acagaagact gcctcatgct  5340
ttagtcctcc accataatga acacccacag agtgactttt cttcattcgt cagcaaattg  5400
aagggcagaa ctgtcctggt ggtcggggaa aagttgtccg tcccaggcaa aatggttgac  5460
tggttgtcag accggcctga ggctaccttc agagctcggc tggatttagg catcccaggt  5520
gatgtgccca aatatgacat aatatttgtt aatgtgagga ccccatataa ataccatcac  5580
tatcagcagt gtgaagacca tgccattaag cttagcatgt tgaccaagaa agcttgtctg  5640
catctgaatc ccggcggaac ctgtgtcagc ataggttatg gttacgctga cagggccagc  5700
gaaagcatca ttggtgctat agcgcggcag ttcaagtttt cccgggtatg caaaccgaaa  5760
tcctcacttg aagagacgga agttctgttt gtattcattg ggtacgatcg caaggcccgt  5820
acgcacaatt cttacaagct ttcatcaacc ttgaccaaca tttatacagg ttccagactc  5880
cacgaagccg gatgtgcacc ctcatatcat gtggtgcgag ggatattgc cacggccacc  5940
gaaggagtga ttataaatgc tgctaacagc aaaggacaac ctggcggagg ggtgtgcgga  6000
```

```
gcgctgtata agaaattccc ggaaagcttc gatttacagc cgatcgaagt aggaaaagcg  6060
cgactggtca aaggtgcagc taaacatatc attcatgccg taggaccaaa cttcaacaaa  6120
gtttcggagg ttgaaggtga caaacagttg gcagaggctt atgagtccat cgctaagatt  6180
gtcaacgata acaattacaa gtcagtagcg attccactgt tgtccaccgg catcttttcc  6240
gggaacaaag atcgactaac ccaatcattg aaccatttgc tgacagcttt agacaccact  6300
gatgcagatg tagccatata ctgcagggac aagaaatggg aaatgactct caaggaagca  6360
gtggctagga gagaagcagt ggaggagata tgcatatccg acgactcttc agtgacagaa  6420
cctgatgcag agctggtgag ggtgcatccg aagagttctt tggctggaag gaagggctac  6480
agcacaagcg atggcaaaac tttctcatat ttggaaggga ccaagtttca ccaggcggcc  6540
aaggatatag cagaaattaa tgccatgtgg cccgttgcaa cggaggccaa tgagcaggta  6600
tgcatgtata tcctcggaga aagcatgagc agtattaggt cgaaatgccc cgtcgaagag  6660
tcggaagcct ccacaccacc tagcacgctg ccttgcttgt gcatccatgc catgactcca  6720
gaaagagtac agcgcctaaa agcctcacgt ccagaacaaa ttactgtgtg ctcatccttt  6780
ccattgccga agtatagaat cactggtgtg cagaagatcc aatgctccca gcctatattg  6840
ttctcaccga aagtgcctgc gtatattcat ccaaggaagt atctcgtgga aacaccaccg  6900
gtagacgaga ctccggagcc atcggcagag aaccaatcca cagaggggac acctgaacaa  6960
ccaccactta taaccgagga tgagaccagg actagaacgc ctgagccgat catcatcgaa  7020
gaggaagaag aggatagcat aagtttgctg tcagatggcc cgacccacca ggtgctgcaa  7080
gtcgaggcag acattcacgg gccgccctct gtatctagct catcctggtc cattcctcat  7140
gcatccgact ttgatgtgga cagtttatcc atacttgaca ccctggaggg agctagcgtg  7200
accagcgggg caacgtcagc cgagactaac tcttacttcg caaagagtat ggagtttctg  7260
gcgcgaccgg tgcctgcgcc tcgaacagta ttcaggaacc ctccacatcc cgctccgcgc  7320
acaagaacac cgtcacttgc acccagcagg gcctgctcga gaaccagcct agtttccacc  7380
ccgccaggcg tgaatagggt gatcactaga gaggagctcg aggcgcttac cccgtcacgc  7440
actcctagca ggtcggtctc gagaaccagc ctggtctcca acccgccagg cgtaaatagg  7500
gtgattacaa gagaggagtt tgaggcgttc gtagcacaac aacaatgacg gtttgatgcg  7560
ggtgcataca tcttttcctc cgacaccggt caagggcatt tacaacaaaa atcagtaagg  7620
caaacggtgc tatccgaagt ggtgttggag aggaccgaat tggagatttc gtatgccccg  7680
cgcctcgacc aagaaaaaga agaattacta cgcaagaaat tacagttaaa tcccacacct  7740
gctaacagaa gcagatacca gtccaggaag gtggagaaca tgaaagccat aacagctaga  7800
cgtattctgc aaggcctagg gcattatttg aaggcagaag gaaaagtgga gtgctaccga  7860
accctgcatc ctgttccttt gtattcatct agtgtgaacc gtgccttttc aagccccaag  7920
gtcgcagtgg aagcctgtaa cgccatgttg aaagagaact ttccgactgt ggcttcttac  7980
tgtattattc cagagtacga tgcctatttg gacatggttg acggagcttc atgctgctta  8040
gacactgcca gtttttgccc tgcaaagctg cgcagctttc caaagaaaca ctcctatttg  8100
gaacccacaa tacgatcggc agtgccttca gcgatccaga acacgctcca gaacgtcctg  8160
gcagctgcca caaaaagaaa ttgcaatgtc acgcaaatga gagaattgcc cgtattggat  8220
tcggcggcct ttaatgtgga atgcttcaag aaatatgcgt gtaataatga atattgggaa  8280
acgtttaaag aaaacccat caggcttact gaagaaaacg tggtaaatta cattaccaaa  8340
ttaaaaggac caaaagctgc tgctcttttt gcgaagacac ataatttgaa tatgttgcag  8400
gacataccaa tggacaggtt tgtaatggac ttaaagagag acgtgaaagt gactccagga  8460
acaaaacata ctgaagaacg gcccaaggta caggtgatcc aggctgccga tccgctagca  8520
acagcgtatc tgtgcggaat ccaccgagag ctggttagga gattaaatgc ggtcctgctt  8580
ccgaacattc atacactgtt tgatatgtcg gctgaagact ttgacgctat tatagccgag  8640
cacttccagc ctggggattg tgttctggaa actgacatcg cgtcgtttga taaaagtgag  8700
gacgacgcca tggctctgac cgcgttaatg attctggaag acttaggtgt ggacgcagag  8760
ctgttgacgc tgattgaggc ggctttcggc gaaatttcat caatacattt gcccactaaa  8820
actaaattta aattcggagc catgatgaaa tctggaatgt tcctcacact gtttgtgaac  8880
acagtcatta acattgtaat cgcaagcaga gtgttgagag aacggctaac cggatcacca  8940
tgtgcagcat tcattggaga tgacaatatc gtgaaaggag tcaaatcgga caaattaatg  9000
gcagacaggt gcgccacctg gttgaatatg gaagtcaaga ttatagatgc tgtggtgggc  9060
gagaaagcgc cttatttctg tggagggttt attttgtgtg actccgtgac cggcacagcg  9120
tgccgtgtgg cagacccccct aaaaaggctg tttaagcttg gcaaacctct ggcagcagac  9180
gatgaacatg atgatgacag gagaagggca ttgcatgaag agtcaacacg ctggaaccga  9240
gtgggtattc tttcagagct gtgcaaggca gtagaatcaa ggtatgaaac cgtaggaact  9300
tccatcatag ttatggccat gactactcta gctagcagtg ttaaatcatt cagctacctg  9360
agagggggccc ctataactct ctacggctaa cctgaatgga ctacgacata gtctagtccg  9420
ccaagttcga aggcgcgcct ctagagccac catggtgagc aagggcgagg agctgttcac  9480
cggggtggtg cccatcctgg tcgagctgga cggcgacgta aacggccaca agttcagcgt  9540
gtccggcgag ggcgagggcg atgccaccta cggcaagctg accctgaagt tcatctgcac  9600
caccggcaag ctgcccgtgc cctggcccac cctcgtgacc accctgacct acggcgtgca  9660
gtgcttcagc cgctaccccg accacatgaa gcagcacgac ttcttcaagt ccgccatgcc  9720
cgaaggctac gtccaggagc gcaccatctt cttcaaggac gacggcaact acaagacccg  9780
cgccgaggtg aagttcgagg gcgacaccct ggtgaaccgc atcgagctga agggcatcga  9840
cttcaaggag gacggcaaca tcctggggca caagctggag tacaactaca acagccacaa  9900
cgtctatatc atggccgaca agcagaagaa cggcatcaag gtgaacttca agatccgcca  9960
caacatcgag gacggcagcg tgcagctcgc cgaccactac cagcagaaca cccccatcgg  10020
cgacggcccc gtgctgctgc ccgacaacca ctacctgagc acccagtccg ccctgagcaa  10080
agaccccaac gagaagcgcg atcacatggt cctgctggag ttcgtgaccg ccgccgggat  10140
cactctcggc atggacgagc tgtacaagta gcatcgatga tatcgcggcc gcatacagca  10200
gcaattggca agctgcttac atagaactcg cggcgattgg catgccgcct taaaattttt  10260
attttatttt tcttttcttt tccgaatcaa attttatttt taatatttca aaaaaaaaaa  10320
aaaaa                                                              10325
```

```
SEQ ID NO: 41          moltype = RNA  length = 2936
FEATURE                Location/Qualifiers
source                 1..2936
                       mol_type = other RNA
                       organism = synthetic construct
SEQUENCE: 41
aaaaaaaaaa cgcgtgataa cgcaggaaag aacatgtgag caaaaggcca gcaaaaggcc  60
aggaaccgta aaaaggccgc gttgctggcg tttttccata ggctccgccc ccctgacgag  120
catcacaaaa atcgacgctc aagtcagagg tggcgaaacc cgacaggact ataaagatac  180
caggcgtttc cccctggaag ctccctcgtg cgctctcctg ttccgaccct gccgcttacc  240
ggatacctgt ccgcctttct cccttcggga agcgtggcgc tttctcatag ctcacgctgt  300
aggtatctca gttcggtgta ggtcgttcgc tccaagctgg gctgtgtgca cgaacccccc  360
gttcagcccg accgctgcgc cttatccggt aactatcgtc ttgagtccaa cccggtaaga  420
cacgacttat cgccactggc agcagccact ggtaacagga ttagcagagc gaggtatgta  480
ggcggtgcta cagagttctt gaagtggtgg cctaactacg gctacactag aagaacagta  540
tttggtatct gcgctctgct gaagccagtt accttcggaa aaagagttgg tagctcttga  600
tccggcaaac aaaccaccgc tggtagcggt ttttttgttt gcaagcagca gattacgcgc  660
agaaaaaaag gatctcaaga agatcctttg atcttttcta cggggtctga cgctcagtgg  720
aacgaaaact cacgttaagg gattttggtc atgagattat caaaaaggat cttcacctag  780
atccttttaa attaaaaatg aagttttaaa tcaatctaaa gtatatatga gtaaacttgg  840
tctgacagtt accaatgctt aatcagtgag gcacctatct cagcgatctg tctatttcgt  900
tcatccatag ttgcctgact ccccgtcgtg tagataacta cgatacggga gggcttacca  960
tctggcccca gtgctgcaat gataccgcga gacccacgct caccggctcc agatttatca  1020
gcaataaacc agccagccgg aagggccgag cgcagaagtg gtcctgcaac tttatccgcc  1080
tccatccagt ctattaattg ttgccgggaa gctagagtaa gtagttcgcc agttaatagt  1140
ttgcgcaacg ttgttgccat tgctacaggc atcgtggtgt cacgctcgtc gtttggtatg  1200
gcttcattca gctccggttc ccaacgatca aggcgagtta catgatcccc catgttgtgc  1260
aaaaaagcgg ttagctcctt cggtcctccg atcgttgtca gaagtaagtt ggccgcagtg  1320
ttatcactca tggttatggc agcactgcat aattctctta ctgtcatgcc atccgtaaga  1380
tgcttttctg tgactggtga gtactcaacc aagtcattct gagaatagtg tatgcggcga  1440
ccgagttgct cttgcccggc gtcaatacgg gataataccg cgccacatag cagaacttta  1500
aaagtgctca tcattggaaa acgttcttcg gggcgaaaac tctcaaggat cttaccgctg  1560
ttgagatcca gttcgatgta acccactcgt gcacccaact gatcttcagc atcttttact  1620
ttcaccagcg tttctgggtg agcaaaaaca ggaaggcaaa atgccgcaaa aaagggaata  1680
agggcgacac ggaaatgttg aatactcata ctcttccttt ttcaatatta ttgaagcatt  1740
tatcagggtt attgtctcat gagcggatac atatttgaat gtatttagaa aaataaacaa  1800
ataggggttc cgcgcacatt tccccgaaaa gtgccacctg agctctaata cgactcacta  1860
taggataggc ggcgcatgag agaagcccag accaattacc tacccaaaac ttccatcata  1920
gttatggcca tgactactct agctagcagt gttaaatcat tcagctacct gagaggggcc  1980
cctataactc tctacggcta acctgaatgg actacgacat agtctagtcc gccaagttcg  2040
aaggcgcgcc tctagagcca ccatggtgag caagggcgag gagctgttca ccggggtggt  2100
gcccatcctg gtcgagctgg acggcgacgt aaacggccac aagttcagcg tgtccggcga  2160
gggcgagggc gatgccacct acggcaagct gaccctgaag ttcatctgca ccaccggcaa  2220
gctgcccgtg ccctggccca ccctcgtgac caccctgacc tacggcgtgc agtgcttcag  2280
ccgctacccc gaccacatga agcagcacga cttcttcaag tccgccatgc ccgaaggcta  2340
cgtccaggag cgcaccatct tcttcaagga cgacggcaac tacaagaccc gcgccgaggt  2400
gaagttcgag ggcgacaccc tggtgaaccg catcgagctg aagggcatcg acttcaagga  2460
ggacggcaac atcctggggc acaagctgga gtacaactac aacagccaca acgtctatat  2520
catggccgac aagcagaaga acggcatcaa ggtgaacttc aagatccgcc acaacatcga  2580
ggacggcagc gtgcagctcg ccgaccacta ccagcagaac acccccatcg gcgacggccc  2640
cgtgctgctg cccgacaacc actacctgag cacccagtcc gccctgagca aagaccccaa  2700
cgagaagcgc gatcacatgg tcctgctgga gttcgtgacc gccgccggga tcactctcgg  2760
catggacgag ctgtacaagt agcatcgatg atatcgcggc cgcatacagc agcaattggc  2820
aagctgctta catagaactc gcggcgattg gcatgccgcc ttaaaatttt tattttattt  2880
ttcttttctt ttccgaatcg gattttgttt ttaatatttc aaaaaaaaaa aaaaaa      2936

SEQ ID NO: 42          moltype = RNA  length = 11522
FEATURE                Location/Qualifiers
source                 1..11522
                       mol_type = other RNA
                       organism = synthetic construct
SEQUENCE: 42
aaaaaaaaaa cgcgtcgagg ggaattaatt cttgaagacg aaagggccag gtggcacttt  60
tcggggaaat gtgcgcggaa cccctatttg tttatttttc taaatacatt caaatatgta  120
tccgctcatg agacaataac cctgataaat gcttcaataa tattgaaaaa ggaagagtat  180
gagtattcaa catttccgtg tcgcccttat tccctttttt gcggcatttt gccttcctgt  240
ttttgctcac ccagaaacgc tggtgaaagt aaaagatgct gaagatcagt tgggtgcacg  300
agtgggttac atcgaactgg atctcaacag cggtaagatc cttgagagtt ttcgccccga  360
agaacgtttt ccaatgatga gcacttttaa agttctgcta tgtggcgcgg tattatcccg  420
tgttgacgcc gggcaagagc aactcggtcg ccgcatacac tattctcaga atgacttggt  480
tgagtactca ccagtcacag aaaagcatct tacggatggc atgacagtaa gagaattatg  540
cagtgctgcc ataaccatga gtgataacac tgcggccaac ttacttctga caacgatcgg  600
aggaccgaag gagctaaccg cttttttgca caacatgggg gatcatgtaa ctcgccttga  660
tcgttgggaa ccggagctga atgaagccat accaaacgac gagcgtgaca ccacgatgcc  720
tgtagcaatg gcaacaacgt tgcgcaaact attaactggc gaactactta ctctagcttc  780
ccggcaacaa ttaatagact ggatggaggc ggataaagtt gcaggaccac ttctgcgctc  840
ggcccttccg gctggctggt ttattgctga taaatctgga gccggtgagc gtgggtctcg  900
cggtatcatt gcagcactgg ggccagatgg taagccctcc cgtatcgtag ttatctacac  960
```

-continued

```
gacggggagt caggcaacta tggatgaacg aaatagacag atcgctgaga taggtgcctc  1020
actgattaag cattggtaac tgtcagacca agtttactca tatatacttt agattgattt  1080
aaaacttcat ttttaattta aaaggatcta ggtgaagatc ctttttgata atctcatgac  1140
caaaatccct taacgtgagt tttcgttcca ctgagcgtca gaccccgtag aaaagatcaa  1200
aggatcttct tgagatcctt tttttctgcg cgtaatctgc tgcttgcaaa caaaaaaacc  1260
accgctacca gcggtggttt gtttgccgga tcaagagcta ccaactcttt ttccgaaggt  1320
aactggcttc agcagagcgc agataccaaa tactgtcctt ctagtgtagc cgtagttagg  1380
ccaccacttc aagaactctg tagcaccgcc tacatacctc gctctgctaa tcctgttacc  1440
agtggctgct gccagtggcg ataagtcgtg tcttaccggg ttggactcaa gacgatagtt  1500
accggataag gcgcagcggt cgggctgaac ggggggttcg tgcacacagc ccagcttgga  1560
gcgaacgacc tacaccgaac tgagatacct acagcgtgag ctatgagaaa gcgccacgct  1620
tcccgaaggg agaaaggcgg acaggtatcc ggtaagcggc agggtcggaa caggagagcg  1680
cacgagggag cttccagggg gaaacgcctg gtatctttat agtcctgtcg ggtttcgcca  1740
cctctgactt gagcgtcgat ttttgtgatg ctcgtcaggg gggcggagcc tatggaaaaa  1800
cgccagcaac gcgagctcta atacgactca ctatagatgg gcggcgcatg agagaagccc  1860
agaccaatta cctacccaaa atggagaaag ttcacgttga catcgaggaa gacagcccat  1920
tcctcagagc tttgcagcgg agcttcccgc agtttgaggt agaagccaag caggtcactg  1980
ataatgacca tgctaatgcc agagcgtttt cgcatctggc ttcaaaactg atcgaaacgg  2040
aggtggaccc atccgacacg atccttgaca ttggaagtgc gcccgcccgc agaatgtatt  2100
ctaagcacaa gtatcattgt atctgtccga tgagatgtgc ggaagatccg gacagattgt  2160
ataagtatgc aactaagctg aagaaaaact gtaaggaaat aactgataag gaattggaca  2220
agaaaatgaa ggagctggcc gccgtcatga gcgaccctga cctggaaact gagactatgt  2280
gcctccacga cgacgagtcg tgtcgctacg aagggcaagt cgctgtttac caggatgtat  2340
acgcggttga cggaccgaca agtctctatc accaagccaa taagggagtt agagtcgcct  2400
actggatagg ctttgacacc accccttta tgtttaagaa cttggctgga gcatatccat  2460
catactctac caactgggcc gacgaaaccg tgttaacggc tcgtaacata ggcctatgca  2520
gctctgacgt tatggagcgg tcacgtagag ggatgtccat tcttagaaag aagtatttga  2580
aaccatccaa caatgttcta ttctctgttg gctcgaccat ctaccacgag aagagggact  2640
tactgaggag ctggcacctg ccgtctgtat ttcacttacg tggcaagcaa aattacacat  2700
gtcggtgtga gactatagtt agttgcgacg ggtacgtcgt taaaagaata gctatcagtc  2760
caggcctgta tgggaagcct tcaggctatg ctgctacgat gcaccgcgag ggattcttgt  2820
gctgcaaagt gacagacaca ttgaacgggg agagggtctc ttttcccgtg tgcacgtatg  2880
tgccagctac attgtgtgac caaatgactg gcatactggc aacagatgtc agtgcggacg  2940
acgcgcaaaa actgctggtt gggctcaacc agcgtatagt cgtcaacggt cgcacccaga  3000
gaaacaccaa taccatgaaa aattaccttt tgcccgtagt ggcccaggca tttgctaggt  3060
gggcaaagga atataaggaa gatcaagaag atgaaaggcc actaggacta cgagatagac  3120
agttagtcat ggggtgttgt tgggctttta gaaggcacaa gataacatct atttataagc  3180
gcccggatac ccaaaccatc atcaaagtga acagcgattt ccactcattc gtgctgccca  3240
ggataggcag taacacattg gagatcgggc tgagaacaag aatcaggaaa atgttagagg  3300
agcacaagga gccgtcacct ctcattaccg ccgaggacgt acaagaagct aagtgcgcag  3360
ccgatgaggc taaggaggtg cgtgaagccg aggagttgcg cgcagctcta ccacctttgg  3420
cagctgatgt tgaggagccc actctggagg cagacgtcga cttgatgtta caagaggctg  3480
gggccggctc agtggagaca cctcgtggct tgataaaggt taccagctac gatggcgagg  3540
acaagatcgg ctcttacgct gtgctttctc cgcaggctgt actcaagagt gaaaaattat  3600
cttgcatcca ccctctcgct gaacaagtca tagtgataac acactctggc cgaaaagggc  3660
gttatgccgt ggaaccatac catggtaaag tagtggtgcc agagggacat gcaatacccg  3720
tccaggactt tcaagctctg agtgaaagtg ccaccattgt gtacaacgaa cgtgagttcg  3780
taaacaggta cctgcaccat attgccacac atggaggagc gctgaacact gatgaagaat  3840
attacaaaac tgtcaagccc agcgagcacg acggcgaata cctgtacgac atcgacagga  3900
aacagtgcgt caagaaagaa ctagtcactg ggctagggct cacaggcgag ctggtggatc  3960
ctcccttcca tgaattcgcc tacgagagtc tgagaacacg accagccgct ccttaccaag  4020
taccaaccat aggggtgtat ggcgtgccag gatcaggcaa gtctggcatc attaaaagcg  4080
cagtcaccaa aaaagatcta gtggtgagcg ccaagaaaga aaactgtgca gaaattataa  4140
gggacgtcaa gaaaatgaaa gggctggacg tcaatgccag aactgtggac tcagtgctct  4200
tgaatggatg caaacacccc gtagagaccc tgtatattga cgaagctttt gcttgtcatg  4260
caggtactct cagagcgctc atagccatta taagacctaa aaaggcagtg ctctgcgggg  4320
atcccaaaca gtgcggtttt tttaacatga tgtgcctgaa agtgcatttt aaccacgaga  4380
tttgcacaca agtcttccac aaaagcatct ctcgccgttg cactaaatct gtgacttcgg  4440
tcgtctcaac cttgttttac gacaaaaaaa tgagaacgac gaatccgaaa gagactaaga  4500
ttgtgattga cactaccggc agtaccaaac ctaagcagga cgatctcatt ctcacttgtt  4560
tcagagggtg ggtgaagcag ttgcaaatag attacaaagg caacgaaata atgacggcag  4620
ctgcctctca agggctgacc cgtaaaggtg tgtatgccgt tcggtacaag gtgaatgaaa  4680
atcctctgta cgcacccacc tcagaacatg tgaacgtcct actgacccgc acggaggacc  4740
gcatcgtgtg gaaaacacta gccggcgacc catggataaa aacactgact gccaagtacc  4800
ctgggaattt cactgccacg atagaggagt ggcaagcaga gcatgatgcc atcatgaggc  4860
acatcttgga gagaccggac cctaccgacg tcttccagaa taaggcaaac gtgtgttggg  4920
ccaaggcttt agtgccggtg ctgaagaccg ctggcataga catgaccact gaacaatgga  4980
acactgtgga ttattttgaa acggacaaag ctcactcagc agagatagta ttgaaccaac  5040
tatgcgtgag gttctttgga ctcgatctgg actccggtct attttctgca cccactgttc  5100
cgttatccat taggaataat cactgggata actccccgtc gcctaacatg tacgggctga  5160
ataaagaagt ggtccgtcag ctctctcgca ggtacccaca actgcctcgg gcagttgcca  5220
ctggaagagt ctatgacatg aacactggta cactgcgcaa ttatgatccg cgcataaacc  5280
tagtacctgt aaacagaaga ctgcctcatg ctttagtcct ccaccataat gaacacccac  5340
agagtgactt ttcttcattc gtcagcaaat tgaagggcag aactgtcctg gtggtcgggg  5400
aaaagttgtc cgtcccaggc aaaatggttg actggttgtc agaccggcct gaggctacct  5460
tcagagctcg gctggattta ggcatcccag gtgatgtgcc caaatatgac ataatatttg  5520
ttaatgtgag gaccccatat aaataccatc actatcagca gtgtgaagac catgccatta  5580
agcttagcat gttgaccaag aaagcttgtc tgcatctgaa tcccggcgga acctgtgtca  5640
gcataggtta tggttacgct gacagggcca gcgaaagcat cattggtgct atagcgcggc  5700
```

-continued

```
agttcaagtt ttcccgggta tgcaaaccga aatcctcact tgaagagacg gaagttctgt  5760
ttgtattcat tgggtacgat cgcaaggccc gtacgcacaa ttcttacaag ctttcatcaa  5820
ccttgaccaa catttataca ggttccagac tccacgaagc cggatgtgca ccctcatatc  5880
atgtggtgcg aggggatatt gccacggcca ccgaaggagt gattataaat gctgctaaca  5940
gcaaaggaca acctggcgga ggggtgtgcg gagcgctgta taagaaattc ccggaaagct  6000
tcgatttaca gccgatcgaa gtaggaaaag cgcgactggt caaaggtgca gctaaacata  6060
tcattcatgc cgtaggacca aacttcaaca aagtttcgga ggttgaaggt gacaaacagt  6120
tggcagaggc ttatgagtcc atcgctaaga ttgtcaacga taacaattac aagtcagtag  6180
cgattccact gttgtccacc ggcatctttt ccgggaacaa agatcgacta acccaatcat  6240
tgaaccattt gctgacagct ttagacacca ctgatgcaga tgtagccata tactgcaggg  6300
acaagaaatg ggaaatgact ctcaaggaag cagtggctag gagagaagca gtggaggaga  6360
tatgcatatc cgacgactct tcagtgacag aacctgatgc agagctggtg agggtgcatc  6420
cgaagagttc tttggctgga aggaagggct acagcacaag cgatggcaaa actttctcat  6480
atttggaagg gaccaagttt caccaggcgg ccaaggatat agcagaaatt aatgccatgt  6540
ggcccgttgc aacggaggcc aatgagcagg tatgcatgta tatcctcgga gaaagcatga  6600
gcagtattag gtcgaaatgc cccgtcgaag agtcggaagc ctccacacca cctagcacgc  6660
tgccttgctt gtgcatccat gccatgactc cagaaagagt acagcgccta aaagcctcac  6720
gtccagaaca aattactgtg tgctcatcct ttccattgcc gaagtataga atcactggtg  6780
tgcagaagat ccaatgctcc cagcctatat tgttctcacc gaaagtgcct gcgtatattc  6840
atccaaggaa gtatctcgtg gaaacaccac cggtagacga gactccggag ccatcggcag  6900
agaaccaatc cacagagggg acacctgaac aaccaccact tataaccgag gatgagacca  6960
ggactagaac gcctgagccg atcatcatcg aagaggaaga agaggatagc ataagtttgc  7020
tgtcagatgg cccgacccac caggtgctgc aagtcgaggc agacattcac gggccgccct  7080
ctgtatctag ctcatcctgg tccattcctc atgcatccga ctttgatgtg gacagtttat  7140
ccatacttga caccctggag ggagctagcg tgaccagcgg ggcaacgtca gccgagacta  7200
actcttactt cgcaaagagt atggagtttc tggcgcgacc ggtgcctgcg cctcgaacag  7260
tattcaggaa ccctccacat cccgctccgc gcacaagaac accgtcactt gcacccagca  7320
gggcctgctc gagaaccagc ctagtttcca ccccgccagg cgtgaatagg gtgatcacta  7380
gagaggagct cgaggcgctt accccgtcac gcactcctag caggtcggtc tcgagaacca  7440
gcctggtctc caacccgcca ggcgtaaata gggtgattac aagagaggag tttgaggcgt  7500
tcgtagcaca acaacaatga cggtttgatg cgggtgcata catcttttcc tccgacaccg  7560
gtcaagggca tttacaacaa aaatcagtaa ggcaaacggt gctatccgaa gtggtgttgg  7620
agaggaccga attggagatt tcgtatgccc cgcgcctcga ccaagaaaaa gaagaattac  7680
tacgcaagaa attacagtta aatcccacac ctgctaacag aagcagatac cagtccagga  7740
aggtggagaa catgaaagcc ataacagcta gacgtattct gcaaggccta gggcattatt  7800
tgaaggcaga aggaaaagtg gagtgctacc gaaccctgca tcctgttcct ttgtattcat  7860
ctagtgtgaa ccgtgccttt tcaagcccca aggtcgcagt ggaagcctgt aacgccatgt  7920
tgaaagagaa ctttccgact gtggcttctt actgtattat tccagagtac gatgcctatt  7980
tggacatggt tgacggagct tcatgctgct tagacactgc cagtttttgc cctgcaaagc  8040
tgcgcagctt tccaaagaaa cactcctatt tggaacccac aatacgatcg gcagtgcctt  8100
cagcgatcca gaacacgctc cagaacgtcc tggcagctgc cacaaaaaga aattgcaatg  8160
tcacgcaaat gagagaattg cccgtattgg attcggcggc ctttaatgtg gaatgcttca  8220
agaaatatgc gtgtaataat gaatattggg aaacgtttaa agaaaacccc atcaggctta  8280
ctgaagaaaa cgtggtaaat tacattacca aattaaaagg accaaaagct gctgctcttt  8340
ttgcgaagac acataatttg aatatgttgc aggacatacc aatggacagg tttgtaatgg  8400
acttaaagag agacgtgaaa gtgactccag gaacaaaaca tactgaagaa cggcccaagg  8460
tacaggtgat ccaggctgcc gatccgctag caacagcgta tctgtgcgga atccaccgag  8520
agctggttag gagattaaat gcggtcctgc ttccgaacat tcatacactg tttgatatgt  8580
cggctgaaga ctttgacgct attatagccg agcacttcca gcctggggat tgtgttctgg  8640
aaactgacat cgcgtcgttt gataaaagtg aggacgacgc catggctctg accgcgttaa  8700
tgattctgga agacttaggt gtggacgcag agctgttgac gctgattgag gcggctttcg  8760
gcgaaatttc atcaatacat ttgcccacta aaactaaatt taaattcgga gccatgatga  8820
aatctggaat gttcctcaca ctgtttgtga acacagtcat taacattgta atcgcaagca  8880
gagtgttgag agaacggcta accggatcac catgtgcagc attcattgga gatgacaata  8940
tcgtgaaagg agtcaaatcg gacaaattaa tggcagacag gtgcgccacc tggttgaata  9000
tggaagtcaa gattatagat gctgtggtgg gcgagaaagc gccttatttc tgtggagggt  9060
ttattttgtg tgactccgtg accggcacag cgtgccgtgt ggcagacccc ctaaaaaggc  9120
tgtttaagct tggcaaacct ctggcagcag acgatgaaca tgatgatgac aggagaaggg  9180
cattgcatga agagtcaaca cgctggaacc gagtgggtat tctttcagag ctgtgcaagg  9240
cagtagaatc aaggtatgaa accgtaggaa cttccatcat agttatggcc atgactactc  9300
tagctagcag tgttaaatca ttcagctacc tgagaggggc ccctataact ctctacggct  9360
aacctgaatg gactacgaca tagtctagtc cgccaagtct agcatatggg cgcgccctca  9420
gcatcgattc aattcgccac catggtgagc aagggcgagg agctgttcac cggggtggtg  9480
cccatcctgg tcgagctgga cggcgacgta aacggccaca agttcagcgt gtccggcgag  9540
ggcgagggcg atgccaccta cggcaagctg accctgaagt tcatctgcac caccggcaag  9600
ctgcccgtgc cctggcccac cctcgtgacc accctgacct acggcgtgca gtgcttcagc  9660
cgctaccccg accacatgaa gcagcacgac ttcttcaagt ccgccatgcc cgaaggctac  9720
gtccaggagc gcaccatctt cttcaaggac gacggcaact acaagacccg cgccgaggtg  9780
aagttcgagg gcgacaccct ggtgaaccgc atcgagctga agggcatcga cttcaaggag  9840
gacggcaaca tcctggggca caagctggag tacaactaca acagccacaa cgtctatatc  9900
atggccgaca agcagaagaa cggcatcaag gtgaacttca agatccgcca caacatcgag  9960
gacggcagcg tgcagctcgc cgaccactac cagcagaaca cccccatcgg cgacggcccc  10020
gtgctgctgc ccgacaacca ctacctgagc acccagtccg ccctgagcaa agaccccaac  10080
gagaagcgcg atcacatggt cctgctggag ttcgtgaccg ccgccgggat cactctcggc  10140
atggacgagc tgtacaagta gtctagagtc gacccgggcg gccgcaacta acttaagcta  10200
gcaacggttt ccctctagcg ggatcaattc cgcccccccc ccctaacgtt actggccgaa  10260
gccgcttgga ataaggccgg tgtgcgtttg tctatatgtt attttccacc atattgccgt  10320
cttttggcaa tgtgagggcc cggaaacctg gccctgtctt cttgacgagc attcctaggg  10380
gtctttcccc tctcgccaaa ggaatgcaag gtctgttgaa tgtcgtgaag gaagcagttc  10440
```

-continued

```
ctctggaagc ttcttgaaga caaacaacgt ctgtagcgac cctttgcagg cagcggaacc  10500
ccccacctgg cgacaggtgc ctctgcggcc aaaagccacg tgtataagat acacctgcaa  10560
aggcggcaca accccagtgc cacgttgtga gttggatagt tgtggaaaga gtcaaatggc  10620
tctcctcaag cgtattcaac aaggggctga aggatgccca gaaggtaccc cattgtatgg  10680
gatctgatct ggggcctcgg tgcacatgct ttacatgtgt ttagtcgagg ttaaaaaaac  10740
gtctaggccc cccgaaccac ggggacgtgg ttttcctttg aaaaacacga taataccatg  10800
accgagtaca agcccacggt gcgcctcgcc acccgcgacg acgtccccag ggccgtacgc  10860
accctcgccg ccgcgttcgc cgactacccc gccacgcgcc acaccgtcga tccggaccgc  10920
cacatcgagc gggtcaccga gctgcaagaa ctcttcctca cgcgcgtcgg gctcgacatc  10980
ggcaaggtgt gggtcgcgga cgacggcgcc gcggtggcgg tctggaccac gccggagagc  11040
gtcgaagcgg gggcggtgtt cgccgagatc ggcccgcgca tggccgagtt gagcggttcc  11100
cggctggccg cgcagcaaca gatggaaggc ctcctggcgc cgcaccggcc caaggagccc  11160
gcgtggttcc tggccaccgt cggcgtctcg cccgaccacc agggcaaggg tctgggcagc  11220
gccgtcgtgc tccccggagt ggaggcggcc gagcgcgccg gggtgcccgc cttcctggag  11280
acctccgcgc cccgcaacct ccccttctac gagcggctcg gcttcaccgt caccgccgac  11340
gtcgaggtgc ccgaaggacc gcgcacctgg tgcatgaccc gcaagcccgg tgcctgagaa  11400
ttggcaagct gcttacatag aactcgcggc gattggcatg ccgccttaaa atttttattt  11460
tatttttct tttcttttcc gaatcggatt ttgtttttaa tatttcaaaa aaaaaaaaaa  11520
aa                                                                11522

SEQ ID NO: 43          moltype = RNA  length = 82
FEATURE                Location/Qualifiers
source                 1..82
                       mol_type = other RNA
                       organism = synthetic construct
SEQUENCE: 43
cgcgtgataa cgcaggaaag aacatgtgag caaaaggcca gcaaaaggcc aggaaccgta  60
aaaaggccgc gttgctggcg tt                                          82

SEQ ID NO: 44          moltype = RNA  length = 31
FEATURE                Location/Qualifiers
source                 1..31
                       mol_type = other RNA
                       organism = synthetic construct
SEQUENCE: 44
cacatttccc cgaaaagtgc cacctgagct c                                31

SEQ ID NO: 45          moltype = RNA  length = 26
FEATURE                Location/Qualifiers
source                 1..26
                       mol_type = other RNA
                       organism = synthetic construct
SEQUENCE: 45
ttcgaaggcg cgcctctaga gccacc                                      26

SEQ ID NO: 46          moltype = RNA  length = 31
FEATURE                Location/Qualifiers
source                 1..31
                       mol_type = other RNA
                       organism = synthetic construct
SEQUENCE: 46
catcgatgat atcgcggccg catacagcag c                                31

SEQ ID NO: 47          moltype = RNA  length = 19
FEATURE                Location/Qualifiers
source                 1..19
                       mol_type = other RNA
                       organism = synthetic construct
SEQUENCE: 47
taatacgact cactatagg                                              19

SEQ ID NO: 48          moltype =   length =
SEQUENCE: 48
000

SEQ ID NO: 49          moltype = RNA  length = 21
FEATURE                Location/Qualifiers
source                 1..21
                       mol_type = other RNA
                       organism = synthetic construct
SEQUENCE: 49
ggattttgtt tttaatattt c                                           21
```

-continued

```
SEQ ID NO: 50          moltype = RNA  length = 21
FEATURE                Location/Qualifiers
source                 1..21
                       mol_type = other RNA
                       organism = synthetic construct
SEQUENCE: 50
ggattttatt tttaatattt c                                            21

SEQ ID NO: 51          moltype = RNA  length = 21
FEATURE                Location/Qualifiers
source                 1..21
                       mol_type = other RNA
                       organism = synthetic construct
SEQUENCE: 51
aaattttgtt tttaatattt c                                            21

SEQ ID NO: 52          moltype = RNA  length = 21
FEATURE                Location/Qualifiers
source                 1..21
                       mol_type = other RNA
                       organism = synthetic construct
SEQUENCE: 52
aaattttatt tttaatattt c                                            21

SEQ ID NO: 53          moltype = RNA  length = 24
FEATURE                Location/Qualifiers
source                 1..24
                       mol_type = other RNA
                       organism = synthetic construct
SEQUENCE: 53
taatacgact cactatagga tagg                                         24

SEQ ID NO: 54          moltype = RNA  length = 95
FEATURE                Location/Qualifiers
source                 1..95
                       mol_type = other RNA
                       organism = Venezuelan equine encephalitis virus
SEQUENCE: 54
catgccgcct taaaattttt attttatttt tcttttcttt tccgaatcgg attttgtttt  60
taatatttca aaaaaaaaaa aaaaaaaaaa aaaaa                             95
```